United States Patent [19]
Schlessinger et al.

[11] Patent Number: 5,858,686
[45] Date of Patent: Jan. 12, 1999

[54] METHODS FOR DETECTING TYROSINE KINASE-BINDING TARGET PROTEINS AND IDENTIFYING SUBSTANCES THAT AFFECT SH2 PHOSPHORYLATED LIGAND REGULATORY SYSTEMS

[75] Inventors: Joseph Schlessinger; Edward Y. Skolnik; Benjamin L. Margolis, all of New York, N.Y.

[73] Assignee: New York University, New York, N.Y.

[21] Appl. No.: 539,005

[22] Filed: Oct. 4, 1995

Related U.S. Application Data

[62] Division of Ser. No. 167,035, Dec. 16, 1993, Pat. No. 5,618,691, which is a division of Ser. No. 906,349, Jun. 30, 1992, Pat. No. 5,434,064, which is a continuation-in-part of Ser. No. 643,237, Jan. 18, 1991, abandoned.

[51] Int. Cl.⁶ .................................................. G01N 33/53
[52] U.S. Cl. .............................. 435/7.8; 435/7.1; 435/15; 435/194; 530/350; 530/352; 436/501
[58] Field of Search ..................................... 435/7.1, 69.1, 435/172.3, 15, 194, 7.8; 514/12, 7; 436/501, 504; 530/350, 352

[56] References Cited

U.S. PATENT DOCUMENTS

| | | | |
|---|---|---|---|
| 5,352,660 | 10/1994 | Pawson | 514/12 |
| 5,434,064 | 7/1995 | Schlessinger | 435/172.3 |

OTHER PUBLICATIONS

Anderson et al, Science 250:979–982, Nov. 1990.
Skolnik et al, Cell 65:83–90, Apr. 5, 1991.
Escobedo et al, Cell 65:75–82, Apr. 5, 1991.
Otsu et al, Cell 65: 91–104, Apr. 5, 1991.
Matuoka et al, Proc.Natl. Acad. Sci USA 89:9015–9019, Oct. 1992.

*Primary Examiner*—Lorraine Spector
*Assistant Examiner*—Eliane Lazar-Wesley
*Attorney, Agent, or Firm*—Pennie & Edmonds LLP

[57] ABSTRACT

A novel expression cloning method is provided for the detection, identification and purification of target proteins capable of binding at least to a tryosine-phosphorylated domain of a eukaryotic tyrosine kinase using novel peptide probes comprising an amino acid sequence substantially corresponding to a portion of a tyrosine-phosphorylated domain of a tyrosine kinase. The probe has at least one phosphorlated tyrosine residue and may be detectably labeled. Also disclosed is a method for preparing the probe, a method for mapping to a chormosome a gene encoding a protein capable of binding to tyrosine-phosphorylated domains of tyrosine kinases, and a method for purifying such a protein with the probe. Non-limiting examples of novel proteins discovered using the above cloning method include GRB-1, GRB-2, GRB-3, GRB-4 and GRB-7, as well as nucleic acid encoding these proteins, and methods for detecting these proteins are also provided.

18 Claims, 59 Drawing Sheets

```
  1 TACAACCAGGCTCAACTGTTGCATGGTAGCAGATTTGCAAACATGAGTGCTGAGGGGTAC   60
    ---------+---------+---------+---------+---------+---------+
    ATGTTGGTCCGAGTTGACAACGTACCATCGTCTAAACGTTTGTACTCACGACTCCCCATG
                                                 M  S  A  E  G  Y

61 CAGTACAGAGCGCTGTATGATTATAAAAAGGAAAGAGAAGAAGATATTGACTTGCACTTG  120
    ---------+---------+---------+---------+---------+---------+
    GTCATGTCTCGCGACATACTAATATTTTTCCTTTCTCTTCTTCTATAACTGAACGTGAAC
     Q  Y  R  A  L  Y  D  Y  K  K  E  R  E  E  D  I  D  L  H  L

121 GGTGACATATTGACTGTGAATAAAGGTCCTTAGTAGCTCTTGGATTCAGTGATGGACAG   180
    ---------+---------+---------+---------+---------+---------+
    CCACTGTATAACTGACACTTATTTCCCAGGAATCATCGAGAACCTAAGTCACTACCTGTC
     G  D  I  L  T  V  N  K  G  S  L  V  A  L  G  F  S  D  G  Q

181 GAAGCCAGGCCTGAAGAATTGGCTGGTTAAATGGCTATAATGAAACCAGGGGAAAGG     240
    ---------+---------+---------+---------+---------+---------+
    CTTCGGTCCGGACTTCTTAACCGACCAATTTACCGATATTACTTTGGTGTCCCCTTTCC
     E  A  R  P  E  E  I  G  W  L  N  G  Y  N  E  T  T  G  E  R

241 GGGGACTTTCCGGGAACTTACGTAGAATATATTGGAAGGAAAAAAATCTCGCCTCCCACA  300
    ---------+---------+---------+---------+---------+---------+
    CCCCTGAAAGGCCCTTGAATGCATCTTATATAACCTTCCTTTTTTTAGAGCGGAGGGTGT
     G  D  F  P  G  T  Y  V  E  Y  I  G  R  K  K  I  S  P  P  T

301 CCAAGCCCCGGCCACCTGGCCTCTTCCTGTTGCACCAGGTTCTTCGAAAACTGAAGCA    360
    ---------+---------+---------+---------+---------+---------+
    GGTTTCGGGGCCGGTGGACCGGAGCCGGAGAAGACAACGTGGTCCAAGAAGCTTTGACTTCGT
     P  K  P  R  P  P  R  P  L  P  V  A  P  G  S  S  K  T  E  A
```

FIG. 4A

```
361  GATGTTGAACAACAAGCTTTGACTCTCCCGGATCTTGCAGAGCAGTTTGCCCCTCCTGAC   420
     ----+----+----+----+----+----+----+----+----+----+----+----+
     CTACAACTTGTTGTTCGAAACTGAGAGGGCCTAGAACGTCTCGTCAAACGGGGAGGACTG

D  V  E  Q  Q  A  L  T  L  P  D  L  A  E  Q  F  A  P  P  D

421  ATTGCCCCGCCCTCTTCTTATCAAGCTCGTCGTTGAAGCCATTGAAAGAAAAGGTCTGGAATGT   480
     ----+----+----+----+----+----+----+----+----+----+----+----+
     TAACGGGGCGGAGAAGAATAGTTCGAGCAGCAACTTCGGTAACTTTCTTTCCAGACCTTACA

I  A  P  P  L  L  I  K  L  V  E  A  I  E  R  K  G  L  E  C

481  TCAACTCTATACAGAACACAGAGCTCCAGCAACCTGGCAGAATTACGACAGCTTCTTGAT   540
     ----+----+----+----+----+----+----+----+----+----+----+----+
     AGTTGAGATATGTCTGTTGTCTCGAGGTCGTTGGACCGTCTTAATGCTGTCGAAGAACTA

S  T  L  Y  R  T  Q  S  S  N  L  A  E  L  R  Q  L  L  D

541  TGTGATACACCCTCCGTGGACTTGGAAATGATCGATGTGCACGTTTTGGCTGACGCTTTC   600
     ----+----+----+----+----+----+----+----+----+----+----+----+
     ACACTATGTGGGAGGCACCCTGAACCTTTACTAGCTACACGTGCAAAACCGACTGCGAAAG

C  D  T  P  S  V  D  L  E  M  I  D  V  H  V  L  A  D  A  F

601  AAACGCTATCTCCCTGGACTTACCAAATCCTGTCATTCCAGCAGCCGTTTACAGTGAAATG   660
     ----+----+----+----+----+----+----+----+----+----+----+----+
     TTTGCGATAGAGGACCTGAATGGTTTAGGACAGTAAGGTCGTCGGCAAATGTCACTTTAC

K  R  Y  L  L  D  L  P  N  P  V  I  P  A  A  V  Y  S  E  M

661  ATTTCTTTAGCTCCAGAAGTCCAGAGTACAAAGCTCCGAAGAATATATTCAGCTATTGAAGAAGCTT   720
     ----+----+----+----+----+----+----+----+----+----+----+----+
     TAAAGAAATCGAGGTCTTCATGTTTCGAGGCTTCTTATATAAGTCGATAACTTCTTCGAA

```
        ATTAGGTCGCCTAGCATACCTCATCAGTATTGGCTTACGCTTCAGTATTTGTTAAAACAT
721     ------+---------+---------+---------+---------+---------+   780
        TAATCCAGCGGATCGTATGGAGTAGTCATAACCGAATGCGAAGTCATAAACAATTTGTA

I  R  S  P  S  I  P  H  Q  Y  W  L  T  L  Q  Y  L  L  K  H

TTCTTCAAGCTCTCTCAAACCTCCAGCAAAAATCTGTTGAATGCAAGAGTACTCTCTGAA
781     ------+---------+---------+---------+---------+---------+   840
        AAGAAGTTCGAGAGAGTTTGGAGGTCGTTTTTAGACAACTTACGTTCTCATGAGAGACTT

F  F  K  L  S  Q  T  S  S  K  N  L  L  N  A  R  V  L  S  E

ATTTTCAGCCCTATGCTTTTCAGATTCTCAGCAGCCTCTGATAATACTGAAAACCTC
841     ------+---------+---------+---------+---------+---------+   900
        TAAAAGTCGGGATACGAAAGTCTAAGAGTCGTCGGAGACTATTATGACTTTTGGAG

I  F  S  P  M  L  F  R  F  S  A  A  S  S  D  N  T  E  N  L

ATAAAAGTTATAGAAATTTTAATCTCAACTGAATGGAATGAACAGCCTGCACCAGCA
901     ------+---------+---------+---------+---------+---------+   960
        TATTTTGAATATGTTTAAAATTAGAGTTGACTTACCTTACTTGCTGTCGGACGTGTCGT

I  K  V  I  E  I  L  I  S  T  E  W  N  E  R  Q  P  A  P  A

CTGCCTCCTAAAATGCTGAATGGTACTGGGGAGATATCTCGAGGGAAGAAGTGAATAACAATATG
961     ------+---------+---------+---------+---------+---------+   1020
        GACGGAGGATTTGTGTGTTTTGGATGATGACATCGGTTGTTGCCATACTTATTGTTATAC

L  P  P  K  P  P  K  P  T  T  V  A  N  N  G  M  N  N  N  M

TCCTTACAAAATGTTTACGACTTACCATGACCCCCTCTATAGAGCTCCCTTCTTCACTTACTTTTT
1021    ------+---------+---------+---------+---------+---------+   1080
        AGGAATGTTTTACAAATGCTGAATGGTACTGGGGAGATATCTCGAGGGAAGAAGTGAATGAAAAA

```
1081 CTTCGAGATACAGCAGACGGGACCTTTTTGGTACGAGATGCGTCTACTAAAATGCATGGT
     ------+---------+---------+---------+---------+---------+ 1140
     GAAGCTCTATGTCGTCTGCCCTGGAAAAACCATGCTCTACGCAGATGATTTTACGTACCA

L   R   D   T   A   D   G   T   F   F   L   V   R   D   A   S   T   K   M   H   G

1141 GATTATACTCTTACACTAAGGAAAGGGGAAATAACAAATTAATCAAATATTTCATCGA
     ------+---------+---------+---------+---------+---------+ 1200
     CTAATATGAGAATGTGATTCCTTTCCCCCTTTATTGTTTAATTAGTTTTATAAAGTAGCT

D   Y   T   L   T   L   R   K   G   G   N   N   K   L   I   K   I   F   H   R

1201 GATGGGAAATATGGCTTCTCTCTGACCCATTAACCTTCAGTTCTGTGGTTGAATTAATAAAC
     ------+---------+---------+---------+---------+---------+ 1260
     CTACCCTTTATACCGAAGAGACTGGGTAATTGGAAGTCAAGACACCAACTTAATTATTTG

D   G   K   Y   G   F   S   D   P   L   T   F   S   S   V   V   E   L   I   N

1261 CACTACCGAATGAATCTCTAGCTCAGTATATAATCCCAAATTGGATGTGAAATTACTTTAT
     ------+---------+---------+---------+---------+---------+ 1320
     GTGATGGCCTTACTTAGAGATCGAGTCATATATTAGGGTTTAACCTACACTTTAATGAAATA

H   Y   R   N   E   S   L   A   Q   Y   N   P   K   L   D   V   K   L   L   Y

1321 CCAGTATCCAAATACCAACAGGATCAAGTTGTCAAAGAAGATAATATTGAAGCTGTAGGG
     ------+---------+---------+---------+---------+---------+ 1380
     GGTCATAGGTTTATGGTTGTCCTAGTTCAACAGTTTCTTCTATTATAACTTCGACATCCC

P   V   S   K   Y   Q   Q   D   Q   V   V   K   E   D   N   I   E   A   V   G

1381 AAAAAATTACATGAATATAACACTCAGTTTCAAGAAAAAGTCGAGAATGATAGATTA
     ------+---------+---------+---------+---------+---------+ 1440
     TTTTTAATGTACTTATATTGTGAGTCAAAGTTCTTTTTCAGCTCTTATACTATCTAAT

```
1441  TATGAAGAATATACCCGCACATCCCAGGAAATCCAAATGAAAAGGACAGCTATTGAAGCA
      ---------+---------+---------+---------+---------+---------+  1500
      ATACTTCTTATATGGGCGTGTAGGGTCCTTTAGTTTACTTTTCCTGTCGATAACTTCGT

Y  E  E  Y  T  R  T  S  Q  E  I  Q  M  K  R  T  A  I  E  A

1501  TTTAATGAAACCATAAAAATATTTGAAGACAGTGCCAGACCCAAGAGAGCGGTACAGCAAA
      ---------+---------+---------+---------+---------+---------+  1560
      AAATTACTTTGGTATTTTTATAAACTTCTGTCACGGTCTGGGTTCTCGCCATGTCGTTT

F  N  E  T  I  K  I  F  E  E  Q  C  Q  T  Q  E  R  Y  S  K

1561  GAATACATAGAAAAGTTTAAACGTGAAGGCAATGAGAAGAAATACAAAGGATTATGCAT
      ---------+---------+---------+---------+---------+---------+  1620
      CTTATGTATCTTTTCAAATTTGCACTTCCGTTACTCTTTCTTATGTTTCCTAATACGTA

E  Y  I  E  K  F  K  R  E  G  N  E  K  E  I  Q  R  I  M  H

1621  AATTATGATAAGTTGAAGTCTCGAATCAGTGAATTATTGACAGTAGAAGAAGATTGGAA
      ---------+---------+---------+---------+---------+---------+  1680
      TTAATACTATTCAACTTCAGAGCTTAGTCACTTTAATAACTGTCATCTTCTTCTAACCTT

N  Y  D  K  L  K  S  R  I  S  E  I  I  D  S  R  R  R  L  E

1681  GAAGACTTGAAGAAGCAGGCAGCTGAGTATCGAGAAATTGACAAACGTATGAACAGCATT
      ---------+---------+---------+---------+---------+---------+  1740
      CTTCTGAACTTCTTCGTCCGTCGACTCATAGCTCTTTAACTGTTTGCATACTTGTCGTAA

E  D  L  K  K  Q  A  A  E  Y  R  E  I  D  K  R  M  N  S  I

1741  AAACCAGACCTTATCCAGCTGAGAAGACGAGACCAATACTTGATGTGGTTGACTCAA
      ---------+---------+---------+---------+---------+---------+  1800
      ATTGGTCTGGAATAGGTCGACTCTTCTGCTCTTCTGGTTATGAACTACACCAACTGAGTT

```
1801  AAAGGTGTTCGGCAAAGAAGTTGAACGAGTGGTTGGGCAATGAAAACTGAAGACCAA
      ----+----|----+----|----+----|----+----|----+----|----+----  1860
      TTTCCACAAGCCGTTTCTTCAACTTGCTCACCAACCGTTACTTTTGACTTCTGGTT
       K  G  V  R  Q  K  K  L  N  E  W  L  G  N  E  N  T  E  D  Q    a

1861  TATTCACTGGTGTGGAAGATGATGAAGATTTGCCCCATCATGATGAGAAGACATGGAATGTT
      ----+----|----+----|----+----|----+----|----+----|----+----  1920
      ATAAGTGACCACACCTTCTACTACTACTTCTAAACGGGGTAGTACTACTCTTCTGTACCTTACAA
       Y  S  L  V  E  D  D  E  D  L  P  H  H  D  E  K  T  W  N  V    a

1921  GGAAGCAGCAACCGAAACAAGCTGAAAACCTGTTGCGAGGGAAGCGAGATGGCACTTTT
      ----+----|----+----|----+----|----+----|----+----|----+----  1980
      CCTTCGTCGTTGGCTTTGTTCGACTTTTGGACAACGCTCCCTTCGCTCTACCGTGAAAA
       G  S  S  N  R  N  K  A  E  N  L  L  R  G  K  R  D  G  T  F    a

1981  CTTGTCCGGGAGAGCAGTAAACAGGGCTGCTATGCCTGCTCTGTAGTGGTGGACGGCGAA
      ----+----|----+----|----+----|----+----|----+----|----+----  2040
      GAACAGGCCCTCTCGTCATTTGTCCCGACGATACGGACGAGACATCACCACCTGCCGCTT
       L  V  R  E  S  S  K  Q  G  C  Y  A  C  S  V  V  V  D  G  E    a

2041  GTAAAGCATTGTGTCATAAACAAAACAGCAACTGGCTTTGCCGAGCCCTATAAC
      ----+----|----+----|----+----|----+----|----+----|----+----  2100
      CATTTCGTAACACAGTATTTGTTTTGTCGTTGACCGAAACGGCTCGGGATATTG
       V  K  H  C  V  I  N  K  T  A  T  G  Y  G  F  A  E  P  Y  N    a

2101  TTGTACAGCTCTCTGAAAGAACTGGTGCTACATTACCAACACACCTCCCTTGTGCAGCAC
      ----+----|----+----|----+----|----+----|----+----|----+----  2160
      AACATGTCGAGAGACTTTCTTGACCACGATGTAATGGTTGTGTGGAGGAACACGTCGTG
       L  Y  S  L  K  E  L  V  L  H  Y  Q  H  T  S  L  V  Q  H       a
```

FIG. 4F

```
2161  AACGACTCCCTCAATGTCACACTAGCCTACCCAGTATATGCACAGCAGAGGCGATGAAGC
      ------+---------+---------+---------+---------+---------+  2220
      TTGCTGAGGGAGTTACAGTGTGATCGGATGGTCATATACGTGTCGTCCGCTACTTCG

N  D  S  L  N  V  T  L  A  Y  P  V  Y  A  Q  Q  R  R   -

2221  GCTTACTCTTGATCCTTCTCCTGAAGTTCAGCCACACCCTGAGGCCTCTGGAAAGCAAAGG
      ------+---------+---------+---------+---------+---------+  2280
      CGAATGAGAAACTAGGAAGAGGACTTCAAGTCGGTGGACTCCGGAGACCTTTCGTTTCC

2281  GCTCCTCTCCAGTCTGATCTGTGAATTGAGCTGCAGAAACGAAGCCATCTTTCTTTGGAT
      ------+---------+---------+---------+---------+---------+  2340
      CGAGGAGAGGTCAGACTAGACACTTAACTCGACGTCTTTGCTTCGGTAGAAAGAAACCTA

2341  GGGACTAGAGCTTTCTTTCACAAAAAGAAGTAGGGGAAGACATGCAGCCTAAGGCTGTA
      ------+---------+---------+---------+---------+---------+  2400
      CCCTGATCTCGAAAGAAAGTGTTTTTTCTTCATCCCCTTCTGTACGTCGGATTCCGACAT

2401  TGATGACCACACGTTCCTAAGCTGGAGTGCTTATCCCTTCTTTTTTCTTTTTTCTTTGGT
      ------+---------+---------+---------+---------+---------+  2460
      ACTACTGGTGTGCAAGGATTCGACCTCACGAATAGGAAGAAAAAGAAAAAAGAAACCA

2461  TTAATTTAAAGCCACACCAACAACATACAACACAAAGAGAAAAAGAAATGCAAAAATCTGC
      ------+---------+---------+---------+---------+---------+  2520
      AATTAAATTTCGGTGTTGGTGTATGTTGTGTTTCTCTTTTTCTTTTACGTTTTAGACG

2521  GTGCAGGGACAAAGAGGCCTTTAACCATGGTGCTTGTTAATGCTTTCTGAAGCTTTACCA
      ------+---------+---------+---------+---------+---------+  2580
      CACGTCCCTGTTTCTCCGGAAATTGGTACCACGAACAATTACGAAAGACTTCGAAATGGT
```

FIG. 4G

```
2581 GCTGAAAGTTGGGACTCTGGAGAGCGGAGGAGAGAGGCAGAGAAGAACCCTGGCCTGAGA  2640
     CGACTTTCAACCCTGAGACCTCTCGCCCTCCTCTCTCCGTCTTCTTGGGACCGGACTCT

2641 AGTTTGGTCCAGCCCTGGTTTAGCCTGGATGTTGCTGTGTGCACGGTGGACCCAGACACATC 2700
     TCCAAACCAGGTCGGACCAAATCGGACCTACAACGACGTGCCACCTGGGTCTGTGTAG

2701 GCACTGTGGATTATTTCATTTTGTAACAAATGAACGATATGTAGCAGAAAGGCACGTCCA  2760
     CGTGACACCTAATAAAGTAAAACATTGTTACTTGCTATACATCGTCTTTCCGTGCAGGT

2761 CTCACAAGGACGCTTTGGGAGAATGTCAGTTCATGTATGTTCAGAAGAAATTCTGTCAT   2820
     GAGTGTTCCCTGCGAAACCCTCTTACAGTCAAGTACACAAGTCTTCTTAAGACAGTA

2821 AGAAAGTGCCAGAAAGTGTTAACTTGTCAAAAAACAAAAACCCAGCAACAGAAAAATGG   2880
     TCTTTCACGGTCTTTCACAAATGAACAGTTTTTGTTTTTGGGTCGTTGTCTTTTTACC

2881 AGTTTGGAAAACAGGACTTAAAATGACATTCAGTATATAAAATATGTACATAATATTGA   2940
     TCAAACCTTTTGTCCTGAATTTTACTGTAAGTCATATATTTTATACATGTATTATAACCT

2941 TGACTAACTATCAAATAGATGGATTTGTATCAATACCAAATAGCTTCTGTTTGTTTTGC   3000
     ACTGATTGATAGTTTATCTACCTAAACATAGTTATGGTTTATCGAAGACAAAACAAAACG
```

FIG. 4H

```
3001  TGAAGGCTAAATTCACAGGCGCTATGCAATTCTTAATTTCATTAAGTTGTTATTCAGTT
      ----+----|----+----|----+----|----+----|----+----|----+----|  3060
      ACTTCCGATTTAAGTGTCCGCGATACGTTAAGAATTAAAGTAATTCAACAATAAGTCAA

3061  TTAAATGTACCTTCAGAATAAGCTTCCCCACCCCAGTTTTTGTGTGCTTGAAAATATTGTT
      ----+----|----+----|----+----|----+----|----+----|----+----|  3120
      AATTTACATGGAAGTCTTATTCGAAGGGGTGGGGTCAAAAACAACGAACTTTATAACAA

3121  GTCCCGGATTTTGTTAATATTCATTTTTGTTATCCTTTTTTAAAAATAAATGTACAGGA
      ----+----|----+----|----+----|----+----|----+----|----+----|  3180
      CAGGGCCTAAAAGAATTATAAGTAAAAACAATAGGAAAAATTTTATTTACATGTCCT

3181  TGCCAGTAAAAAAAAAAAATGGCTTCAGAATTAAAACTATGAAATATTTACAGTTTTCT
      ----+----|----+----|----+----|----+----|----+----|----+----|  3240
      ACGGTCATTTTTTTTTTTTACCGAAGTCTTAATTTTGATACTTTATAAAATGTCAAAAGA

3241  TGTACAGAGTACTTGCTGTTAGCCCAAGGTTAAAAAGTTCATAACAGATTTTTTTGGAC
      ----+----|----+----|----+----|----+----|----+----|----+----|  3300
      ACATGTCTCATGAACGACAATCGGGTTCCAATTTTTCAAGTATTGTCTAAAAAAACCTG

3301  TGTTTGTTGGGCAGTGCCTGATAAGCTTCAAAGCTGCTTTATTCAATAAAAAAAACC
      ----+----|----+----|----+----|----+----|----+----|----+----|  3360
      ACAAAACAACCCGTCACGGACTATTCGAAGTTTCGACGAAATAAGTTATTTTTTTTGG

3361  CGAATTCACTGG
      ----+--  3372
      GCTTAAGTGACC
```

```
GRB-1 N 333  WYWGDIS -- R EE--- VN E-- KL RDTAD------ GTFLVRDST KM HGDY T LT LRK-----GG---NN LIKI
GRB-1 C 624  WNVGSSN -- R NK--- AE N-- LL RGKRD------ GTFLVRESS K- QGCY A CS VVV-----DG--EV KHCV c-src   150  WYFGKIT -- R RE--- SE RL LL NPENPR----- GTFLVRESE TT KGAY C LS VSDF-DNAKGLNVK HYKI
v-abl   248  WYHGPVS -- R NA--- AE YK KS SGIN------- GSFLVRESE SS PG-Q R -S ISLRYE---G-RVY HYRI
PLC N   550  WFHGKLG AG R DGRHI AE R-- LL TEYCIETGAPD GSFLVRESE TF VGDY T LS F--WR-N--G-KVQ HCRI
PLC C   668  WYHASLT -- R AQ--- AE H-- ML MRVPRD----- GAFLVRKRN -E PNSY A IS F--RAE--G-KIK HCRV
GAP N   178  WYHGKLD -- R TI--- AE E-- RL RQAGKS----- GSYLIRESD RR PGSF V LS FRSQM-N-V---VN HPRI
GAP C   348  WYHGKIS -- K QE--- AY N-- LL MTVGQVC---- -SFLVRPSD NT PGDY S LY F-RTNENIQ----R-- -FKI
v-crk   248  WYWGRLS -- R GD--- AV S-- LL QGQRH------ GTFLVRDSG SI PGDF V LS VSES----S----RVS HYIV GRB-1 N 384  --FHRD G KYGFSDPLT--------------- F S  SV V ELI N HY RNESLAQYNPKLDV- RL LY PVSK -VCP
GRB-1 C 672  INKTAT G -YGFAEPYNL--------------- Y S  SL K ELV L HY QHTSLVQHNDSLNV- TL AY PVYA c-src   207  RKLDSG G FYITSRTQ---------------- F S  SL Q QLV A YY SKHADGLCH------ RL TN -VCP
v-abl   298  -NTASD G KLYVSSESR--------------- F N  TL A ELV H HH STVADGLITT---- LH YP --AP
PLC N   611  HSRQDA G TPKFFLTDNLV------------- F D  SL Y DLI T HY QQVPLRCA-EFEM- RL SL PV-P
PLC C   718  ---QQE G QTVMLGNSE--------------- F D  SL V DLI S YY EKHPLYRK----M- KL RY PI--
GAP N   230  --IAMC G DYYIGGRR---------------- F S  SL S DLI G YY SHVSCLLKGE---- KL LY PVAP
GAP C   399  -CPTPN N QFMMGGRY---------------- Y N  SI G DII D HY RKEQIVEG-YY--- -L KE PV-P
v-crk   298  NSLGPA G GRRAGEGPFAPGLNPTRFLIGDNV F D  SL P SLL E FY KIHYLDT--TT---- -L IE PV--

GRB-1    10  ALYDY KKEREE D IDLHLGDI LT VNK G SLVALGFSDPEARPEDIG WL NGYNETTGER GDFP GT YVE YIGRK c-src    88  ALYDY ESRTET D -------- LA FKK G ERLQIV-----MNTEGD WW LAHSLTTGQT GYIP SN YVA PS-DS
v-abl    68  ALYDF VASGDN T -------- LS ITK G EKLRVLG----YNHNGE WC EAQTK-NGQ- GWVP SN YIT PV-NS
PLC     148  ALFDY KAGRED E -------- LT FTK S AIIQNV-----EKQEGG WW RGDYHHKKQ- LWFP SN YVE EMV-S
GAP     284  AILDY TKVPDT D E------- IS FLK G DMFIVN-----NELEDG WM WVTNLRTDEQ GLIV ED LVE EV-GR
v-crk   375  ALFDF KGNDDG D -------- LP FKK G DILKIR-----DKPEEQ WW NAEDMDGKR- GMIP VP YVE KCRPS
```

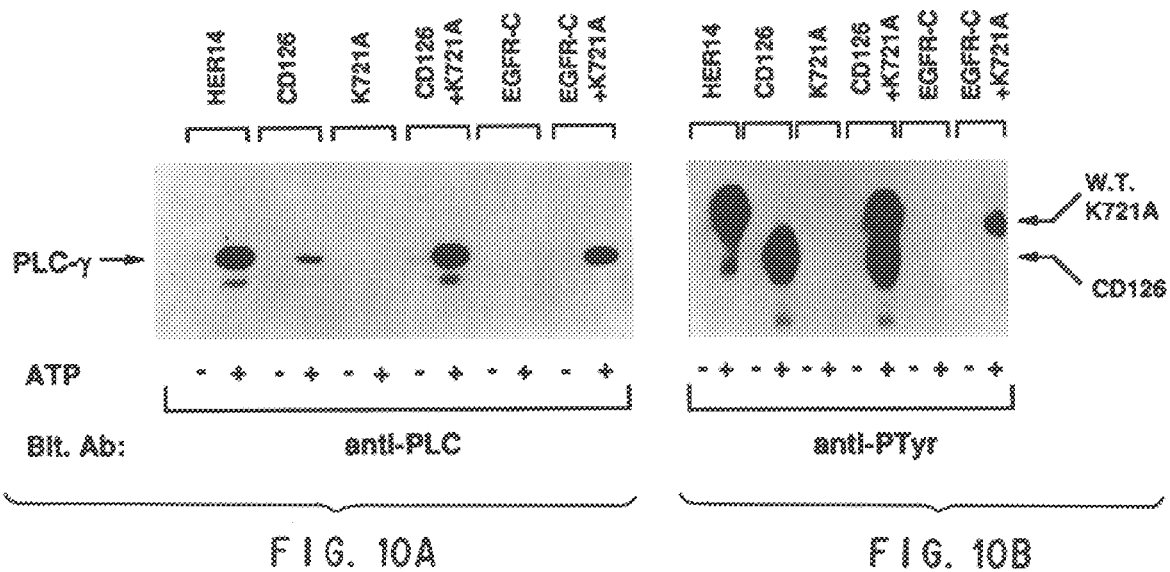

```
    GCCAGTGAATTCGGGCCCGAATTGGCAGAGCTTAATGGAAAGACGGCTTCATTCCCAAG
1   ------+---------+---------+---------+---------+---------+  60
    CGGTCACTTAAGCCCGGGCTTAACCGTCTCGAATTACCTTTCTGCCGAAGTAAGGGTTC a    A  S  E  F  G  P  E  L  A  E  L  N  G  K  D  G  F  I  P  K  -

AACTACATAGAAATGAAACCACATCCGTGGTTTTTTGGCAAAATCCCAGAGCCAAGGCA
61  ------+---------+---------+---------+---------+---------+  120
    TTGATGTATCTTTACTTTGGTGTAGGCACCAAAAACCGTTTTAGGGTCTCGGTTCCGT
                              →SH2 DOMAIN
a    N  Y  I  E  M  K  P  H  P  W  F  F  G  K  I  P  R  A  K  A  -

GAAGAAATGCTTAGCAAACAGCGGCACGATGGGGCCTTTCTTATCCGAGAGAGTGAGAGC
121 ------+---------+---------+---------+---------+---------+  180
    CTTCTTTACGAATCGTTTGTCGCCGTGCTACCCCGGAAAGAATAGGCTCTCTCACTCTCG a    E  E  M  L  S  K  Q  R  H  D  G  A  F  L  I  R  E  S  E  S  -

GCTCCTGGGGACTTCTCCCTCTCTGTCAAGTTTGGAACGATGTGCAGCACTTTCAAGGTG
181 ------+---------+---------+---------+---------+---------+  240
    CGAGGACCCCTGAAGAGGGAGAGACAGTTCAAACCTTGCTACACGTCGTGAAAGTTCCAC a    A  P  G  D  F  S  L  S  V  K  F  G  T  M  C  S  T  F  K  V  -

CTCCCGAGATGGAGCCGGGAAGTACTTCCTCTGGTGGTGAAGTTCAATTCTTTGAATGAG
241 ------+---------+---------+---------+---------+---------+  300
    GAGGGCTCTACCTCGGCCCTTCATGAAGGAGACCACCACTTCAAGTTAAGAAACTTACTC a    L  P  R  W  S  R  E  V  L  P  L  V  V  K  F  N  S  L  N  E  -
```

FIG. 16A

```
     CTGGTGGATTATCACAGATCTACATCTGTCTCCAGAAACCAGCAGATATTCCTGCGGGAC
301  ------+---------+---------+---------+---------+---------+ 360
     GACCACCTAATAGTGTCTAGATGTAGACAGAGGTCTTTGGTCGTCTATAAGGACGCCCTG a    L  V  D  Y  H  R  S  T  S  V  S  R  N  Q  Q  I  F  F  L  R  D  -

ATAGAACAGGTGCCACAGCAGCCGACATACGTCCAGGCCCTCTTTGACTTTGATCCCCAG
361  ------+---------+---------+---------+---------+---------+ 420
     TATCTTGTCCACGGTGTCGTCGGCTGTATGCAGGTCCGGGAGAAACTGAAACTAGGGGTC
                                            SH3 DOMAIN
                                          ┌─────────
 a    I  E  Q  V  P  Q  Q  P  T  Y  V  Q  │A  L  F  D  F  D  P  P  Q  -

GAGGATGGAGAGCTGGGCTTCCGCCGGGGAGATTTTATCCATGTCATGGATAACTCAGAC
421  ------+---------+---------+---------+---------+---------+ 480
     CTCCTACCTCTCGACCCGAAGGCGGCCCCTCTAAAATAGGTACAGTACCTATTGAGTCTG a    E  D  G  E  L  G  F  R  R  G  D  F  I  H  V  M  D  N  S  D  -

CCCAACTGGTGGAAAGGAGCTTGCCACGGGCAGACCGGCATGTTTCCCCGGGAATTATGT
481  ------+---------+---------+---------+---------+---------+ 540
     GGGTTGACCACCTTTCCTCGAACGGTGCCCGTCTGGCCGTCTGGCCGTACAAAGGGGCGCTTAATACA a    P  N  W  W  K  G  A  C  H  G  Q  T  G  M  F  P  R  E  L  C  -

CTCCCCCXGTGAACCGGAACTTGCCTTGCAGATTCTCAGTTCTTCGTTAATAAATTCTTTCACTTTT
541  ------+---------+---------+---------+---------+---------+ 600
     GAGGGGGXCACTTGGCCTTGAACGGAACGTCTAAGAGTCAAGAAGCAATTATTTAAAGAAAGTGAAAA a    L  P  ?  *  T  G  T  S  K  S  Q  E  A  I  I  *  R  K  *  K  -
```

FIG. 16B

```
601  ATGTAAAACACATACAAAGAATTAAACCCACAAGCTGCCTCTGACAGCAGCCTGTGAGG
     ----+---------+---------+---------+---------+---------+ 660
     TACATTTGTGTATGTTTCTTAATTTGGGTGTTCGACGGAGACTGTCGTCGGACACTCC

M  *  N  T  Y  K  R  I  K  P  T  S  C  L  *  Q  Q  P  V  R  -

661  GAGTGCAGAACACCTGGCCGGGTCACCCTCTCACTTTGGTTGGAACTTTAGG
     ----+---------+---------+---------+---------+---------+ 720
     CTCACGTCTTGTGGACCGGCCCAGTGGGAGAGTGAAACCAACCTTGAAATCC

E  C  R  T  P  G  R  V  T  L  *  P  S  H  F  G  W  N  F  R  -

721  GGGTGGGAGGGGCGTTGGATTAAAAATGCCAAAACTTACCTATAAATTAAGAAGAGTT
     ----+---------+---------+---------+---------+---------+ 780
     CCCACCCTCCCCGCAACCTAAATTTTACGGTTTGAATGGATATTTAATTCTTCTCAA

G  W  E  G  A  L  D  L  K  M  P  K  L  T  Y  K  L  R  R  V  -

781  TTTATTACAAATTTCACTGCTGCTCCTCTTTCCCCTCCTTGTCTTTTTTTCATCCT
     ----+---------+---------+---------+---------+---------+ 840
     AAATAATGTTTAAAAGTGACGACGAGGAGAAGGGGAGGAAACAGAAAAAAGTAGGA

```
841  TTTTCTCTTCTGTCCATCAGTGCATGACGTTTAAGGCCACGTATAGTCCTAGCTGACGC
     ---------+---------+---------+---------+---------+---------+ 900
     AAAAGAGAAGACAGGTAGTCACGTACTGCAAATTCCGGTGCATATCAGGATCGACTGCG

F  F  S  S  V  H  Q  C  M  T  F  K  A  T  Y  S  P  S  *  R  -

901  CAATAATAAAAACCGAATTCGAGCTCGGGGATCCCTCTAGAGTC
     ---------+---------+---------+---------+---- 949
     GTTATTATTTTTGGCTTAAGCTCGAGCCCCTAGGGAGATCTCAG

```
GRB-3   1   PDTGAGPLGAGARAGGARVPAAAQRESAEAAMAGNFDSEERSSWYWGRLSRQEAVALLQG   60
v-crk  205  QPRAGRGA.HRGLRRP.GRGQRVRPAGGA.I....Q....D.G.........GD..S....  264

GRB-3  61   QRDGVFLVRDSSTSPGDYVLSVSENSRVSHYIINSSGPRPPVPPSPAQP-PPGVSPSRLR  120
v-crk  265  ..H.T......GSI...F......S.......V..L..AGGRRAGGEG.GA...LN.T.FL  324

GRB-3  121  IGDQEFDSLPALLEFYKIHYLDTTTLIEPVARSRQGSGVILRQEEAEYVRALFDFNGNDE  180
v-crk  325  ....V.....S..................S....N.........V.........K...D   384

GRB-3  181  EDLPFKKGDILRIRDKPEEQWWNAEDSEGKRGMIPVPYVEKYRPASASVSALIGGNQEGS  240
v-crk  385  G..........K.............MD............C..S.....T.T..R*     444
```

FIG.17

```
GRB-4   1   VIEKPENDPEWWKCKNARGQVGLVPKNYVVVLSDGP...ALHPAHTPQISYTGPSASGRF   60
nck    219  .............RKIN.M.........T.MQNN.LTSG.E.S.P..CD.IR..LT.K.  278

GRB-4  61   AGREWYYGNVTRHQAECALNERGVEGDFLIRDSESSPSDFSVSLKASGRNKHFKVQLVDS  120
nck    279  ..NP....K......M......H..............N........Q.K........KET  338

GRB-4  121  VYCIGQRRFHSMDELVEHYKKAPIFTSEHGEKLYLVRALQ*                     161
nck    339  .......K.ST.E................Q.......KH.S*                   379
```

FIG.18

| | |
|---|---|
| 1 | MELDLSPTHLSSSPEDVCPTPATPPETPPPPDNPPPGDVKRSQPLPIPSSRKLREEFQA | 60 |
| 61 | TSLPSIPNPFPELCSPPSQKPILGGSSGARGLLPRDSSRLCVVKVYSEDGACRSVEVAAG | 120 |
| 121 | ATARHVCEMLVQRAHALSDESWGLVESHPYLALERGLEDHEFVVEVQEAWPVGGDSRFIF | 180 |
| 181 | RKNFAKYELFKSPPHTLFPEKMVSSCLDAQTGISHEDLIQNFLNAGSFPEIQGFLQLRGS | 240 |
| 241 | GRGSGRKLWKRFFCFLRRSGLYYSTKGTSKDPRHLQYVADVNESNVYVVTQGRKLYGMPT | 300 |
| 301 | DFGFCVKPNKLRNGHKGLHIFCSEDEQSRTCWLAAFRLFKYGVQLYKNYQQAQSRHLRLS | 360 |
| 361 | YLGSPPLRSVSDNTLVAMDFSGHAGRVIDNPREALSAAMEEAQAWRKKTNHRLSLPTTCS | 420 |
| 421 | GSSLSAAIHRTQPWFHGRISREESQRLIGQQGLVDGVFLVRESQRNPQGFVLSLCHLQKV | 480 |
| 481 | KHYLILPSEDEGCLYFSMDEGQTRFTDLLQLVEFHQLNRGILPCLLRHCCARVAL | 535 |

FIG. 19

| | | | | | | | |
|---|---|---|---|---|---|---|---|
| c-src | 148 | WYFGKITR | RE--SE R--LL | LNPENPR | GTFLVR | ESETTKGAYC- | LSV SDFDNAKGLN--- | VKH--Y KI | RKLDS---
| p85α-N | 333 | WYWKGDISR | EE--VN E--KL | RDTA--D | GTFLVR | DASTKMHGDYT | LTL RKGGNNKLIK--- | IFH --- | RV QQE---
| PLCγ1-C | 668 | WYHASLTR | AQ--AE H--ML | MRVPR-D | GAFLVR | KRNEPNSYA--- | ISF RAEGK--- | IKH --C | RD GKY---
| fyn | 149 | WYFGKLG | RKD AE RQ--LL | SFGNPR- | GTFLIR | ESETTKGAYS- | LSI RDWDDMKGDH | VKH --Y KI | RKLDN---
| GRB-3 | 44 | WYMKGRLSR | QE--AV A--LL | QGQR--D | GTFLVR | DSSTSPGDYV- | LSV SENR | VSH --Y II | NSS---
| GRB-4 | 65 | WYYGNVTR | HQ--AE C--AL | NERGV-E | GDFLIR | DSESSPSDFS- | VSL KASGR | NKH --F | KV QLVDSYYCI---
| GRB-7 | 434 | WFHGRISR | EE--SQ R--LI | GQQGLVD | GVFLVR | ESQRNPQGFV- | LSL CHLQK | VKH --Y II | LPSEDE---

| | | | | | | | |
|---|---|---|---|---|---|---|---|
| c-src | 212 | G G--F | YITSRTQ | FSSL QQ | LV A YY | SKHADG L | CH--- | RL TNV
| p85α-N | 387 | G Q--T | VMLGNSE | FDSL VD | LI S YY | EKHP--- | L YRKM--- | KL RYPI
| PLCγ1-C | 721 | G--- F | SDPLT- | FSSV VE | LI N HY | RNES--- | L AQYNPKLDV | KL LYPV
| fyn | 211 | G G--Y | YITTRAQ | FETL QQ | LV Q HY | SERAAG L | CC--- | RL W
| GRB-3 | 98 | G P--R | GPRPPVPPSPAQPPPGVSPSRLRIGDQE | FDSL PS | LL E FY | KIHY--- | I DTT--- | TL IEPV
| GRB-4 | 125 | G Q R | R | FHSM DE | LV E HY | KKAP--- | I FTSEHGE--- | KL YLV
| GRB-7 | 492 | G CL Y | FSMDEGQTR | FTDL LQ | LV E FH | QLNRG--- | I LP--- | LL RHCCARV

FIG. 21

```
GRB-7    242  RG S GRKL L WK R FF CF L RR S G——    LYY STKGTSKD PR H L QYVA DV NESN VYVV TQCRK LYG M
Ras GAP  484  KG K GKR- L WK N LY FI L EG S DAQL   IYF KSEKRATK PK G L —-I DL SVCS VYVV HDS—- LFG R

GRB-7    299  P TD F GFC V KPNK L RNC H KG L HIFCSKD EQ SRTC W LAA F RL F
Ras GAP  538  P NC F QIV V QH——  F SEE H YI F YFAGETP EQ AED— W MKG L QA F
```

FIG.22

```
GRB-7    19   P T PA TPPET PPPP DN PPPG DV RSQP LP IPSSR KL RK EE -F QATS LP S I PNPFPK L C—SPP
P2B2     4    P E PA RAAPP PPPP PP PPPG AD R VVKA VP FPPTH RL TS EE V F DLDG IP R V DVLKNH L VKEGRV

GRB-7    78   SQKPI L GGSSGARG LL P RD SSRLCV V K V YSEDGA C RS V EVAAGATARH V C E ML VQR A HALSDESW
P2B2     66   DEEIA L RIINEGAA IL R RE KT—M I E V EAPITV C GD I H-GQFFDLMK L F E VGGSP A NT-RYLFL

GRB-7    143  G LVESHP YL A LE RG L EDHE F V V EVQEAMP V GGDSRF IFR K N F AK Y EL FK SPPHTL F P EK
P2B2     126  G DYVDRG YF S IE CV L YLWV L K I LYPSTLF L LRGNHEC—- R H L TE Y FT FK QECKIK Y S ER

GRB-7    202  MVSS C L DA QTG I SHED LI — Q N FL —NA G SF PEI QC F LQ LR GSG R
P2B2     183  VTEA C M EA FDS L PLAA LL N Q FL CVHG G LS PEI HT L DD IR RLD R
```

FIG.23

```
  1 GCCAGTGAATTCGGGGCTCAGCCCCTCCTCCCTGCTTCCCTGCTTCAGGCTGCTGAG    60
    CGGTCACTTAAGCCCCGAGTCGGGGAGGAGGGAGGAAGTCCGACGACTC

61 CACTGAGCAGCGCTCAGAATGGAAGCCATCGCCAAATATGACTTCAAAGCTACTGCAGAC   120
    GTGACTCGTCGCGAGTCTTACCTTCGGTAGCGGTTTATACTGAAGTTTCGATGACGTCTG
                  M  E  A  I  A  K  Y  D  F  K  A  T  A  D

121 GACGAGCTGAGCTTCAAAAGGGGACATCCTCAAGGTTTTGAACGAAGAATGTGATCAG    180
    CTGCTCGACTCGAAGTTTTCCCCCTGTAGGAGTTCCAAAACTTGCTTCTTACACTAGTC
     D  E  L  S  F  K  R  G  D  I  L  K  V  L  N  E  E  C  D  Q

181 AACTGGTACAAGGCAGAGCTTAATGGAAAAGACGGCTTCATTCCCAAGAACTACATAGAA   240
    TTGACCATGTTCCGTCTCGAATTACCTTTTCTGCCGAAGTAAGGGTTCTTGATGTATCTT
     N  W  Y  K  A  E  L  N  G  K  D  G  F  I  P  K  N  Y  I  E

241 ATGAAACCACATCCGTGGTTTTTTGGCAAAATCCCAGAGCCAAGGGCCAAGAAGAAATGCTT   300
    TACTTTGGTGTAGGCACCAAAAAACCGTTTTAGGGTCTCGGTTCCGTTCTTCTTTACGAA
     M  K  P  H  P  W  F  F  G  K  I  P  R  A  K  A  E  E  M  L

301 AGCAAACAGCGGCACGATGGGGCCTTTCTTATCCGAGAGAGTGAGAGCGCTCCTGGGGAC   360
    TCGTTTGTCGCCGTGCTACCCCGGAAAGAATAGGCTCTCTCACTCTCGCGAGGACCCCTG
     S  K  Q  R  H  D  G  A  F  L  I  R  E  S  E  S  A  P  G  D
```

```
361  TTCTCCCTCTGTCAAGTTTGGAAACGATGTGCAGCACTTCAAGTGTGCTCCGAGATGA
     ----+----+----+----+----+----+----+----+----+----+----+----  420
     AAGAGGGAGACAGTTCAAACCTTTGCTACACGTCGTGAAGTTCCACGAGGCTCTACCT
     F  S  L  S  V  K  F  G  N  D  V  Q  H  F  K  V  L  R  D  G

421  GCCGGGAAGTACTTCCTCTGGGTGGTGAAGTTCAATTCTTTGAATGAGCTGGTGGATTAT
     ----+----+----+----+----+----+----+----+----+----+----+----  480
     CGGCCCTTCATGAAGGAGACCCACCACTTCAAGTTAAGAAACTTACTCGACCACCTAATA
     A  G  K  Y  F  L  W  V  V  K  F  N  S  L  N  E  L  V  D  Y

481  CACAGAGATCTACATCTGTCTCCAGAAACCAGACAGATATTCCTGCGGGACATAGAACAGGTG
     ----+----+----+----+----+----+----+----+----+----+----+----  540
     GTGTCTAGATGTAGACAGAGGTCTTGGTCGTCTATAAGGACGCCCTGTATCTTGTCCAC
     H  R  S  T  S  V  S  R  N  Q  Q  I  F  L  R  D  I  E  Q  V

541  CCACAGCAGCCGACATACGTCCAGGCCCTCTTTGATCCCAGGAGGATGGAGAG
     ----+----+----+----+----+----+----+----+----+----+----+----  600
     GGTGTCGTCGGCTGTATGCAGGTCCGGGAGAAACTGAAACTAGGGGTCCTCCTACCCTC
     P  Q  Q  P  T  Y  V  Q  A  L  F  D  F  D  P  P  Q  E  D  G  E

601  CTGGGCTTCCGCCGGGGAGATTTTATCCATGTCATGGATAACTCAGACCCCAACTGTGG
     ----+----+----+----+----+----+----+----+----+----+----+----  660
     GACCCGAAGGCGGCCCCTCTAAAATAGGTACAGTACCTATTGAGTCTGGGGTTGACCACC
     L  G  F  R  R  G  D  F  I  H  V  M  D  N  S  D  P  N  W  W
```

```
661  AAAGGAGCTTGCCACGGGCAGACCGGCATGTTCCCCGCAATTATGTCACCCCGTGAAC
     ----------+---------+---------+---------+---------+---------+  720
     TTTCCTCGAACGGTGCCCGTCTGGCCGTACAAGGGGCGTTAATACAGTGGGGCACTTG
      K  G  A  C  H  G  Q  T  G  M  F  P  P  R  N  Y  V  T  P  V  N  -

721  CGGAACGTCTAAGAGTCAAGAAGCAATTATTTAAAGAAGTGAAAAATGTAAACACATA
     ----------+---------+---------+---------+---------+---------+  780
     GCCTTGCAGATTCTCAGTTCTTCGTTAATAAATTCTTCACTTTTTACATTTGTGTAT
      R  N  V  *

781  CAAAAGAATTAAACCCACAAGCTGCCTCTGACAGCAGCCTGTGAGGGAGTGCAGAACACC
     ----------+---------+---------+---------+---------+---------+  840
     GTTTTCTTAATTTGGGTGTTCGACGGAGACTGTCGTCGGACACTCCCTCACGTCTTGTGG

841  TGGCCGGGTCACCCTGTGACCCTCTCACTTGGTTGGAACTTTAGGGGTGGGAGGGGGC
     ----------+---------+---------+---------+---------+---------+  900
     ACCGGCCCAGTGGGACACTGGGAGAGTGAACCTTGAAATCCCCACCCTCCCCCG

901  GTTGGATTTAAAAATGCCAAACTTACCTATAAATTAAGAAGAGTTTTATTACAAATTT
     ----------+---------+---------+---------+---------+---------+  960
     CAACCTAAATTTTACGGTTTGAATGGATATTTAATTCTTCAAAATAATGTTAAA

961  TCACTGCTGCTCCCTTCCCCTTGTCTTTTTTCATCCTTTTTTCTCTCTGTC
     ----------+---------+---------+---------+---------+---------+  1020
     AGTGACGACGAGGAGGGAAAGGGGAACAGAAAAAAGTAGAAAAAGAGAGACAG

1021 CATCAGTGCATGACGTTTAAGGCCACGTATAGTCCTAGCTGACGCCAATAAT
     ----------+---------+---------+---------+--        1072
     GTAGTCACGTACTGCAAATTCCGGTGCATATCAGGATGACTGCGGTTATTA
```

FIG. 26C

```
GRB2    60    WFFGKIP-- R AK--- AE E- ML SKQRHD------          GAPLIRESE SA PGDF  S  LS  VKF----- -GNDVQ- HFKV p85 N   333   WYWGDIS-- R EE--- VN E- KL RDTAD-------          GTFLVRDST KM HGDY  T  LT  LRK----- -GG--NN- LIKI
p85 C   624   WNVGSSN-- R NK--- AE N- LL RGKRD-------          GTFLVRESS K- QGCY  A  CS  VVV----- -DG--EV- KHCV
c-src   150   WFPGKIT-- R RE--- SE RL LL NPENPR------          GTFLVRESE TT KGAY  C  LS  VSDFDNAK-GLNVK- HYKI
v-abl   248   WEHGPVS-- R NA--- AE YK KS SGIN---------          GSFLVRESE SS PG-Q  R  -S  ISLRYE-- -G-RVY- HYRI
PLC N   550   WFHGKLG AG R DGRHI AE R- LL TEYCIETGAPD          GSFLVRESE TF VGDY  T  LS  ----F--- -WRN-G-KVQ- HCRI
PLC C   668   WFHASLT-- R AQ--- AE H- ML MRVPRD------          GAFIVRKRN -E PNSY  A  IS  --FRAE-- -G-KIK- HCRV
GAP N   178   WYHGKLD-- R TI--- AE E- RL RQAGKS------          GSYLIRESD RR PGSF  V  LS  --FRSQMN- V- -VN- HPRI
GAP C   348   WFHGKIS-- R QE--- AY N- LL MTVGQVC-----          -SFLVRPSD NT PGDY  S  LY  --FRTNENIQ-R--- -FKI
v-crk   248   WYWGRLS-- R GD--- AV S- LL QRERH-------          GTFLVRDSG SI PGDF  V  LS  VSES--- -S-- -RVS- HYIV GRB2    111   LRDGA-  G KY-FLWVVK----------------------         F N SL N ELV D YH RSTSVSRNQQIFLRD IE QV PQQP p85 N   384   --FHRD  G KYGFSDPLT----------------------         F S SV V ELI N HY RNESLAQYNPKLDV- KL LY PVSK
p85 C   672   INKTAT  G -YGFAEPY-----------------------         -NL- Y S SL K ELV L HY QHTSLVQHNDSLNV- TL AY PVYA
c-src   207   RKLDSG  G FYITSRTQ-----------------------         F S SL Q QLV A YY SKHADGLCH------ RL TN -VCP
v-abl   611   HSRQDA  G TPKF--------FLTDNLV------------         F D SL Y DLI T HY QQVPLRCN-EFEM-- RL SE PV-P
PLC C   718   ---QQE  G QTVMLGNSE----------------------         F D SL V DLI S YY EKHPLYRK----M-- KL RY PI--
GAP N   230   --IAMC  G DYYIGGRR-----------------------         F S SL S DLI G YY SHVSCLLKGE----- KL LY PVAP
GAP C   399   -CPTPN  N QFMGGRY------------------------         Y N SI G DII D HY RKEQIVEG-YY---- -L KE PV-P
v-crk   298   NSLGPA  G GRRAGGEGPFAPGLNPTRFLIGDNV------         F D SL P SLL E FY KIHYLDT--TT---- -L IE PV--
```

FIG. 26E

|         |     |       |        |   |                   |    |     |    |              |      |    |     |
|---------|-----|-------|--------|---|-------------------|----|-----|----|--------------|------|----|-----|
| GRB2 N  | 5   | AKYDF | KATADD | E | ----------        | LS | FKR | G  | DILKVL------ | NEECDQN | WY | KAELN--GKD | GFIP | KN | YIE |
| GRB2 C  | 163 | ALFDF | DPQEDG | E | ----------        | LG | FRR | G  | DFIHVM------ | DNSDPN  | WW | KGACH----- | GQTG | MF | PRN |
|         |     |       |        |   |                   |    |     |    |              |         |    |            |      |    |     |
| P85     | 10  | ALYDY | KKEREE | D | IDLHLGDI          | LT | VNK | G  | SLVALGFSDGQEARPEEIG | WL | NGYNETTGER | GDFP | GT | YVE |
| c-src   | 88  | ALYDY | ESRTET | D | ----------        | LA | FKK | G  | ERLQIV------ | MNTEGD  | WW | LAHSLTTGQT | GYIP | SN | YVA |
| v-abl   | 68  | ALYDF | VASGDN | T | ----------        | LS | ITK | G  | EKLRVLG----- | YNHNGE  | WC | EAQTK-NGQ- | GWVP | SN | YIT |
| PLC     | 148 | ALFDY | KAGRED | E | ----------        | LT | FTK | S  | AIIQNV------ | EKQEGG  | WW | RGDYHHKKQ- | LWFP | SN | YVE |
| GAP     | 284 | AILDY | TKVPDT | D | E---------        | IS | FLK | G  | DMFIVN------ | NELEDG  | WM | WVTNLRTDEQ | GLIV | ED | LVE |
| v-crk   | 375 | ALFDF | KGNDDG | D | ----------        | LP | FKK | G  | DILKIR------ | DKPEEQ  | WW | NAEDMDGKR- | GMIP | VP | YVE |

FIG. 26F

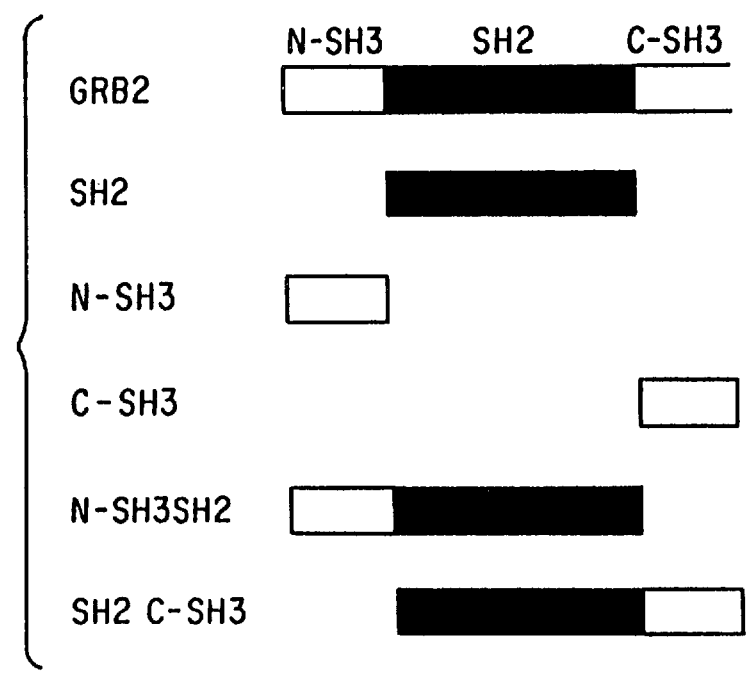
F I G. 29

| | | |
|---|---|---|
| GRB2  | M E A I A k y D F k A l o d D E L S F K R G d i L | 25 |
| SEM-5 | M E A V A e h D F q A g s p D E L S F K R G n l L | 25 |
| GRB2  | K V L N e E c D q n W Y K A E L n G k D G F I P k | 50 |
| SEM-5 | K V L N k D e D p h W Y K A E L d G n E G F I P s | 50 | SH3
| GRB2  | N Y I e M k p h p W F f G K I p R a k A E e m L s | 75 |
| SEM-5 | N Y I r M t e c n W Y I G K I t R n d A E v I L k | 75 |
| GRB2  | K q r h - D G a F L I R e s E S a P G D F S L S V | 99 |
| SEM-5 | K p l v r D G h F L V R q c E S s P G E F S I S V | 100 |
| GRB2  | k F g n d V Q H F K V L R D g a G K Y F L W v V K | 124 |
| SEM-5 | r F q d s V Q H F K V L R D q n G K Y Y L W a V K | 125 | SH2
| GRB2  | F N S L N E L V d Y H R s t S V S R n q q I f L r | 149 |
| SEM-5 | F N S L N E L V a Y H R t a S V S R h l I I L s | 150 |
| GRB2  | D i e q v p q q p l Y V Q A L F D F d P Q E d G E | 174 |
| SEM-5 | D m n v e l k - - - F V Q A L F D F n P Q E s G E | 172 |
| GRB2  | L g F r R G D f I h V m d n s D P N W W k G a c h | 199 |
| SEM-5 | L a F k R G D v I t L i n k d D P N W W e G q l n | 197 | SH3
| GRB2  | g q t G m F P r N Y V t P v N r N v | 217 |
| SEM-5 | n r r G i F P s N Y V c P y N s N k s n s n v a p | 222 |
| SEM-5 | g f n f g n | 228 |

FIG.32

```
  1   AGCCTGACACCGGAGCCGGTCCGCTGGGCGCCGGTCCGCTGGAGGGGCGCGTGC
      TCGGACTGTGGCCTCGGCCAGGCGACCCGCGGCCAGCGACCTCCCCGCGCACG   +60
          P  D  T  G  A  G  P  L  G  A  G  A  R  A  G  G  A  R  V  P  -

61   CGGCGGGGCCCAGCGCCGTGAAAGCGCGGAGGCGGCCATGGCGCAACTTCGACTCGGAGG
      GCCGCCGCCGGGTCGCGGCACTTTCGCGCCTCCGCCGGTACCGCCGTTGAAGCTGAGCCTCC   +120
          A  A  Q  R  E  S  A  E  A  A  M  A  G  N  F  D  S  E  E  -

121   AGCGGAGTAGCTGGTACTGGGCCTGAGCCGGAGGCCGTGGCGCTATTGCAGG
      TCGCCTCATCGACCATGACCCGGACTCGGCCTCCGCCACCGCGATAACGTCC   +180
          R  S  W  Y  W  G  R  L  S  R  Q  E  A  V  A  L  L  Q  G  -

181   GCCAGCGGCGACGGGGTGTTCCTGGTGCGGGACTCGAGCACCAGCCCCGGGGACTATGTGC
      CGGTCGCCGCTGCCCCACAAGGACCACGCCCTGAGCTCGTGGTCGGGGCCCCTGATACACG   +240
          Q  R  D  G  V  F  L  V  R  D  S  S  T  S  P  G  D  Y  V  L  -

241   TTAGCGTCTCCGAAAACTCGGCGTCTCCCACTACATCATCAACAGCAGCCCGCGCC
      AATCGCAGAGGCTTTTGAGCGCGCAGAGGGTGATGTAGTAGTTGTCGTCGGGCGCGG   +300
          S  V  S  E  N  S  R  V  S  H  Y  I  I  N  S  S  G  P  R  P  -

301   CTCCAGTGCCTCCGTCGCCGCTCAGCCCTCCGCCGGGAGTGAGTCCCTCCAGGCTCCGAA
      GAGGTCACGGAGGCAGCGGCGAGTCGGGAGGCGGCCCTCACTCAGGAGGTCCGAGGCTT   +360
          P  V  P  P  S  P  A  Q  P  P  P  G  V  S  P  P  S  R  L  R  I  -
```

FIG. 34A

```
     TAGGAGATCAAGAATTTGATTCATTGCCTGCTTTACTGGAATTCTACAAAATACACTATT
361  ------------+---------+---------+---------+---------+---------+  +420
     ATCCTCTAGTTCTTAAACTAAGTAACGGACGAAATGACCTTAAGATGTTTATGTGATAA
      G  D  Q  E  F  D  S  L  P  A  L  L  E  F  Y  K  I  H  Y  L  -

TGGACACTACAACATTGATAGAACCAGTGGCCAGATCAAGGCAGGGTAGTGGAGTGATTC
421  ------------+---------+---------+---------+---------+---------+  +480
     ACCTGTGATGTTGTAACTATCTTGGTCACCGGTCTAGTTCCGTCCCATCACCTCACTAAG
      D  T  T  T  L  I  E  P  V  A  R  S  R  Q  G  S  G  V  I  L  -

TCAGGCAGGAGGCAGAGTATGTGCGGGCCCTCTTTGACTTTAATGGAATGATGAAG
481  ------------+---------+---------+---------+---------+---------+  +540
     AGTCCGTCCTCCTCCGTCTCATACACGCCCGGGAGAAACTGAAATTACCCTTACTACTTC
      R  Q  E  E  A  E  Y  V  R  A  L  F  D  F  N  G  N  D  E  E  -

AAGATCTTCCCTTTAAGAAGAAGGGAGACATCCTGAGAATCCGGGATAAGCCTGAAGAGCAGT
541  ------------+---------+---------+---------+---------+---------+  +600
     TTCTAGAAGGGAAATTCTTCTGTCGTAGGACTCTTAGGCCTATTCGGACTTCTCGTCA
      D  L  P  F  K  K  G  D  I  L  R  I  R  D  K  P  E  E  Q  W  -

GGTGGAATGCAGAGGACAGCGAAGGAAAGAGGGGATGATTCCTGTCCCTTACGTGGAGA
601  ------------+---------+---------+---------+---------+---------+  +660
     CCACCTTACGTCTCCTGTCGCTTCCTTTCTCCCCTACTAAGGACAGGAATGCACCTCT
      W  N  A  E  D  S  E  G  K  R  G  M  I  P  V  P  Y  V  E  K  -

AGTATATAGACCTGCCTCCGCTTCCCGCCTCAGTATCGGCTCTGATTGGAGGTAACCAGGAGGGTTCCC
661  ------------+---------+---------+---------+---------+---------+  +720
     TCATATCTGGACGGAGGCGGAGTCATAGCCGAGACTAACCTCCATTGGTCCTCCCAAGGG
      Y  R  P  A  S  A  S  V  S  A  L  I  G  G  N  Q  E  G  S  H  -
```

FIG. 34B

```
721 ACCCACAGCCACTGGGGTGGCCGGAGCCTGGGCCCTATGCCAACCCAGCGT
    --------+---------+---------+---------+---------+ 770
    TGGGTGTCGGTGACCCCACCGGCCTCGGACCCGGGATACGGTTGGGTCGCA
     P  Q  P  L  G  G  R  S  L  G  P  M  P  T  Q  R  -
```

FIG. 34C

```
     GTGATTGAGAAGCCGGAGAATGACCCTGAATGGTGGAAAATGCCAAAAATGCCGAGGCCAA
1    ------:------:------:------:------:------:------:------:------:------:------:------+60
     CACTAACTCTTCGGCCTCTTACTGGGACTTACCACCTTTTACGTTTTTACGGGCTCCGGTT
     V  I  E  K  P  E  N  D  P  E  W  W  K  C  K  N  A  R  G  Q  -

GTGGGCCTGGTCCCCAAAAACTACGTGGTTGTTCTCAGTGATGGGCCTGCTCTGCACCCC
61   ------:------:------:------:------:------:------:------:------:------:------:------+120
     CACCCGGACCAGGGGTTTTGATGCACCAACAAGAGTCACTACCCGGACGAGACGTGGGG
     V  G  L  V  P  K  N  Y  V  V  V  L  S  D  G  P  A  L  H  P  -

GCTCACACCCCAGATCAGCTACACCGGGCCTTCAGCCAGGGGCGCTTTGCTGGTCgg
121  ------:------:------:------:------:------:------:------:------:------:------:------+180
     CGAGTGTGGGGGTCTAGTCGATGTCGGCCCGGAAGTCGTCCCCGAAACGACCAGCC
     A  H  T  P  Q  I  S  Y  T  G  P  S  A  S  G  R  F  A  G  R  -

GAGTGGTACTATGGCAACGTGACACGGCACCAGGCCGAGTGTGCGCTCAATGAGCGGGGC
181  ------:------:------:------:------:------:------:------:------:------:------:------+240
     CTCACCATGATACCGTTGCACTGTGCCGTGGTCCGGCTCACACGCGAGTTACTCGCCCCG
     E  W  Y  Y  G  N  V  T  R  H  Q  A  E  C  A  L  N  E  R  G  -

GTCGAGGGCGACTTCCTCATTAGGGACTCCGAGAGCTCCTGCCCAGTGACTTCTCCGTGTCT
241  ------:------:------:------:------:------:------:------:------:------:------:------+300
     CAGCTCCCGCTGAAGGAGTAATCCCTGTCGTCGAGGAGCGGGTCACTGAAGAGGCACAGA
     V  E  G  D  F  L  I  R  D  S  E  S  S  P  S  D  F  S  V  S  -

CTCAAAGCGTCAGGGAGAAACAAGCACTTCAAGGTGCAGCTGGTGGACAGCGTCTACTGC
301  ------:------:------:------:------:------:------:------:------:------:------:------+360
     GAGTTTCGCAGTCCCTCTTTGTTCGTGAAGTTCCACGTCGACCACCTGTCGCAGATGACG
     L  K  A  S  G  R  N  K  H  F  K  V  Q  L  V  D  S  V  Y  C  -
```

FIG. 35A

```
361  ATTGGGCAGCGGCGTTCCACAGCATGGACGAGAGCTTGTGGAGCACTACAAGAAGGCCCCC
     ------+---------+---------+---------+---------+---------+ 420
     TAACCCGTCGCCGCAAGGTGTCGTACCTGCTCGAACACCTCGTGATGTTCTTCCGGGGG
      I  G  Q  R  R  F  H  S  M  D  E  L  V  E  H  Y  K  K  A  P  -

421  ATCTTCACCAGCGAGCACGGGGAGAAGCTCTACCTTGTCCGAGCCCTACAGTGAAAGCAG
     ------+---------+---------+---------+---------+---------+ 480
     TAGAAGTGGTCGCTCGTGCCCCTCTTCGAGATGGAACAGGCTCGGGATGTCACTTTCGTC
      I  F  T  S  E  H  G  E  K  L  Y  L  V  R  A  L  Q  *  -

481  CCATTGGCCCCTCATGCCCTGTGGGCCTGCCACTCTGCTCTGCCACCTCTGCTCCCAGAG
     ------+---------+---------+---------+---------+---------+ 540
     GGTAACCGGGGAGTACGGGACACCCGGACGCCGAGCGTGAGACGAGACGGAGGGTCTC

541  CCCAGCACTTCTGCTCCACCTCCACCCATGTGGCTTGATCACCTCTGTGCCCAGTCTGT
     ------+---------+---------+---------+---------+---------+ 600
     GGGTCGTGAAGACGAGGTGGAGGTGGGTACACCGAACCTAGTGGAGACACCGGGTCAGACA

601  CCTTTCTTTTTCAGCCCTGTTGGTCAACCACGGCTACCTAGG
     ------+---------+---------+---------+--- 642
     GGAAAGAAAAAGTCGGGACAACCAGTTGGTGCCGATGGATCC
```

FIG. 35B

```
  1   CTCTCTCTCTCTCTCTCTCCCTCTCTCCTAGCACCTGCTGCTCAGTAGGAAGGGCAAG    60
      ----+----+----+----+----+----+----+----+----+----+----+----+
      GAGAGAGAGAGAGAGAGAGAGGGAGAGAGAGGATCGTGGACGAGTCATCCTTCCCGTTC

61   AGCAATTCGAGGCCGGTGCATTGTGAGGAGTCTCCACCCCTCCTGCGCTTCCTTCTC    120
      ----+----+----+----+----+----+----+----+----+----+----+----+
      TCGTTAAGCTCCGGCCACGTAACACTCCTCAGAGGTGGGGAGGACGCGAAGGAAGAG

121   CAGGGAGCCTCTCAGCCCGCCCTCACCTGCCCGAGATAATTTAGTTCCCTGGGCCTGG    180
      ----+----+----+----+----+----+----+----+----+----+----+----+
      GTCCCTCGGAGAGTCCGGCGGAGTGGACGGGCTCTATTAAATCAAAGGACCCGGACC

181   AATCTGGATACGCAGGGCCTCTGCTCTATATTCTCCCGCCTCAACATTCAAAGGCGGAT    240
      ----+----+----+----+----+----+----+----+----+----+----+----+
      TTAGACCTATGCGTCCCGGAGCGAGATATAAGAGGGCGGAGTTGTAAGTTTCCGCCCTA

241   AGCCTTTCTACCATCTGTAGAGAAGAGAGAAAGGATTCGAAATCAAATCCAAGTGTCTGG    300
      ----+----+----+----+----+----+----+----+----+----+----+----+
      TCGGAAAGATGGTAGACATCTCTTCTCTTTCCTAAGCTTTAGTTTAGGTTCACAGACC

301   GATCTCTAGACAGAGCCAGACTTTGGGCCGGGTGTCCGGCTCCTTCTGTTGGAGGTGCTC    360
      ----+----+----+----+----+----+----+----+----+----+----+----+
      CTAGAGATCTGTCTCGGTCTGAAACCCGGCCCACAGGCCGAGGAAGACAACCTCCACGAG

361   CAGGTGCCATGGAACTGGATCTGAGCCCGACTCATCTCAGCAGCTCCCCAGAAGATGTGT    420
      ----+----+----+----+----+----+----+----+----+----+----+----+
      GTCCACGGTACCTTGACCTAGACTCGGGCTGAGTAGAGTCGTCGAGGGTCTTCTACACA
        M  E  L  D  L  S  P  T  H  L  S  S  S  P  E  D  V  C -
```

FIG. 36A

```
421  GCCCAACTCCTCCTGCTACCCCTCCTGAGACTCCTCCGCCCCTCGATAACCCTCCGCCAGGGG
     ----+----+----+----+----+----+----+----+----+----+----+----+  480
     CGGGTTGAGGAGGACGATGGGGAGGACTCTGAGGAGGCGGGGACTATTGGGAGGCGGTCCCC
      P  T  P  A  T  P  P  E  T  P  P  P  P  D  N  P  P  P  G  D  -

481  ATGTGAAGCGGTCGCAGCCTTTGCCCATCCCCAGCAGCAGGAAACTTCGAGAAGAGGAGT
     ----+----+----+----+----+----+----+----+----+----+----+----+  540
     TACACTTCGCCAGCGTCGGAAACGGGTAGGGGTCGTCGTCCTTTGAAGCTCTTCTCCTCA
      V  K  R  S  Q  P  L  P  I  P  S  S  R  K  L  R  E  E  E  F  -

541  TTCAGGCAACTCTCTGCCCTCCATCCCCAACCCTTCCCTGAGCTCTGCAGCCCCACCTT
     ----+----+----+----+----+----+----+----+----+----+----+----+  600
     AAGTCCGTTGAGAGACGGGAGGTAGGGGTTGGGAAGGGACTCGAGACGTCGGGTGGAA
      Q  A  T  S  L  P  S  I  P  N  P  F  P  E  L  C  S  P  P  S  -

601  CACAGAAACCCATTCTTGGTGTTCCTCGGTGTGCAAGGGGTTGCTTCCTGAGACTCCA
     ----+----+----+----+----+----+----+----+----+----+----+----+  660
     GTGTCTTTGGGTAAGAACCACAAGGAGGCACGTTCCCAACGAAGGAGTCTGAGGT
      Q  K  P  I  L  G  G  S  S  G  A  R  G  L  L  P  R  D  S  S  -

661  GCCGGCCTCTGTGTGGTGAAGGTGTACAGTGAGGATGGGGCCTGCCGGTCTGTGGAGGTGG
     ----+----+----+----+----+----+----+----+----+----+----+----+  720
     CGGCCGGAGACACACCACTTCCACATGTCACTCCTACCCCGACGGCCAGACACCTCCACC
      R  L  C  V  V  K  V  Y  S  E  D  G  A  C  R  S  V  E  V  A  -
```

FIG. 36B

```
721   CAGCGGGGCGCCACAGCTCGTCGTGTGTGAGATGCTGGTACAACGAGCTCACGCCCTGA
      ----+---------+---------+---------+---------+---------+ 780
      GTCGCCCCGCGGTGTCGAGCAGTGCACACACTCTACGACCATGTTGCTCGAGTGCGGGACT
       A  G  A  T  A  R  H  V  C  E  M  L  V  Q  R  A  H  A  L  S -

781   GCGACGAGAGTCTGGGGACTAGTGTGGGAATCCCCACCCTACCTGGCACTGGAGCGGGTCTGG
      ----+---------+---------+---------+---------+---------+ 840
      CGCTGCTCTCGACCCCTGATCACCTTAGGGTGGGATGACCGTGACCTCGCCCAGACC
       D  E  S  W  G  L  V  E  S  H  P  Y  L  A  L  E  R  G  L  E -

841   AGGACCATGAATTTGTGGAAGTGCAGGAGGCCTGGCCTGTGGGTGGAGATAGCCGCT
      ----+---------+---------+---------+---------+---------+ 900
      TCCTGGTACTTAAACACCTTCACGTCCTCCGGACCACCCACCTCTATCGGCGA
       D  H  E  F  V  V  E  V  Q  E  A  W  P  V  G  G  D  S  R  F -

901   TCATCTTCCGTAAAAACTTCGCCAAGTATGAACTATTCAAGAGCCCCCACACCCTGT
      ----+---------+---------+---------+---------+---------+ +960
      AGTAGAAGGCATTTTTGAAGCGGTTCATACTTGATAAGTTCTCGGGGGTGTGGACA
       I  F  R  K  N  F  A  K  Y  E  L  F  K  S  P  P  H  T  L  F -

961   TTCCAGAAAAGATGGTCTCGAGCTGTCTGGATGCACAAACAGGCATATCCCATGAAGACC
      ----+---------+---------+---------+---------+---------+ +1020
      AAGGTCTTTTCTACCAGAGCTCGACAGACTACGTGTTTGTCCGTATAGGGTACTTCTGG
       P  E  K  M  V  S  S  C  L  D  A  Q  T  G  I  S  H  E  D  L -

1021  TCATCCAGAACTTCCTGAACGCTGGCAGCTTCCCTGAGATCCAGGGCTTCCTGCAGCTGC
      ----+---------+---------+---------+---------+---------+ +1080
      AGTAGGTCTTGAAGGACTTGCGACCGTCGAAGGGACTCTAGGTCCCGAAGACGTCGACG
       I  Q  N  F  L  N  A  G  S  F  P  E  I  Q  G  F  L  Q  L  R -
```

FIG. 36C

```
1081  GGGGATCAGGCCCGGGGGGTCAGGTCGAAAGCTTTGGAAACGTTTCTTCTGCTTTCTGCGTC
      CCCCTAGTCCGCGCCCCCAGTCCAGTCCAGCTTTCGAAACCTTTGCAAAGAAGACGAAAGACGCAG  +1140
      G   S   G   R   G   S   G   R   K   L   W   K   R   F   F   C   F   L   R   R   -

1141  GATCTGGCCTCTACTACTCTACCAAGGGTACCTCCAAGGATACCCCAGAGACCCACAGTATG
      CTAGACCGGAGATGATGAGATGGTTCCCATGGAGGTTCCTGGGGTCTGTGGATGTCATAC  +1200
      S   G   L   Y   Y   S   T   K   G   T   S   K   D   P   R   H   L   Q   Y   V   -

1201  TGGCAGATGTGAATGAGTCCAATGTCTATGTGGTGACCCAGGGCCGCAAGCTGTATGGGA
      ACCGTCTACACTTACTCAGGTTACAGATACACCACTGGTCCGGCGTTCGACATACCCT  +1260
      A   D   V   N   E   S   N   V   Y   V   V   T   Q   G   R   K   L   Y   G   M   -

1261  TGCCCCACTGACTTCGGCTTCTGTGTCAAGCCCAACAAGCTTCGAAACGGCCACAAGGGC
      ACGGGGTGACTGAAGCCGAAGACACAGTTCGGTTGTTGAAGCTTTGCCGGTGTTCCCG  +1320
      P   T   D   F   G   F   C   V   K   P   N   K   L   R   N   G   H   K   G   L   -

1321  TCCACATCTTCTGCAGTGAGGATGAGCAGAGTCGGACGTCGCTCTCAGCCTGCTGGCTTCCGC
      AGGTGTAGAAGACGTCACTCCTACTCGTCTCAGCGAGACGTCGGACGACCGACGAAGGCCG  +1380
      H   I   F   C   S   E   D   E   Q   S   R   T   C   W   L   A   A   F   R   L   -

1381  TCTTCAAGTACGGGGTACAGTCTATATAAGAATTATCAGCAGGCCCAGTCTCGTCACCTGC
      AGAAGTTCATGCCCCATGTCGATATATTCTTAATAGTCGTCCGGGTCAGAGCAGTGGACG  +1440
      F   K   Y   G   V   Q   L   Y   K   N   Y   Q   Q   A   Q   S   R   H   L   R   -
```

FIG. 36D

```
      GCCTATCCTATTTGGGTCTCCACCCTTGAGGAGCGTCTCAGACAATACCCTAGTGGCTA
1441  ------+---------+---------+---------+---------+---------+ +1500
      CGGATAGGATAAACCCCAGAGGTGGGAACTCCTCGCAGAGTCTGTTATGGGATCACCGAT
       L  S  Y  L  G  S  P  P  L  R  S  V  S  D  N  T  L  V  A  M -

TGGACTTCTCTGGCCATGCGGGGGGTGTCATTGATAACCCCGGGAAGCTCTGAGTGCCG
1501  ------+---------+---------+---------+---------+---------+ +1560
      ACCTGAAGAGACCGGTACGCCCCCACAGTAACTATTGGGGCCCTTCGAGACTCACGGC
       D  F  S  G  H  A  G  R  V  I  D  N  P  R  E  A  L  S  A  A -

CCATGGAGGAGCCCAGGCTCGAGCTCCTCCGGACCTCCTCCTTCTGTTGGTGCAGACTCGGACGGTGT
1561  ------+---------+---------+---------+---------+---------+ +1620
      GGTACCTCCTCCGGGTCCGAGTCGGAGGAGGAAGACAAACCACGTCTGAGCCTGCCACCA
       M  E  E  A  Q  A  W  R  K  K  T  N  H  R  L  S  L  P  T  T -

CATGCTCTGGCTCGAGCCTCAGCGCCAGCCATTCATCGCACCCAGCCCTGGTTTCATGAC
1621  ------+---------+---------+---------+---------+---------+ +1680
      GTACGAGACCGAGCTCGGAGTCGCGGTCGGTAAGTAGCGTGGGTCGGGACCAAAGTACCTG
       C  S  G  S  S  L  S  A  A  I  H  R  T  Q  P  W  F  H  G  R -

GCATCTCTCGGGAGGAGAGCCTAATTGGACACAGCAGGGCCTGGTGGATGGTGTGT
1681  ------+---------+---------+---------+---------+---------+ +1740
      CGTAGAGAGCCCTCCTCTCGGATTAACCTGTGTCGTCCGACCACTACCACACA
       I  S  R  E  E  S  Q  R  L  I  G  Q  Q  G  L  V  D  G  V  F -

TCCTGGTCCGGAGAGCCAGAGGAACCCACAGGGCTTTGTCCTTGTCCATCTGC
1741  ------+---------+---------+---------+---------+---------+ +1800
      AGGACCAGGCCCTCTCGGTCTCCGGGTGTCCCGAAACAGGAACACGGTAGACG
       L  V  R  E  S  Q  R  N  P  Q  G  F  V  L  S  L  C  H  L  Q -
```

FIG. 36E

```
1801  AGAAAGTCAAGCATTATCTCATTTGCCAAGTGAAGATGAAGGTTGCCTTTACTTCAGCA
      ----+----+----+----+----+----+----+----+----+----+----+----+  +1860
      TCTTTCAGTTCGTAATAGAGTAAACGGTTCACTTCTACTTCCAACGGAAATGAAGTCGT
       K  V  K  H  Y  L  I  L  P  S  E  D  E  G  C  L  Y  F  S  M  -

1861  TGGATGAGGGCCAGACCCGTTTCACAGACCTGCTGCAGCTGGTAGAATTCCACCAGCTGA
      ----+----+----+----+----+----+----+----+----+----+----+----+  +1920
      ACCTACTCCCGGTCTGGGCAAAGTGTCTGGACGACGTCGACCATCTTAAGGTGGTCGACT
       D  E  G  Q  T  R  F  T  D  L  L  Q  L  V  E  F  H  Q  L  N  -

1921  ACCGAGGCATCCTGCCCTGCCTGCTGCGCCACTGCTGTGCCCGTGTGGCCCCTCTGAGCC
      ----+----+----+----+----+----+----+----+----+----+----+----+  +1980
      TGGCTCCGTAGGACGGGACGGACGACGCGGTGACGACACGGGCACACCGGGAGACTCCGG
       R  G  I  L  P  C  L  L  R  H  C  C  A  R  V  A  L  *  -

1981  GCACAAGCTACTGCAGCCATGGGTTTGCCTACCACCCTTCTGTGTCCTGTGACTGGTGCA
      ----+----+----+----+----+----+----+----+----+----+----+----+  +2040
      CGTGTTCGATGACGTCGGTACCCAAACGGATGGTGGGAAGACACAGGACACTGAGCCACGT

2041  GGTGGGTGGGGTGGTAAACAGTGGAAGAGCTCCCCCCAATTTATCCCATTTTTTT
      ----+----+----+----+----+----+----+----+----+----+----+----+  +2100
      CCACCCACCCCACCATTGTCACCTTCTCGAGGGGGGGTTAAAATAGGTAAAAAAA

2101  AACCTCTCTCAACCAGTGAAACATCCCCTGTCCATCCCTGACTCCTGTCCCCAA
      ----+----+----+----+----+----+----+----+----+----+----+----+  +2160
      TTGGAGAGAGTTGGTCACTTTGTAGGGATTGGGACAGGTAGGACTGAGGACAGGGTT
```

FIG. 36F

```
2161  GGGAGGCATTGTGGTCCTGTCCCTTGGTAGAGCTCCTGAGGTACTGTTCCAGTGAGGGG
      ----+---------+---------+---------+---------+---------+  +2220
      CCCTCCGTAACACCAGGACAGGGAACCATCTCGAGGACTCCATGACAAGGTCACTCCCC

2221  CATTATGAGAGAGGAGCGGGGCAGCCCAGGAGGTCTCATACCCCACCCATAATCTGTACAGA
      ----+---------+---------+---------+---------+---------+  +2280
      GTAATACTCTCTCCTCGCCCCGTCGGGTCCTCCAGAGTATGGGGTGGTATTAGACATGTCT

2281  CTGAGAGGCCAGTTGATCTGCTCTGTTTTATACCAGTAACAATAAAGATTATTTTTGAT
      ----+---------+---------+---------+---------+---------+  +2340
      GACTCTCCGGTCAACTAGACGAGACAAAATATGGTCATTGTTATTTCTAATAAAAACTA

2341  ACAAA
      -----  2345
```

FIG. 36G

METHODS FOR DETECTING TYROSINE KINASE-BINDING TARGET PROTEINS AND IDENTIFYING SUBSTANCES THAT AFFECT SH2 PHOSPHORYLATED LIGAND REGULATORY SYSTEMS

This is a divisional application of U.S. application Ser. No. 08/167,035, filed Dec. 16, 1993, now U.S. Pat. No. 5,618,691 which is a divisional application of U.S. Ser. No. 07/906,349, filed Jun. 30, 1992, and issued on Jul. 18, 1995 as U.S. Pat. No. 5,434,064, which is a continuation-in-part of U.S. application Ser. No. 07/643,237, filed Jan. 18, 1991, now abandoned, each of which is incorporated herein by reference in its entirety.

BACKGROUND OF THE INVENTION

1. Field of the Invention

The invention, in the field of molecular and cell biology, relates to a novel method, based on direct expression cloning, for identifying target proteins capable of binding to and/or serving as substrates for receptor or cytoplasmic tyrosine kinases. The invention also relates to novel proteins identified using this method.

2. Description of the Background Art

A variety of polypeptide growth factors and hormones mediate their cellular effects by interacting with cell surface receptors and soluble or cytoplasmic polypeptide containing molecules having tyrosine kinase enzymatic activity (for review, see Williams, L. T. et al., *Science* 243:1564–1570 (1989); Ullrich, A. et al., *Cell* 61:203–212 (1990); Carpenter, G. et al. *J. Biol. Chem.* 265:7709–7712 (1990)). The interaction of these ligands with their receptors induces a series of events which include receptor dimerization and stimulation of protein tyrosine kinase activity. For the epidermal growth factor receptor (EGFR) as well as other receptors with tyrosine kinase activity, such as the platelet-derived growth factor receptor (PDGFR), kinase activation and receptor autophosphorylation result in the physical association of the receptor with several cytoplasmic substrates (Ullrich et al., supra).

Two substrates for the EGFR kinase have now been definitively identified in living cells: (a) the phosphatidylinositol specific phospholipase C-γ (PLC-γ) and (b) the GTPase activating protein (GAP), a protein which may be in the effector loop of the ras protein (Margolis, B. et al. *Cell* 57:1101–1107 (1989b); Meisenhelder, J. et al. *Cell* 57:1109–1122 (1989); Molloy, C. J. et al. *Nature* 342:711–714 (1989); Wahl, M. I. et al. *J. Biol. Chem.* 265:3944–3948 (1990); Ellis, C. et al. *Nature* 343:377–381 (1990); Kaplan, D. R. et al. *Cell* 61 121–133 (1990)).

Similarly, activated PDGFR was shown to tyrosine phosphorylate, and to become associated with PLC-γ, GAP, and cellular tyrosine kinases such as pp60$^{RTC}$ (Gould, K. L. et al., *Molec. Cell. Biol.* 8:3345–3356 (1988); Meisenhelder, J. et al., *Cell* 57:1109–1122 (1989); Molloy, C. J. et al., *Nature* 342:711–714 (1989); Kaplan, D. R. et al., *Cell* 61:121–133 (1990); Kazlauskas, A. et al., *Science* 247:1578–1581 (1990); Krypta, R. M. et al., *Cell* 62:481–492 (1990); Margolis, B. et al., *Science* 248:607–610 (1990)). While the exact sites responsible for the association of EGFR with either PLC-γ or GAP have not been completely clarified, recent work has begun to identify regions on both the substrate and receptor which contribute to the association.

SH2 (src homology 2) domains appear to be the regions responsible for the association of several tyrosine kinase substrates with activated growth factor receptors. SH2 domains are conserved sequences of about 100 amino acids found in cytoplasmic non-receptor tyrosine kinases such as pp60src, PLC-γ, GAP and v-crk (Mayer, B. J. et al., *Nature* 332:272–275 (1988); Pawson, T. *Oncogene* 3:491–495 (1988)). While having distinct catalytic domains, all these molecules share conserved SH2 and SH3 (src homology 3) domains and the ability to associate with receptors with tyrosine kinase activity (Anderson, D. et al., *Science* 250:979–982 (1990)).

Tyrosine kinase activation and receptor autophosphorylation are prerequisites for the association between growth factor receptors and SH2 domain-containing proteins (Margolis, B. et al., *Mol. Cell. Biol.* 10:435–441 (1990); Kumjian et al., *Proc. Natl. Acad. Sci. USA* 86:8232–8239 (1989); Kazlauskas, A. et al., *Science* 247:1578–1581 (1990)). In particular, the carboxy-terminal (C-terminal) fragment of the EGFR, which contains all the known autophosphorylation sites, binds specifically to the SH2 domains of GAP and PLC-γ (see below). Hence, a major site of association exists between the SH2 domain of these substrate proteins and the tyrosine phosphorylated C-terminal tail of the EGFR.

With the recognition that binding to the activated tyrosine kinase receptor is conserved among several substrate proteins, efforts to identify additional substrates which share these properties have been undertaken. Target proteins which bind to activated receptors have been identified by analysis of proteins that co-immunoprecipitate with growth factor receptors, or that bind to receptors attached to immobilized matrices (Morrison, D. K. et al., *Cell* 58:649–657 (1989); Kazlauskas, A. et al., *EMBO J.* 9:3279–3286 (1990)). While the identity of some of these proteins is known, several others detected utilizing these approaches have not been fully characterized. Moreover, it is possible that rare target molecules which interact with activated receptors have not been detected due to the limited sensitivity of these techniques; the actual stoichiometry of binding may be low, and the detergent solution necessary to solubilize proteins may disrupt binding.

Conventional approaches to isolate and clone these proteins have been arduous, requiring the use of large quantities of tissue or cells lines to purify sufficient amounts of protein for microsequence analysis and subsequent conventional cDNA cloning. Therefore, a need for new approaches for the cloning and subsequent isolation and identification of these proteins is recognized in the art.

SUMMARY OF THE INVENTION

It is an object of the present invention to overcome the deficiencies of the related art.

It is also an object of the present invention to understand and gain control over the regulation of cell growth and oncogenesis by providing the ability to identify target proteins for tyrosine kinases, including both receptor and cytoplasmic tyrosine kinases in eukaryotic organisms.

It is a further object of the present invention to provide a novel expression/cloning system for the rapid cloning of target proteins which bind tyrosine kinase proteins which are present intracellularly and in cell receptors of eukaryotes. The cloning method is based on the ability of a certain class of substrates to bind specifically to the tyrosine-phosphorylated carboxy-terminus (C-terminus) of the proteins having tyrosine kinase activity. Non-limiting examples include proteins that bind at least one of cytoplasmic and receptor tyrosine kinases, such as a receptor tyrosine kinase found in epidermal growth factor receptor (EGFR) (see Example VI, below).

Another object of the present invention is to provide a method of cloning tyrosine kinase target proteins, which method important advantages over conventional cloning methods, including avoidance of the laborious and costly task of purifying potential target proteins for microsequencing analysis.

Another object of the present invention is to provide a method for identifying receptor target molecules having tyrosine kinase activity whose association with activation receptors could not otherwise be detected using conventional techniques.

Another object of the present invention is to provide for the identification of structurally or functionally related proteins which, though only weakly homologous at the nucleic acid level, are similar in their property of binding to activated receptors with tyrosine kinase activity, which latter ability is important since conventional screening methods used to identify related genes are typically based on low stringency nucleic acid hybridization. Conventional hybridization-based screening would not have been successful in cloning and identifying such tyrosine kinase target proteins of the present invention, exemplified as non limiting examples as GRB-1, GRB-2, GRB-3, GRB-4 or GRB-7, because of their lack of similarity at the DNA level.

The methods of the present invention take advantage of the discovery that the C-terminus of the EGFR protein in which the tyrosine residues are phosphorylated can bind substrates as described herein. By creating a labelled polypeptide which substantially corresponds to at least a portion of phosphorylation domain of a tyrosine kinase, a probe is provided having at least one phosphorylated tyrosine. Such a probe can be used to detect, identify and/or purify target proteins from solutions or as part of screening of cDNA expression libraries from eukaryotic cells or tissues. Such tyrosine kinase target proteins, discovered according to the present invention, ar termed "GRB" (for Growth factor Receptor Bound) for the initial receptor tyrosine kinases used, but which target proteins are not limited to growth factor receptors. Accordingly, GRBs of the present invention include target proteins for any eukaryotic tyrosine kinase which are provided according to the present invention.

The novel cloning methodology of the present invention has been designated, "CORT" (for Cloning Of Receptor Targets), and may also be applied to detecting, identifying, cloning or purifying target proteins for any tyrosine kinase, such as a soluble, cytoplasmic or receptor tyrosine kinase.

The method of the present invention is proposed as a novel approach having both generality and rapidity for the identification and cloning of target molecules for tyrosine kinases.

The present invention is thus directed to a method for detecting a target protein in solution, which is a target of a receptor or cytoplasmic tyrosine kinase, the target protein being capable of binding to at least a portion of a tyrosine-phosphorylated polypeptide of the receptor or cytoplasmic tyrosine kinase, the method comprising:

(a) contacting the solution (as a cell, an extract thereof, a lysate thereof, or a supernatant thereof) with a solid phase carrier, causing the binding of the protein to the carrier to provide a carrier-bound target protein;

(b) incubating the carrier-bound target protein with the tyrosine-phosphorylated polypeptide, which has been detectably labeled, allowing the polypeptide to bind to the carrier-bound protein;

(c) removing materials not bound to the carrier-bound target protein;

(d) detecting the presence or measuring the amount of the tyrosine-phosphorylated polypeptide bound to the carrier, thereby quantitatively or qualitatively detecting the target protein in said solution.

In one embodiment, the receptor or cytoplasmic tyrosine kinase is any eukaryotic tyrosine kinase, such as epidermal growth factor receptor, the platelet-derived growth factor receptor, or the fibroblast growth factor receptor, $pp60^{v-src}$, $pp160^{gag-abl}$, $pp130^{gag-fps}$, $pp59^{c-fyn}$, PDGF receptor B, CSF-1 receptor, $pp150^{c-fms}$, $pp150^{v-fms}$, EGF receptor, Insulin Receptor, IGF-1 receptor, $pp68^{gag-ros}$, PLC-γ, middle t-$pp60^{c-src}$ middle t-$pp62^{c-yes}$, and the consensus sequences EEEEEY(PO$_4$)MPMXX (SEQ ID NO:11), EEEEEY(PO$_4$)VPMXX (SEQ ID NO:12), DDDDDY(PO$_4$)MPMXX (SEQ ID NO:13), and DDDDDY(PO$_4$)VPMXX (SEQ ID NO:14) or a phosphorylatable fragment thereof, preferably a polypeptide of about 10 to 250 amino acid residues, more preferably 10 to 40 or 15 to 50 residues, wherein the polypeptide is produced recombinantly, synthetically or by enzymatic digestion of a purified tyrosine kinase molecule.

This method is preferably performed using a prokaryotic cell, most preferably a bacterial cell such as $E.\ coli$. The cell may also be eukaryotic, such as a yeast or a mammalian cell.

Preferably, the phosphorylated polypeptide is detectably labeled.

The solid phase carrier can be any material which can be used to bind a target protein for a tyrosine kinase. The carrier may preferably be a nitrocellulose membrane, such as to which are transferred proteins released for lysed bacterial cells when a library is being screened.

The present invention also provides a method for mapping to a eukaryotic, such a mammalian, human, murine, or other eukaryotic chromosome a gene encoding a protein which is capable of binding to a tyrosine-phosphorylated polypeptide portion of a receptor or cytoplasmic tyrosine kinase molecule, the method comprising:

(a) infecting a host or host cells which a eukaryotic gene expression library;

(b) detecting a clone expressing the protein using a method according to claim 1;

(c) sequencing the DNA of the clone; and (d) mapping the sequence to a eukaryotic chromosome.

The present invention is also directed to a polypeptide probe useful in the detection of the expression of a protein capable of binding to a tyrosine-phosphorylated polypeptide portion of a receptor or cytoplasmic tyrosine kinase. The probe comprises an amino acid sequence derived from the tyrosine-phosphorylated portion of the receptor or cytoplasmic molecule, or a functional derivative thereof, lacks the tyrosine kinase domain, and the sequence must contain at least one phosphotyrosine residue, such as 1,2,3,4,5,6,7,8, 9,10 or 11 phosphotyrosines. The probe should be detectably labeled with known labels.

A preferred probe has between about 10 and 250 amino acid residues, preferably 10–35, 16–30, 21–35, 15–35, or 20–40 residues.

The probe of the present invention is useful for detecting target proteins for receptor or cytoplasmic tyrosine kinases including but not limited to, epidermal growth factor receptor (EGFR), platelet-derived growth factor receptor (PDGFR), fibroblast growth factor receptor (FGFR), colony stimulating factor-1, (CSF-1), insulin receptor, phospholipase C-γ (PLC-γ) and insulin like growth factor-1, (IGF-1), pp60$^{v\text{-}src}$, pp160$^{gag\text{-}abl}$, pp130$^{gag\text{-}fps}$, pp59$^{c\text{-}fyn}$, PDGF receptor B, CSF-1 receptor, pp150$^{c\text{-}fms}$, pp150$^{v\text{-}fms}$, EGF receptor, insulin receptor, IGF-1 receptor, pp68$^{gag\text{-}ros}$, PLC, middle t-pp60$^{c\text{-}src}$, middle t-62$^{c\text{-}yes}$, and the consensus sequence EEEEY(PO$_4$)MPMXX (SEQ ID NO:11), EEEEY (PO4) VPMXX (SEQ ID NO:12), DDDDY(PO4)MPMMXX (SEQ ID NO:13), and DDDDDY(PO4) VPMXX (SEQ ID NO:14) or a phosphorylatable fragment thereof, e.g., as described Cantley et al., Cell 64:281–302 (1991) or Ulrich and Schlessinger Cell 61:203–312 (1990), which references are entirely herein incorporated by reference.

The present invention also includes a method for preparing the above probe, comprising (a) providing the receptor or cytoplasmic tyrosine kinase, or a recombinantly, enzymatically or synthetically produced fragment thereof, wherein the receptor or cytoplasmic tyrosine kinase, or fragment thereof, has both a tyrosine kinase domain and a tyrosine-phosphorylated domain, the tyrosine-phosphorylated domain including at least one tyrosine residue capable of being phosphorylated by the tyrosine kinase;

(b) incubating the receptor or cytoplasmic tyrosine kinase, or fragment, with detectably labeled adenosine triphosphate under conditions permitting phosphorylation of the tyrosine residue, causing phosphorylation of the tyrosine residue thereby producing the probe. In a preferred embodiment, the method includes the step of:

(c) additionally treating the phosphorylated receptor or cytoplasmic tyrosine kinase molecule with an agent capable of cleaving the molecule between the tyrosine kinase domain and the tyrosine-phosphorylated domain.

A preferred cleaving agent is cyanogen bromide.

In another embodiment, the above method involves a genetically engineered receptor-like derivative which is a polypeptide encoded by a DNA molecule comprising a DNA sequence encoding tyrosine kinase, linked to a DNA sequence encoding a selective enzymatic cleavage site, linked to a DNA sequence encoding the tyrosine-phosphorylated domain, and wherein the agent is an enzyme capable of cleaving at this cleavage site. Preferred enzymes are Factor Xa and thrombin.

Also provided is a method for purifying from a complex mixture a protein which is capable of binding to a tyrosine-phosphorylated polypeptide portion of a receptor or cytoplasmic tyrosine kinase molecule, the method comprising:

(a) contacting the complex mixture with a solid phase carrier to which a probe is bound, allowing the protein to bind to the probe;

(b) removing materials not bound to the carrier; and (c) eluting the bound protein from the carrier, thereby purifying the protein.

The present invention is also directed to a protein, GRB-1, having the amino acid sequence shown in FIG. 4 (SEQ ID NO:2). The invention also includes polypeptides having an amino acid sequence substantially corresponding to the amino acid sequence of a protein, GRB-2, which includes the amino acid sequence shown in FIG. 26 ((SEQ ID NO:6). The invention also includes polypeptides having an amino acid sequence substantially corresponding to the amino acid sequence of a protein, GRB-3, which includes the amino acid sequence shown in FIG. 34 (SEQ ID NO:4). The invention also includes polypeptides having an amino acid sequence substantially corresponding to the amino acid sequence of a protein, GRB-4, which includes the amino acid sequence shown in FIG. 35 (SEQ ID NO:8). The invention also includes polypeptides having an amino acid sequence substantially corresponding to the amino acid sequence of a protein, GRB-7, which includes the amino acid sequence shown in FIG. 36 (SEQ ID NO:10).

The invention is also directed to a DNA molecule encoding a polypeptide having a amino acid sequence substantially corresponding to the amino acid sequence of at least one of GRB-1, GRB-2, GRB-3, GRB-4 or GRB-7 proteins. Included are DNA molecules encoding functional derivatives of these proteins. When the DNA molecule naturally occurs, it is substantially free of the nucleotide sequences with which it is natively associated. The DNA molecules of this invention may be expression vehicles, such as plasmids.

Also provided is a host transformed with each of the above DNA molecules.

The present invention also includes a process for preparing a target protein substantially corresponding to the amino acid sequence GRB-1, GRB-2, GRB-3, GRB-4 or GRB-7 protein, comprising:

(a) culturing a host comprising a recombinant nucleic acid having a nucleotide sequence encoding the target protein under culturing conditions such that the target protein is expressed in recoverable amounts; and (b) recovering the protein from the culture.

BRIEF DESCRIPTION OF THE DRAWINGS

FIGS. 4A–4I shows the DNA sequence and predicted amino acid sequence of GRB-1 (SEQ ID NOS:1–2; complementary strand is SEQ ID NO:48). The protein has 724 amino acid residues.

FIG. 5 compares the sequences of the SH2 domains of GRB-1 with other proteins with similar motifs. A) SH2 domains of GRB-1(N=SEQ ID NO:17C=SEQ ID NO:18), c-src, (SEQ ID NO:19), v-abl (SEQ ID NO:20), PLC-γ (N=SEQ ID NO:21; C=SEQ ID NO:22), GAP (N=SEQ ID NO:23; C=SEQ ID NO:24), and v-crk (SEQ ID NO: 25). N and C refer to N-Terminal and C-terminal SH2 domains respectively. Conservation amino acid substitutions are as defined by Schwartz and Dayhoff: (A,G,P,S,T); (L,I,V,M); (D,E,N,Q); (K,R,H); (F,Y,W); and C. Bold letters identify those position were the same or a conservative amino acid substitution is present at 5 or more position. Boxes identify conserved motifs. B) A similar comparison of the SH3 domain of GRB-1 (SEQ ID NO:26); c-srk (SEQ ID NO:27);

v-abl (SEQ ID NO:28); PLC (SEQ ID NO:29); GAP (SEQ ID NO:30); v-crk (SEQ ID NO:31)

Figure 6:
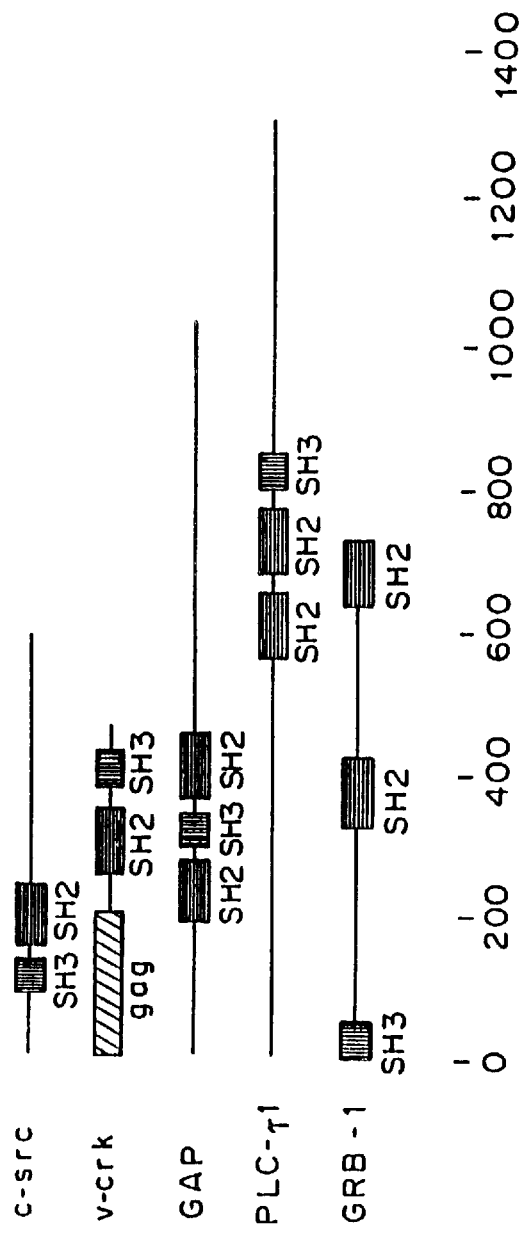

FIG. 6 is a schematic diagram comparing the structural organization of the SH2 and SH3 domains. The scheme includes known proteins containing SH2 and SH3 domains, such as c-src, v-crk, PLC-γ, GAP1 and GRB-1.

Figure 7:
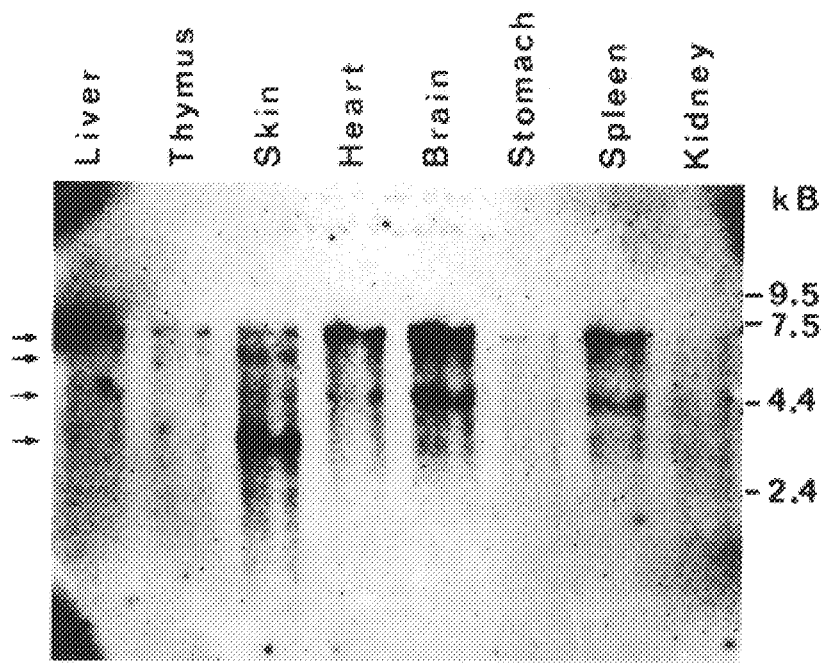

FIG. 7 is a Northern blot of monkey mRNA with GRB-1 probe. 5 μg of poly (A)+MRNA, obtained from various monkey tissue, was electrophoresed on 1.2%,/2.2M agarose-formaldehyde gel. The blot was hybridized with a ($^{32}$P)-nick translated DNA probe corresponding to the insert from clone ki4.

Figure 8:
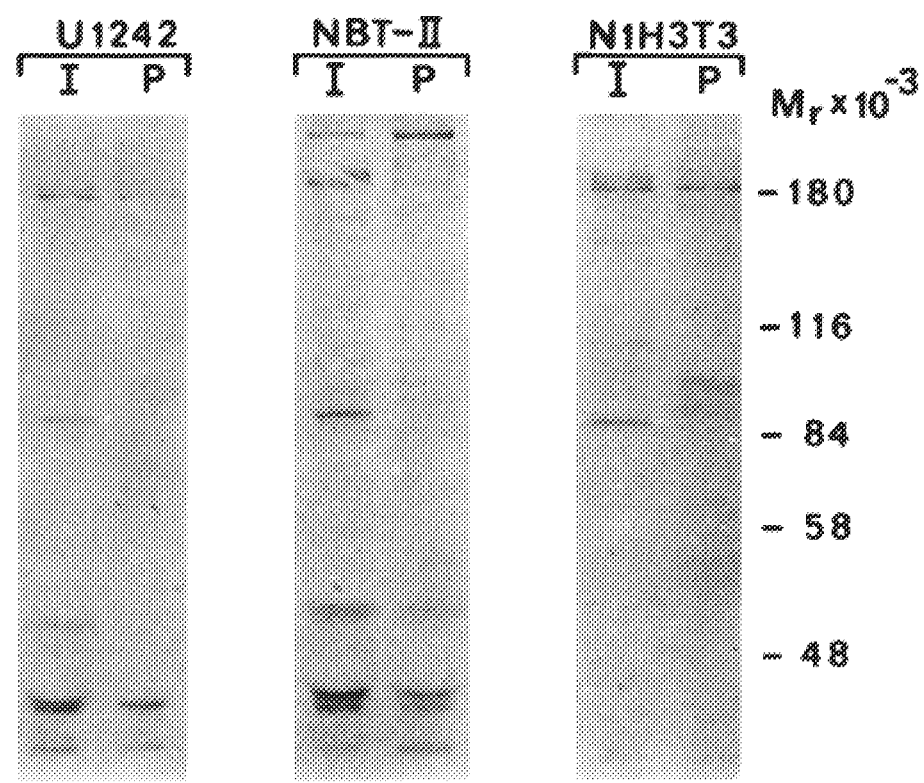

FIG. 8 is a gel pattern showing that antibodies to GRB-1 immunoprecipitate a protein of 85 kDa from biosynthetically labelled cells. Cells were metabolically labelled with ($^{35}$S) methionine, after which lysates were prepared and immunoprecipitated with either immune (I) or preimmune (P) serum. The immunoprecipitated protein was separated on a 8% SDS/PAGE. Autoradiography was performed overnight. Cell lines used include human glioblastoma cell line, U1242, rat bladder carcinoma cell line, NBT-II and NIH-3T3 cells.

Figure 9A:
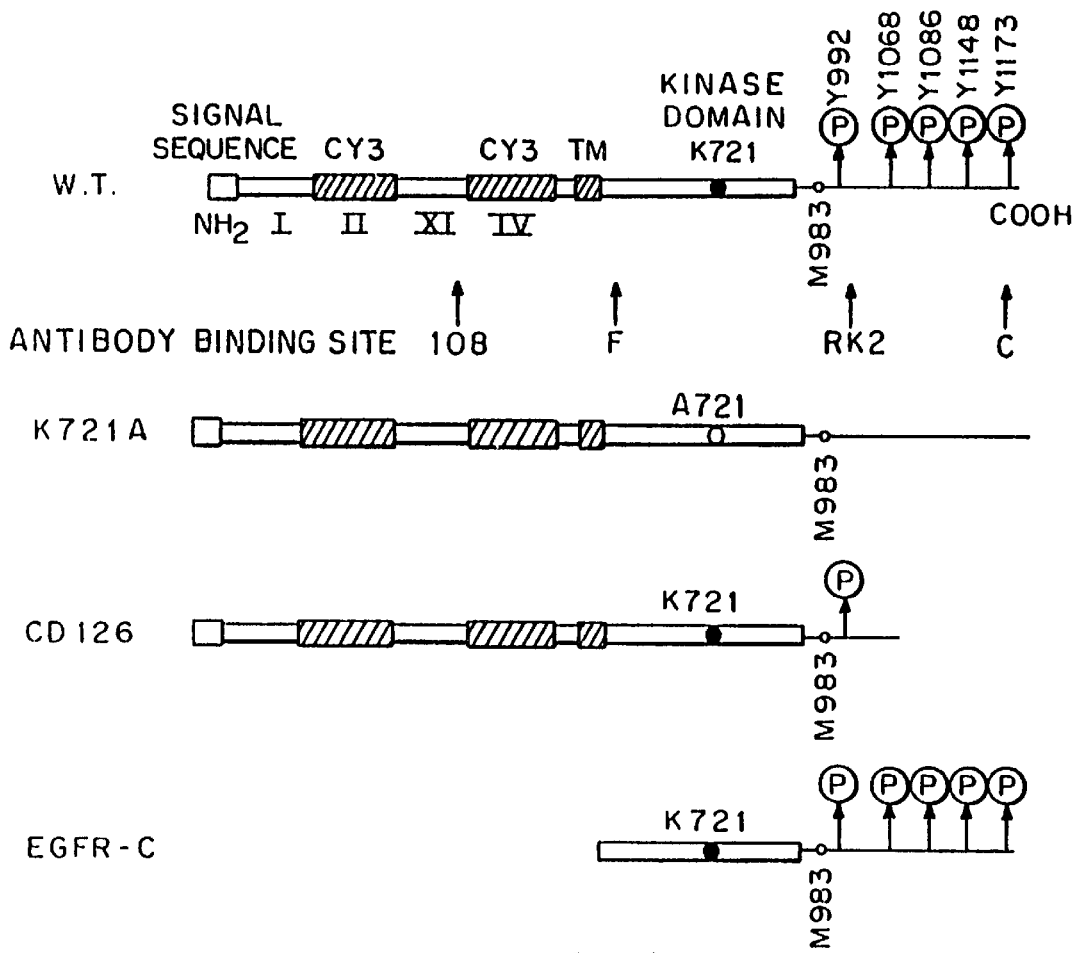
Figure 9B:
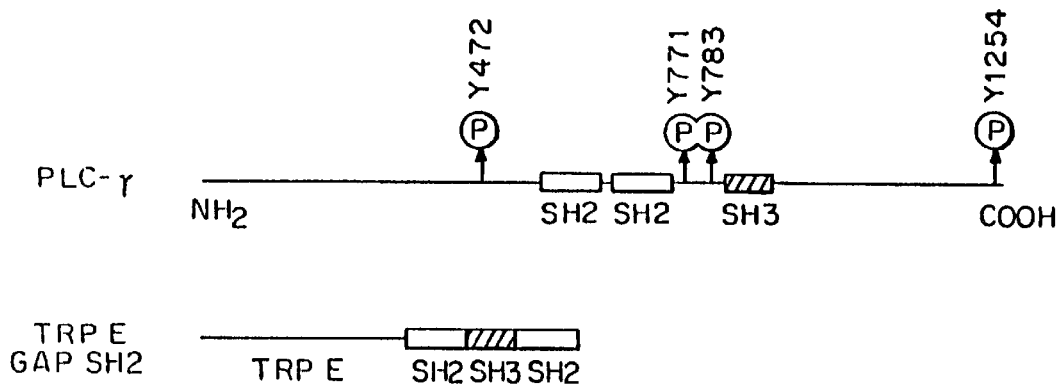

FIGS. 9A and 9B depicts several wild-type and mutant proteins used in the studies. (A) EGF receptor constructs with their known or predicted autophosphorylation sites. Wild-type (W. T.), Kinase negative (K721A), and carboxy-terminal deletion (CD126), were immunoprecipitated from previously-described transfected NIH373 cells expressing –300,000 EGF receptors. EGFR-C represents a deletion mutant containing the cytoplasmic domain of the EGF receptor produced by baculovirus-infected SF9 cells. (B) Structure of PLC-γ and trpE/GAP SH2 proteins indicating location of the SH2 and SH3 domains and PLC-γ tyrosine phosphorylation sites.

FIG. 10 is a gel pattern showing association of PLC-γ with EGFR mutants. Wild-type (HER14), carboxy-terminal deletion (DC126), or kinase-negative (K721A) EGFR were immunoprecipitated with anti-EGFR mAb108. Receptors were autophosphorylated with (γ-$^{32}$P-ATP. Concomitantly EGFR-C was added to protein A-Sepharose beads alone or to immunoprecipitated K721A receptors either with or without ATP. After further washes to remove ATP, lysate from– 15×10 6 PLC-γ overexpressing 3T-P1 cells was added and mixed for 90 min at 4 C. After washing to remove unbound PLC-γ, proteins were separated on a 6% SDS-gel and transferred to nitrocellulose for immunoblotting. One eighth of the sample was utilized for anti-PTyr blotting, the remainder for anti-PLC-γ blotting (exposure time 14 h).

Figure 11:
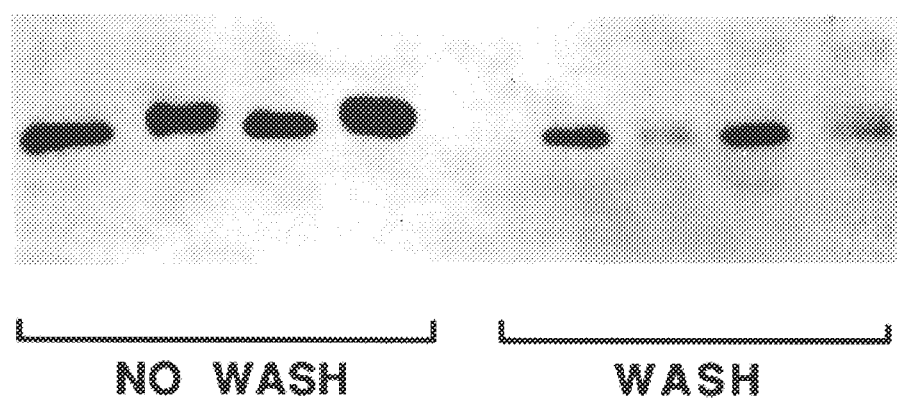

FIG. 11 is a gel pattern showing that phosphorylation of PLC-γ reduces its binding to the EGF receptor. Full length EGFR was immunoprecipitated with mAb108, and allowed to autophosphorylate. Lysate from PLC-γ overexpressing 3T-P1 cells was added and mixed for 90 min at 4° C. After binding, ATP was added to one half of the samples allowing the PLC-γ molecules to be phosphorylated by the EGF receptor. SDS-PAGE sample buffer was then added to one half of the EGFR-PLC-γ complexes (NO WASH, left panel) and directly loaded onto the 6% gel. The other half was washed three times with HNTG and then loaded on the gel (WASH, right panel. After running duplicate samples on SDS-PAGE, the proteins were transferred to nitrocellulose and probed with anti-PLC-γ and ($^{125}$I)protein A. The bands were subsequently cut from the nitrocellulose and quantitated in a γ counter. After three washes with HNTG, 50±5% (Mean±SEM, n=4) of the non-phosphorylated PLC-γ remained bound to the EGFR while only 22±4% of the phosphorylated PLC-γ remained (exposure time: 12 h).

Figures 12A, 12B:
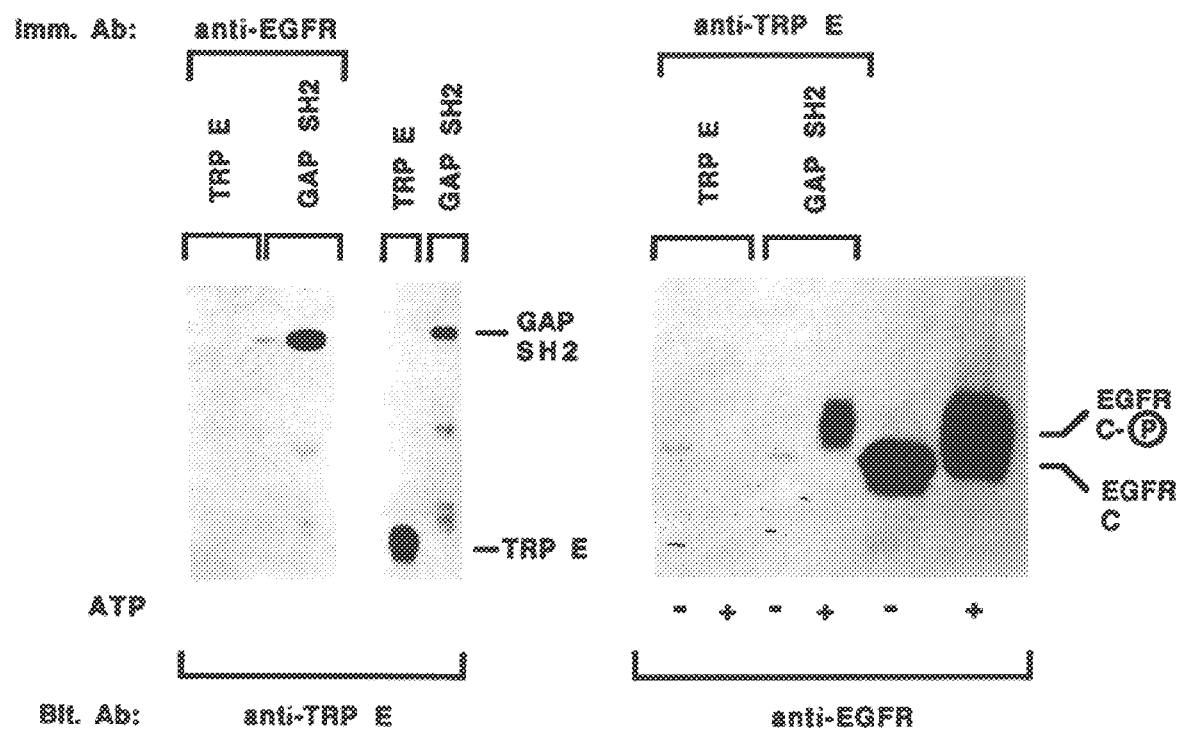

FIGS. 12A and 12B are representations of a gel pattern showing binding of EGFR-C to trpE proteins. In FIG. 12A, EGFR-C (0.5 μg) was immunoprecipitated with antibody C and washed. MnCl$_2$ alone or MnCl$_2$ and ATP were then added to facilitate autophosphorylation of TrpE or trpE/GAP SH2 (approximately 2 μg). The immunoprecipitates were separated on a 10% SDS-gel, transferred to nitrocellulose and immunoblotting was performed with anti-trpE. For comparison, about 0.1 μg of trpE or trpE/GAP SH2 lysate was loaded directly on to the gel (right panel of A). In FIG. 12B, trpE or trpE/GAP SH2 was immunoprecipitated with anti-trpE antibodies and washed. Phosphorylated or non-phosphorylated EGFR-C (0.5 μg) was then added and allowed to bind as above. After washing, samples were separated on a 10% gel, transferred to nitrocellulose and probed with antibody C. The two samples on the right represent 0.5 μg of phosphorylated and non-phosphorylated kinase loaded directly onto the gel (exposure time: 2 h).

Figure 13A:
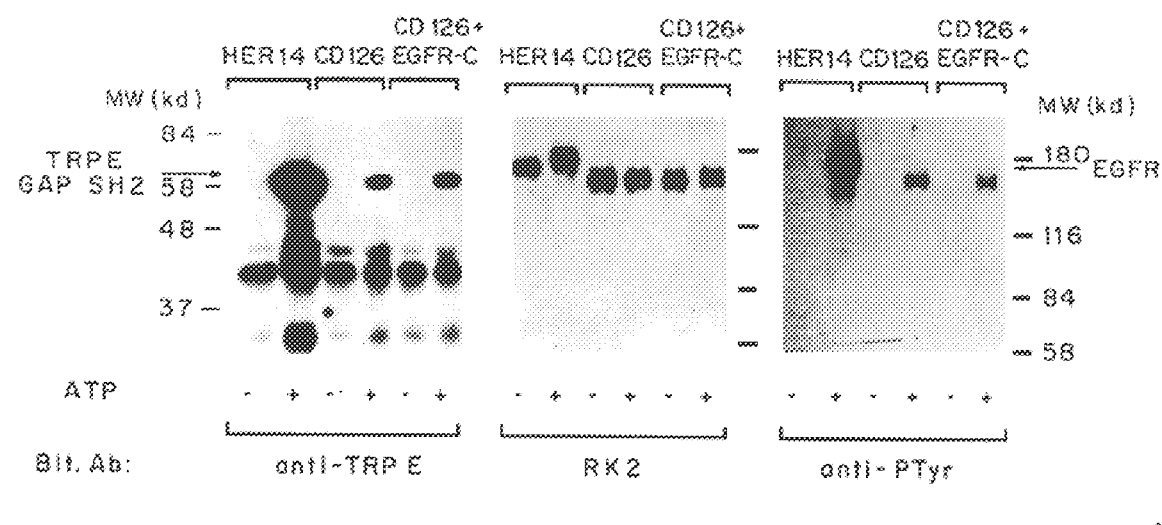
Figure 13B:
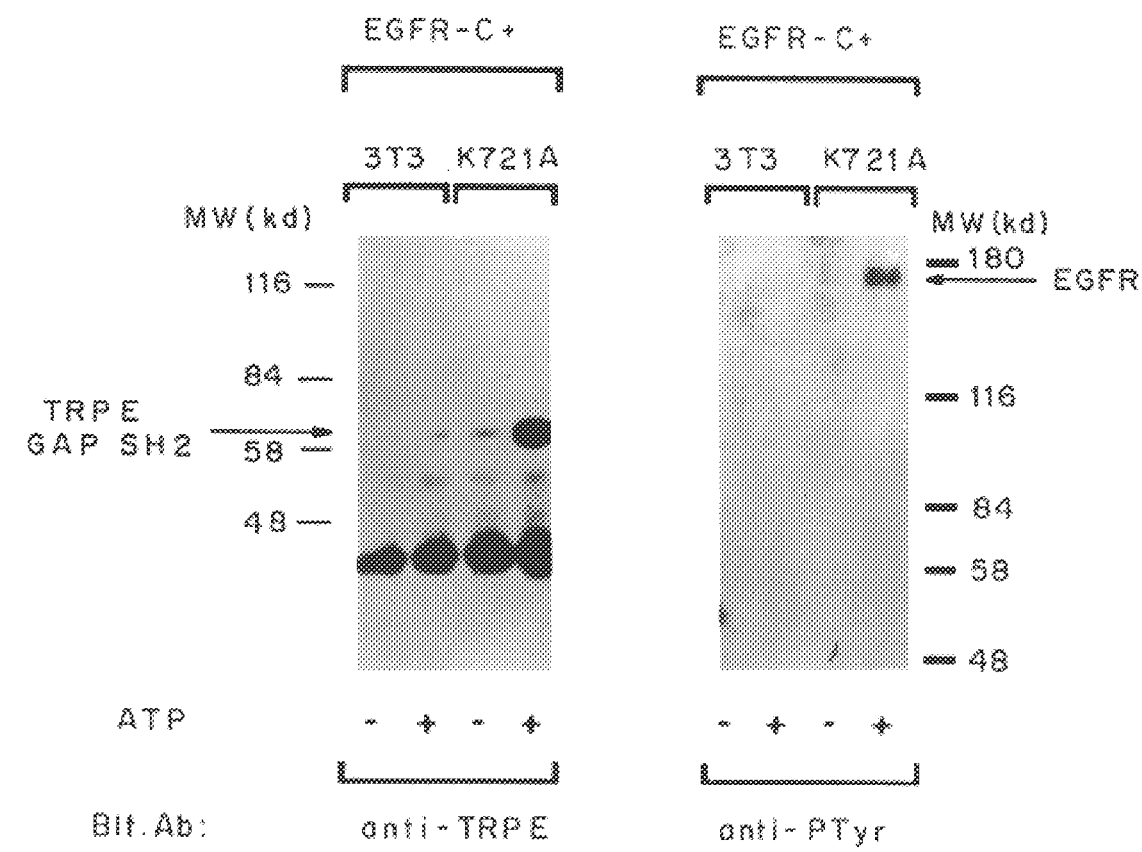

FIGS. 13A and 13B are representations of a gel pattern showing binding of trpE/GAP SH2 to wild-type and mutant EGFR. In FIG. 13A, wild-type receptor (HER14) or the carboxy-terminal deletion CD126 receptor were immunoprecipitated with mAb 108. MnCl$_2$ alone or MnCl$_2$ and ATP were then added to the autophosphorylated half of the receptor-containing samples. One set of CD126 was also cross-phosphorylated with 0.5 μg of EGFR-C. TrpE/GAP SH2 was then added for 90 min at 4° C. and, after three more washes, loaded onto SDS-PAGE. After transfer to nitrocellulose, blots were probed with anti-trpE (left panel), anti-EGFR RK2 (center panel), or anti-PTyr (right panel). RK2 and anti-PTyr are both ⅛ of the total sample and were separated on 7% SDS-PAGE. The remaining sample was loaded on a 10% gel for the anti-trpE blot (exposure time 14 h).

In FIG. 13B, lysates from NIH3T3 2.2 cells containing no EGFR (3T3) or from cells with kinase-negative receptors (K21A) were immunoprecipitated with mAb108. To all immunoprecipitates, 0.5 μg of EGFR-C was added and then MnCl$_2$ alone or MnCl$_2$ and ATP. trpE/GAP SH2 was added and samples prepared and immunoblotted as in (A) (exposure time 19 h).

Figure 14:
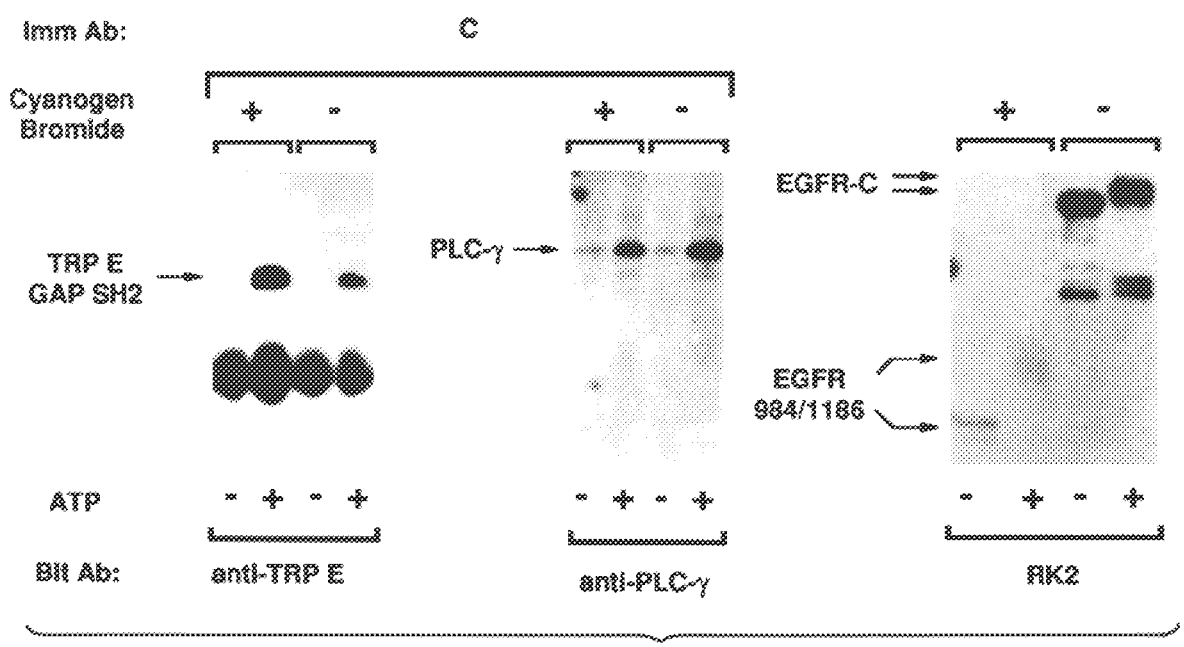

FIG. 14 is a gel pattern showing binding of PLC-γ and trpE/GAP SH2 to the CNBr cleaved C-terminal fragment of EGFR. EGFR-C (10 μg) was incubated in a Centricon 30 in 20 mM HEPES, pH 7.5 with 100 μg BSA as a carrier protein. The phosphorylated and non-phosphorylated EGFR-C were then each divided in two with one half being stored in buffer while the other half was cleaved with CNBr. The four samples either with or without ATP, and with or without CNBr were then each brought up in 500 μl 1% Triton X-100 lysis buffer, split in two, and immunoprecipitated with anti-C antibody. After washing the immunoprecipitates, lysates containing PLC-γ or trpE/GAP SH2 were added. Immunoblotting was then performed on the samples as above with anti-trpE or anti-PLC-γ. For the right panel, a fraction of the cleaved and uncleaved EGFR-C (0.1 μg) was loaded directly on the gel without immunoprecipitation and immunoblotted with RK2 (exposure time 14 h). The dark band seen in all lines of the anti-trpE blot runs at about 40 kDa (also seen in FIG. 13) and represents ($^{125}$I)protein A binding to the heavy chain of the immunoprecipitating antibody.

Figure 15:
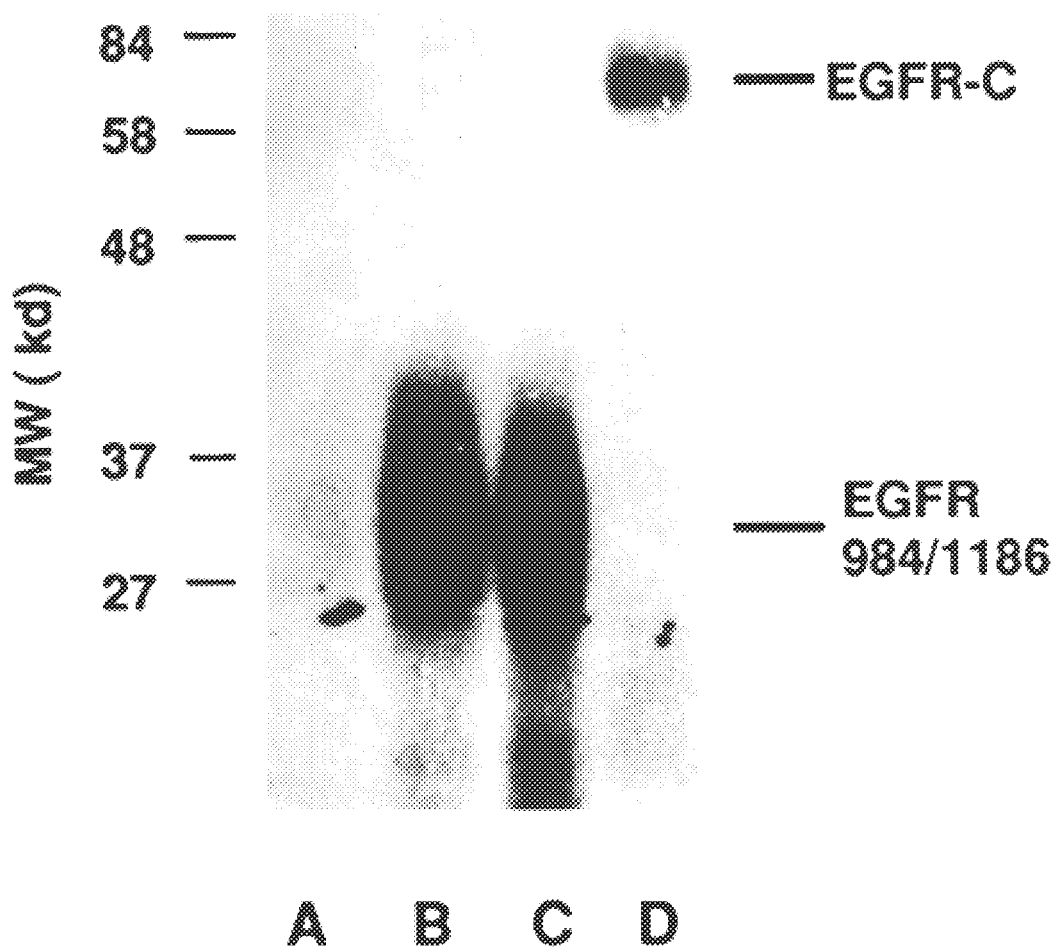

FIG. 15 is a gel pattern showing binding of the tyrosine phosphorylated C-terminal EGFR fragment to trpE/GAP SH2 but not to trpE. EGFR-C (5 μg) was autophosphorylated by the addition of (γ-32P)ATP. The phosphorylated EGFR-C was concentrated in a Centricon 30, and then cleaved with CNBr in 70% formic acid. One half of the sample (350,000 c.p.m.) was allowed to bind to trpE or trpE/GAP SH2 as in FIG. 12B, washed and run on a 10% SDS-gel. (A) Binding of phosphorylated CNBr cleaved EGFR-C to trpE (B) Binding of phosphorylated CNBr cleaved EGFR-C to trpE GAP SH2 (C) 3000 c.p.m. of CNBr-cleaved EGFR-C (D) for comparison 3000 c.p.m. of cleaved EGFR-C (exposure time 20 h). EGFR 984/1186 indicates the sequence of the tyrosine autophosphorylated fragment generated by CNBr.

FIGS. 16A–B shows the partial nucleotide sequence (SEQ ID NO:32; complementary strand is SEQ ID NO:50) and predicted amino acid sequence of GRB-2.

FIG. 17 is a comparison of sequence homology of avian crk (SEQ ID NO:39) to GRB-3 (SEQ ID NO:4) with dots indicating homologous amino acids.

FIG. 18 is a protein sequence of nck (SEQ ID NO:40) compared to that of GRB-4 (SEQ ID NO:8) for amino acid sequence homology.

FIG. 19 is a GRB-7 (SEQ ID NO:10) protein sequence.

Figure 20:
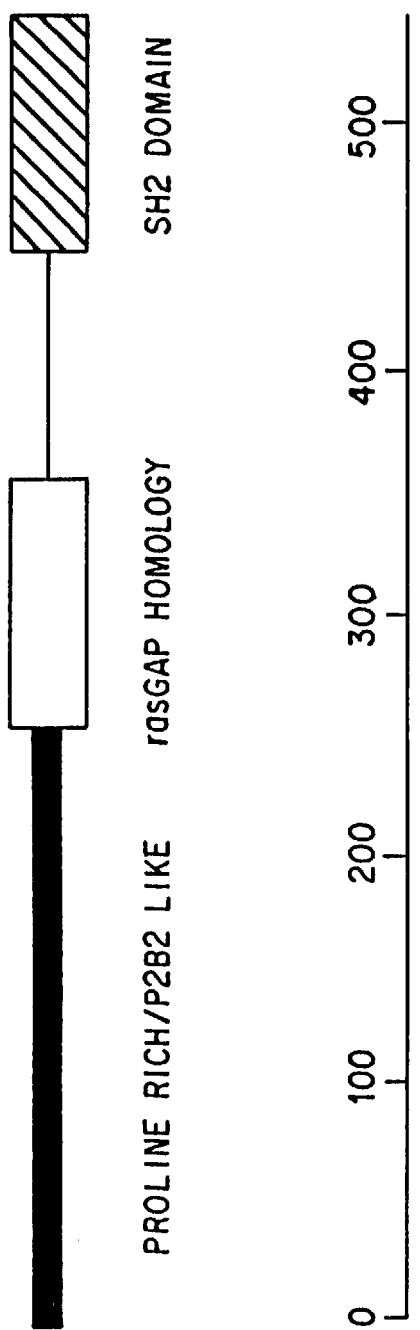

FIG. 20 is a schematic representation of GRB-7 to include the proline rich, P2B2, rasGAP and SH2 domain homology.

FIG. 21 is a comparison of a GRB-7 amino acid sequences (SEQ ID NO:10) with SH2 domains from avian c-src (SEQ ID NO:19), human PLC-γ1(SEQ ID NO:22), GRB-1/p85 (SEQ ID NO:17), mouse fyn (SEQ ID NO:41), GRB-3 (SEQ ID NO:3) and GRB-4(SEQ ID NO:8).

FIG. 22 is a comparison of a GRB-7 amino acid sequence (SEQ ID NO:10) with rasGAP (SEQ ID NO:42).

FIG. 23 is a comparison of a GRB-7 amino acid sequence (SEQ ID NO:10) with P2B2 (SEQ ID NO:43).

Figure 24:
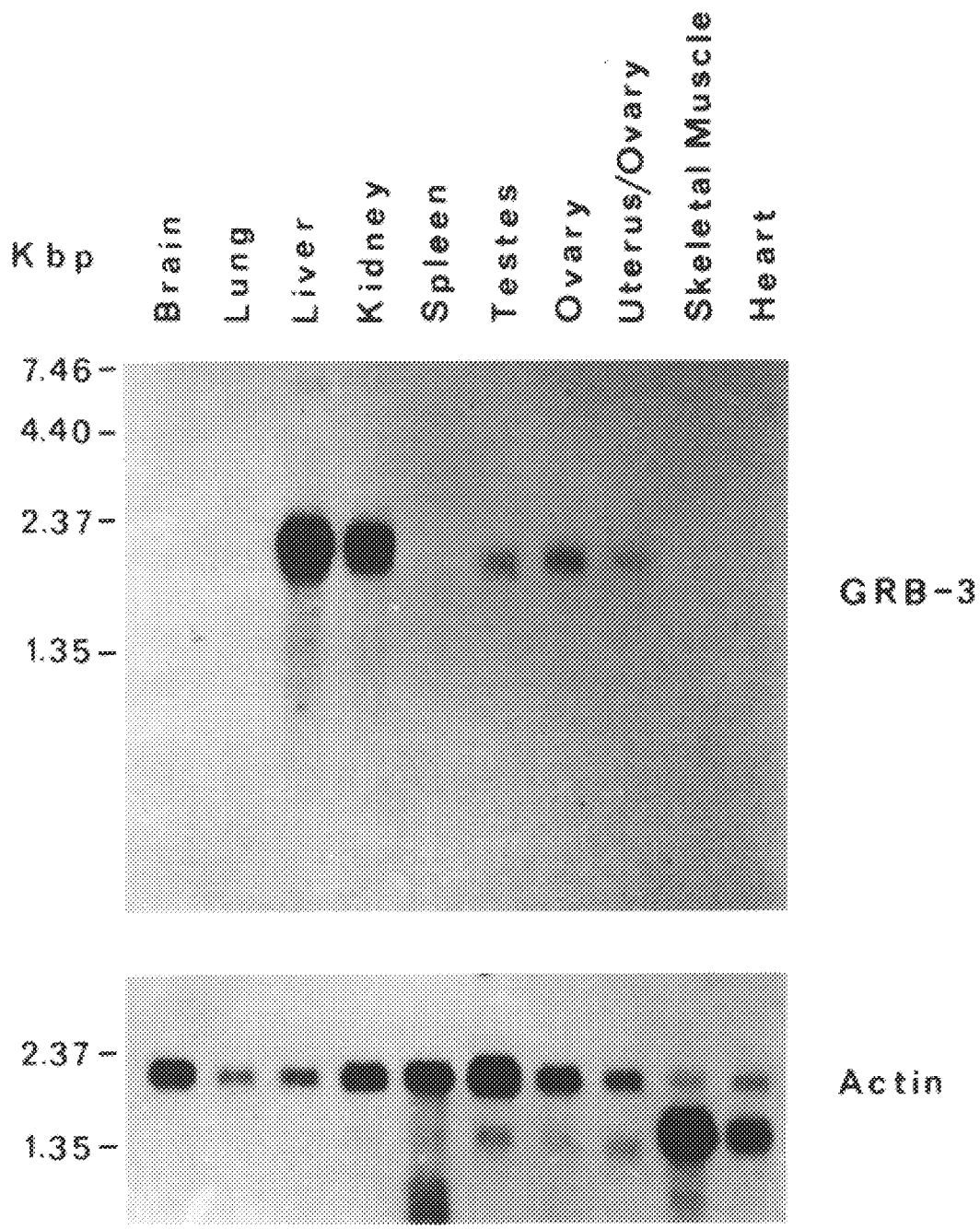

FIG. 24 is a representation of a Northern blot analysis of GRB-7 mRNA.

FIG. 25 is a comparison of binding of the phosphorylated EGFR carboxy-terminus to PLC-g fragments expressed in a λgt11 or T7 polymerase based library.

Figure 1:
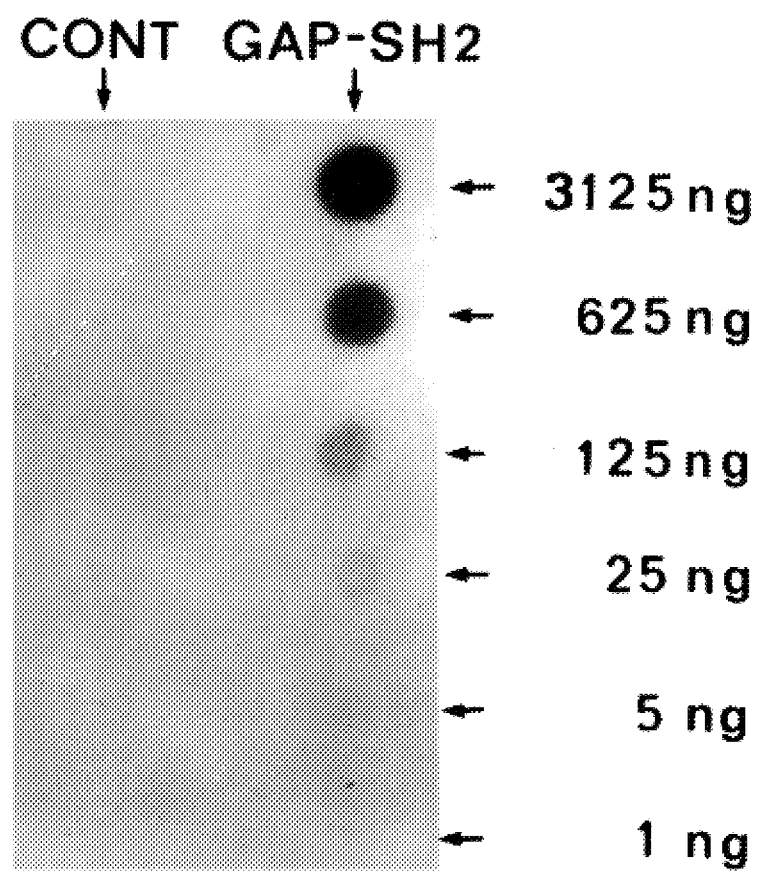
FIG. 1 is a filter blot pattern showing that the carboxy-terminus of the EGFR interacts with GAP-SH2 immobilized on nitrocellulose filters. Bacterially-expressed trpE/GAP-SH2 fusion protein or trpE as a control was spotted at various concentrations onto nitrocellulose filters. The filters were hybridized overnight with ($^{32}$P) -labelled C-terminal domain of the EGFR. Autoradiography was for 2 hours.
Figure 2:
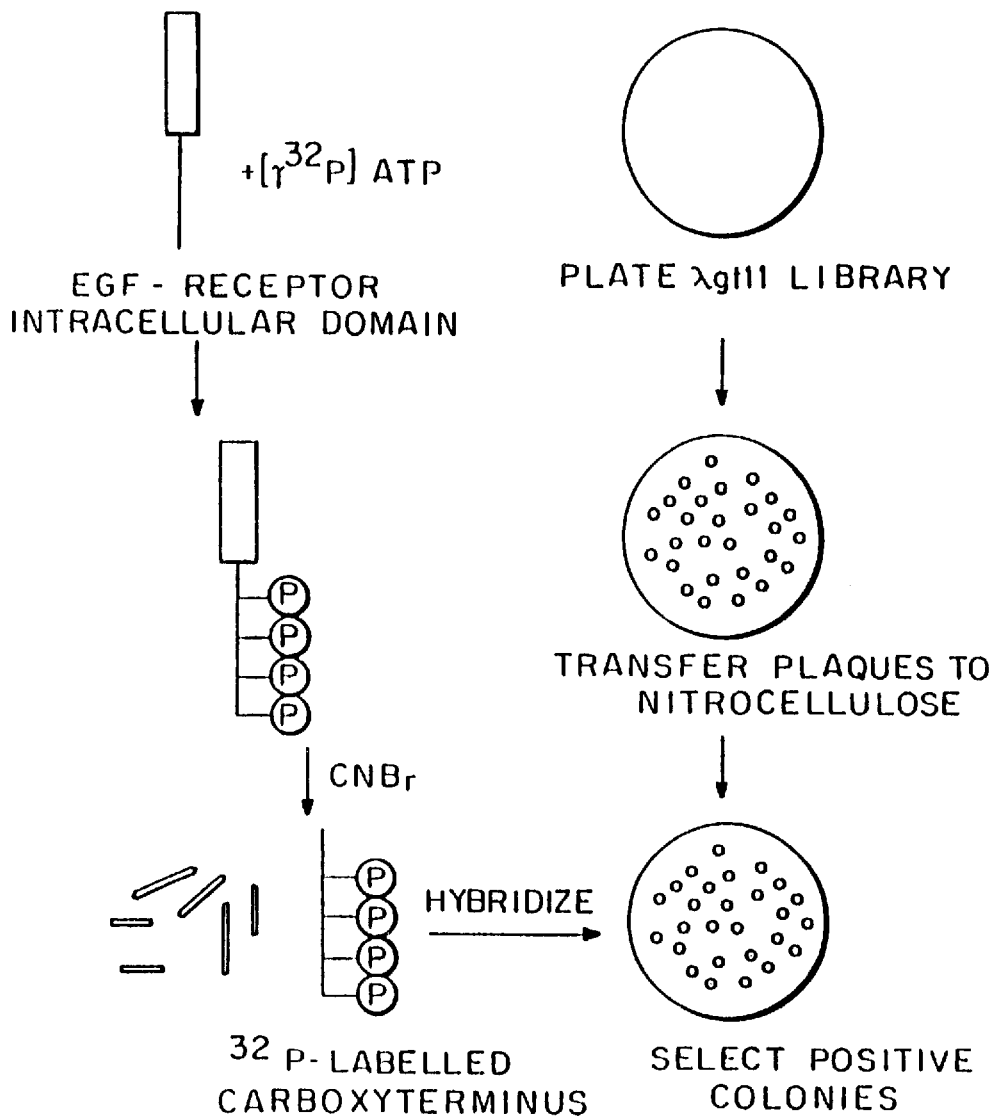
FIG. 2 is a schematic diagram depicting the method of cloning of receptor or cytoplasmic tyrosine kinase targets (CORT). C-terminal domain of the EGFR is phosphorylated with radiolabelled phosphorous. Lambda gt11 library was plated at a density of 4×10$^4$ plaques per 150 ml plate. The plaques were overlaid with IPTG-impregnated nitrocellulose filters for 12 hours, after which the plaques were transferred to nitrocellulose and incubated with the labelled probe. Positive colonies are then selected for further analysis.

FIGS. 26A1 and 26A2 include a cDNA (SEQ ID NO:5; complementary strand is (SEQ ID NO:49) and protein sequence (SEQ ID NO:6) of GRB2 clone 10–53, with '5 and '3 untranslated flanking sequences; SH2 (thick line) and SH3 (thin lines) domains are indicated.

FIG. 26B is a schematic representation of the overall domain structure of GRB2.

Figure 26D:
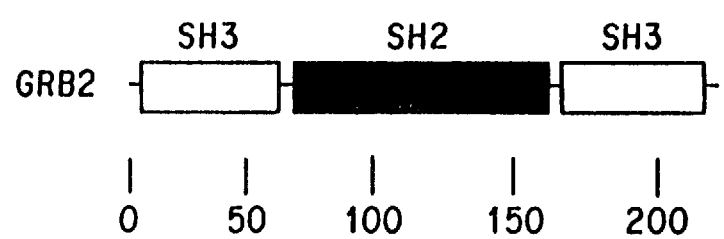

FIGS. 26C and 26D are sequence alignments of GRB2 SH2 (SEQ ID NO:44) and SH3 (N=SEQ ID NO:45; C=SEQ ID NO:46) domains, respectively, with other proteins. N and C refer to N-terminal and C-terminal domains, respectively. The one letter code is used to indicate amino acid residues. Bold letters identify those positions where the same or a conservative amino acid substitution is present at that position. Compared are PLCγ1, GAP, v-src, v-abl, v-crk and p85. The SH2 domain of GRB2 is most similar to the SH2 domain of v-fgr (43% similarity) and the N-terminal SH3 domain is most similar to the SH3 domain of human vav (48% similarity).

Figure 27A:
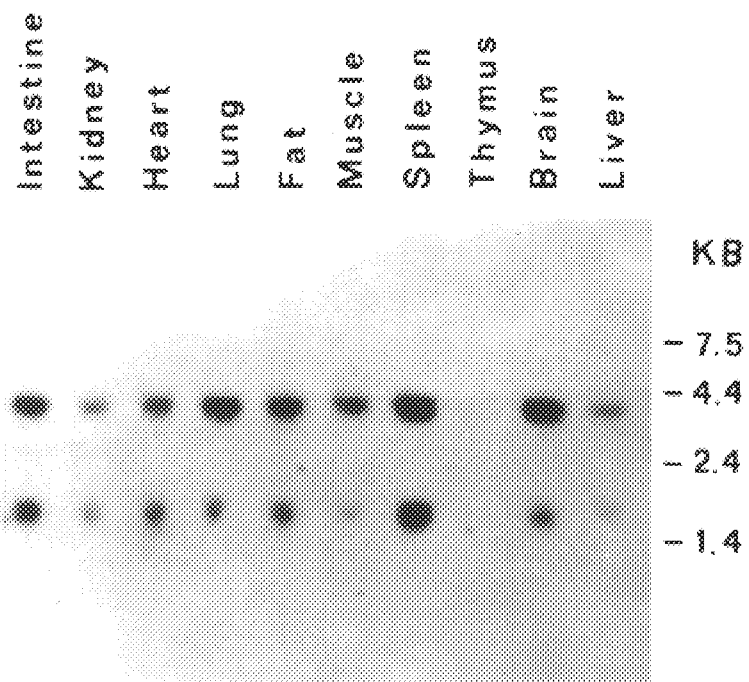
Figure 27B:
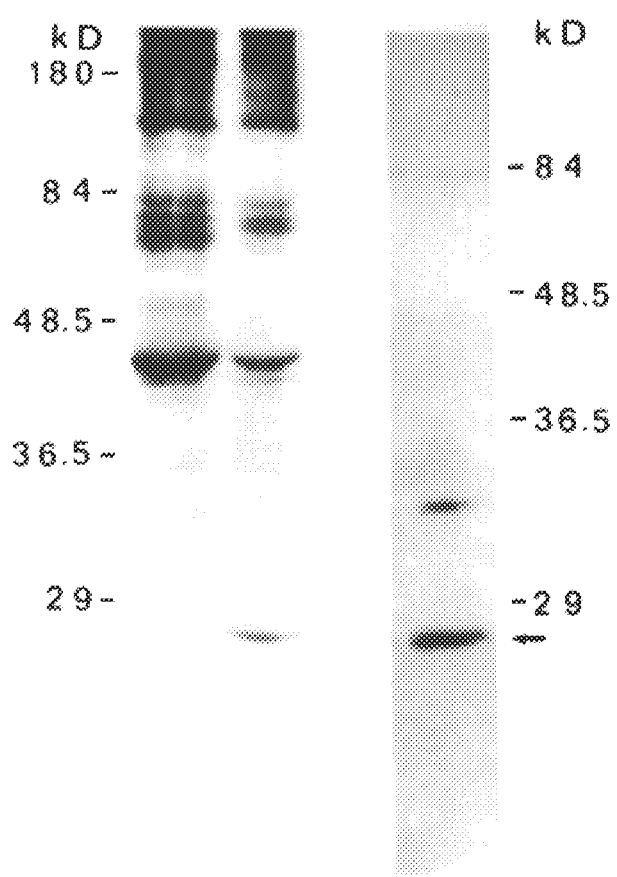

FIGS. 27A–27B show the analysis of expression of GRB2 in various murine tissues and cell lines. 27A shows a Northern analysis in murine tissues, with tissue of origin as indicated, with 20 μg total RNA loaded per lane. The sizes of the GRB2 transcripts (relative to BRL size markers indicated) are 3.8 kb and 1.5 kb.

FIG. 27B shows immunoprecipitation of GRB2 from ($^{35}$S)methionine labeled HER14 lysates with preimmune (lane 1) and immune GRB2 antiserum (Ab50) (lane 2).

Immunoblot analysis of GRB2 from lysates of HER14 cells with Ab86 (lane 3). Molecular weight markers (sized in kDa) are indicated. Arrow indicates band corresponding to GRB2 protein. Exposure times are 24 hours.

Figure 28:
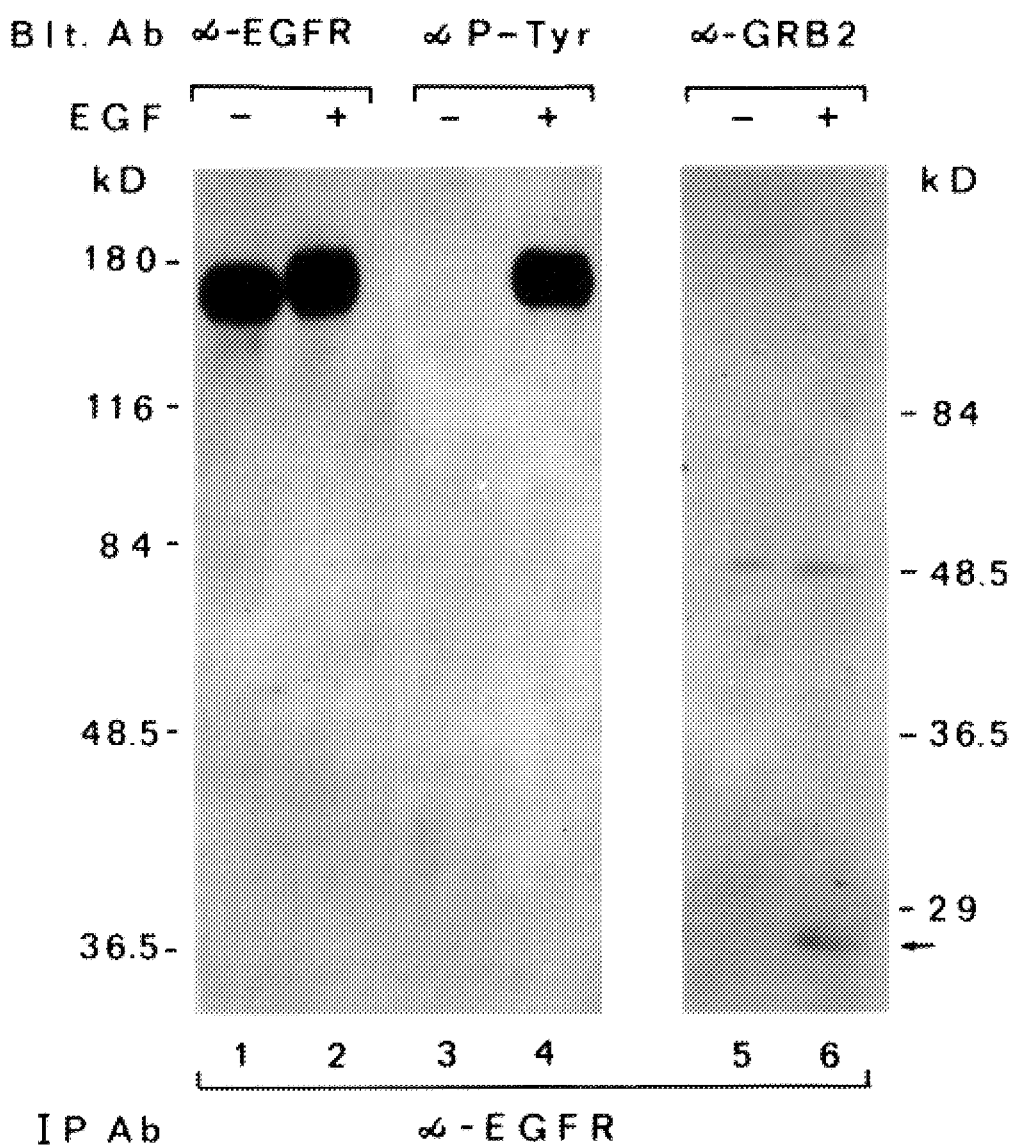

FIG. 28 shows the association of endogenous GRB2 with EGFR in HER14 cells. HER14 cells mock treated lanes 1, 3, 5) or EGF treated (lanes 2, 4, 6) were lysed and immunoprecipitated with anti-EGF receptor antibodies (mAb 108), subjected to SDS-PAGE, and after transfer to nitrocellulose, blotted with polyclonal anti-EGFR antibodies (Anti-C) lanes 1 and 2), anti-phosphotyrosine antibodies (lanes 3 and 4), or anti-GRB2 antibodies (Ab86 ) (lanes 5 and 6). The immunoblots were labeled with $^{125}$I-protein A followed by autoradiography at −70° C. Anti-GRB2 blot were exposed for 24 hrs. Anti-EGFR and antiP-tyr blots were exposed for 16 hrs. The positions of molecular weight markers (sized in kDa) are indicated.

FIG. 29 is a schematic representation of GRB2-GST fusion proteins. Gluthatione-S-transferase fusion proteins of full size GRB2 and various regions of GRB2 were generated and purified by affinity chromatography utilizing glutathione agarose beads, as described in methods. Shown are the SH2 domain of GRB2 (SH2), the amino terminal SH3 (N-SH3), carboxy terminal SH3 (C-SH3), the amino terminal SH3 and SH2 domains (N-SH3 SH2), and the SH domain with the carboxy terminal SH3 domain (SH2C-SH3). GST region of fusion proteins is not shown.

Figure 30:
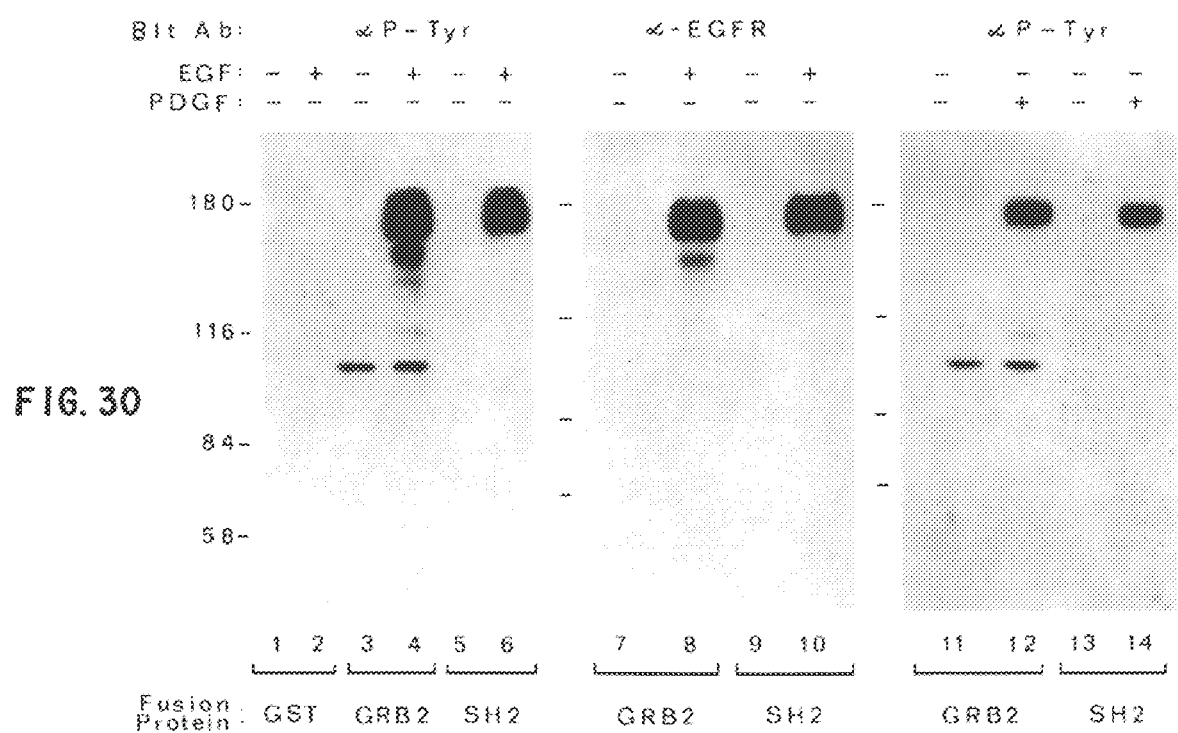

FIG. 30 represents the binding of GST-GRB2 fusion proteins to activated growth factor receptors in vitro. Binding of fusion proteins to the tyrosine phosphorylated proteins (lanes 1 through 6) and EGFR (lanes 7 through 10) in control and EGF stimulated HER14 cell lysates, and tyrosine phosphorylated proteins in control and PDGF stimulated lysates (lanes 11 through 14). Lysates were incubated with equal amounts of fusion proteins immobilized on glutathione-agarose beads. Bound proteins were washed, subjected to SDS-PAGE and immunoblotted with antiphosphotyrosine (lanes 1 through 6, 11 through 14)) or anti EGF-receptor (lanes 7 through 10) antibodies. The immunoblots were labelled with $^{125}$I-proteins a followed by autoradiography at −70° C. exposure time 16 hrs. The positions of the molecular weight markers are indicated (sizes in kDA).

Figure 31:
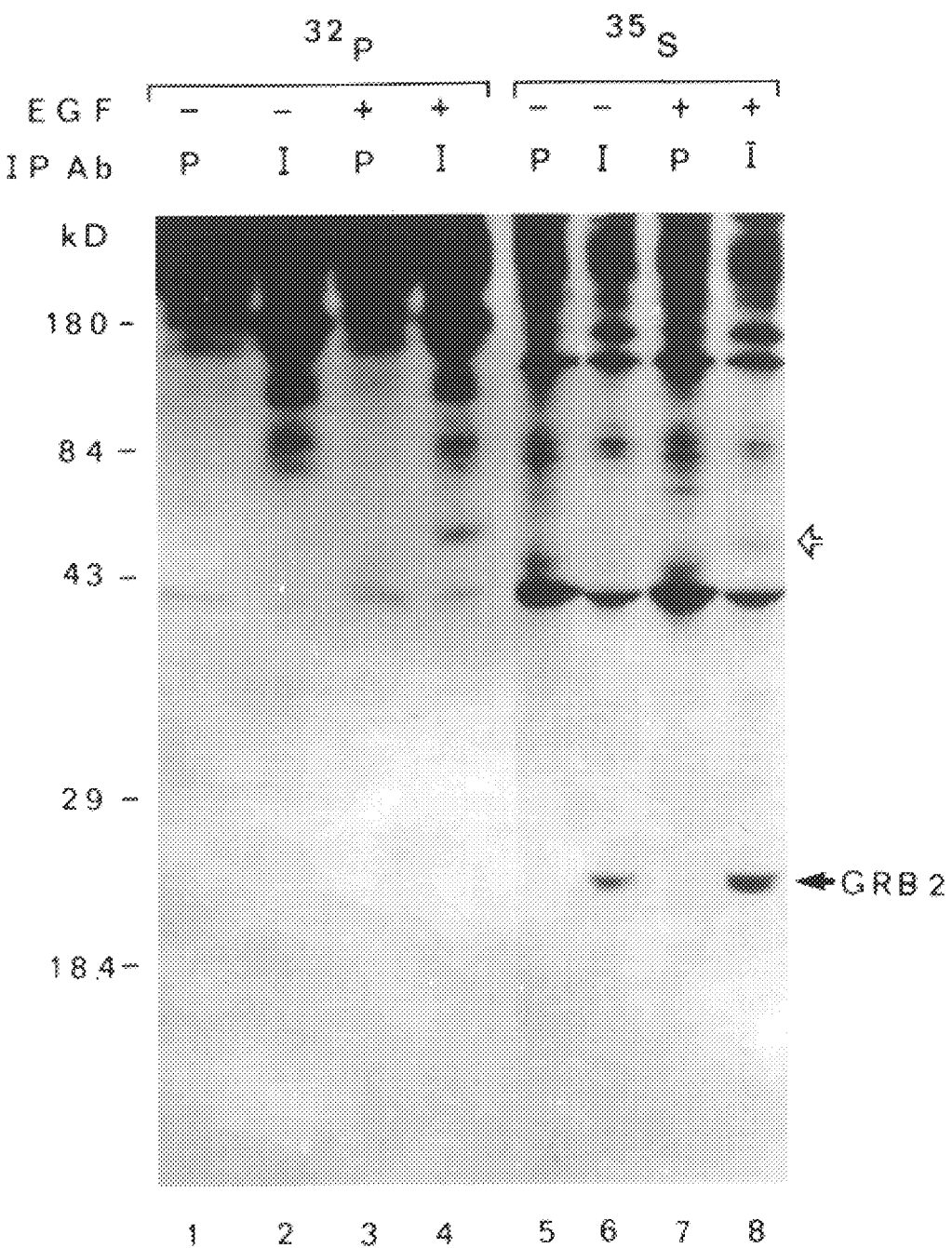

FIG. 31 shows data representing the lack of significant phosphorylation of GRB2 in HER14 cells following stimulation with EGF. ($^{32}$P) orthophosphate (lanes 1 through 4) or ($^{35}$S) methionine (lanes 5 through 8) metabolically labeled HER14 cells were lysed following mocked EGF treatment. The precleared lysates were immunoprecipitated with either preimmune or anti-GRB2 antibodies (Ab50), and subjected to SDS-PAGE and autoradiography. Two hour ($^{32}$P) and two day ($^{35}$S) exposure times are shown. The position of GRB2 and the co-immunoprecipitating 55 kDa phosphoprotein are marked with arrows.

FIG. 32 presents the alignment of amino acid sequences of GRB2 (SEQ ID NO:6)and sem-5 (SEQ ID NO:47) (single letter code). Boxes surround the SH2 and SH3, domains, as indicated. Bold capital letters indicate identical amino acids, capital letter indicate conservative substitutions.

Figure 33:
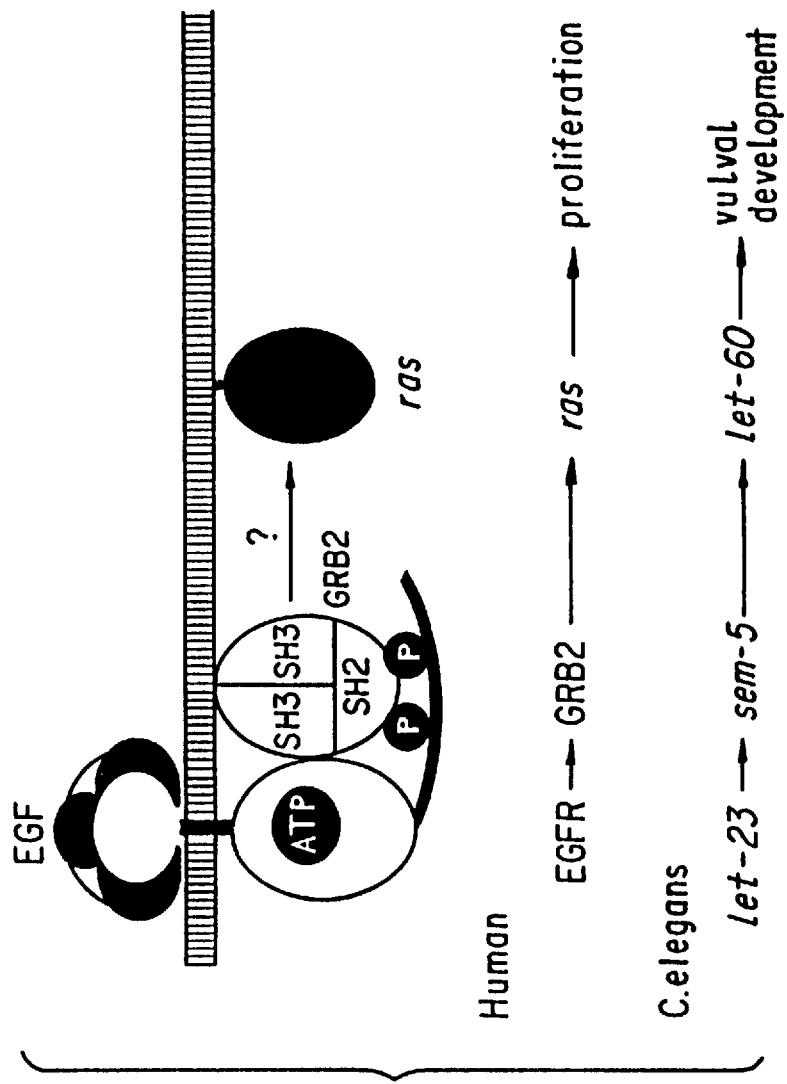

FIG. 33 is a representation showing a model for the interaction between EGF receptor and GRB2 and their *C. elegans* counterparts. Tyrosine autophosphorylated EGFR (or let-23) binds to the SH domain of GRB2 (or sem-5). Ras (or let-60) acts downstream leading to either cell proliferation or vulval development.

FIG. 34 is a cDNA (SEQ ID NO:3) and protein sequence (SEQ ID NO:4) of GRB-3.

FIG. 35 is a cDNA (SEQ ID NO:4) and protein (SEQ ID NO:8) sequence of GRB-4.

FIGS. 36A–C is a cDNA (SEQ ID NO:9) and protein (SEQ ID NO:10) sequence of GRB-7.

DETAILED DESCRIPTION OF THE PREFERRED EMBODIMENTS

Methods, compounds and compositions have now been discovered to provide a means to understand and gain control over the regulation of cell growth and oncogenesis by providing the ability to identify target proteins for tyrosine kinases, including both receptor and cytoplasmic tyrosine kinases in eukaryotic organisms.

One embodiment of the present invention is to provide a novel expression/cloning system for the rapid cloning of target proteins which bind tyrosine kinase proteins which are present intracellularly and in cell receptors of eukaryotes. The cloning method is based on the discovery that certain class of substrates can bind specifically to the phosphorylated domain of proteins having tyrosine kinase activity.

According to another embodiment of the present invention, novel probes and methods using such probes for rapid expression cloning of DNA encoding proteins which have the characteristic of binding to the tyrosine-phosphorylated portion, such as the C-terminus, of a receptor tyrosine kinase molecule, which molecule is present in the cytoplasm or in cell receptors of eukaryotic receptors.

By the term "eukaryote" or "eurkaryotic" is intended any organism considered to have the attributes of a eukaryote, including a cell nucleus, mitochondria, chromosomes, etc., which are attributes which do not occur in bacteria, blue-green algae or viruses. Non-limiting examples of eukaryotes include yeast, fungi, insects, plants, mammals, birds, reptiles, amphibians. Mammals include, but are not limited to, humans, mice, rats, rabbits, cows, pigs, goats, sheep, horses, cats, dogs, etc.

Expression cloning is a method wherein the DNA being cloned encodes a protein which is expressed from a cloned library from a cell known or expected to have the desired protein. The desired DNA, typically in the form of a cDNA library, is detected by means of its expression and/or direct detection of the protein which it encodes. Expression cloning systems and library cloning are well-known in the art (see: Sambrook, J. et al. (*Molecular Cloning: A Laboratory Manual*, 2nd Edition, Cold Spring Harbor Press, Cold Spring Harbor, N.Y. (1989), and Ausubel et al, eds. (*Current Protocols in Molecular Biology* Wiley Interscience, N.Y. (1987, 1992)), which references are hereby entirely incorporated by reference).

According to the present invention, the protein is expressed according to known method steps from a library and the expressed protein, released from the cell it is expressed in is transferred to a solid carrier or support, such as a nitrocellulose filter as a non-limiting example, and detected using a detectable label for the expressed protein by known method steps.

One of the ways in which the polypeptide probe target protein can be detectably labeled is by providing peptide probes or anti-target protein antibodies and linking the peptide probes or antibodies to an enzyme for use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may additionally be accomplished using any of a variety of other immunoassays or detectably labeled peptide probes. For example, by radioactively labeling the peptide probes, anti-target protein antibodies or antibody fragments, such that the labeled target protein may also be detected through the use of a radioimmunoassay (RIA). A good description of RIA may be found in *Laboratory Techniques and Biochemistry in Molecular Biology*, by Work, T. S., et al., North Holland Publishing Company, New York (1978) with particular reference to the chapter entitled "An Introduction to Radioimmune Assay and Related Techniques" by T. Chard, incorporated by reference herein. A radioactive isotope, such as $^{32}$P, $^{35}$S, $^{12}$C or $^{3}$H, can be detected by such means as the use of a gamma counter, a liquid scintillation counter or by autoradiography.

It is also possible to label the peptide probe or anti-target protein antibody with a fluorescent compound. When the fluorescently labeled peptide or antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine. Suitable fluorescent probes are well known or commercially available, such as from Molecular Probes, Inc., Eugene, Oreg.

The peptide probe or anti-target protein antibody can also be detectably labeled using fluorescence emitting metals such as $^{132}$Eu, or others of the lanthanide series. These metals can be attached to the peptide probe or anti-target protein antibody using such metal chelating groups as diethylenetriaminepentaacetic acid (DTPA) or ethylenediaminetetraacetic acid (EDTA).

The peptide probe or anti-target protein antibody also can be detectably labeled by coupling it to a chemiluminescent compound. The presence of the chemiluminescent-tagged peptide probe or anti-target protein antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the peptide probe or anti-target protein antibody of the present invention. Bioluminescence is a type of chemiluminescence found in biological systems in which a catalytic peptide probe or anti-target protein antibody increases the efficiency of the chemiluminescent reaction. The presence of a bioluminescent peptide probe or anti-target protein antibody is determined by detecting the presence of luminescence. Important bioluminescent compounds for purposes of labeling are luciferin, luciferase and aequorin.

The expression cloning method of the present invention for detecting and cloning a target protein for tyrosine kinase cytoplasmic or receptor protein may be used for detecting such target proteins from any eukaryotic cell source. For example, certain target molecules bind to the tyrosine phosphorylated portion of PDGFR and the colony stimulating factor-1 (CSF-1) (Coughlin, S. R. et al., *Science* 243:1191–1194 (1989); Kazlauskas, A. et al., *Cell* 58:1121–1133 (1989); Shurtleff, S. A. et al., *EMBO J.* 9:2415–2421 (1990); and Reedjik, M. et al., *Mol. Cell. Biol.* 10:5601–5608 (1990)). In these receptors, the tyrosine phosphorylation occurs in a kinase insert domain, rather than in the C-terminal domain as is the case with the EGFR. Therefore, specific polypeptide probes in the range of 10–250, such as 10–20, 20–30, 40–50, 70–100, or 100–200, amino acids utilizing the kinase insert domain, or a portion thereof as defined herein, and cytoplasmic or receptor or PDGFR or CSF-1 receptor can be similarly used for expression cloning. Similar probes can also be constructed for the fibroblast growth factor (FGF) receptor (which is tyrosine phosphorylated in the C-terminal domain) or the HER 2/neu receptor, both of the which are also able to interact with SH2 containing proteins such as PLC-γ. In other receptors, such as the insulin receptor, tyrosine phosphorylation occurs in the kinase domain itself.

Accordingly, any tyrosine kinase protein or fragment thereof of 10–250 amino acids, e.g., as described in Cantley et al. *Cell* 64:281–302 (1991) (the entire contents of which are herein incorporated by reference), can be used to bind a target protein in solution which is contacted to the tyrosine kinase protein bound or associated with a carrier or support. The carrier or support can be any known material that associates with a tyrosine kinase or fragment thereof, such that, once the target protein is bound, the non-bound material can be removed from the carrier without dissociated the tyrosine kinase bound to the target protein.

Thus the tyrosine kinase protein is used as a protein probe to bind target proteins. Alternatively, a polypeptide of 10–250 amino acids, corresponding to at least a phosphorylation domain of the tyrosine kinase; or corresponding to a consensus sequence of a class or group of tyrosine kinases, can be used as the protein or polypeptide probe and may be detectably labeled.

Thus, while it will be appreciated that different sites are tyrosine-phosphorylated in different proteins, e.g., the C-terminal domain in the EGFR, the kinase domain in insulin receptor, and a kinase domain insert in PDGFR, the present invention recognizes the common features of all these structures, the presence of one or more phosphotyrosine residues, and the ability of certain cellular proteins to bind on the basis of affinity to a polypeptide containing one or more phosphotyrosines. While reference will generally be made below to a probe which is a C-terminal domain, with reference to the EGFR, this language is not intended to be limiting and is intended to include all of the other alternative tyrosine-phosphorylated domains discussed above.

The methods and approach of the present invention can be applied to the cloning and identification of all target molecules which are capable of interacting in a specific manner with tyrosine is phosphorylated polypeptides, such as cytoplasmic tyrosine kinases or the activated phosphorylated receptors described herein. Additional proteins which bind to tyrosine-phosphorylated sequences, such as the tyrosine-specific phosphatases, e.g., R-PTPases (Sap, J. et al., *Proc. Natl. Acad. Sci. USA* 87:6112–6116 (1990); Kaplan, R. et al., *Proc. Natl. Acad. Sci. USA* 87:7000–7004 (1990) may also be use according to a method of the present invention. The methods are also applicable in the cloning and identification of proteins which bind to phosphorylated serine/threonine residues, as with serine/threonine-specific phosphatases as a non-limiting example.

Use of a polypeptide or protein probe of the present invention allows the rapid cloning of DNA and identification of the encoded proteins from eukaryotic DNA or RNA libraries., such as a gene expression library. The method is particularly useful with a bacteriophage lambda gt11 library or a T7 library. As a non-limiting example of a eukaryotic library, screening a human fetal brain lambda gt11 expression library has permitted the present inventors to clone several target protein genes and to characterize the proteins they encode. One, termed GRB-1, was fully DNA sequenced (SEQ ID NO:1) and found to encode novel human protein with an amino acid sequence as shown in FIG. 4 (SEQ ID NO:2) and a molecular weight of about 85 kDa which contained two SH2 domains and one SH3 domain (FIG. 4 and FIG. 5). GRB-2 DNA (FIG. 26) (SEQ ID NO:5) also contains unique SH2 and SH3 domains in the amino acid sequence, (FIG. 26) (SEQ ID NO:6). GRB-3 DNA (SEQ ID NO:3) was also sequenced (FIG. 34) and the GRB-3 amino acid sequence (SEQ ID NO:4). GRB-4 DNA (SEQ ID NO:7) (FIG. 35) encoded a protein composed of three SH3 domains and one SH2 domain having the GRB-4 amino acid sequence (SEQ ID NO:8).

Several overlapping clones were identified which were used for DNA sequencing of GRB-7 (FIGS. 36A–C) (SEQ ID NO:9) to obtain the full length GRB-7 amino acid sequence shown in FIGS. 36A–C (SEQ ID NO:10). A schematic representation of GRB-7 is displayed in FIG. 20 depicting the regions of similarity to known proteins. The GRB-7 protein is 535 amino acids in length (FIGS. 36A–C) (SEQ ID NO:10) and has one SH2 domain at its extreme carboxy-terminus. In FIG. 21, the SH2 domain of GRB-7 is compared to other SH2 domains including mouse fyn, human PLC-γ 1 and the crk and nck-like proteins of the present invention. Other protein motifs in GRB-7 were determined using Swissprot and GenEmbl databases, using software such as the University of Wisconsin Genetics Computer Group Sequence Analysis Software package (Devereaux et al *Nucl. Acid Res.* 12:387 (1984)). The Swissprot and GenEMBL database can be searched using known software, such as the FASTA and TFASTA respectively. Pearson and Lipman, *Proc. Natl. Acad. Sci. USA* 85, 2444 (1988). Protein alignments can be performed using known software, such as BESTFIT, e.g., with conservative substitutions defined as a score of $\geq 0.8$ using the symbol comparison table for proteins. Gribskov and Burgess, *Nucleic Acid Research* 14, 6745 (1984).

From such analysis, amino acids 242 to 339 of GRB-7 showed similarity to a sequence from the central region of ras GAP (21). Over this region of 91 amino acids from ras GAP, GRB-7 has 26% identity and 42% similarity allowing for conservative substitutions (FIG. 22). This region of ras GAP lies between the SH2/SH3 domains and the GTPase activating carboxy terminal region and has not been assigned a specific function (Martin et al *Science* 255:192 (1992)). The amino-terminal sequence of GRB-7 was found to be proline rich and thus has similarity to many other proline rich proteins. GRB-7 does have an extended region of limited similarity to the catalytic domain of protein phosphatase 2B (Guerini and Klee, *Proc. Natl. Acad. Sci. USA* 87:6112 (1990)) including this proline rich region (FIG. 23) but no significant similarity was found to other serine/threonine phosphatase such as protein phosphatase 1 or 2A.

A northern blot of GRB-7 in mouse tissues is presented in FIG. 25. Oligo dt selected mRNA was probed with GRB-7 cDNA using known methods. See Ausubel et al eds., *Current Protocols in Molecular Biology*, Wiley Interscience, New York (1987, 1992) and Sap et al *Proc. Natl. Acad. Sci. USA* 87:6112 (1990), which are entirely incorporated herein by reference. The highest signal was detected in liver and kidney, but a signal was also detected in ovary and testes. On longer exposure, a weak signal was detectable in lung but not in heart, muscle, spleen or brain. The major transcript was seen at 2.4 kb which closely corresponds to the longest cDNA clone obtained.

GRB-7 represents another novel gene cloned using the CORT technology, according to the present invention. It belongs to a relatively rare group of proteins with SH2 domains but no SH3 domains including the fps tyrosine kinase, (I. Sadowski, J. C. Stone and T. Pawson, *Mol. Cell. Biol.* 6:4396 (1986)), protein tyrosine phosphatase 1C (Shen et al *Nature(Lond.)* 352:736 (1991)) and possibly tensin (Davis et al., *Science* 252:712 (1991)).

CORT methodology of the present invention provides proteins that interact with the EGFR and lie downstream of the EGFR signalling pathway. In general, in vitro associations between SH2 domain and tyrosine phosphorylated proteins correlate with interactions in living cells (McGlade et al., *Mol. Cell. Biol.* 12:991 (1992)). CORT methodology of the present invention is therefore expected to yield commercially important downstream signalling components of cytoplasmic tyrosine kinase target proteins, as well as growth factor receptors, as demonstrated by the finding that the C. elegans gene sem-5 is the homolog of human GRB-2. Sem-5 is crucial for vulval development, a process that requires the activity of let-23, an EGFR like tyrosine kinase. Accordingly, it is expected that sem-5 lies downstream of the activated let-23, and that GRB-2 serves a similar crucial function in EGFR signalling.

CORT methodology of the present invention can also be used to identify new SH2 proteins that interact with the EGFR. Seven different exemplary SH2 domain proteins are expected to have important signalling functions. With the use of the T7 polymerase based library, this methodology may be more easily applied, due to relatively higher levels of expressions which increase detectability, to any eukaryotic cytoplasmic or receptor tyrosine kinase proteins, such as growth factor receptor systems. Hence such a method of the present invention can also be used to clone other novel SH2 domain proteins using other growth factor receptor tyrosine kinases, including the use of T7 polymerase based libraries, by performing expression/cloning techniques involving protein-protein interactions and DNA binding proteins.

SH2 domains, such as in the GAP and PLC-γ proteins, are responsible for the association of these proteins with the phosphorylated C-terminus of the EGFR (see Example VI, below). Thus, one function of SH2 domains is to juxtapose the intracellular portion of receptor tyrosine kinase molecules with their substrates to facilitate efficient tyrosine phosphorylation.

Detailed analysis of one of the cDNA clones of the present invention, GRB-1, identified using methods of the present invention, reveals a novel sequence containing two SH2 domains and one SH3 domain. This protein is expressed in various tissues and cell lines. Its predicted molecular weight, 85 kDa, is consistent with its migration on sodium dodecyl sulfate polyacrylamide gel electrophoresis (SDS-PAGE).

By the term "cytoplasmic tyrosine kinase" is meant a soluble form of protein or polypeptide having tyrosine kinase which can be found in the intracellular portion of a cell. By the term "receptor tyrosine kinase" is intended a transmembrane protein having an extracellular receptor domain, and one or more intracellular domains, including at least one extracellular or intracellular domain having tyrosine kinase enzymatic activity. Additional intracellular domains may have sequence homology to SH2. These molecules are well known in the art (Williams, L. T. et al., *Science* 243:1564–1570 (1989); Ullrich, A. et al., *Cell* 61:203–212 (1990); Carpenter, G. et al. *J. Biol. Chem.* 265:7709–7712 (1990), which are entirely incorporated by reference).

The proteins which interact with, and which may be phosphorylated by, tyrosine kinases are referred to as "target" proteins for these kinases, as distinguished from the "ligands" for these receptors, which bind to the kinase.

According to the present invention, an expression cloning method is performed directly on a gene expression library, such as lambda gt11 or T7 expression library. In a preferred embodiment, the DNA is human cDNA. More preferably, the DNA is human fetal brain DNA. Using such a source as the starting material for the cloning of human genes has a great advantage over the alternative known means, in which a large amount of tissue is taken, and antibodies produced, or the protein purified and partially sequenced, and oligonucleotide probes are then prepared from this sequence and used to screen a genomic DNA or cDNA library. The advantage of bypassing these steps is of most relevance in the case of human genes, since tissue is generally not available in large quantities, with the exception of placenta.

The expression library may be screened in a single step. Preferably, the lambda plaques are blotted onto a solid carrier, preferably nitrocellulose, allowing the transfer of library DNA-encoded proteins which are expressed in the infected bacteria and transferred to the carrier. This carrier is then incubated with the probe of the present invention, as described herein. The probe is allowed to bind to proteins which have the capability of binding to the tyrosine-phosphorylated polypeptide. Based on the label used in the probe, such as an enzymatic, radioisotope or fluorescent label, an appropriate detection system is used to identify the plaques containing the protein of interest. The phage in these plaques are then selected, and the DNA inserts can then be re-cloned, excised and placed into other vectors, used for large scale expression of the protein, and the like, according to known method steps.

One of ordinary skill in the art will appreciate that the concentrations, times, temperatures can be varied depending on the precise nature of the system used, and will know how to vary the appropriate parameters without undue experimentation. Furthermore, general methods in this area are set forth in Sambrook et al. (supra).

Materials of which solid phase carrier can be made include, but are not limited to, nitrocellulose, cellulose, paper, substituted polystyrenes, acrylonitriles, polycarbonate, polypetene, or silicone oxide.

The probe of the present invention is a tyrosine-phosphorylated polypeptide molecule derived from the C-terminal domain of a cytoplasmic or receptor tyrosine kinase. The polypeptide can have between about 10 and about 250 amino acids in length. The probe can be a phosphorylated native sequence or a functional derivative thereof (defined below).

Highly efficient phosphorylation is obtained by using the tyrosine kinase domain present on the tyrosine kinase molecule to autophosphorylate the C-terminal region at between 1 and 5 tyrosine residues. Known methods and conditions (described in detail in Example I) are used to phosphorylate the tyrosine residues. A preferred substrate is detectably labeled substrate such as ($\gamma$-P$^{32}$-adenosine triphosphate).

The source of tyrosine molecule used as the source material to make the probe can include molecules chemically purified from tissues or cells, or molecules produced recombinant DNA methods.

When using recombinant techniques, a native cytoplasmic or receptor tyrosine kinase may be produced, or alternatively, a tyrosine kinase derivative may be produced. A preferred tyrosine kinase derivative includes the tyrosine kinase domain linked to the C-terminal domain. In another embodiment, the two domains may be produced as separate molecules, and mixed together to achieve tyrosine phosphorylation of the C-terminus-derived polypeptide.

The probe comprising a tyrosine-phosphorylated C-terminal portion of the tyrosine kinase, as described herein can be produced by recombinant means in the form of a fusion protein.

As used herein, a "fusion protein" may refer to a fused protein comprising a bacterial protein and a polypeptide of interest such as a protein having an SH2 domain. Alternatively, a fusion protein may also be an artificially constructed tyrosine kinase-like derivative, wherein a DNA sequence encoding the tyrosine kinase domain has been linked to a selective enzymatic cleavage site, which, in turn, is linked to a tyrosine kinase C-terminal domain having one or more tyrosine residues which can be phosphorylated by the kinase. Such a genetic construct encoding this type of "fusion protein" can be inserted into an expression vehicle and expressed in a bacterial or eukaryotic host. Once expressed, such a fusion protein can be allowed-to autophosphorylate, wherein the kinase acts to phosphorylate the tyrosine residues in the C-terminal domain. Following this phosphorylation, use of the appropriate enzyme will cleave at the selective cleavage site, thus separating the N-terminal kinase from the C-terminal phosphorylated polypeptide, which can now serve as a probe.

Expression of fusion proteins and modifications to increase yields ans to provide cleavage sites, etc., are well known. See, e.g., Ausubel, supra; Itakura et al. *Science* 198:1056–1063 (1977)) and Riggs (U.S. Pat. No. 4,366,246 (1982); Marston, *Biochem. J.* 240:1–12 (1986); Nagai et al. (*Nature* 309:810–812 (1984); (Germino et al., *Proc. Natl. Acad. Sci. USA* 81:692–4696 (1984); Scholtissek et al., *Gene* 62:55–64 (1988); Smith et al., *Gene* 67:31–40 (1988); Knott et al., *Eur. J. Biochem.* 174:405–410 (1988); and Dykes et al., *Eur. J. Biochem.* 174:411–416 (1988), which references are all entirely incorporated herein by reference.

The term "selective cleavage site" refers to an amino acid residue or residues which can be selectively cleaved with either chemicals or enzymes and where cleavage can be achieved in a predictable manner. A selective enzymatic cleavage site is an amino acid or a peptide sequence which is recognized and hydrolyzed by a proteolytic enzyme. Examples of such sites include trypsin or chymotrypsin cleavage sites. In a preferred embodiment of this invention, the selective cleavage site is comprised of the sequence Ile-Glu-Gly-Arg (SEQ ID NO:15), which is recognized and cleaved by blood coagulation factor Xa. In another embodiment, the selective cleavage site has the sequence Leu-Val-Pro-Arg (SEQ ID NO:16), which is recognized and cleaved by thrombin.

In constructing the tyrosine kinase-like derivative, an oligonucleotide sequence, 5' to the sequence coding for the enzyme recognition site can be included, and may vary in length. For example, in one embodiment, 13 nucleotides are situated between the codon for Ile (the start of the factor Xa recognition site) and the 3' end of the sequence encoding the tyrosine kinase domain.

Thus, in one embodiment of the present invention, the Ile-Glu-Gly-Arg (SEQ ID NO:15) sequence is introduced between the tyrosine kinase domain and the C-terminal domain. In another embodiment, the Leu-Val-Pro-Arg (SEQ ID NO:16) sequence is introduced. The proteins having this cleavage site are expressed in bacteria using standard methods. Thereafter, autophosphorylation of the C-terminal domain, preferably with (γ32P) adenosine triphosphate, is allowed to occur, followed by selective cleavage of the tyrosine-phosphorylated C-terminal domain with the appropriate cleaving agent, e.g., factor Xa.

The present invention also provides a method for mapping a gene, preferably a human gene, which encodes a target protein for a tyrosine kinase (such as a GRB protein as defined herein), to a particular human chromosome. This method combines the new expression cloning method described herein with one of several known techniques for mapping a gene to a particular chromosome. Thus, according to the present invention, a clone, such as a lambda gt11 clone, containing a DNA insert encoding a GRB protein, is identified using the expression cloning methods disclosed herein. The insert may be further subcloned, if desired, using methods well-known in the art, and a probe constructed, either by direct labeling of the nucleic acid of the clone or by producing an oligonucleotide probe corresponding to a unique portion of the clone's sequence (see: Sambrook, J. et al. (*Molecular Cloning: A Laboratory Manual,* 2nd Edition, Cold Spring Harbor Press, Cold Spring Harbor, N.Y. (1989); and Ausubel, supra). This labeled probe can is then used in a hybridization assay with commercially available blots, such Chromosome Blots from Bios Corporation (New Haven, Conn.) which contain DNA from a panel of human-hamster somatic cell hybrids (Kouri, R. E. et al., *Cytogenet. Cell Genet.* 51:1025 (1989)). By comparison of which human chromosomes remain in the human-hamster hybrid cell and the hybridization of the probe specific for the GRB gene of interest, the gene is mapped to a particular human chromosome. In this way, linkage is established to known human genes (or diseases caused by mutations therein) present on this chromosome. Using methods well-known in the art for finer mapping, e.g., using known human deletion mutations, the GRB gene can be mapped more precisely to other human genes.

The tyrosine-phosphorylated tyrosine kinase C-terminal probe polypeptide of the present invention, as well as the GRB proteins of the present invention, and additional yet unknown GRB proteins which are discovered using the methods of this invention, are useful in methods for screening drugs and other agents which are capable of modulating cell growth control that occurs via signal transduction through tyrosine kinases. By attaching a tyrosine-phosphorylated probe polypeptide or a GRB protein, or fragments thereof, to a solid phase carrier matrix, an affinity probe is created which can be used to isolate and purify molecules from complex mixtures which are capable of binding to the affinity probe. Furthermore, such an affinity probe is useful for detecting the presence in a biological fluid of a molecule capable of binding the tyrosine-phosphorylated probe or the GRB protein. Similarly, chemical agents can be tested for their capacity to interact with the probe or GRB.

Methods for coupling proteins and peptides to the solid phase, the solid phase substances useful in these methods, and means for elution, are well known to those of skill in the art.

In the case of growth factor receptors which are receptor tyrosine kinases (including as non-limiting examples EDGFR, PDGFR and FGFR), tyrosine phosphorylation is linked to cell growth and to oncogenic transformation. Disruption of the action of a GRB in the cell may prevent or inhibit growth, and might serve as means to counteract development of a tumor. Furthermore, a mutation in the C-terminal portion of the tyrosine kinase or the GRB, or a disregulation in their mutual interactions, may promote susceptibility to cancer.

The insulin receptor (InsR) is also a receptor tyrosine kinase, and tyrosine phosphorylation in cells bearing InsR is associated with normal physiological function. In contrast to the case of cell growth and cancer, disruption of normal interactions between of the tyrosine-phosphorylated portion of the receptor and the GRB would counteract insulin effects. Subnormal levels or activity of a GRB protein may act to remove a normal counterregulatory mechanisms. It is expected that overexpression or overactivity of a GRB protein could inhibit or totally prevent the action of insulin on cells, leading to diabetes (of an insulin-resistant variety). Thus susceptibility to diabetes may be associated with GRB protein dysregulation.

Therefore methods of the present invention for identifying normal or mutant GRB protein genes, or for detecting the presence or the amount of GRB protein in a cell, can serve as methods for identifying susceptibility to cancer, diabetes, or other diseases associated with alterations in cellular metabolism mediated by tyrosine kinase pathways.

The present invention provides methods for evaluating the presence, and the level of normal or mutant GRB protein in a subject. Altered expression of these proteins, or presence of a mutant GRB protein, in an individual may serve as an important predictor of susceptibility to oncogenic transformation and the development of cancer. Alternatively, altered expression of GRB protein may serve as an important predictor of susceptibility to diabetes.

Oligonucleotide probes encoding various portions of the GRB protein are used to test cells from a subject for the presence DNA or RNA sequences encoding the GRB protein. A preferred probe would be one directed to the nucleic acid sequence encoding at least 4 amino acid residues, and preferably at least 5 amino acid residues of the GRB-1, GRB-2, GRB-3, GRB-4 or GRB-7, protein of the present invention, such as 6, 7, 8, 9, 10, 11, 12, 13, 14, 15, 16, 17, 18, 19, 20, 25, 30, 35, 40, 45, or 50 amino acids. Qualitative or quantitative assays can be performed using such probes. For example, Northern analysis (see Example III, below) is used to measure expression of an GRB protein mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. (supra), Ausubel et al, supra, etc.

Recently, an in vitro, enzymatic method has been described which is capable of increasing the concentration of such desired nucleic acid molecules. This method has been referred to as the "polymerase chain reaction or "PCR" (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194; Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Meth. Enzymol.* 155:335–350 (1987), which references are entirely incorporated herein by reference).

In one embodiment, the invention is directed to target proteins of eukaryotic tyrosine kinases, which include, as non-limiting examples, GRB proteins such as GRB-1, GRB-2, GRB-3, GRB-4 or GRB-7 proteins are included. In another embodiment, the invention is directed to recombinant eukaryotic GRB proteins. The invention provides the naturally occurring protein molecule substantially free of other proteins with which it is natively associated. "Substantially free of other proteins or glycoproteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluids containing the GRB-1, GRB-2, GRB-3, GRB-4 or GRB-7 protein to standard protein purification techniques such as immunoadsorbent columns bearing monoclonal antibodies reactive against the protein.

The nucleotide sequence of the GRB-1 gene (SEQ ID NO:1), and the amino acid sequence of the GRB-1 protein (SEQ ID NO:2), are shown in FIG. 4 (SEQ ID NO:5). The partial nucleotide sequence of GRB-2 (1–949 of SEQ ID NO:32) and the partial amino acid sequence, are shown in FIG. 16, and the complete amino acid sequence is shown in FIG. 26 (SEQ ID NO:6), as well as the complete nucleotide sequence.

In a preferred embodiment, GRB-1, GRB-2, GRB-3, GRB-4 or GRB-7, or other eukaryotic GRB protein, can be isolated and purified using as an affinity probe, the probe of the present invention which is a tyrosine-phosphorylated C-terminal domain of a tyrosine kinase, or a functional derivative thereof.

Alternatively, the purification can be achieved by a combination of standard methods, such as ammonium sulfate precipitation, molecular sieve chromatography, and ion exchange chromatography.

It will be understood that the GRB-1 proteins of the present invention can be biochemically purified from a variety of cell or tissue sources. For preparation of naturally occurring GRB protein, tissues such as mammalian placenta or brain are preferred.

Alternatively, because the gene for GRB1, GRB-2, GRB-3, GRB-4 or GRB-7 can be isolated or synthesized, the polypeptide can be synthesized substantially free of other proteins or glycoproteins of mammalian origin in a prokaryotic organism or in a non-mammalian eukaryotic organism, if desired. As intended by the present invention, a recombinant GRB-1, GRB-2, GRB-3, GRB-4 or GRB-7 molecule produced in mammalian cells, such as transfected COS, NIH-3T3, or CHO cells, for example, is either a naturally occurring protein sequence or a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support or carrier. In particular, the tyrosine-phosphorylated C-terminal domain probe of the present invention, or a functional derivative thereof, can be synthesized using a peptide synthesis method wherein phosphotyrosine is provided in place of tyrosine, resulting in direct synthesis of the phosphorylated form of the polypeptide. See, e.g., Staerkaer et al, *Tetrahedron Letters* 32:5289–5392 (1991); Shoelson et al *Tetrahedron Letters* 32:6061 (1991), which references are entirely incorporated herein by reference).

The present invention also provides "functional derivatives" of the tyrosine-phosphorylated C-terminal domain polypeptide and or the GRB-1, GRB-2, GRB-3, GRB-4 or GRB-7 proteins.

By "functional derivative" is meant a "fragment," "variant," "analog," or "chemical derivative" of the GRB protein, which terms are defined below. A functional derivative retains at least a portion of the function of the native protein which permits its utility in accordance with the present invention.

A "fragment" of any of the proteins or polypeptides of the present invention refers to any subset of the molecule, that is, a shorter peptide.

A "variant" of the protein refers to a molecule substantially similar to either the entire peptide or a fragment thereof. Variant peptides may be conveniently prepared by direct chemical synthesis of the variant peptide, using methods well-known in the art.

The term "substantially corresponding to the amino acid sequence of" in the context of the present refers to a protein containing conservative amino acid substitutions, known in the art and as described herein, that would be expected to maintain the functional biological activity of the referenced sequence, and/or target protein binding characteristics.

Such substitutions can be readily determined without undue experimentation by using known conservative substitutions, as known in the art. Alternatively, known software can be used to provide such conservative substitutions according to the present invention. As a non-limiting example the program "BESTFIT" can be used to provide conservative amino acid substitutions of a define sequence, e.g., defined as having a score of $\geq 0.4$, 0.6, 0.8 or 1.0 depending on the type of protein used. See e.g., Gribskov and Burgess, *Nucl. Acid. Res.* 14:6745 (1984), which is entirely incorporated by reference. Variant peptides may be conveniently prepared by direct chemical synthesis of the variant peptide using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

Amino acid substitutions in the context of the present invention include substitutions wherein at least one amino acid residue in the peptide molecule, and preferably, only one, has been removed and a different residue inserted in its place. For a detailed description of protein chemistry and structure, see Schulz, G. E. et al., *Principles of Protein Structure*, Springer-Verlag, N.Y. 1978, and Creighton, T. E., *Proteins: Structure and Molecule Properties*, W. H. Freeman & Co., San Francisco, 1983, which are hereby incorporated by reference. The types of substitutions which may by made in the protein or peptide molecule of the present invention may be based on analysis of the frequencies of amino acid changes between a homologous protein of different species, such as those presented in Table 1–2 of Schultz et al. (supra) and FIGS. 3–9 of Creighton (supra). Base on such an analysis, conservative substitutions are defined herein as exchanges within one of the following five groups:

1. Small aliphatic, nonpolar or slightly polar residues: ala, ser, thr (pro, gly);
2. Polar, negatively charged residues and their amides: asp, asn, glu, gly;
3. Polar, positively charged residues: his, arg, lys;
4. Large aliphatic, nonpolar residues: Met, leu, ile, val (cys); and
5. Large aromatic residues: phe, tyr, trp.

Accordingly, amino acid sequences substantially corresponding to a given sequence can be made without undue experimentation and then routinely screened for tyrosine kinase binding activity using known methods or those disclosed herein, such that one of ordinary skill in the art can determine which substitutions provide tyrosine kinase target proteins according to the present invention. For example, once target protein sequences are determined, such as for GRB-1, GRB-2, GRB-3, GRB-4 or GRB-7, conservative amino acid substitutions can be made to provide target proteins having amino acid sequences which substantially correspond to the determined target protein sequences.

The preferred bacterial host for this invention is *E. coli*. In other embodiments, other bacterial species can be used. In yet other embodiments, eukaryotic cells may be utilized, such as, for example, yeast, filamentous fungi, or the like. Use of these cell types are well known in the art. Any host may be used to express the protein which is compatible with replicon and control sequences in the expression plasmid. In general, vectors containing replicon and control sequences are derived from species compatible with a host cell are used in connection with the host. The vector ordinarily carries a replicon site, as well as specific genes which are capable of providing phenotypic selection in infected or in transformed cells. The expression of the fusion protein can also be placed under control with other regulatory sequences which may be homologous to the organism in its untransformed state. Preferred promoters can include a T7 promoter. Such preferred promoters express the human gene as a fusion protein such as the T7 capsid protein P10 under control of the T7 promoter. Such expression systems are commercially available, e.g, as the λEXlox vector from Novagen, Inc. (Madison, Wis.). In such fusion protein expression systems, the recombinant T7 vector containing a human gene, encoding such proteins obtainable by methods of the present invention, such as GRB-1, GRB-2, GRB-3, GRB-4 and GRB-7, as, e.g., a T10 fusion protein. The recombinant T7 vector can then be used to transform a bacteria, such-as *E. coli*, by infection with a phage containing the recombinant T7 vector under lac control, such lacUV5 control. Induction of the infected, successfully transformed bacteria or other suitable host cell, by IPTG generates the T7 polymerase which then initiates transcription of the fusion protein encoded by the phage library. Because such resulting T7 vector infected bacteria provide human gene library plaques that have stronger signals than obtained by the use of bacterial RNA polymerases, such as E. coli RNA polymerase. According to the present invention, the use of a T7 polymerase expression system is particularly suitable for library screening when there as thousands of small plaques per plate. The major advantage of the use of a T7 expression system is the high level of protein expression due to the greater activity of the T7 polymerase versus E. coli RNA polymerase, and because fusion proteins using the smaller phage fusion protein gene, such as the T10 gene fragment (26 kd versus the 110 kd B-galactosidase of λgt11 expression library) yields more stable expression and that its hydrophobic character promotes binding to nitrocellulose. In addition to directional cloning, the use of T7 phages also allow for automatic conversion to a PET plasmid (see, e.g., Palazzalo et al., *Gene* 88, 25 (1990)) which can be useful for expression of a fusion protein for antibody production.

This invention is also directed to an antibody specific for an epitope of the GRB-1, GRB-2, GRB-3, GRB-4 or GRB-7 protein and the use of such an antibody to detect the presence of, or measure the quantity or concentration of, the GRB protein in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, GILD and any subclass thereof. The hybridoma producing the mabs of this invention may be cultivated in vitro or in vivo. Production of high titers of mabs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane ANTIBODIES: A LABORATORY MANUAL Cold Spring Harbor Laboratory (1988)). These references are hereby entirely incorporated by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the GRB protein of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a GRB protein epitope.

The anti-Id mAbs thus have their own idiotypic epitopes, or "idiotopes" structurally similar to the epitope being evaluated, such as GRB protein-α.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of GRB protein according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which express the GRB protein. This can be accomplished by immunofluorescence techniques employing a fluorescently labeled antibody (see below) coupled with light microscopic, flow cytometric, or fluorometric detection.

The antibodies (of fragments thereof) useful in the present invention may be employed histologically, as in immunofluorescence or immunoelectron microscopy, for in situ detection of GRB proteins. In situ detection may be accomplished by removing a histological specimen form a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the GRB protein but also its distribution on the examined tissue. Using the present invention, those of ordinary skill will readily perceive that any of wide variety of histological methods (such as staining procedures) can be modified in order to achieve such in situ detection.

Such assays for GRB protein typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying GRB protein, and detecting the antibody by any of a number of techniques well-known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with the detectably labeled GRB protein-specific antibody. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of anti-GRB-1, anti-GRB-2, anti-GRB-3, Anti-GRB-4 or anti-GRB-7, antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which a GRB-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in *Laboratory Techniques and Bio chemistry in Molecular Biology*, by Work, T. S. et al., North Holland Publishing Company, N.Y. (1978) with particular reference to the chapter entitled "An Introduction to Radioimmune Assay and Related Techniques" by Chard, T., incorporated by reference herein. The radioactive isotope can be detected by such means as the use of a $\gamma$ counter or a scintillation counter or by autoradiography.

It is also possible to label the antibody with a fluorescent compound. When the fluorescently labeled antibody is exposed to light of the proper wave length, its presence can be then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The following example are presented by way of further explanation of the present invention, and not by way of limitation.

EXAMPLE I

A study was performed to determine the detectability of binding of the C-terminal domain of EGFR to a protein containing the SH2 domain immobilized on nitrocellulose filters. For this purpose, the binding of the C-terminal domain to a bacterially expressed fusion protein was assessed (see FIG. 1).

A. Isolation and Labelling of the Carboxyterminal Domain of the EGFR

The intracellular portion of the EGFR, which includes the tyrosine kinase domain and the carboxy terminal domain, was purified from recombinant baculovirus which expressed cDNA complementary to the intracellular domain of the human EGFR, as described previously (Hsu, C-Y. et al., *Cell Growth and Differentiation* 1:191–200 (1990)). The recombinant protein (2 μg) was then phosphorylated with ($\gamma$-$^{32}$P) ATP (200 μCi, 6000 Ci/Mmol)., at 4° C. in HNTG (20 mM HEPES, pH 7.5, 150 mM NaCl, 0.1% Triton X-100, and 10% glycerol) buffer which contained 5 mM MnCl$_2$. In order to remove unincorporated (y-32P) ATP, the phosphorylated kinase was diluted to 1 ml with 20 mM HEPES, pH 7.5, containing 100 μg BSA and then concentrated in a Centricon-10 to a volume of 50 μl. This procedure was repeated 3 times resulting in the removal of >99% of the unincorporated ATP. To separate the C-terminal domain from the kinase domain, the concentrated protein was then digested with cyanogen bromide (CNBr) in 70% formic acid for 14 hours at room temperature (see also Example VI, below). Samples were then washed three times with water, dried and resuspended in binding buffer to a concentration of 2×10$^6$ cpm/ml.

B. Binding of the C-terminal Domain of the EGFR to Bacterially Expressed TrpE/GAP-SH2 Fusion Protein Immobilized on Nitrocellulose TrpE and TrpE/GAP-SH2 were obtained from the laboratory of Dr. Tony Pawson and/or prepared as previously described (Moran, M. F. et al., *Proc. Natl. Acad. Sci. USA* 87:8622–8626 (1990)). Filter binding studies were performed according to published methods (Schneider, W. J. et al., *Proc. Natl. Acad. Sci.* 76:5577–5581 (1979); Daniel, T. O. et al., *J. Biol. Chem.* 258:4606–4611 (1983)) with minor modifications. Various concentrations of either bacterially expressed TrpE fusion protein or bacterial protein alone were spotted onto nitrocellulose filters. After blocking the filters for 1 hour at 4° C. in PBS containing 5% Carnation dry milk, $_{32}$P-labelled C-terminal domain of the EGFR was added and incubation was continued overnight at 4° C. After 24 hours, the nitrocellulose filters were washed 3 times at room temperature with PBS containing 0.2% Triton X-100. The filters were dried and exposed to Kodak XAR-5 film at −80° C.

C. Results

The above method permitted detection of specific binding of the EGFR C-terminal domain to less than 5 ng of a bacterially expressed GAP-SH2 fusion protein. The binding was specific, since it required tyrosine phosphorylation of the probe and did not occur when irrelevant proteins were applied to nitrocellulose filters.

The demonstration that the EGFR C-terminal domain could bind specifically to an SH2-containing protein immobilized on nitrocellulose filters encouraged the present inventors to apply this approach to the screening of lambda gt11 expression libraries with the goal of identifying novel EGFR binding proteins.

EXAMPLE II

Screening of Expression Libraries and Isolation of a cDNA Clone Encoding a Novel SH2-Containing Protein The tyrosine phosphorylated C-terminal tail of the EGFR was used as a probe to screen expression libraries from several different human tissues as described above. The approach to screening is outlined in FIG. 2. Numerous positive clones have been identified so far using this approach, of which two have been analyzed in detail.

A. Screening of cDNA Library

A lambda gt11, library, constructed from mRNA isolated from human brain stem, was obtained from M. Jaye. To screen the library, lambda gt11 phage were plated at a density sufficient to produce 4×10$^4$ plaques per 150 mm agar plate. A total of six plates were initially screened. After incubation of the plates for 4 hours at 42° C., the plates were overlaid with nitrocellulose filters which had been impregnated with isopropyl-B-D-thiogalactopyranoside (IPTG), as previously described (MacGregor, P. F. et al., *Oncogene*

5:451–458 (1990)). Incubation was continued overnight at 37° C., The filters were then removed, washed with tBST (10 mM Tris-HCl, pH8, 150 mM NaCl, and 0.05% triton X-100) at room temperature, and then blocked in HBB (20 mM HEPES, pH 7.5, 5 mM Mg/Cl, 1 mM KCl) buffer containing 5% carnation dry milk for 1 hour at 4° C., as described (MacGregor et al., supra). Following blocking, labelled tyrosine phosphorylated carboxy- terminus (C-terminus) probe was added at a concentration of 1.6×10−4 µg/ml, and incubation was continued overnight. The filters were then washed 3 times at room temperature in PBS containing 0.2% Triton X-100. Filters were dried and exposed to Kodak XAR-5 film at −80° C.

Agar plugs, corresponding to the positive clones, were collect from the plates and placed in 1 ml of SM media. After allowing the phages to diffuse from the agar, the phages were replated and rescreened as described above. Those phages that demonstrated enrichment on subsequent screening were isolated and sequence. Lambda gt11 phage DNA was isolated by the plate lysate method according to Maniatis et al., and subcloned into EcoRI-digested M13 MP19 (Maniatis et al., 1982). Single stranded DNA was isolated and sequenced by the dideoxy chain termination method using the Sequenase DNA sequencing kit (United States Biochemical).

Figure 3A:
FIGS. 3A and 3B shows autoradiograms of phage expressing GRB-1 protein. A) Primary screen demonstrating one positive signal (arrow) out of 40,000 phage plated. B) Plaque purification of phage expressing GRB-1. All plaques bound to the ($^{32}$P) -labelled C-terminal domain of the EGFR.
Figure 3B:
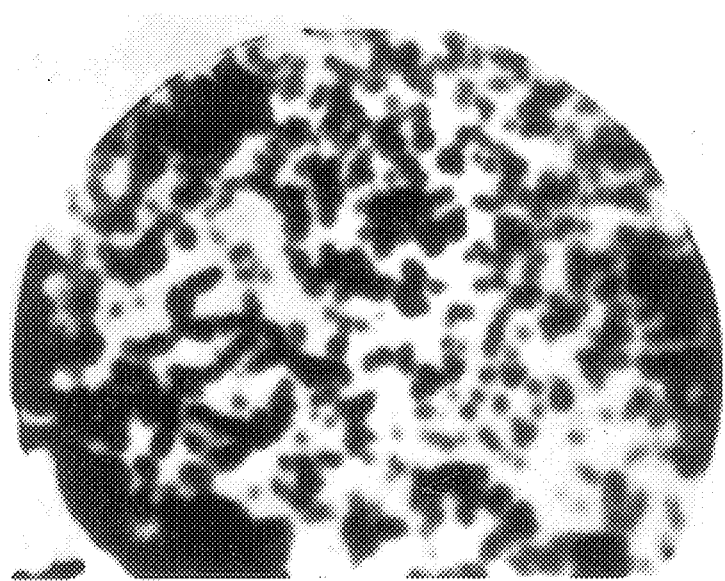

In one experiment, 240,000 pfu from a human brainstem lambda gt11 library were screened. A single plaque, clone ki4 (FIG. 3A) was isolated. On subsequent screening this clone demonstrated enrichment, and on tertiary screening all plaques bound the probe (FIG. 3B). Clone ki4 contained an insert of about 900 nucleotides, which, upon induction of the lac promoter with IPTG, produced a fusion protein which could bind the EGFR. The size of the fusion protein predicted that the cDNA insert coded for a protein of about 300 amino acids, which was the size expected if the cDNA contained a single large open reading frame. To analyze clone ki4 in more detail, DNA was isolated and the EcoRI fragment, corresponding to the human cDNA insert, was subcloned into M13 and sequenced. Translation of the sequence from this insert demonstrated a single large open reading frame which, upon analysis using the Genbank database, was found to contain a single stretch of about 100 amino acids with sequence homology to SH2 domains of other known proteins (FIGS. 4 and 5A). However, in other regions, no sequence homology was noted. Thus, using this screening approach, a new SH2-containing protein which could bind to the EGFR was identified.

B. Isolated of Full Length cDNA

The initial clone isolated encoded for an SH2 domain, but did not contain the 3' or 5' ends of the gene. To isolated the full length cDNA, the library was rescreened using DNA isolated from the initial positive phage. DNA, from recombinant M13 bacteriophage which expressed the positive clone, was amplified using a thermal cycler, Taq1 polymerase and oligonucleotides complementary to the EcoR1 flanking regions of the M13 sequence in information, a second amplified DNA product, corresponding to the most 5'250 nucleotides of the initial isolated phage, was also generated by using oligonucleotides complementary to sequences at both ends of this region. ($^{32}$P) -labelled DNA probes were then prepared by nick translation of the amplified products.

To rescreen the cDNA library, the library was replated as described above. After incubation of the plates for 8 hours at 37° C., the plates were cooled for 1 hour at 4° C. following which the phage DNA was transferred to nitrocellulose filters. The filters were denatured in a solution of 0.2N NaOH and 1.5M NaCl and then baked in vacuo for 2 hours at 80° C. (Sambrook, J. et al., (*Molecular Cloning: A Laboratory Manual,* 2nd Edition, Cold Spring Harbor Press, Cold Spring Harbor, N.Y. (1989)). After prehybridization of the filters for 1 hour at 42° C., 32P-labelled DNA probe was added and hybridization was continued overnight at 42° C. in a solution containing 5×Denhardt's, 50% formamide, 5×SSC, 0.1% SDS, 200 mM Tris-HCl, pH 7.6 and 100 µg/ml salmon sperm DNA. The filters were then washed in a solution containing 0.1×SSC and 0.1% SDS, dried and exposed to Kodak XAR-5 film at −70° C. Positive clones were then isolated and sequenced as described above.

Since the insert from clone ki4 lacked the 3' and 5' ends of the gene, the library was rescreened using two DNA probes which were generated by amplifying DNA from clone ki4. This approach enabled the identification of five additional clones. Three of the clones extended 3' from the initial clone ki4, two of which, clones, ki2.2 and ki2.4, contained a polyadenylation signal and a long 3' untranslated region (>1000 nucleotides). In addition, these clones encoded a protein which contained a second SH2 domain (FIGS. 4 and 5A).

The other two clones, ki3.0 and ki5.3, extended 5' from clone ki4. Both clones contained long open reading frames and an AUG codon which met the translation initiation criteria as defined by Kozak (Kozak, M. *J. Cell. Biol.* 108:229–241 (1989)). However, only clone ki3.0, when translated into protein and compared with known sequences in Genbank, was found to contain a domain of 50 amino acids which was homologous to SH3 domains present in other known proteins. The predicted molecular weight of the full length protein encoded by the overlapping clones, ki2.2 and ki3.0, was about 84 kDa. This new protein was termed GRB-1.

EXAMPLE III

GRB-1 Protein Contains SH2 and SH3 domains

Analysis of the GRB-1 protein sequence by comparison to sequences in the Genbank database revealed the presence of two stretches of about 100 amino acids, starting at amino acids 333 and 624, with sequence homology to SH2 domains of other proteins known to interact with the EGFR (FIG. 5A). While GRB-1 displayed striking homology to other SH2 domains at the protein level, it revealed no significant homology at the DNA level. GRB-1 also contained a segment of about 50 amino acids, located in the N-terminal region, which had sequence homology to SH3 domains (FIGS. 4 and 5B).

A comparison of the structural organization of GRB-1 with several other SH2/SH3 containing proteins is shown in FIG. 6. It is apparent from this scheme that the localization of the SH2 and SH3 domains vary from protein to protein. Despite this there are certain similarities and differences among these SH2 containing proteins. GRB-1 is similar to some other substrates which have been found to interact with the EGFR, such as PLC-γ and GAP, in that GRB-1 contains two SH2 domains and a single SH3 domain. However, unlike these substrates, GRB-1 contains no homology to any known catalytic domain, and in this regard resembles the protein encoded by the avian sarcoma virus, v-crk.

Out side of these regions there was no sequence homology with other protein sequences present in Genbank. In particular, GRB-1 lacked a consensus ATP-binding domain, and did nod display sequence homology with any serine/threonine kinase or tyrosine kinase.

The SH2 domain is thought to provide a common motif by which enzymatically distinct signalling molecules can be coupled to activated receptors with tyrosine kinase activity (Moran, M. F. et al., *Proc. Natl. Acad. Sci. USA* 87:8622–8626 (1990); Anderson, D. et al., *Science* 250:979–982 (1990)).

The presence of SH2 domains in GRB-1 (FIG. 4) and in GRB-2 further reinforces the importance of this domain in mediating the interaction of these proteins with the C-terminal tail of the EGFR. Moreover, since many proteins capable of interacting with cytoplasmic or receptor tyrosine kinases remain to be identified, this suggests that additional members of this protein family remain to be discovered.

In addition to containing two SH2 domains, GRB-1 also contains an SH3 domain. The SH3 domain is a non-catalytic domain of about 50 amino acid residues which is shared among many SH2-containing proteins. Since SH3 domains are also found in cytoskeletal proteins, such as spectrin and fodrin, the function of this domain could be to localize these proteins to the membrane or submembrane cytoskeleton where they would interact with other molecules.

Comparison of the deduced amino acid sequence of GRB-1 with the protein product encoded by the avian oncogene v-crk may shed light on GRB-1 function. The gene v-crk encodes a protein which is composed primarily of a viral gag protein fused to an SH2 and SH3 domain (Mayer, B. J. et al., *Nature* 332:272–275 (1988)). Both GRB-1 and the $p47^{gag-crk}$ protein have no homology with any known catalytic domains. However, chicken embryo fibroblasts transformed with $p47^{gag-crk}$ display elevated levels of phosphotyrosine-containing proteins (Mayer, B. J. et al., supra; *Proc. Natl. Acad. Sci. USA* 87:2638–2642 (1990); Matsuda, M. et al., *Science* 248:1537–1539 (1990)).

Since the v-crk product has been shown to bind several phosphotyrosine-containing proteins in v-crk transformed cells, it may be that the function of c-crk is to act as a bridge between kinases and substrates. In this regard, it is intriguing that GRB-1, like GAP and PLC-γ, contains two SH2 domains, the combination of which may be ideally suited for linking other proteins to activated tyrosine kinase molecules.

EXAMPLE IV

Northern Analysis of GRB-1 Expression

A. Methods

Total cellular RNA was prepared from monkey tissue by the guanidinium isothiocyanate/cesium chloride method described by Sambrook, J. et al., (supra). Poly (A)+RNA was prepared by oligo(dT) cellulose chromatography. For Northern analysis, RNA was size fractionated by electrophoresis in a 1.2% agarose/2.2M formaldehyde gel, transferred onto a nylon membrane by capillary action and baked at 80° C. for 2 hours. Following prehybridization, the blot was hybridized with a ($^{32}$P) -nick-translated DNA probe which was prepared as described above. Hybridization was carried out overnight at 42° C. in the presence of 50% formamide, 5×SSC, 0.1% SDS, and 5×Denhardt's. The membrane was then washed in 0.1×SSC, 0.1% SDS at 42° C., and exposed to Kodak XAR film at −70° C. for 12 hours using an intensifying screen.

B. Results

To test for the expression of mRNA corresponding to the newly isolated cDNA, Northern blot analysis of different monkey tissue mRNA, probed with DNA corresponding to the insert from clone ki4, demonstrated the presence of two major bands of 4.4 kb and 7.0 kb in most tissues examined (FIG. 7). Expression was highest in the brain, with heart, spleen, liver and thymus displaying decreasing levels of expression. The 4.4 kb message corresponds to the expected size of the transcript which would encode the isolated clones. In contrast to the 4.4 and 7.0 kb transcripts observed in most tissues, the skin contained two slightly smaller sized mRNAs of 3.6 and 6.6 kb.

The 3.6, 6.6 and 7.0 kb transcripts may represent alternatively spliced forms of MRNA, or may encode for distinct but related mRNA species.

EXAMPLE V

Production of anti-GRB-1 Antibodies and Analysis of GRB-1 Fusion Protein

A. Methods

Polyclonal antibodies were produced by immunizing rabbits with the β-galactosidase fusion protein expressed by the initial isolated phage clone, ki4. *E. coli* CAG 456 bacteria (obtained from Dr. Michael Snyder, Yale University) were infected with recombinant phage ki4 at a multiplicity-of-infection of 10 and β-galactosidase fusion protein was recovered from the protein pellet after 1.5 hours. Protein extracts were prepared, separated on a 6% SDS-gel, and the band corresponding to the fusion protein excised from gel and used for immunization.

Human glioblastoma cell line U1242, rat bladder carcinoma cell line NBT II, and NIH3T3 cells were grown to confluence in DMEM medium supplemented with 10% fetal bovine serum. Cells were labelled with ($^{35}$S)-methionine (50 μCi/ml) in 0.5% fetal bovine serum and lysed after 12 hours as previously described (Margolis, B. et al., *Cell* 57:1101–1107 (1989)). After immunoprecipitation with 10 μl of antibody coupled to protein A-Sepharose, the beads were washed three times with a solution containing 20 mM HEPES, pH 7.5, 300 mM NaCl, 10% glycerol, 1% Triton X-100, 0.1% SDS, and 1% sodium deoxycholate. After boiling in sample buffer proteins were separated on a 8% SDS-gel.

B. Results

Polyclonal antibodies were raised against the β-galactosidase fusion protein expressed by the initial isolated phage. Immunoprecipitation experiments, using biosynthetically labelled cells, demonstrated that these antibodies recognized an 85 kDa protein in three different cell lines (FIG. 8, lanes designated "I"). Recognition of the 85 kDa protein by this antiserum was specific since preimmune serum did not recognize this protein (lanes designated "P"). These results provided support for the predicted molecular weight based on the amino acid sequence of cloned GRB-1.

C. Discussion

The finding that the gene for GRB-1 encodes for a protein with an expected molecular weight of 85 kDa, together with the demonstration that antibodies to GRB-1 immunoprecipitated an 85 kDa protein from three different cell lines, suggest that GRB-1 may represent a particular protein which had previously been shown to associate with activated growth factor receptors, namely p85. While the exact function of p85 was unknown, it was presumed to be phosphatidylinositol (PI3)-kinase, since PI3-kinase activity copurified with an 85 kDa protein found in PDGF-stimulated as well as middle T-antigen (MTAg)-transformed cells (Kaplan, D. R. *Cell* 50:1021–1029 (1987); Whitman, M. et al., *Nature* 315:239–242 (1985); Coughlin, S. R. et al., *Science* 243:1191–1194 (1989)). The absence of an ATP binding site argues that GRB-1 is most likely not a phospholipid kinase. GRB-1 exhibits 97% sequence identity with murine and bovine p85. Hence, GRB-1 is the human counterpart of p85. Recombinant p85 is able to bind to the activated PDGFR or EGFR, but does not itself contain intrinsic PI3 kinase activity. p85, however, is found associated with a 110 kDa tyrosine phosphorylated protein which may be the catalytic subunit of the PI3 Kinase. While the exact relationship between PI3 kinase and p85 is not known, overexpression of p85 modulates the interaction between PI3 kinase and the PDGFR. p85 could function as a regulatory subunit or as a bridge between activated receptors and the PI3 kinase.

EXAMPLE VI

The Tyrosine Phosphorylated Carboxy-terminus of the EGF Receptor is a Binding Site for GAP and PLC-γ

The studies described below confirm that binding of PLC-γ and a fusion protein containing the SH2 and SH3 domains of GAP (trpE/GAP SH2) are specifically controlled by autophosphorylation of the EGFR. The results show that phosphorylation of PLC-γ actually reduces its association with the EGFR. Evidence is presented demonstrating that both PLC-γ and the trpE/GAP SH2 fusion protein bind specifically to the tyrosine phosphorylated C-terminus of the EGFR. In sum, these results indicate that the SH2/SH3 domains interact directly with phosphotyrosine containing regions of the EGF receptor.

A. Materials and Methods

1. Cell lines, mutant receptors and fusion proteins

The cell lines CD126 (Margolis, B. L. et al., *J. Biol. Chem.* 264:10667–10671 (1989a), HER14, K721 (Honegger, A. M. et al., *Cell* 51:199–209 (1987); Honegger, A. M. et al., *Mol. Cell. Biol.* 7:4567–4571 (1987)) were used as sources for wild-type EGF receptor, kinase-negative (kin$^{31}$) EGF receptor and C-terminal (C-terminal) truncated EGF receptor, respectively. The intracellular domain of the EGF receptor (EGFR-C) was purified from a baculovirus expression system (Hsu, C.-J. et al., *Cell Growth Differ* 1:191–200 (1990)) (FIG. 9A). 3TP1, a cell line which overexpresses transfected PLC-γ cDNA but has no EGF receptor was used as a source of PLC-γ (Margolis, B. et al., *Science* 248:607–610 (1990b)).

The preparation of trpE fusion proteins containing the GAP SH2 domain (GAP residues 171–448, FIG. 9B) has been described by Moran, M. F. et al., *Proc. Natl. Acad. Sci. USA* 87:8622–8626 (1990). Bacterial lysates containing trpE/GAP SH2 fusion proteins were prepared by resuspending 1 g of bacteria in 3 ml of 50 mM Tris pH 7.5, 0.5 mM EDTA, 0.1 mM PMSF. After incubation at 4° C. in 1 mg/ml lysozyme and 0.2% NP-40, cells were sonicated 5 times for 5 seconds, and the lysate was clarified by centrifugation for 30 min at 10,000 g. Bacterial lysates were diluted 1:100 in the 1% Triton lysis buffer with proteinase and phosphatase inhibitors as described above and were precleared with protein A-Sepharose.

2. Antibodies, immunoprecipitation and immunoblotting

The following anti-EGFR antibodies (FIG. 9A) were used: (a) mAb108, a monoclonal antibody directed against domain III of the extracellular domain (Lax, I. et al., *EMBO J.* 8:421–427 (1989)); (b) antipeptide antibody RK2 specific for residues 984–996; (c) antipeptide antibody C specific for residues 1176–1186; and (d) antipeptide antibody F, specific for residues 656–676. For immunoprecipitating the trpE fusion proteins, a mouse monoclonal antibody against trpE (Oncogene Science) bound to agarose linked anti-mouse IgG (Sigma) was utilized. For immunoblotting, a polyclonal rabbit antibody against trpE was used (Moran, M. F. et al., *Proc. Natl. Acad. Sci. USA* 87:8622–8626 (1990)). PLC-γ was immunoblotted and immunoprecipitated with a polyclonal rabbit anti-peptide antibody described previously (Margolis, B. et al., *Cell* 57:1101–1107 (1989b)).

The techniques used are described in several references from the present inventors' laboratory (Margolis, B. L. et al., *J. Biol. Chem.* 264:10667–10671 (1989); *Cell* 57:1101–1107 (1989)). Unstimulated cells were grown to confluence in Dulbecco's Modified Eagle Medium with 10% calf serum and starved overnight in 1% fetal calf serum prior to lysis in a 1% Triton X-100 lysis buffer containing proteinase and phosphatase inhibitors. EGF receptors were immunoprecipitated utilizing antibodies bound to protein A-Sepharose. After washing the receptor material with HNTG (20 mM Hepes, pH 7.5, 150 mM NaCl, 0.1% Triton X-100 and 10% glycerol), autophosphorylation was induced by the addition of 5 mM MnCl$_2$ and 30 μM ATP. Controls were incubated with Mn$^{2+}$only. After further washes with HNTG, lysate containing either PLC-γ (from 3TP1 cells) or the bacterial fusion proteins was added. After allowing binding to proceed for 90 min, three further washes with HNTG were performed and samples were run on an SDS gel and immunoblotted.

3. Cyanogen bromide (CNBr) cleavage

EGFR-C was phosphorylated at 4° C. with MnCl$_2$ and ATP sometimes in the presence of (γ-$^{32}$P)ATP (NEN/Dupont, 6000 Ci/mmol). The receptor preparation was then resuspended in 20 mM HEPES, pH 7.5, with 100 μg BSA and concentrated in a Centricon 10 (Amicon) to 50 μl. Then 240 μl 88% formic acid was added with two grains of CNBr and the samples were stored under nitrogen in the dark for 14 h at room temperature. Samples were dried and washed three times with water in a Speed-Vac (Savant) and then resuspended in 1% Triton lysis buffer.

B. RESULTS

A comparison was performed of the binding of PLC-γ to wild-type and mutant EGFRs (FIG. 9A). First, wild-type and mutant receptors from transfected NIH-3T3 cells were immunoprecipitated and some of the receptor immunoprecipitates were allowed to undergo in vitro autophosphorylation with ATP and Mn$^{2+}$(Margolis, B. et al., *Mol. Cell. Biol.* 10:435–441 (1990a)). Then, lysates from NIH-3T3 cells which overexpress PLC-γ (Margolis, B. et al., *Science* 248:607–610 (1990b)) were added and binding allowed to proceed for 90 min. at 4° C. After washing the immunoprecipitates with HNTG, the amount of PLC-γ bound was assessed by immunoblotting. As illustrated in FIG. 10, PLC-γ bound only to the tyrosine phosphorylated wild-type receptor but not to the non-phosphorylated receptor.

To assess the importance of autophosphorylation, two studies with mutant receptors were then undertaken. First to be examined was the binding of PLC-γ to a truncated EGF receptor missing 126 amino acids from the C-terminus (CD126, FIG. 9A) and devoid of four major autophosphorylation sites (Downward, J. et al., *Nature* 311:483–485 (1984)). This truncated receptor was autophosphorylated, probably at tyrosine 992 (Walton, G. M. et al.,*J. Biol. Chem.* 265:1750–1754 (1990)). However, despite this level of tyrosine autophosphorylation, the binding of PLC-γ was markedly reduced compared to the full length receptor. Reduced association was also observed with CD63, a deletion mutant EGF receptor lacking 63 C-terminal residues containing two autophosphorylation sites. These results suggested a role for the receptor C-terminus in either binding or modulating the binding of PLC-γ to the EGF receptor.

FIG. 10 also demonstrates that PLC-γ cannot bind to the kin-mutant receptor. To explore the importance of autophosphorylation in this effect, the kin-receptor was cross-phosphorylated with the CD126 receptor (Honegger, A. M.

et al., Proc. Natl. Acad. Sci. USA 86:925–929 (1989)). This resulted in normalization of PLC-γ binding to wild-type levels. This suggested that phosphorylation of the kin-receptor was sufficient to normalize binding to PLC-γ.

To confirm that the kin-receptor alone could bind PLC-γ after phosphorylation, this receptor was cross-phosphorylated with a soluble, baculovirus-expressed EGFR cytoplasmic domain (EGFR-C) that does not bind to the mAb 108 (FIG. 9A).

Although cross-phosphorylation was not as strong as with the CD126 mutant, tyrosine phosphorylation of the K721A mutant and binding of PLC-γ were clearly detected. This finding confirms that tyrosine phosphorylation of the EGFR promotes binding of PLC-γ.

The role of PLC-γ tyrosine phosphorylation in the interaction between wild-type EGFR and PLC-γ was examined. Tyrosine phosphorylated PLC-γ could be dissociated from the EGFR more readily than non-phosphorylated PLC-γ (FIG. 11), suggesting a lower affinity of tyrosine phosphorylated PLC-γ for the EGFR.

These findings were extended to examination of the binding of a fusion protein containing trpE/GAP SH2 domain (FIG. 9B) to the baculovirus expressed EGFR-C, As with the full length EGFR and PLC-γ, the trpE/GAP SH2 fusion protein domain bound only to the tyrosine phosphorylated EGFR-C (FIG. 12A). The trpE protein alone did not bind to EGFR-C. Similarly, phosphorylated EGFR-C bound only to trpE/GAP SH2; however, non-specific binding of non-phosphorylated EGFR-C was high (FIG. 12B). These results demonstrated that the binding site of the EGFR is situated in its intracellular domain.

In general, the trpE/GAP SH2 fusion protein bound with a higher stoichiometry to full length EGFR than did PLC-γ. However, the fusion protein was not tyrosine phosphorylated by the EGFR. The trpE/GAP SH2 protein much better to the phosphorylated full length receptor compared to the CD126 deletion mutant (FIG. 13A). As shown in FIG. 13B, cross-phosphorylation of the kin-full length EGF receptor by the EGFR-C allowed it to bind the trpE/GAP SH2 protein.

In control groups, the EGFR-C was shown not to enhance the binding to the CD126 receptor probably because this receptor was already maximally tyrosine phosphorylated (FIG. 13A). Also, no binding was observed when EGFR-C was tested in the presence of mAb 108 immunoprecipitate from cells containing no EGF receptor (FIG. 13B). This indicates that the effects of EGFR-C could not be attributed to non-specific binding of tyrosine phosphorylated EGFR-C to sepharose. These studies confirm the importance of autophosphorylation in mediating binding and show that for EGF receptor binding, the GAP SH2 domain behaves similarly to intact PLC-γ.

The poor binding to the CD126 deletion mutant suggested that at least part of the binding site for the molecule was in the C-terminus. Yet an effect, possibly allosteric, of this deletion on the overall conformation of the receptor could not be excluded. Therefore, the binding of PLC-γ and trpE/GAP SH2 to a C-terminal fragment of the EGFR was examined. In the EGFR, the most C-terminal methionine residue is found at position 983; CNBr cleavage therefore generates a 203 amino acid fragment which contains all the known autophosphorylation sites. This protein fragment is recognized by an antibody specific for the EGFR C-terminus, anti-C (FIG. 9A).

When this C-terminal fragment was specifically immunoprecipitated and tyrosine phosphorylated, it bound PLC-γ and the trpE/GAP SH2 fusion protein (FIG. 14). CNBr cleavage was complete; no full-length EGFR-C could be detected after proteolysis that could account for the binding. Again, no binding was seen to the non-phosphorylated C-terminal CNBr fragment. CNBr cleavage of EGFR-C also generated a 97 amino acid N-terminal peptide identified by antibody F (FIG. 9A, EGFR residues 645–742). This fragment, immunoprecipitated by antibody F, did not bind trpE/GAP SH2. Additionally, EGFR-C was autophosphorylated with (γ-$^{32}$P)ATP and a $^{32}$P-labelled CNBr C-terminal fragment was generated. As shown in FIG. 15, this fragment bound to the trpE/GAP SH2 fusion protein but not to trpE. In total, these findings demonstrate that direct binding to the tyrosine phosphorylated C-terminus contributes at least in part to the specific binding of SH2 and SH3 domain proteins to the EGFR.

C. Discussion

When taken together, the above findings and several additional lines of evidence argue strongly that the phosphotyrosine residues are part of the actual binding site of the EGFR for SH2 domains. First, P47$^{gag-crk}$ was found to bind to nearly all phosphotyrosine-containing proteins in v-crk transformed cells (Matsuda, M. et al., Science 248:1537–1539 (1990)). Second, mutations of two autophosphorylation sites on the PDGF receptor greatly decreased the binding of GAP (Kazlauskas, A. et al., Science 247:1578–1581 (1990)). Finally, the results presented above demonstrate specific binding to the C-terminus of the EGFR only when phosphotyrosine is present. Thus, it is concluded that the phosphotyrosine residues either comprise a part of the binding site or locally alter the conformation of this region, allowing binding. It is unlikely that phosphotyrosine alone constitutes the binding site. For example, phosphotyrosine alone cannot interfere with the binding of P47$^{gag-crk}$ to phosphotyrosine-containing proteins (Matsuda et al., supra). Additionally, PLC-γ does not bind to activated all molecules that contain phosphotyrosine residues, such as the CSF-1 receptor (Downing, J. R. et al., EMBO J. 8:3345–3350 (1989)). Similarly, the binding of PLC-γ to PDGFR does not appear to be identical to GAP binding; different SH2 and SH3 domain-containing proteins may have different binding specificities (Kazlauskas et al., supra).

EXAMPLE VII

Cloning, Isolation & Characterization of a Target Protein for Receptor Tyrosine Kinase METHODS: The intracellular domain of the EGFR, which includes the tyrosine kinase and carboxy terminal domain, was purified from a recombinant baculovirus expression system as described (Margolis Mol. Cell. Biol. 10:435–441 (1990) and EMBO J. 9:4375–4390 (1990); Skolnik et al. Cell 65:83–90 (1991). The recombinant protein was phosphorylated with ($^{32}$P) γ-ATP, washed, and cyanogen bromide digested to yield a 204 residue carboxy terminal tail containing all five phosphorylated tyrosine residues (Margolis Mol. Cell. Biol. 10:435–441 (1990a) and EMBO J. 9:4375–4390 (1990b). The ($^{32}$P) -carboxyterminal tail was then used as probe to screen a λgt11 human brainstem expression library, as previously described (Skolnik et al. Cell 65:83–90 (1991)).

An oligo (dT) λgt11, constructed from mRNA isolated from human brain stem, was obtained from M. Jaye (Rhone Poulenic-Rorer Pharmaceuticals) and is readily available from commercial sources. Screening of the library was performed as previously described (Skolnik et al. Cell 65:83–90 (1991)). cDNA inserts isolated from positive recombinant phage that bound the EGFR were subcloned into M13 and sequenced by the dideoxy chain termination method, using the Sequenase 2.0 kit (U.S.B). Since the initial clone isolated by expression/cloning did not contain the 5' ends of the gene, the library was rescreened, using the clone 2–4 insert as a DNA probe.

Total cellular RNA was prepared with the Stratagene RNA isolation kit. For Northern analysis, RNA was size fractionated on a 1.2% agarose-2.2M formaldehyde gel, transferred by capillary action to a Nytran membrane (Schleicher and Schuell), and prehybridized and hybridized at 65° in 0.5M sodium phosphate pH 7.2, 7% SDS, 1 mM EDTA, 100 µg/ml salmon sperm DNA. The membrane was then washed 1×at room temp and then 2×at 65° C. in 40 mM sodium phosphate pH 7.2, 1 SDS, 1 mM EDTA.

HER14 are NIH 3T3 cells (clone 2.2) which express approximately 400,000 wild type human EGF receptors per cell (Honeggar et al. *Cell* 51:199–209 (1987)). HER14 cells were maintained in Dulbecco's modified Eagles medium (DMEM) containing 10% calf serum (CS). Prior to stimulation, cells were cultured for 18 hours in DMEM/1% CS. Cells were then stimulated with either EGF (275 ng/ml) or PDGF-BB (50 ng/ml) Intergen, Purchase, N.Y.) for 2 minutes in DMEM containing 1 mg/ml BSA and 20 mM HEPES pH 7.5, following which the cells were immediately washed and lysed. Lysate protein content was normalized as described (Bradford, 1976). Cell lysis, immunoprecipitation, and immunoblotting were performed as previously described (Margolis et al. *Cell* 57:1101–1107 (1989)). 293 cells were transfected using a modification of the calcium phosphate precipitation method (Chen and (Okayama *Mol. Cell. Biol.* 7:2745–272 (1987).

Several polyclonal antibodies were generated against GRB2. A synthetic peptide derived from the N-terminal SH3 domain (residues 36–50) and the full length GRB2-GST (glutathione-S-transferase) fusion protein were used to produce rabbit polyclonal antisera called Ab 86 and Ab 55, respectively. Both of these antisera are effective at recognizing denatured GRB2 in immunoblots. A third polyclonal rabbit antisera called Ab50 was generated against the GRB2-GST fusion protein containing the C-terminal SH3 domain of GRB2 (residues 167–221), and is capable of immunoprecipitating GRB2 from solubilized cells. Monoclonal antiphosphotyrosine antibodies (1G2) covalently coupled to agarose were purchased from Oncogene Science (Manhasset, N.Y.). Anti-P-Tyr immunoblots were performed with a rabbit polyclonal antibody. Anti-EGF receptor immunoprecipitates were performed with monoclonal antibody mAb m108 (Bellot et al. *J. Cell Biol.* 110:491–502 (1990).

Anti-EGF receptor immunoblots were performed with anti-C terminus peptide (residues 1176–1186) antisera (Margolis et al. *Cell* 57:1101–1107 (1989)).

Using the cDNA of GRB2 as a template, DNA fragments corresponding to the various GRB2 domains were synthesized using PCR and oligonucleotides which contained appropriate restriction sites and bordered the domains of interest. The amplified DNA was isolated, digested with BamHI and EcoRI and cloned into pGEX3X (Pharmacia), which was then used to transform *E. coli* HB 101 to ampicillin resistance. Large scale cultures were then grown, induced with IPTG, and the glutathione S-transferase (GST) fusion proteins purified on glutathione agarose beads as previously described (Smith and Johnson *Gene* 67:31–40 (1988)).

The following fusion proteins were prepared: GST-GRB2 full length (FL) (amino acids {AA} 2–217); GST-SH2 (AA 50–161); GST-N-terminal SH3 (AA 2–59); GST-C-terminal SH3 (AA 156–217); GST-N-terminal SH3-SH2 (AA-161); GST-SH22-C-terminal SH3 (AA 50–217).

To assay the binding of native growth factor receptors to GST-fusion proteins 500 ul of HER14 cell lysate was incubated for 90 min at 4° C. with approximately 5 ug of fusion protein coupled to glutathione agarose beads. The beads were then washed three times with HNTG, and after boiling in sample buffer, the proteins were separated on 8% SDS-PAGE. Bound proteins were transferred to nitrocellulose and blotted with antibodies as described (Margolis et al. *Mol. Cell. Biol.* 10:435–411 (1990a), Margolis et al. *EMBO J.* 9:4375–4380 (1990B); Margolis *Cell Growth and Differentiation* 3:73–80 (1992); and Margolis et al. *Nature* 356:71–74 (1992).

Labeling cells with ($^{32}$P) -orthophosphate were carried out as previously described (Li et al. *Mol. Biol. Cell* 2:641–649, 1991). Briefly, confluent HER14 cells starved for 16 hrs in 1% FCS/DMEM were incubated for two hours in $P_i$-free media, and labeled for two hours in $P_i$-free media, 1% dialyzed FBS, 1 mCi/ml orthophosphate (carrier free, 314.5–337.5 TBq/mmole, purchased form NEN, Wilmington, Del.), at 37° C., Where appropriate, cells were incubated with vanadate (200 uM) at 37° C. for the last 20 minutes of cell labeling. Cells were then stimulated for two minutes with EGF (250 ng/ml) or PDGF (50 ng/ml), rapidly washed 2 times with ice cold phosphate-buffered saline (PBS), and solubilized immediately in lysis buffer (10 mM Tris-Cl pH 7.6, 50 mM NaCl, 30 mM sodium pyrophosphate, 50 mM sodium fluoride, 100 uM sodium orthovanadate, 5 uM $ZnCl_2$, 1 mM PMSF and 0.5% Triton-X-100). After nuclei were removed by centrifugation, the lysates where precleared for 1 hour with 50 ul Sepharose G25, and then incubated overnight with anti-GRB2 antiserum (Ab50) at 4° C. The immune complexes were then precipitated with protein A-Sepharose for 45 min at 4° C., washed 8–15 times with RIPA buffer (20 mM Tris-Cl pH 7.6, 300 mM NaCl, 2 mM EDTA, 1% Triton-X-100 1% sodium deoxycholate and 0.1% SDS), heated in Laemmli sample buffer containing 0.1M B-mercaptoethanol and 1% SDS at 95° C. for 5 min, resolved by SDS PAGE (8–15% gradient), and visualized by autoradiography of dried gels. To isolate tyrosine phosphorylated proteins, the cell lysates were incubated with anti-PY antibody (Oncogene Science) beads for 2 hours at 4° C. The anti-PY beads were washed 5 times with lysis buffer, followed by elution with phenylphosphate (2 mM) in the presence of ovalbumin.

RESULTS: Isolation of a cDNA clone encoding a protein with novel SH2 and SH3 domains.

The carboxy-terminal tail of the EGFR was used as a probe to screen a human brain stem λgt11 protein expression library as previously described (Skolnik et al. *Cell* 6:4396–4408, 1991). One of the clones isolated utilizing this technique, clone 2–4, contained an insert of 1100 nucleotides found to contain a reading frame encoding novel SH2 and SH3 domains. The insert from clone 2–4 contained a 3' stop codon followed by a polyadenylation signal, but did not contain the 5' start site. To isolate the 5' end of the gene, the library was rescreened using DNA probes generated by amplifying DNA from clone 2–4. This approach enabled identification of clone 10–53, which was found to encode the full length protein. Clone 10–53, while overlapping with clone 2–4 at the 3' end contained a 5' ATG codon meeting Kozak translation initiation criteria (Kozak *J. Cell. Biol.* 108:229–241 (1989)), giving a 660 bp open reading frame from the initiating methionine (Ficket et el. *Nucleic Acids Research* 10:5303–5318 (1982)) (FIG. 26A). Analysis of the protein sequence of clone 10–53 using Genbank revealed that the full length protein contained a single SH2 domain flanked by two SH3 domains, and that these three domains comprise the bulk of the protein (FIG. 26B). The SH2 and SH3 domains of GRB2 are compared to those in other proteins in FIGS. 26C and 26D. The full length protein encoded by clone 10–53 was named GRB2 (for the second growth factor receptor binding protein identified by the CORT method), and encoded a protein with a predicted molecular weight of about 24.5 kDa. The sequence also contains two potential protein kinase C phosphorylation sites (aa 22 and 102), two potential casein kinase 2 phosphorylation consensus sequences (aa 16 and 131) (Woodget et al. *Eur. J. Biochem.* 161:177–184 1986; Kishimoto et al. *J. Biol. Chem.* 260:12492–12499 1985; Marin et al. *Eur. J. Biochem.* 160:239–244 1986; Kuenzel et al. *J. Biol. Chem.* 262:9136–9140 1987) and two RGD motifs.

Northern Analysis and Protein Expression

To determine tissue distribution of GRB2, Northern hybridization analysis of various mouse tissue RNAs was performed, using as a probe the insert from clone 10–53. This analysis demonstrated GRB2 expression in every tissue examined, with the highest expression in the brain, spleen, lung, and intestine (FIG. 27A). GRB2 transcripts were visible in the thymus upon longer exposure. We have thus far been unable to identify a tissue or cell line which does not express GRB2, further demonstrating the ubiquitous nature of GRB2 expression. GRB2 hybridized to two transcripts of 1.5 and 3.8 kb. The 1.5 kb transcript corresponds to the expected size of clone 10–53.

Several polyclonal rabbit antisera against GRB2 were generated (see methods section) and used to analyze the GRB2 protein by immunoblotting or immunoprecipitation experiments. FIG. 27B shows that a protein of 25 kDa is recognized by the immune, but not by the preimmune antiserum utilizing either immunoprecipitation analysis of ($^{35}$S) methionine labelled cells or an immunoblotting approach. The various antisera recognized a 25 kDa protein in every cell line and tissue examined, consistent with the distribution of the GRB2 transcript found in Northern analysis.

GRB2 associates with growth factor receptors in living cells. Receptor substrates which contain SH2 domains are endowed with the ability to physically associate with certain activated growth factor receptors. Since the goal of the CORT cloning technique is to identify target proteins for particular growth factor receptors, we assessed whether GRB2 associates with the EGF receptor. HER 14 cells were treated with or without EGF, lysed, and subjected to immunoprecipitation analysis, according to published procedures (Margolis et al. 1990b, 1991b).

Immunoblotting of anti-EGFR immunoprecipitates with antibodies to GRB-2 demonstrated association of the 25 kDa (GRB-2 protein with activated EGFR (FIG. 28, lane 6). As shown for PLCγ, the association between EGFR and GRB2 was strictly dependent upon ligand activation and tyrosine autophosphorylation (FIG. 28, lanes 5 and 6) (Anderson et al. *Science* 250:979–982 (1990); Margolis et al. *Cell* 57:1101–1107 1989, *Mol. Cell. Biol.* 10:435–441 1990a, *EMBO J.* 9:4375–4380 1990b; Wahl et al. *Natl. Acad. Sci. USA* 86:1568–1572 1989, Meisenhelder *Cell* 57:1109–1122 1989). Thus, GRB2 associates only with the activated tyrosine phosphorylated EGFR. GRB2 was also demonstrated to have an association with EGFR by immunoprecipitation of GRB2 followed by immunoblotting with anti EGF-receptor antibodies (data not shown). Similar results were obtained with PDGF receptor; activated PDGF receptor associated with GRB2 in HER14 cell sin growth factor dependent manner.

However, no association between GRB2 and the FGF receptor was detected when similar experiments, using anti GRB2 for immunoprecipitation and anti FGF receptor antibodies for immunoblotting, were performed with cell lines expressing FGF-receptor (Mohammadi et al. *Mol. Cell. Biol.* 11:5068–5078 1991).

Interaction of GRB2 with growth factor receptors is mediated via the SH2 domain. It has been shown that SH2 domains mediate the interaction of signalling molecules, such as PLC-γ or GAP, with tyrosine phosphorylated growth factor receptors (Koch et al. *Science* 252:668–674 (1991); Heldin et al. *Trends in Biol. Sci.* 16:450–452 (1991); Margolis et al. *Cell Growth and Differentiation* 3:73–80 (1992), Margolis et al. *Nature* 3556:71–74 1992). In order to determine whether the interaction between GRB2 and growth factor receptors is mediated via the SH$_2$ domain of GRB2, we constructed bacterial expression vectors which were designed to express GRB2 as well as the various domains of GRB2 as GST-fusion protein (FIG. 4). These fusion proteins were purified by affinity chromatography on glutathione agarose beads (Smith et al. *Gene* 67:31–40 1988), and subsequently incubated with lysates from EGF- or PDGF-treated HER 14 cells. The ability of the fusion proteins to bind the activated EGF or PDGF receptors was assessed by immunoblotting the washed complexes with either antiphosphotyrosine or anti-receptor antibodies.

Both the full length GRB2 fusion protein and a fusion protein containing only the SH2 domain of GRB2 were each capable of binding tyrosine phosphorylated proteins which comigrated with the activated EGF or PDGF receptors (FIG. 30, lanes 4, 6, 12 and 14). In contrast, neither receptor bound GST alone (FIG. 30, lane 2) nor a GST-fusion protein containing either the amino or carboxy terminal SH3 domains could bind to activated receptors. Binding was ligand dependent, since immunoblotting with anti-EGFR antibodies revealed association of the EGFR with the fusion proteins only when incubated with lysates from growth factor stimulated cells (FIG. 30, lanes 7 through 10). Thus, in agreement with data about other SH2 domain containing proteins, the association between GRB2 and growth factor receptors is mediated by the SH2 domain (Koch et al. *Science* 252:668–674 1991); Heldin et al. *Trends in Biol. Sci.* 16:450–452 (1991); Margollis et al. *Cell Growth and Differentiation* 3:73–80 (1992) and *Nature* 356:71–74 (1992).

It is noteworthy that the full length GRB2 fusion protein bound several other tyrosine phosphorylated proteins in EGF- and PDGF-stimulated cell lysates (FIG. 30, lanes 3, 4, 11 and 12). While these bound proteins failed to interact with the SH2-GST fusion protein (FIG. 30, lane 6) or either SH3 domain of GRB2 expressed independently, they did interact with a fusion protein containing both the N-terminal SH3 and SH2 domains. The ability of SH3 domain of GRB2 to enhance the binding activity of the SH2 domain suggests that the N-terminal SH3 domain is important for binding to various cellular proteins and that binding to these proteins may require the concerted action of both SH2 and SH3 domains. GRB2 binds to activated growth factor receptors without being phosphorylated in living cells.

After demonstrating that GRB2 was able to bind to activated EGF and PDGF receptors, we were next interested in determining if GRB2 was a substrate for receptor tyrosine kinases. We examined the capacity of EGF to stimulate phosphorylation of GRB2 in HER14 labelled with ($^{32}$P)-orthophosphate. These cells were treated with EGF, lysed and immunoprecipitated with antibodies to GRB2. While anti-GRB2 antibodies immunoprecipitated GRB2 from ($^{35}$S) methionine labeled cell lysates (FIG. 31, lanes 6 and 8), phosphorylated GRB2 was not detected in the anti-GRB2 immunoprecipitates from orthophosphate labelled cells. Despite marked overexposure of this gel, no detectable band corresponding to GRB2 was evident in the orthophosphate labelled immunoprecipitates. In similar experiments, stimulation of HER14 cells with PDGF also did not result in detectable phosphorylation of GRB2. The failure of detect phosphorylated GRB2 was not due to poor stimulation of the cells by EGF, since anti-P-Tyr immunoprecipitation of the ($^{32}$P$_i$) -labeled lysates demonstrated a marked increase in tyrosine phosphorylation of numerous cellular substrates following EGF stimulation. Similarly anti-phosphotyrosine immunoblotting of GRB2 immunoprecipitated from EGF- or PDGF-stimulated HER14 cell lysates, did not reveal tyrosine phosphorylated GRB2 (data not shown).

To determine if the failure to detect tyrosine phosphorylated GRB2 was due to the rapid dephosphorylation by a protein tyrosine phosphatase, a potent tyrosine phosphatase inhibitor, vanadate, was tested for its effects upon GRB2 phosphorylation. ($^{32}$P)-orthophosphate-labelled cells were incubated with or without vanadate at 37° C. for 20 min prior to the addition of EGF, and GRB2 phosphorylation was assessed as described above. Vanadate treatment of EGF stimulated cells similarly did not result in detectable GRB2 phosphorylation.

The inability to demonstrate GRB2 phosphorylation was further corroborated in a double immunoprecipitation experiment. ($^{32}$P) -labeled HER 14 lysates were immunoprecipitated with anti-PTyr antibodies bound to beads, eluted and the eluates subjected to a second immunoprecipitation with anti-GRB2 antibodies. While clear stimulation of tyrosine phosphorylation was demonstrated in these lysates no significant phosphorylation of the antiP-Tyr-associated GRB2 fraction was detected. Thus, our data demonstrates that while GRB2 associates with the EGF and PDGF-receptors it is not a good substrates for either receptors, and that GRB2 is not phosphorylated by a tyrosine or serine/threonine kinase acting later in the signaling pathway induced by ligand binding. This data suggests that growth factor regulation of GRB2 is not mediated through GRB2 phosphorylation.

GRB2 tyrosine phosphorylation was detected in 293 cells transiently overexpressing PDGFR and GRB2 as determined by anti-PTyr and anti-GRB2 blotting (data not shown). A shift in the mobility of GRB2 was detected on anti-GRB2 (Ab86) blots, in the presence of activated PDGF receptor and the lower mobility form was shown to be tyrosine phosphorylated by anti-PTyr blotting. Similar experiments have confirmed that the immunoprecipitating antibody (Ab 50) will recognize tyrosine phosphorylated GRB2. This data suggest that it is possible to tyrosine phosphorylate GRB2 under conditions of overexpression of both receptor and GRB2 protein.

Interestingly, a phosphoprotein of approximately 55 kDa was found to con-immunoprecipitate with GRB2 using immune, but not preimmune sera, in lysates from EGF or PDGF stimulated HER14 cells (FIG. 31, lanes 3, 4 and 7, 8). The association of the 55 kDa protein with GRB2 immunoprecipitates was dependent upon growth factor stimulation, since this interaction was not observed in GRB2 immunoprecipitates from unstimulated cell lysates. The identity of this protein is unknown. GRB2 represents the human homologue of the C. elegans gene product sem-5.

As mentioned earlier, GRB2 is composed of one SH2 domain flanked by two SH3 domains in the order of SH3, SH2, SH3. A C. elegans gene encoding for a protein with similar size and domain order has been cloned in the laboratory of R. Horvitz (Clark et al., 1992). This gene, called sem-5, plays a crucial role in C. elegans development as mutations in sem-5 impair both vulval development and sex myoblast migration. FIG. 32 shows a comparison of the amino acid sequences of GRB2 and sem-5. The N-SH3 domains are 58% (63%) and the C-terminal SH3 domains are 58% identical (60%), respectively. The overall sequence identity (similarity) is 58% (63%). Considering the evolutionary distance between human and nematode, these two genes are very similar suggesting the sem-5 represents the C. elegans homologue of GRB2.

DISCUSSION

A novel EGF receptor binding protein of the present invention was cloned by the CORT expression cloning method of the present invention, designated as GRB2. This 25 kDa protein contains on SH2 domain and two SH3 domains. GRB2 is widely expressed, as determined by Northern analysis in ten different murine tissues. It is also expressed in every human, monkey and murine cell line tested as revealed by Northern blotting, immunoprecipitation and immunoblotting experiments. Also shown is that GRB2 associates with EGF and PDGF receptors in a ligand-dependent manner, both in vitro and in living cells. Like other SH2-domain containing proteins, the association between GRB2 and growth factor receptors is mediated by the SH2 domain, can be dependent upon receptor tyrosine autophosphorylation, and involves a direct interaction between GRB2 and the tyrosine phosphorylated receptors.

Despite the fact that GRB2 forms stable complexes with tyrosine phosphorylated, on tyrosine, serine, or threonine residues at physiologic levels of expression to any significant extent. The fact that pretreatment of cells with vanadate did not increase GRB2 phosphorylation indicates that GRB2 is not rapidly dephosphorylated by tyrosine phosphatases.

The extent of sequence homology between GRB2 and sem-5 is striking considering the evolutionary distance between nematode and man. The 58% sequence identity (63% similarity) and the conserved overall architecture of these tow proteins suggest that sem-5 and C. elegans homologue of GRB2 or a closely related member of the same gene family. the similarity between GRB2 and sem-5 is higher than the similarity between let-23 and EGFR; approximately 44% and 28.7% sequence similarities in the catalytic kinase and ligand binding domain, respectively (Aroian et al. Nature 348:693–699 1990).

By detailed genetic studies the laboratories of Horvitz and Sternberg have identified gene crucial for C. elegans vulval development and sex myoblast migration (Horvitz and Sternberg Nature 351:535–341 1991; Aroian et al. Nature 348693–699 1990; Clark et al. Nature In press 1992). It was shown that mutation sin let-23 (EGFR like), sem-5 (GRB2) or let-60 (ras like) lead to defects in vulval development, while sem-5 also functions in sex myoblast migration. It was therefore proposed that the products of these genes lie along the same signal transduction pathway crucial for normal vulval development. Hence, on the basis of genetic studies of C. elegans (Horvitz and Sternberg Nature 351:535–541; Aroian et al. Nature 348:693–699; Clark Nature in press 1992), previous studies on growth factor receptors (Ullrich and Schlessinger Cell 61:203–211 (1990)) and the results presented in this report it is possible to propose a model for the information flow and interaction among these proteins in C. elegans and mammalian cells (FIG. 33). Because of the similarity of sem-5 with GRB2 and let-23 with the EGFR it is likely that sem-5 with GRB2 and let-23 with the EGFR it is likely that sem-5 will bind tyrosine phosphorylated let-23 via its SH2 domain according to the scheme presented in FIG. 8. Since mutations in let-60 cause a similar phenotype as mutations in either let-23 and Sem-5, and since activated ras can rescue let-23 and sem-5 mutations, it is reasonable to assume the let-60/ras functions downstream from EGFR and GRB2 and that GRB2 is somehow involved in regulation of ras activity. In this regard, the 55 kDa phosphoprotein which binds to GRB2 in response to growth factor stimulation is expected to be a downstream signaling molecule regulated upon GRB2 binding to activated growth factor receptors.

EXAMPLE VIII:

Utilization of an Alternative Phage Library Expression System For Detecting Proteins of the Present Invention A T7 phage library expression system, used an alternative to the phage λgt11 system described in Example II above, was used to express tyrosine kinase target proteins, as presented in the above Examples, with modifications as described below. A T7 polymerase system (Palazzalo et al., Gene 88, 25 (1990); λEXlox vector, Novagen, Inc.), based on the PET expression systems of Studier and coworkers (Studier et al Meth. Enzymol. 185:60 (1990)) fusing cDNA clones to a fragment of the T7 capsid protein T10 under the control of the T7 promoter. These phages were then used to infect E. coli harboring the T7 polymerase under lacUV5 control. Induction with IPTG generated the T7 polymerase which then initiated transcription of the fusion protein encoded by the phage library. The SH2 domain fragment of PLC-γ1 was incorporated into this phage and analyzed the binding of the phosphorylated EGFR, as described in the above Examples. The DNA fragment containing the human PLC-γ1 (Burgess et al., Mol. Cell. Biol. 10, 4770 (1990)) was amplified by PCT with primers that incorporated EcoR1 sites such that the PLC-γ1 fragment would be in the correct reading frame for λgt11. The amplified DNA was cut with EcoR1 and ligated into EcoR1 digested λgt11 DNA (Promega). After packaging (Gigapack, Stragene), the phages were plated and screened with PLC-γ1 antibody using known techniques (Huynh, T. V. et al. In: DNA CLONING, ed. Glover, IRL Press, Oxford, 1:49–78 (1985)). This phage was then tested for binding to a cyanogen bromide generated fragment from $^{32}$P-ATP labelled EGFR as described in the above Examples. An identical approach was taken to clone the two SH2 domains into λgt11 or λEXlox vectors.

Figure 25A:
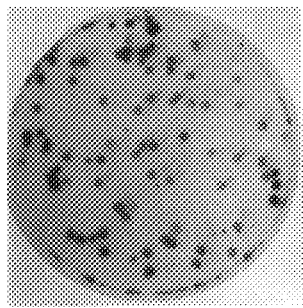
Figure 25B:
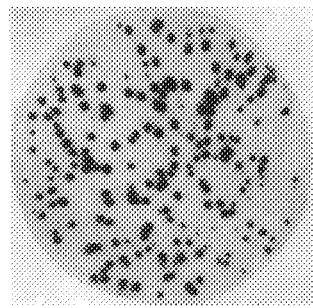
Figure 25C:
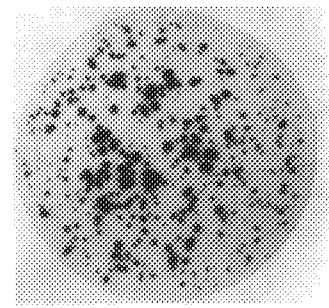

As can be seen in FIGS. 25A–C, uniform binding of the EGFR was seen in the that appeared stronger than was seen with the λgt11 system (compare FIGS. 25A and 25B). We also cloned in a longer fragment which ran from 532–1290 of PLC-γ1 and this was also easily seen in the T7 system (FIG. 25C). The T7 plaques although mostly smaller than the λgt11 plaques gave stronger signals. This makes this system particularly suitable for library screening when there as thousands of small plaques per plate. The major advantage of this system is the high level of protein expression due to the greater activity of the T7 polymerase versus E. coli RNA polymerase. It may also be that the fusion proteins using the smaller T10 gene fragment (26 kd versus the 110 kd B-galactosidase of λgt11) yields more stable expression and that its hydrophobic character promotes binding to nitrocellulose. In addition to directional cloning, the λEXlox phages also allow for automatic conversion to a PET plasmid (Palazzalo et al., Gene 88, 25 (1990)) which can be useful for expression of a fusion protein for antibody production. Accordingly, screening an T7 expression library is expected to give superior results than for λgt11 for such a cloning strategy of the present invention.

Of 1.6 million clones of a directional oligo dT primed mouse T7 (λEXlox) library screened, nine positive clones were obtained. The library from a 16 day mouse embryo was obtained from Novagen. The library was plated at 40,000 phages per plate in E. coli pLysS according to known methods. After growth for 8 hours, plates were covered with nitrocellulose impregnated with 1 mM IPTG. Plates were grown overnight and the filters probed as described in the above Examples. Positive clones were selected and reprobed until plaques were purified. Phages were then converted to plasmids utilizing the bacterial strain Bm25.5 per manufacturer's instruction. These plasmids were used to transform bacterial strain DH5∝ and the resultant plasmids subjected to double stranded sequencing using known techniques (Sequenase Version 2, U.S. Biochemical). Six of nine clones encoded proteins that were similar or identical to other known genes which contained SH2 domains TABLE I—see attached. Figures). The comparison of two of these protein sequences of the present invention, GRB-3 and GRB-4, to their known counterparts is displayed in FIGS. 17 and 18. Partial sequence of three clones revealed that they were closely related to the avian oncogene v-crk. GRB-3 has a high degree of identity with v-crk beginning with the methionine at residue 32 and this methionine has been found to be the start site of avian c-crk. In the sequence carboxy-terminus to this methionine, there is 77% amino acid homology (FIG. 17) and 80% DNA similarity between v-crk and GRB-3. GRB-4, was similar to nck (FIG. 18), a human protein composed of three SH3 domains and one SH2 domain. Our clone contained one SH3 domain and one SH2 domain and was 74% identical at the protein level and 66% similar at the DNA level in the open reading frame. We also cloned two SH2 domain proteins with intrinsic enzymatic activity.

TABLE I

| SH2 DOMAIN PROTEIN | CLONES ISOLATED | DESCRIPTION |
|---|---|---|
| GRB-3 | #19,#76,#80 | crk-like |
| GRB-4 | #64 | nck-like |
| GRB-5 | #63B | fyn |
| GRB-6 | #88 | PLC-γ1 |
| GRB-7 | #63A,#66,#88 | novel protein |

A remaining clone encoded a new protein with a unique SH2 domain as GRB-7. To obtain a full length DNA clone, the T7 (λEXlox) library was plated in an E. coli strain without T7 polymerase gene and routine DNA hybridization performed with a 700 base pair EcoR1 fragment from the GRB-7 clone using standard published techniques (Ausubel et al eds., Current Protocols in Molecular Biology, Wiley Interscience, N.Y. (1987, 1992)). Several overlapping clones were identified which were used for DNA sequencing to obtain the full length GRB-7 protein sequence shown in FIG. 19. A schematic representation of GRB-7 is displayed in FIG. 20 depicting the regions of similarity to known proteins as discussed below. The protein is 535 amino acids in length and has one SH2 domain at its extreme carboxy-terminus. In FIG. 21, the SH2 domain of GRB-7 is compared to other SH2 domains including mouse fyn, human PLC-γ1 and the crk and nck-like proteins we cloned in this project. One interesting aspect is that GRB-7 has an isoleucine at amino acid 448, whereas other SH2 domains have a leucine at this position. To look for other protein motifs in GRB-7, a sequence of 433 amino acids from GRB-7 which excluded the SH2 domain was used to scan the Swissprot and GenEmbl databases, as described herein. Amino acids 242 to 339 of GRB-7, showed similarity to a sequence from the central region of ras GAP. Over this region of 91 amino acids from ras GAP, GRB-7 has 26% identity and 42% similarity allowing for conservative substitutions (FIG. 22). This region of ras GAP lies between the SH2/SH3 domains and he GTPase activating carboxy-terminal region and has not been assigned a specific function. The amino-terminal sequence of GRB-7 was found to be proline rich and thus has similarity to many other proline rich proteins. GRB-7 does have an extended region of limited similarity to the catalytic domain of protein phosphatase 2B including this proline rich region (FIG. 23) but no significant similarity was found to other serine/threonine phosphatase such as protein phosphatase 1 or 2A.

A northern blot of GRB-7 in mouse tissues is presented in FIG. 24. Oligo dt selected MRNA was probed with the same EcoR1 fragment used to isolate full length GRB-7. See Ausubel et al eds., *Current Protocols in Molecular Biology*, Wiley Interscience, N.Y. (1987, 1992) and Sap et al *Proc. Natl. Acad. Sci. USA* 87:6112 (1990). The MRNA was extracted from six week old mice tissues by known methods, e.g., as described by Sap et al *Proc. Natl. Acad. Sci. USA* 87:6112 (1990). Approximately 3 µg was run on a 1.2% agarose formaldehyde gel and blotted to nytran (Schleicher and Scheull). The blot was probed with a DNA fragment that encodes amino acids 297 to 515 and labelled with $^{32}$P-dCTP using a random priming labeling kit (U.S. Biochemical). Blots were probed in 0.5M sodium phosphate, pH 7.2, 7% sodium dodecyl sulfate and 1 mM EDTA at 65° C. overnight. Blots were washed in 40 mM sodium phosphate, pH 7.2, 1% SDS and 1 mM EDTA at 65° C. After exposure of the GRB-7 blot for 4 days, blots were stripped and reprobed with actin (exposure 36 hours). The highest signal was detected in liver and kidney, but was also detected in ovary and testes. On longer exposure, a weak signal was detected in lung.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

What is claimed is:

1. A method for identifying a substance that affects a Src homology region 2-phosphorylated ligand regulatory system, comprising:
  (a) contacting a peptide comprising a Src homology region 2 domain having the amino acid sequence depicted in SEQ ID NO. 10, SEQ ID NO. 17, SEQ ID NO:18 or SEQ ID NO. 44, a phosphorylated ligand and a test substance under conditions which permit the formation of a Src homology region 2-phosphorylated ligand complex;
  (b) measuring the level of complex formed; and
  (c) comparing the level in (b) with the level of complex formed when the peptide and the phosphorylated ligand are contacted as in (a) but in the absence of test substance, such that a difference in the two levels identifies a test substance that affects a Src homology region 2-phosphorylated ligand regulatory system.

2. The method of claim 1 wherein the peptide comprises a Src homology region 2 domain having the amino acid sequence depicted in SEQ ID NO. 10.

3. The method of claim 1 wherein the peptide comprises a Src homology region 2 domain having the amino acid sequence depicted in SEQ ID NO. 17.

4. The method of claim 1 wherein the peptide comprises a Src homology region 2 domain having the amino acid sequence depicted in SEQ ID NO. 18.

5. The method of claim 1 wherein the peptide comprises a Src homology region 2 domain having the amino acid sequence depicted in SEQ ID NO. 44.

6. The method of claim 1, wherein the test substance affects a Src homology region 2-phosphorylated ligand regulatory system by disrupting or inhibiting the action of a GRB-1 protein comprising the amino acid sequence depicted in SEQ ID NO. 17 or SEQ ID NO 18, a GRB-2 protein comprising the amino acid sequence depicted in SEQ ID NO. 44 or a GRB-7 protein comprising the amino acid sequence depicted in SEQ ID NO. 10.

7. A method for identifying a substance that affects a Src homology region 2-phosphorylated ligand regulatory system, comprising:
  (a) contacting a known concentration of peptide comprising a Src homology region 2 domain having the amino acid sequence depicted in SEQ ID NO. 10, SEQ ID NO. 17, SEQ ID NO:18 or SEQ ID NO. 44, a known concentration of phosphorylated ligand and a test substance under conditions which permit the formation of a Src homology region 2-phosphorylated ligand complex;
  (b) measuring the level of complex formed, the level of non-complexed peptide and the level of non-complexed phosphorylated ligand; and
  (c) comparing the levels in (b) with the level of complex formed, the level of non-complexed peptide and the level of non-complexed phosphorylated ligand, when the peptide and the phosphorylated ligand are contacted as in (a) but in the absence of test substance, such that a difference in the levels identifies a test substance that affects a Src homology region 2-phosphorylated ligand regulatory system.

8. The method of claim 7 wherein the peptide comprises a Src homology region 2 domain having the amino acid sequence depicted in SEQ ID NO. 10.

9. The method of claim 7 wherein the peptide comprises a Src homology region 2 domain having the amino acid sequence depicted in SEQ ID NO. 17.

10. The method of claim 7 wherein the peptide comprises a Src homology region 2 domain having the amino acid sequence depicted in SEQ ID NO. 18.

11. The method of claim 7 wherein the peptide comprises a Src homology region 2 domain having the amino acid sequence depicted in SEQ ID NO. 44.

12. The method of claim 7, wherein the test substance affects a Src homology region 2-phosphorylated ligand regulatory system by disrupting or inhibiting the action of a GRB-1 protein comprising the amino acid sequence depicted in SEQ ID NO. 17 or SEQ ID NO. 18, a GRB-2 protein comprising the amino acid sequence depicted in SEQ ID NO. 44 or a GRB-7 protein comprising the amino acid sequence depicted in SEQ ID NO. 10.

13. A method for identifying a substance that affects a Src homology region 2-phosphorylated ligand regulatory system, comprising:
(a) contacting a known concentration of Src homology region 2-phosphorylated ligand complex, said complex comprising a peptide comprising a Src homology region 2 domain having the amino acid sequence depicted in SEQ ID NO. 10, SEQ ID NO. 17, SEQ ID NO. 18 or SEQ ID NO:44 and phosphorylated ligand, with a test substance; and
(b) measuring disruption of the complex by comparing the concentration of complex in (a) to the known concentration of complex present prior to contacting with test substance, so that if complex is disrupted, a substance that affects a Src homology region 2-phosphorylated ligand regulatory system is identified.

14. The method of claim 13 wherein the peptide comprises a Src homology region 2 domain having the amino acid sequence depicted in SEQ ID NO. 10.

15. The method of claim 13 wherein the peptide comprises a Src homology region 2 domain having the amino acid sequence depicted in SEQ ID NO. 17.

16. The method of claim 13 wherein the peptide comprises a Src homology region 2 domain having the amino acid sequence depicted in SEQ ID NO. 18.

17. The method of claim 13 wherein the peptide comprises a Src homology region 2 domain having the amino acid sequence depicted in SEQ ID NO. 44.

18. The method of claim 13, wherein said substance disrupts the action of a GRB-1 protein having the amino acid sequence of SEQ ID NO. 17 or SEQ ID NO. 18, a GRB-2 protein having the amino acid sequence of SEQ ID NO. 44, or a GRB-7 protein comprising the amino acid sequence of SEQ ID NO. 10.

* * * * *

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 3372 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 43..2214

( x i ) SEQUENCE DESCRIPTION: SEQ ID NO:1:

```
TACAACCAGG  CTCAACTGTT  GCATGGTAGC  AGATTTGCAA  AC ATG AGT GCT GAG          54
                                                  Met Ser Ala Glu
                                                   1

GGG TAC CAG TAC AGA GCG CTG TAT GAT TAT AAA AAG GAA AGA GAA GAA           102
Gly Tyr Gln Tyr Arg Ala Leu Tyr Asp Tyr Lys Lys Glu Arg Glu Glu
 5              10                  15                  20

GAT ATT GAC TTG CAC TTG GGT GAC ATA TTG ACT GTG AAT AAA GGG TCC          150
Asp Ile Asp Leu His Leu Gly Asp Ile Leu Thr Val Asn Lys Gly Ser
         25                 30                  35
```

```
TTA GTA GCT CTT GGA TTC AGT GAT GGA CAG GAA GCC AGG CCT CGA AGA       198
Leu Val Ala Leu Gly Phe Ser Asp Gly Gln Glu Ala Arg Pro Arg Arg
         40                  45                  50

AAT GGC TGG TTA AAT GGC TAT AAT GAA ACC ACA GGG GAA AAG GGG GAC       246
Asn Gly Trp Leu Asn Gly Tyr Asn Glu Thr Thr Gly Glu Lys Gly Asp
         55                  60                  65

TTT CCG GGA ACT TAC GTA GAA TAT ATT GGA AGG AAA AAA ATC TCG CCT       294
Phe Pro Gly Thr Tyr Val Glu Tyr Ile Gly Arg Lys Lys Ile Ser Pro
     70                  75                  80

CCC ACA CCA AAG CCC CGG CCA CCT CGG CCT CTT CCT GTT GCA CCA GGT       342
Pro Thr Pro Lys Pro Arg Pro Pro Arg Pro Leu Pro Val Ala Pro Gly
 85                  90                  95                  100

TCT TCG AAA ACT GAA GCA GAT GTT GAA CAA CAA GCT TTG ACT CTC CCG       390
Ser Ser Lys Thr Glu Ala Asp Val Glu Gln Gln Ala Leu Thr Leu Pro
                 105                 110                 115

GAT CTT GCA GAG CAG TTT GCC CCT CCT GAC ATT GCC CCG CCT CTT CTT       438
Asp Leu Ala Glu Gln Phe Ala Pro Pro Asp Ile Ala Pro Pro Leu Leu
             120                 125                 130

ATC AAG CTC GTG GAA GCC ATT GAA AAG AAA GGT CTG GAA TGT TCA ACT       486
Ile Lys Leu Val Glu Ala Ile Glu Lys Lys Gly Leu Glu Cys Ser Thr
         135                 140                 145

CTA TAC AGA ACA CAG AGC TCC AGC AAC CTG GCA GAA TTA CGA CAG CTT       534
Leu Tyr Arg Thr Gln Ser Ser Ser Asn Leu Ala Glu Leu Arg Gln Leu
     150                 155                 160

CTT GAT TGT GAT ACA CCC TCC GTG GAC TTG GAA ATG ATC GAT GTG CAC       582
Leu Asp Cys Asp Thr Pro Ser Val Asp Leu Glu Met Ile Asp Val His
165                 170                 175                 180

GTT TTG GCT GAC GCT TTC AAA CGC TAT CTC CTG GAC TTA CCA AAT CCT       630
Val Leu Ala Asp Ala Phe Lys Arg Tyr Leu Leu Asp Leu Pro Asn Pro
                 185                 190                 195

GTC ATT CCA GCA GCC GTT TAC AGT GAA ATG ATT TCT TTA GCT CCA GAA       678
Val Ile Pro Ala Ala Val Tyr Ser Glu Met Ile Ser Leu Ala Pro Glu
             200                 205                 210

GTA CAA AGC TCC GAA GAA TAT ATT CAG CTA TTG AAG AAG CTT ATT AGG       726
Val Gln Ser Ser Glu Glu Tyr Ile Gln Leu Leu Lys Lys Leu Ile Arg
         215                 220                 225

TCG CCT AGC ATA CCT CAT CAG TAT TGG CTT ACG CTT CAG TAT TTG TTA       774
Ser Pro Ser Ile Pro His Gln Tyr Trp Leu Thr Leu Gln Tyr Leu Leu
     230                 235                 240

AAA CAT TTC TTC AAG CTC TCT CAA ACG TCC AGC AAA AAT CTG TTG AAT       822
Lys His Phe Phe Lys Leu Ser Gln Thr Ser Ser Lys Asn Leu Leu Asn
245                 250                 255                 260

GCA AGA GTA CTC TCT GAA ATT TTC AGC CCT ATG CTT TTC AGA TTC TCA       870
Ala Arg Val Leu Ser Glu Ile Phe Ser Pro Met Leu Phe Arg Phe Ser
                 265                 270                 275

GCA GCC AGC TCT GAT AAT ACT GAA AAC CTC ATA AAA GTT ATA GAA ATT       918
Ala Ala Ser Ser Asp Asn Thr Glu Asn Leu Ile Lys Val Ile Glu Ile
             280                 285                 290

TTA ATC TCA ACT GAA TGG AAT GAA CGA CAG CCT GCA CCA GCA CTG CCT       966
Leu Ile Ser Thr Glu Trp Asn Glu Arg Gln Pro Ala Pro Ala Leu Pro
         295                 300                 305

CCT AAA CCA CCA AAA CCT ACT ACT GTA GCC AAC AAC GGT ATG AAT AAC      1014
Pro Lys Pro Pro Lys Pro Thr Thr Val Ala Asn Asn Gly Met Asn Asn
     310                 315                 320

AAT ATG TCC TTA CAA AAT GCT GAA TGG TAC TGG GGA GAT ATC TCG AGG      1062
Asn Met Ser Leu Gln Asn Ala Glu Trp Tyr Trp Gly Asp Ile Ser Arg
325                 330                 335                 340

GAA GAA GTG AAT GAA AAA CTT CGA GAT ACA GCA GAC GGG ACC TTT TTG      1110
Glu Glu Val Asn Glu Lys Leu Arg Asp Thr Ala Asp Gly Thr Phe Leu
                 345                 350                 355
```

| | | | | | | | | | | | | | | | |
|---|---|---|---|---|---|---|---|---|---|---|---|---|---|---|---|
| GTA | CGA | GAT | GCG | TCT | ACT | AAA | ATG | CAT | GGT | GAT | TAT | ACT | CTT | ACA | CTA | 1158 |
| Val | Arg | Asp | Ala | Ser | Thr | Lys | Met | His | Gly | Asp | Tyr | Thr | Leu | Thr | Leu | |
| | | | 360 | | | | | 365 | | | | 370 | | | | |
| AGG | AAA | GGG | GGA | AAT | AAC | AAA | TTA | ATC | AAA | ATA | TTT | CAT | CGA | GAT | GGG | 1206 |
| Arg | Lys | Gly | Gly | Asn | Asn | Lys | Leu | Ile | Lys | Ile | Phe | His | Arg | Asp | Gly | |
| | | 375 | | | | | 380 | | | | | 385 | | | | |
| AAA | TAT | GGC | TTC | TCT | GAC | CCA | TTA | ACC | TTC | AGT | TCT | GTG | GTT | GAA | TTA | 1254 |
| Lys | Tyr | Gly | Phe | Ser | Asp | Pro | Leu | Thr | Phe | Ser | Ser | Val | Val | Glu | Leu | |
| | 390 | | | | | 395 | | | | | 400 | | | | | |
| ATA | AAC | CAC | TAC | CGG | AAT | GAA | TCT | CTA | GCT | CAG | TAT | AAT | CCC | AAA | TTG | 1302 |
| Ile | Asn | His | Tyr | Arg | Asn | Glu | Ser | Leu | Ala | Gln | Tyr | Asn | Pro | Lys | Leu | |
| 405 | | | | | 410 | | | | | 415 | | | | | 420 | |
| GAT | GTG | AAA | TTA | CTT | TAT | CCA | GTA | TCC | AAA | TAC | CAA | CAG | GAT | CAA | GTT | 1350 |
| Asp | Val | Lys | Leu | Leu | Tyr | Pro | Val | Ser | Lys | Tyr | Gln | Gln | Asp | Gln | Val | |
| | | | | 425 | | | | | 430 | | | | | 435 | | |
| GTC | AAA | GAA | GAT | AAT | ATT | GAA | GCT | GTA | GGG | AAA | AAA | TTA | CAT | GAA | TAT | 1398 |
| Val | Lys | Glu | Asp | Asn | Ile | Glu | Ala | Val | Gly | Lys | Lys | Leu | His | Glu | Tyr | |
| | | | 440 | | | | | 445 | | | | | 450 | | | |
| AAC | ACT | CAG | TTT | CAA | GAA | AAA | AGT | CGA | GAA | TAT | GAT | AGA | TTA | TAT | GAA | 1446 |
| Asn | Thr | Gln | Phe | Gln | Glu | Lys | Ser | Arg | Glu | Tyr | Asp | Arg | Leu | Tyr | Glu | |
| | | 455 | | | | | 460 | | | | | 465 | | | | |
| GAA | TAT | ACC | CGC | ACA | TCC | CAG | GAA | ATC | CAA | ATG | AAA | AGG | ACA | GCT | ATT | 1494 |
| Glu | Tyr | Thr | Arg | Thr | Ser | Gln | Glu | Ile | Gln | Met | Lys | Arg | Thr | Ala | Ile | |
| | 470 | | | | | 475 | | | | | 480 | | | | | |
| GAA | GCA | TTT | AAT | GAA | ACC | ATA | AAA | ATA | TTT | GAA | GAA | CAG | TGC | CAG | ACC | 1542 |
| Glu | Ala | Phe | Asn | Glu | Thr | Ile | Lys | Ile | Phe | Glu | Glu | Gln | Cys | Gln | Thr | |
| 485 | | | | | 490 | | | | | 495 | | | | | 500 | |
| CAA | GAG | CGG | TAC | AGC | AAA | GAA | TAC | ATA | GAA | AAG | TTT | AAA | CGT | GAA | GGC | 1590 |
| Gln | Glu | Arg | Tyr | Ser | Lys | Glu | Tyr | Ile | Glu | Lys | Phe | Lys | Arg | Glu | Gly | |
| | | | | 505 | | | | | 510 | | | | | 515 | | |
| AAT | GAG | AAA | GAA | ATA | CAA | AGG | ATT | ATG | CAT | AAT | TAT | GAT | AAG | TTG | AAG | 1638 |
| Asn | Glu | Lys | Glu | Ile | Gln | Arg | Ile | Met | His | Asn | Tyr | Asp | Lys | Leu | Lys | |
| | | | 520 | | | | | 525 | | | | | 530 | | | |
| TCT | CGA | ATC | AGT | GAA | ATT | ATT | GAC | AGT | AGA | AGA | AGA | TTG | GAA | GAA | GAC | 1686 |
| Ser | Arg | Ile | Ser | Glu | Ile | Ile | Asp | Ser | Arg | Arg | Arg | Leu | Glu | Glu | Asp | |
| | | 535 | | | | | 540 | | | | | 545 | | | | |
| TTG | AAG | AAG | CAG | GCA | GCT | GAG | TAT | CGA | GAA | ATT | GAC | AAA | CGT | ATG | AAC | 1734 |
| Leu | Lys | Lys | Gln | Ala | Ala | Glu | Tyr | Arg | Glu | Ile | Asp | Lys | Arg | Met | Asn | |
| | 550 | | | | | 555 | | | | | 560 | | | | | |
| AGC | ATT | AAA | CCA | GAC | CTT | ATC | CAG | CTG | AGA | AAG | ACG | AGA | GAC | CAA | TAC | 1782 |
| Ser | Ile | Lys | Pro | Asp | Leu | Ile | Gln | Leu | Arg | Lys | Thr | Arg | Asp | Gln | Tyr | |
| 565 | | | | | 570 | | | | | 575 | | | | | 580 | |
| TTG | ATG | TGG | TTG | ACT | CAA | AAA | GGT | GTT | CGG | CAA | AAG | AAG | TTG | AAC | GAG | 1830 |
| Leu | Met | Trp | Leu | Thr | Gln | Lys | Gly | Val | Arg | Gln | Lys | Lys | Leu | Asn | Glu | |
| | | | | 585 | | | | | 590 | | | | | 595 | | |
| TGG | TTG | GGC | AAT | GAA | AAC | ACT | GAA | GAC | CAA | TAT | TCA | CTG | GTG | GAA | GAT | 1878 |
| Trp | Leu | Gly | Asn | Glu | Asn | Thr | Glu | Asp | Gln | Tyr | Ser | Leu | Val | Glu | Asp | |
| | | | 600 | | | | | 605 | | | | | 610 | | | |
| GAT | GAA | GAT | TTG | CCC | CAT | CAT | GAT | GAG | AAG | ACA | TGG | AAT | GTT | GGA | AGC | 1926 |
| Asp | Glu | Asp | Leu | Pro | His | His | Asp | Glu | Lys | Thr | Trp | Asn | Val | Gly | Ser | |
| | | 615 | | | | | 620 | | | | | 625 | | | | |
| AGC | AAC | CGA | AAC | AAA | GCT | GAA | AAC | CTG | TTG | CGA | GGG | AAG | CGA | GAT | GGC | 1974 |
| Ser | Asn | Arg | Asn | Lys | Ala | Glu | Asn | Leu | Leu | Arg | Gly | Lys | Arg | Asp | Gly | |
| | 630 | | | | | 635 | | | | | 640 | | | | | |
| ACT | TTT | CTT | GTC | CGG | GAG | AGC | AGT | AAA | CAG | GGC | TGC | TAT | GCC | TGC | TCT | 2022 |
| Thr | Phe | Leu | Val | Arg | Glu | Ser | Ser | Lys | Gln | Gly | Cys | Tyr | Ala | Cys | Ser | |
| 645 | | | | | 650 | | | | | 655 | | | | | 660 | |
| GTA | GTG | GTG | GAC | GGC | GAA | GTA | AAG | CAT | TGT | GTC | ATA | AAC | AAA | ACA | GCA | 2070 |
| Val | Val | Val | Asp | Gly | Glu | Val | Lys | His | Cys | Val | Ile | Asn | Lys | Thr | Ala | |
| | | | | 665 | | | | | 670 | | | | | 675 | | |

```
ACT  GGC  TAT  GGC  TTT  GCC  GAG  CCC  TAT  AAC  TTG  TAC  AGC  TCT  CTG  AAA       2118
Thr  Gly  Tyr  Gly  Phe  Ala  Glu  Pro  Tyr  Asn  Leu  Tyr  Ser  Ser  Leu  Lys
               680                      685                      690

GAA  CTG  GTG  CTA  CAT  TAC  CAA  CAC  ACC  TCC  CTT  GTG  CAG  CAC  ACC  GAC       2166
Glu  Leu  Val  Leu  His  Tyr  Gln  His  Thr  Ser  Leu  Val  Gln  His  Thr  Asp
               695                      700                      705

TCC  CTC  AAT  GTC  ACA  CTA  GCC  TAC  CCA  GTA  TAT  GCA  CAG  CAG  AGG  CGA       2214
Ser  Leu  Asn  Val  Thr  Leu  Ala  Tyr  Pro  Val  Tyr  Ala  Gln  Gln  Arg  Arg
          710                      715                      720

TGAAGCGCTT  ACTCTTTGAT  CCTTCTCCTG  AAGTTCAGCC  ACCCTGAGGC  CTCTGGAAAG            2274

CAAAGGGCTC  CTCTCCAGTC  TGATCTGTGA  ATTGAGCTGC  AGAAACGAAG  CCATCTTTCT            2334

TTGGATGGGA  CTAGAGCTTT  CTTTGACAAA  AAAGAAGTAG  GGGAAGACAT  GCAGCCTAAG            2394

GCTGTATGAT  GACCACACGT  TCCTAAGCTG  GAGTGCTTAT  CCCTTCTTTT  TCTTTTTTTC            2454

TTTGGTTTAA  TTTAAAGCCA  CAACCACATA  CAACACAAAG  AGAAAAAGAA  ATGCAAAAAT            2514

CTCTGCGTGC  AGGGACAAAG  AGGCCTTTAA  CCATGGTGCT  TGTTAATGCT  TTCTGAAGCT            2574

TTACCAGCTG  AAAGTTGGGA  CTCTGGAGAG  CGGAGGAGAG  AGAGGCAGAA  GAACCCTGGC            2634

CTGAGAAGGT  TTGGTCCAGC  CTGGTTTAGC  CTGGATGTTG  CTGTGCACGG  TGGACCCAGA            2694

CACATCGCAC  TGTGGATTAT  TTCATTTTGT  AACAAATGAA  CGATATGTAG  CAGAAAGGCA            2754

CGTCCACTCA  CAAGGGACGC  TTTGGGAGAA  TGTCAGTTCA  TGTATGTTCA  GAAGAAATTC            2814

TGTCATAGAA  AGTGCCAGAA  AGTGTTTAAC  TTGTCAAAAA  ACAAAAACCC  AGCAACAGAA            2874

AAATGGAGTT  TGGAAAACAG  GACTTAAAAT  GACATTCAGT  ATATAAAATA  TGTACATAAT            2934

ATTGGATGAC  TAACTATCAA  ATAGATGGAT  TTGTATCAAT  ACCAAATAGC  TTCTGTTTTG            2994

TTTTGCTGAA  GGCTAAATTC  ACAGCGCTAT  GCAATTCTTA  ATTTTCATTA  AGTTGTATT             3054

TCAGTTTTAA  ATGTACCTTC  AGAATAAGCT  TCCCCACCCC  AGTTTTGTT   GCTTGAAAAT            3114

ATTGTTGTCC  CGGATTTTTG  TTAATATTCA  TTTTTGTTAT  CCTTTTTTAA  AAATAAATGT            3174

ACAGGATGCC  AGTAAAAAAA  AAAATGGCTT  CAGAATTAAA  ACTATGAAAT  ATTTTACAGT            3234

TTTTCTTGTA  CAGAGTACTT  GCTGTTAGCC  CAAGGTTAAA  AAGTTCATAA  CAGATTTTTT            3294

TTGGACTGTT  TTGTTGGGCA  GTGCCTGATA  AGCTTCAAAG  CTGCTTTATT  CAATAAAAAA            3354

AAAACCCGAA  TTCACTGG                                                              3372
```

( 2 ) INFORMATION FOR SEQ ID NO:2:

( i ) SEQUENCE CHARACTERISTICS:
        ( A ) LENGTH: 724 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met  Ser  Ala  Glu  Gly  Tyr  Gln  Tyr  Arg  Ala  Leu  Tyr  Asp  Tyr  Lys  Lys
 1                   5                        10                       15

Glu  Arg  Glu  Glu  Asp  Ile  Asp  Leu  His  Leu  Gly  Asp  Ile  Leu  Thr  Val
               20                       25                       30

Asn  Lys  Gly  Ser  Leu  Val  Ala  Leu  Gly  Phe  Ser  Asp  Gly  Gln  Glu  Ala
          35                       40                       45

Arg  Pro  Arg  Arg  Asn  Gly  Trp  Leu  Asn  Gly  Tyr  Asn  Glu  Thr  Thr  Gly
     50                       55                       60

Glu  Lys  Gly  Asp  Phe  Pro  Gly  Thr  Tyr  Val  Glu  Tyr  Ile  Gly  Arg  Lys
65                       70                       75                       80
```

```
Lys  Ile  Ser  Pro  Pro  Thr  Pro  Lys  Pro  Arg  Pro  Pro  Arg  Pro  Leu  Pro
               85                  90                       95

Val  Ala  Pro  Gly  Ser  Ser  Lys  Thr  Glu  Ala  Asp  Val  Glu  Gln  Gln  Ala
               100                 105                      110

Leu  Thr  Leu  Pro  Asp  Leu  Ala  Glu  Phe  Ala  Pro  Asp  Ile  Ala
               115                 120                      125

Pro  Pro  Leu  Leu  Ile  Lys  Leu  Val  Glu  Ala  Ile  Glu  Lys  Lys  Gly  Leu
          130                 135                      140

Glu  Cys  Ser  Thr  Leu  Tyr  Arg  Thr  Gln  Ser  Ser  Asn  Leu  Ala  Glu
145                      150                 155                           160

Leu  Arg  Gln  Leu  Leu  Asp  Cys  Asp  Thr  Pro  Ser  Val  Asp  Leu  Glu  Met
                    165                 170                      175

Ile  Asp  Val  His  Val  Leu  Ala  Asp  Ala  Phe  Lys  Arg  Tyr  Leu  Leu  Asp
                180                      185                 190

Leu  Pro  Asn  Pro  Val  Ile  Pro  Ala  Ala  Val  Tyr  Ser  Glu  Met  Ile  Ser
               195                 200                      205

Leu  Ala  Pro  Glu  Val  Gln  Ser  Ser  Glu  Glu  Tyr  Ile  Gln  Leu  Leu  Lys
          210                      215                      220

Lys  Leu  Ile  Arg  Ser  Pro  Ser  Ile  Pro  His  Gln  Tyr  Trp  Leu  Thr  Leu
225                      230                      235                      240

Gln  Tyr  Leu  Leu  Lys  His  Phe  Phe  Lys  Leu  Ser  Gln  Thr  Ser  Ser  Lys
                    245                      250                      255

Asn  Leu  Leu  Asn  Ala  Arg  Val  Leu  Ser  Glu  Ile  Phe  Ser  Pro  Met  Leu
               260                      265                      270

Phe  Arg  Phe  Ser  Ala  Ala  Ser  Ser  Asp  Asn  Thr  Glu  Asn  Leu  Ile  Lys
          275                           280                      285

Val  Ile  Glu  Ile  Leu  Ile  Ser  Thr  Glu  Trp  Asn  Glu  Arg  Gln  Pro  Ala
290                      295                      300

Pro  Ala  Leu  Pro  Pro  Lys  Pro  Pro  Lys  Pro  Thr  Thr  Val  Ala  Asn  Asn
305                      310                      315                      320

Gly  Met  Asn  Asn  Asn  Met  Ser  Leu  Gln  Asn  Ala  Glu  Trp  Tyr  Trp  Gly
                    325                      330                      335

Asp  Ile  Ser  Arg  Glu  Glu  Val  Asn  Glu  Lys  Leu  Arg  Asp  Thr  Ala  Asp
               340                      345                      350

Gly  Thr  Phe  Leu  Val  Arg  Asp  Ala  Ser  Thr  Lys  Met  His  Gly  Asp  Tyr
          355                      360                      365

Thr  Leu  Thr  Leu  Arg  Lys  Gly  Gly  Asn  Asn  Lys  Leu  Ile  Lys  Ile  Phe
370                      375                      380

His  Arg  Asp  Gly  Lys  Tyr  Gly  Phe  Ser  Asp  Pro  Leu  Thr  Phe  Ser  Ser
385                      390                      395                      400

Val  Val  Glu  Leu  Ile  Asn  His  Tyr  Arg  Asn  Glu  Ser  Leu  Ala  Gln  Tyr
                    405                      410                      415

Asn  Pro  Lys  Leu  Asp  Val  Lys  Leu  Leu  Tyr  Pro  Val  Ser  Lys  Tyr  Gln
               420                      425                      430

Gln  Asp  Gln  Val  Val  Lys  Glu  Asp  Asn  Ile  Glu  Ala  Val  Gly  Lys  Lys
          435                      440                      445

Leu  His  Glu  Tyr  Asn  Thr  Gln  Phe  Gln  Glu  Lys  Ser  Arg  Glu  Tyr  Asp
     450                      455                      460

Arg  Leu  Tyr  Glu  Glu  Tyr  Thr  Arg  Thr  Ser  Gln  Glu  Ile  Gln  Met  Lys
465                      470                      475                      480

Arg  Thr  Ala  Ile  Glu  Ala  Phe  Asn  Glu  Thr  Ile  Lys  Ile  Phe  Glu  Glu
                    485                      490                      495

Gln  Cys  Gln  Thr  Gln  Glu  Arg  Tyr  Ser  Lys  Glu  Tyr  Ile  Glu  Lys  Phe
               500                      505                      510
```

| | | | | | | | | | | | | | | |
|---|---|---|---|---|---|---|---|---|---|---|---|---|---|---|
| Lys | Arg | Glu | Gly | Asn | Glu | Lys | Glu | Ile | Gln | Arg | Ile | Met | His | Asn | Tyr |
| | | 515 | | | | 520 | | | | | 525 | | | | |
| Asp | Lys | Leu | Lys | Ser | Arg | Ile | Ser | Glu | Ile | Ile | Asp | Ser | Arg | Arg | Arg |
| | 530 | | | | | 535 | | | | | 540 | | | | |
| Leu | Glu | Glu | Asp | Leu | Lys | Lys | Gln | Ala | Ala | Glu | Tyr | Arg | Glu | Ile | Asp |
| 545 | | | | | 550 | | | | | 555 | | | | | 560 |
| Lys | Arg | Met | Asn | Ser | Ile | Lys | Pro | Asp | Leu | Ile | Gln | Leu | Arg | Lys | Thr |
| | | | | 565 | | | | | 570 | | | | | 575 | |
| Arg | Asp | Gln | Tyr | Leu | Met | Trp | Leu | Thr | Gln | Lys | Gly | Val | Arg | Gln | Lys |
| | | | 580 | | | | | 585 | | | | | 590 | | |
| Lys | Leu | Asn | Glu | Trp | Leu | Gly | Asn | Glu | Asn | Thr | Glu | Asp | Gln | Tyr | Ser |
| | | 595 | | | | | 600 | | | | | 605 | | | |
| Leu | Val | Glu | Asp | Asp | Glu | Asp | Leu | Pro | His | His | Asp | Glu | Lys | Thr | Trp |
| | 610 | | | | | 615 | | | | | 620 | | | | |
| Asn | Val | Gly | Ser | Ser | Asn | Arg | Asn | Lys | Ala | Glu | Asn | Leu | Leu | Arg | Gly |
| 625 | | | | | 630 | | | | | 635 | | | | | 640 |
| Lys | Arg | Asp | Gly | Thr | Phe | Leu | Val | Arg | Glu | Ser | Ser | Lys | Gln | Gly | Cys |
| | | | | 645 | | | | | 650 | | | | | 655 | |
| Tyr | Ala | Cys | Ser | Val | Val | Val | Asp | Gly | Glu | Val | Lys | His | Cys | Val | Ile |
| | | | 660 | | | | | 665 | | | | | 670 | | |
| Asn | Lys | Thr | Ala | Thr | Gly | Tyr | Gly | Phe | Ala | Glu | Pro | Tyr | Asn | Leu | Tyr |
| | | 675 | | | | | 680 | | | | | 685 | | | |
| Ser | Ser | Leu | Lys | Glu | Leu | Val | Leu | His | Tyr | Gln | His | Thr | Ser | Leu | Val |
| | 690 | | | | | 695 | | | | | 700 | | | | |
| Gln | His | Thr | Asp | Ser | Leu | Asn | Val | Thr | Leu | Ala | Tyr | Pro | Val | Tyr | Ala |
| 705 | | | | | 710 | | | | | 715 | | | | | 720 |
| Gln | Gln | Arg | Arg | | | | | | | | | | | | |

(2) INFORMATION FOR SEQ ID NO:3:

(i) SEQUENCE CHARACTERISTICS:
        (A) LENGTH: 770 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 3..770

(xi) SEQUENCE DESCRIPTION: SEQ ID NO:3:

| | | | | | | | | | | | | | | | | |
|---|---|---|---|---|---|---|---|---|---|---|---|---|---|---|---|---|
| AG | CCT | GAC | ACC | GGA | GCC | GGT | CCG | CTG | GGC | GCG | GGC | GCC | AGG | GCT | GGA | 47 |
| | Pro | Asp | Thr | Gly | Ala | Gly | Pro | Leu | Gly | Ala | Gly | Ala | Arg | Ala | Gly | |
| | 1 | | | 5 | | | | | 10 | | | | | 15 | | |
| GGG | GCG | CGC | GTG | CCG | GCG | GCG | GCC | CAG | CGT | GAA | AGC | GCG | GAG | GCG | GCC | 95 |
| Gly | Ala | Arg | Val | Pro | Ala | Ala | Ala | Gln | Arg | Glu | Ser | Ala | Glu | Ala | Ala | |
| | | | 20 | | | | | 25 | | | | | 30 | | | |
| ATG | GCG | GGC | AAC | TTC | GAC | TCG | GAG | GAG | CGG | AGT | AGC | TGG | TAC | TGG | GGC | 143 |
| Met | Ala | Gly | Asn | Phe | Asp | Ser | Glu | Glu | Arg | Ser | Ser | Trp | Tyr | Trp | Gly | |
| | | | 35 | | | | | 40 | | | | | 45 | | | |
| CGC | CTG | AGC | CGG | CAG | GAG | GCG | GTG | GCG | CTA | TTG | CAG | GGC | CAG | CGC | GAC | 191 |
| Arg | Leu | Ser | Arg | Gln | Glu | Ala | Val | Ala | Leu | Leu | Gln | Gly | Gln | Arg | Asp | |
| | | 50 | | | | | 55 | | | | | 60 | | | | |
| GGG | GTG | TTC | CTG | GTG | CGG | GAC | TCG | AGC | ACC | AGC | CCC | GGG | GAC | TAT | GTG | 239 |
| Gly | Val | Phe | Leu | Val | Arg | Asp | Ser | Ser | Thr | Ser | Pro | Gly | Asp | Tyr | Val | |
| | 65 | | | | | 70 | | | | | 75 | | | | | |

| | | | | | | | | | | | | | | | | |
|---|---|---|---|---|---|---|---|---|---|---|---|---|---|---|---|---|
| CTT | AGC | GTC | TCC | GAA | AAC | TCG | CGC | GTC | TCC | CAC | TAC | ATC | ATC | AAC | AGC | 287 |
| Leu | Ser | Val | Ser | Glu | Asn | Ser | Arg | Val | Ser | His | Tyr | Ile | Ile | Asn | Ser | |
| 80 | | | | 85 | | | | | | 90 | | | | | 95 | |
| AGC | GGC | CCG | CGC | CCT | CCA | GTG | CCT | CCG | TCG | CCC | GCT | CAG | CCT | CCG | CCG | 335 |
| Ser | Gly | Pro | Arg | Pro | Pro | Val | Pro | Pro | Ser | Pro | Ala | Gln | Pro | Pro | Pro | |
| | | | 100 | | | | | 105 | | | | | 110 | | | |
| GGA | GTG | AGT | CCC | TCC | AGG | CTC | CGA | ATA | GGA | GAT | CAA | GAA | TTT | GAT | TCA | 383 |
| Gly | Val | Ser | Pro | Ser | Arg | Leu | Arg | Ile | Gly | Asp | Gln | Glu | Phe | Asp | Ser | |
| | | | 115 | | | | | 120 | | | | | 125 | | | |
| TTG | CCT | GCT | TTA | CTG | GAA | TTC | TAC | AAA | ATA | CAC | TAT | TTG | GAC | ACT | ACA | 431 |
| Leu | Pro | Ala | Leu | Leu | Glu | Phe | Tyr | Lys | Ile | His | Tyr | Leu | Asp | Thr | Thr | |
| | | 130 | | | | | 135 | | | | | 140 | | | | |
| ACA | TTG | ATA | GAA | CCA | GTG | GCC | AGA | TCA | AGG | CAG | GGT | AGT | GGA | GTG | ATT | 479 |
| Thr | Leu | Ile | Glu | Pro | Val | Ala | Arg | Ser | Arg | Gln | Gly | Ser | Gly | Val | Ile | |
| | 145 | | | | | 150 | | | | | 155 | | | | | |
| CTC | AGG | CAG | GAG | GAG | GCA | GAG | TAT | GTG | CGG | GCC | CTC | TTT | GAC | TTT | AAT | 527 |
| Leu | Arg | Gln | Glu | Glu | Ala | Glu | Tyr | Val | Arg | Ala | Leu | Phe | Asp | Phe | Asn | |
| 160 | | | | | 165 | | | | | 170 | | | | | 175 | |
| GGG | AAT | GAT | GAA | GAA | GAT | CTT | CCC | TTT | AAG | AAA | GGA | GAC | ATC | CTG | AGA | 575 |
| Gly | Asn | Asp | Glu | Glu | Asp | Leu | Pro | Phe | Lys | Lys | Gly | Asp | Ile | Leu | Arg | |
| | | | | 180 | | | | | 185 | | | | | 190 | | |
| ATC | CGG | GAT | AAG | CCT | GAA | GAG | CAG | TGG | TGG | AAT | GCA | GAG | GAC | AGC | GAA | 623 |
| Ile | Arg | Asp | Lys | Pro | Glu | Glu | Gln | Trp | Trp | Asn | Ala | Glu | Asp | Ser | Glu | |
| | | | 195 | | | | | 200 | | | | | 205 | | | |
| GGA | AAG | AGG | GGG | ATG | ATT | CCT | GTC | CCT | TAC | GTG | GAG | AAG | TAT | AGA | CCT | 671 |
| Gly | Lys | Arg | Gly | Met | Ile | Pro | Val | Pro | Tyr | Val | Glu | Lys | Tyr | Arg | Pro | |
| | | 210 | | | | | 215 | | | | | 220 | | | | |
| GCC | TCC | GCC | TCA | GTA | TCG | GCT | CTG | ATT | GGA | GGT | AAC | CAG | GAG | GGT | TCC | 719 |
| Ala | Ser | Ala | Ser | Val | Ser | Ala | Leu | Ile | Gly | Gly | Asn | Gln | Glu | Gly | Ser | |
| | | 225 | | | | | 230 | | | | | 235 | | | | |
| CAC | CCA | CAG | CCA | CTG | GGT | GGC | CGG | AGC | CTG | GGC | CCT | ATG | CCA | ACC | CAG | 767 |
| His | Pro | Gln | Pro | Leu | Gly | Gly | Arg | Ser | Leu | Gly | Pro | Met | Pro | Thr | Gln | |
| 240 | | | | | 245 | | | | | 250 | | | | | 255 | |
| CGT | | | | | | | | | | | | | | | | 770 |
| Arg | | | | | | | | | | | | | | | | |

( 2 ) INFORMATION FOR SEQ ID NO:4:

( i ) SEQUENCE CHARACTERISTICS:
        ( A ) LENGTH: 256 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Pro | Asp | Thr | Gly | Ala | Gly | Pro | Leu | Gly | Ala | Gly | Ala | Arg | Ala | Gly | Gly |
| 1 | | | | 5 | | | | | 10 | | | | | 15 | |
| Ala | Arg | Val | Pro | Ala | Ala | Ala | Gln | Arg | Glu | Ser | Ala | Glu | Ala | Ala | Met |
| | | | 20 | | | | | 25 | | | | | 30 | | |
| Ala | Gly | Asn | Phe | Asp | Ser | Glu | Glu | Arg | Ser | Ser | Trp | Tyr | Trp | Gly | Arg |
| | | 35 | | | | | 40 | | | | | 45 | | | |
| Leu | Ser | Arg | Gln | Glu | Ala | Val | Ala | Leu | Leu | Gln | Gly | Gln | Arg | Asp | Gly |
| | 50 | | | | | 55 | | | | | 60 | | | | |
| Val | Phe | Leu | Val | Arg | Asp | Ser | Ser | Thr | Ser | Pro | Gly | Asp | Tyr | Val | Leu |
| 65 | | | | | 70 | | | | | 75 | | | | | 80 |
| Ser | Val | Ser | Glu | Asn | Ser | Arg | Val | Ser | His | Tyr | Ile | Ile | Asn | Ser | Ser |
| | | | | 85 | | | | | 90 | | | | | 95 | |
| Gly | Pro | Arg | Pro | Pro | Val | Pro | Pro | Ser | Pro | Ala | Gln | Pro | Pro | Pro | Gly |
| | | | 100 | | | | | 105 | | | | | 110 | | |

```
Val  Ser  Pro  Ser  Arg  Leu  Arg  Ile  Gly  Asp  Gln  Glu  Phe  Asp  Ser  Leu
          115                      120                      125

Pro  Ala  Leu  Leu  Glu  Phe  Tyr  Lys  Ile  His  Tyr  Leu  Asp  Thr  Thr  Thr
     130                      135                     140

Leu  Ile  Glu  Pro  Val  Ala  Arg  Ser  Arg  Gln  Gly  Ser  Gly  Val  Ile  Leu
145                           150                     155                     160

Arg  Gln  Glu  Glu  Ala  Glu  Tyr  Val  Arg  Ala  Leu  Phe  Asp  Phe  Asn  Gly
                    165                      170                     175

Asn  Asp  Glu  Glu  Asp  Leu  Pro  Phe  Lys  Lys  Gly  Asp  Ile  Leu  Arg  Ile
               180                      185                          190

Arg  Asp  Lys  Pro  Glu  Glu  Gln  Trp  Trp  Asn  Ala  Glu  Asp  Ser  Glu  Gly
          195                      200                     205

Lys  Arg  Gly  Met  Ile  Pro  Val  Pro  Tyr  Val  Glu  Lys  Tyr  Arg  Pro  Ala
     210                      215                     220

Ser  Ala  Ser  Val  Ser  Ala  Leu  Ile  Gly  Gly  Asn  Gln  Glu  Gly  Ser  His
225                           230                     235                     240

Pro  Gln  Pro  Leu  Gly  Gly  Arg  Ser  Leu  Gly  Pro  Met  Pro  Thr  Gln  Arg
                    245                      250                     255
```

(2) INFORMATION FOR SEQ ID NO:5:

(i) SEQUENCE CHARACTERISTICS:
        (A) LENGTH: 1072 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 79..729

(xi) SEQUENCE DESCRIPTION: SEQ ID NO:5:

```
GCCAGTGAAT  TCGGGGGCTC  AGCCCTCCTC  CCTCCCTTCC  CCCTGCTTCA  GGCTGCTGAG              60

CACTGAGCAG  CGCTCAGA ATG  GAA  GCC  ATC  GCC  AAA  TAT  GAC  TTC  AAA  GCT         111
                     Met  Glu  Ala  Ile  Ala  Lys  Tyr  Asp  Phe  Lys  Ala
                      1                  5                          10

ACT  GCA  GAC  GAC  GAG  CTG  AGC  TTC  AAA  AGG  GGG  GAC  ATC  CTC  AAG  GTT    159
Thr  Ala  Asp  Asp  Glu  Leu  Ser  Phe  Lys  Arg  Gly  Asp  Ile  Leu  Lys  Val
               15                      20                      25

TTG  AAC  GAA  GAA  TGT  GAT  CAG  AAC  TGG  TAC  AAG  GCA  GAG  CTT  AAT  GGA    207
Leu  Asn  Glu  Glu  Cys  Asp  Gln  Asn  Trp  Tyr  Lys  Ala  Glu  Leu  Asn  Gly
          30                           35                          40

AAA  GAC  GGC  TTC  ATT  CCC  AAG  AAC  TAC  ATA  GAA  ATG  AAA  CCA  CAT  CCG    255
Lys  Asp  Gly  Phe  Ile  Pro  Lys  Asn  Tyr  Ile  Glu  Met  Lys  Pro  His  Pro
     45                       50                           55

TGG  TTT  TTT  GGC  AAA  ATC  CCC  AGA  GCC  AAG  GCA  GAA  GAA  ATG  CTT  AGC    303
Trp  Phe  Phe  Gly  Lys  Ile  Pro  Arg  Ala  Lys  Ala  Glu  Glu  Met  Leu  Ser
60                       65                           70                       75

AAA  CAG  CGG  CAC  GAT  GGG  GCC  TTT  CTT  ATC  CGA  GAG  AGT  GAG  AGC  GCT    351
Lys  Gln  Arg  His  Asp  Gly  Ala  Phe  Leu  Ile  Arg  Glu  Ser  Glu  Ser  Ala
               80                           85                          90

CCT  GGG  GAC  TTC  TCC  CTC  TCT  GTC  AAG  TTT  GGA  AAC  GAT  GTG  CAG  CAC    399
Pro  Gly  Asp  Phe  Ser  Leu  Ser  Val  Lys  Phe  Gly  Asn  Asp  Val  Gln  His
               95                          100                         105

TTC  AAG  GTG  CTC  CGA  GAT  GGA  GCC  GGG  AAG  TAC  TTC  CTC  TGG  GTG  GTG    447
Phe  Lys  Val  Leu  Arg  Asp  Gly  Ala  Gly  Lys  Tyr  Phe  Leu  Trp  Val  Val
          110                          115                         120
```

```
AAG  TTC  AAT  TCT  TTG  AAT  GAG  CTG  GTG  GAT  TAT  CAC  AGA  TCT  ACA  TCT       495
Lys  Phe  Asn  Ser  Leu  Asn  Glu  Leu  Val  Asp  Tyr  His  Arg  Ser  Thr  Ser
     125                      130                     135

GTC  TCC  AGA  AAC  CAG  CAG  ATA  TTC  CTG  CGG  GAC  ATA  GAA  CAG  GTG  CCA       543
Val  Ser  Arg  Asn  Gln  Gln  Ile  Phe  Leu  Arg  Asp  Ile  Glu  Gln  Val  Pro
140                      145                     150                          155

CAG  CAG  CCG  ACA  TAC  GTC  CAG  GCC  CTC  TTT  GAC  TTT  GAT  CCC  CAG  GAG       591
Gln  Gln  Pro  Thr  Tyr  Val  Gln  Ala  Leu  Phe  Asp  Phe  Asp  Pro  Gln  Glu
                    160                     165                     170

GAT  GGA  GAG  CTG  GGC  TTC  CGC  CGG  GGA  GAT  TTT  ATC  CAT  GTC  ATG  GAT       639
Asp  Gly  Glu  Leu  Gly  Phe  Arg  Arg  Gly  Asp  Phe  Ile  His  Val  Met  Asp
               175                     180                     185

AAC  TCA  GAC  CCC  AAC  TGG  TGG  AAA  GGA  GCT  TGC  CAC  GGG  CAG  ACC  GGC       687
Asn  Ser  Asp  Pro  Asn  Trp  Trp  Lys  Gly  Ala  Cys  His  Gly  Gln  Thr  Gly
          190                      195                     200

ATG  TTT  CCC  CGC  AAT  TAT  GTC  ACC  CCC  GTG  AAC  CGG  AAC  GTC                 729
Met  Phe  Pro  Arg  Asn  Tyr  Val  Thr  Pro  Val  Asn  Arg  Asn  Val
     205                     210                     215

TAAGAGTCAA  GAAGCAATTA  TTTAAAGAAA  GTGAAAAATG  TAAAACACAT  ACAAAAGAAT              789

TAAACCCACA  AGCTGCCTCT  GACAGCAGCC  TGTGAGGGAG  TGCAGAACAC  CTGGCCGGGT              849

CACCCTGTGA  CCCTCTCACT  TTGGTTGGAA  CTTTAGGGGG  TGGGAGGGGG  CGTTGGATTT              909

AAAAATGCCA  AAACTTACCT  ATAAATTAAG  AAGAGTTTTT  ATTACAAATT  TTCACTGCTG              969

CTCCTCTTTC  CCCTCCTTTG  TCTTTTTTTT  CATCCTTTTT  TCTCTTCTGT  CCATCAGTGC              1029

ATGACGTTTA  AGGCCACGTA  TAGTCCTAGC  TGACGCCAAT  AAT                                 1072
```

( 2 ) INFORMATION FOR SEQ ID NO:6:

( i ) SEQUENCE CHARACTERISTICS:
         ( A ) LENGTH: 217 amino acids
         ( B ) TYPE: amino acid
         ( D ) TOPOLOGY: unknown ( i i ) MOLECULE TYPE: protein ( x i ) SEQUENCE DESCRIPTION: SEQ ID NO:6:

```
Met  Glu  Ala  Ile  Ala  Lys  Tyr  Asp  Phe  Lys  Ala  Thr  Ala  Asp  Asp  Glu
1                    5                    10                       15

Leu  Ser  Phe  Lys  Arg  Gly  Asp  Ile  Leu  Lys  Val  Leu  Asn  Glu  Glu  Cys
               20                   25                       30

Asp  Gln  Asn  Trp  Tyr  Lys  Ala  Glu  Leu  Asn  Gly  Lys  Asp  Gly  Phe  Ile
          35                        40                  45

Pro  Lys  Asn  Tyr  Ile  Glu  Met  Lys  Pro  His  Pro  Trp  Phe  Phe  Gly  Lys
     50                        55                   60

Ile  Pro  Arg  Ala  Lys  Ala  Glu  Glu  Met  Leu  Ser  Lys  Gln  Arg  His  Asp
65                        70                   75                        80

Gly  Ala  Phe  Leu  Ile  Arg  Glu  Ser  Glu  Ser  Ala  Pro  Gly  Asp  Phe  Ser
                    85                   90                        95

Leu  Ser  Val  Lys  Phe  Gly  Asn  Asp  Val  Gln  His  Phe  Lys  Val  Leu  Arg
               100                      105                 110

Asp  Gly  Ala  Gly  Lys  Tyr  Phe  Leu  Trp  Val  Val  Lys  Phe  Asn  Ser  Leu
          115                      120                      125

Asn  Glu  Leu  Val  Asp  Tyr  His  Arg  Ser  Thr  Ser  Val  Ser  Arg  Asn  Gln
     130                      135                      140

Gln  Ile  Phe  Leu  Arg  Asp  Ile  Glu  Gln  Val  Pro  Gln  Gln  Pro  Thr  Tyr
145                      150                      155                      160

Val  Gln  Ala  Leu  Phe  Asp  Phe  Asp  Pro  Gln  Glu  Asp  Gly  Glu  Leu  Gly
                    165                      170                      175
```

| | | | | | | | | | | | | | |
|---|---|---|---|---|---|---|---|---|---|---|---|---|---|
| Phe | Arg | Arg | Gly | Asp | Phe | Ile | His | Val | Met | Asp | Asn | Ser | Asp | Pro | Asn |
| | | | 180 | | | | | 185 | | | | | 190 | | |
| Trp | Trp | Lys | Gly | Ala | Cys | His | Gly | Gln | Thr | Gly | Met | Phe | Pro | Arg | Asn |
| | | 195 | | | | | 200 | | | | | 205 | | | |
| Tyr | Val | Thr | Pro | Val | Asn | Arg | Asn | Val |
| | 210 | | | | | 215 | | |

( 2 ) INFORMATION FOR SEQ ID NO:7:

( i ) SEQUENCE CHARACTERISTICS:
        ( A ) LENGTH: 642 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..471

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| GTG | ATT | GAG | AAG | CCG | GAG | AAT | GAC | CCT | GAA | TGG | TGG | AAA | TGC | AAA | AAT | 48 |
| Val | Ile | Glu | Lys | Pro | Glu | Asn | Asp | Pro | Glu | Trp | Trp | Lys | Cys | Lys | Asn | |
| 1 | | | | 5 | | | | | 10 | | | | | 15 | | |
| GCC | CGA | GGC | CAA | GTG | GGC | CTG | GTC | CCC | AAA | AAC | TAC | GTG | GTT | GTT | CTC | 96 |
| Ala | Arg | Gly | Gln | Val | Gly | Leu | Val | Pro | Lys | Asn | Tyr | Val | Val | Val | Leu | |
| | | | 20 | | | | | 25 | | | | | 30 | | | |
| AGT | GAT | GGG | CCT | GCT | CTG | CAC | CCC | GCT | CAC | ACC | CCC | CAG | ATC | AGC | TAC | 144 |
| Ser | Asp | Gly | Pro | Ala | Leu | His | Pro | Ala | His | Thr | Pro | Gln | Ile | Ser | Tyr | |
| | | 35 | | | | | 40 | | | | | 45 | | | | |
| ACC | GGG | CCT | TCA | GCC | AGC | GGG | CGC | TTT | GCT | GGT | CGG | GAG | TGG | TAC | TAT | 192 |
| Thr | Gly | Pro | Ser | Ala | Ser | Gly | Arg | Phe | Ala | Gly | Arg | Glu | Trp | Tyr | Tyr | |
| 50 | | | | | 55 | | | | | 60 | | | | | | |
| GGC | AAC | GTG | ACA | CGG | CAC | CAG | GCC | GAG | TGT | GCG | CTC | AAT | GAG | CGG | GGC | 240 |
| Gly | Asn | Val | Thr | Arg | His | Gln | Ala | Glu | Cys | Ala | Leu | Asn | Glu | Arg | Gly | |
| 65 | | | | | 70 | | | | | 75 | | | | | 80 | |
| GTC | GAG | GGC | GAC | TTC | CTC | ATT | AGG | GAC | AGC | GAG | TCC | TCG | CCC | AGT | GAC | 288 |
| Val | Glu | Gly | Asp | Phe | Leu | Ile | Arg | Asp | Ser | Glu | Ser | Ser | Pro | Ser | Asp | |
| | | | | 85 | | | | | 90 | | | | | 95 | | |
| TTC | TCC | GTG | TCT | CTC | AAA | GCG | TCA | GGG | AGA | AAC | AAG | CAC | TTC | AAG | GTG | 336 |
| Phe | Ser | Val | Ser | Leu | Lys | Ala | Ser | Gly | Arg | Asn | Lys | His | Phe | Lys | Val | |
| | | | 100 | | | | | 105 | | | | | 110 | | | |
| CAG | CTG | GTG | GAC | AGC | GTC | TAC | TGC | ATT | GGG | CAG | CGG | CGG | TTC | CAC | AGC | 384 |
| Gln | Leu | Val | Asp | Ser | Val | Tyr | Cys | Ile | Gly | Gln | Arg | Arg | Phe | His | Ser | |
| | | 115 | | | | | 120 | | | | | 125 | | | | |
| ATG | GAC | GAG | CTT | GTG | GAG | CAC | TAC | AAG | AAG | GCC | CCC | ATC | TTC | ACC | AGC | 432 |
| Met | Asp | Glu | Leu | Val | Glu | His | Tyr | Lys | Lys | Ala | Pro | Ile | Phe | Thr | Ser | |
| | 130 | | | | | 135 | | | | | 140 | | | | | |
| GAG | CAC | GGG | GAG | AAG | CTC | TAC | CTT | GTC | CGA | GCC | CTA | CAG | TGAAAGCAGC | | | 481 |
| Glu | His | Gly | Glu | Lys | Leu | Tyr | Leu | Val | Arg | Ala | Leu | Gln | | | | |
| 145 | | | | | 150 | | | | | 155 | | | | | | |

| | | | | |
|---|---|---|---|---|
| CATTGGCCCC | CTCATGCCCT | GCCCACTGTG | GGCCTCGCTG | CCACCTCTGC | CTCCCAGAGC | 541 |
| CCAGCACTTC | TGGCCACCTC | CACCCATGTG | GCTTGGATCA | CCTCTGTGGC | CCAGTCTGTC | 601 |
| CTTTCTTTTT | CAGCCCTGTT | GGTCAACCAC | GGCTACCTAG | G | | 642 |

( 2 ) INFORMATION FOR SEQ ID NO:8:

( i ) SEQUENCE CHARACTERISTICS:
        ( A ) LENGTH: 157 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

| Val | Ile | Glu | Lys | Pro | Glu | Asn | Asp | Pro | Glu | Trp | Trp | Lys | Cys | Lys | Asn |
|---|---|---|---|---|---|---|---|---|---|---|---|---|---|---|---|
| 1 | | | | 5 | | | | | 10 | | | | | 15 | |

| Ala | Arg | Gly | Gln | Val | Gly | Leu | Val | Pro | Lys | Asn | Tyr | Val | Val | Leu |
|---|---|---|---|---|---|---|---|---|---|---|---|---|---|---|
| | | | 20 | | | | | 25 | | | | | 30 | |

| Ser | Asp | Gly | Pro | Ala | Leu | His | Pro | Ala | His | Thr | Pro | Gln | Ile | Ser | Tyr |
|---|---|---|---|---|---|---|---|---|---|---|---|---|---|---|---|
| | | 35 | | | | | 40 | | | | | 45 | | | |

| Thr | Gly | Pro | Ser | Ala | Ser | Gly | Arg | Phe | Ala | Gly | Arg | Glu | Trp | Tyr | Tyr |
|---|---|---|---|---|---|---|---|---|---|---|---|---|---|---|---|
| | 50 | | | | | 55 | | | | | 60 | | | | |

| Gly | Asn | Val | Thr | Arg | His | Gln | Ala | Glu | Cys | Ala | Leu | Asn | Glu | Arg | Gly |
|---|---|---|---|---|---|---|---|---|---|---|---|---|---|---|---|
| 65 | | | | | 70 | | | | | 75 | | | | | 80 |

| Val | Glu | Gly | Asp | Phe | Leu | Ile | Arg | Asp | Ser | Glu | Ser | Ser | Pro | Ser | Asp |
|---|---|---|---|---|---|---|---|---|---|---|---|---|---|---|---|
| | | | | 85 | | | | | 90 | | | | | 95 | |

| Phe | Ser | Val | Ser | Leu | Lys | Ala | Ser | Gly | Arg | Asn | Lys | His | Phe | Lys | Val |
|---|---|---|---|---|---|---|---|---|---|---|---|---|---|---|---|
| | | | 100 | | | | | 105 | | | | | 110 | | |

| Gln | Leu | Val | Asp | Ser | Val | Tyr | Cys | Ile | Gly | Gln | Arg | Arg | Phe | His | Ser |
|---|---|---|---|---|---|---|---|---|---|---|---|---|---|---|---|
| | | 115 | | | | | 120 | | | | | 125 | | | |

| Met | Asp | Glu | Leu | Val | Glu | His | Tyr | Lys | Lys | Ala | Pro | Ile | Phe | Thr | Ser |
|---|---|---|---|---|---|---|---|---|---|---|---|---|---|---|---|
| | 130 | | | | | 135 | | | | | 140 | | | | |

| Glu | His | Gly | Glu | Lys | Leu | Tyr | Leu | Val | Arg | Ala | Leu | Gln |
|---|---|---|---|---|---|---|---|---|---|---|---|---|
| 145 | | | | | 150 | | | | | 155 | | |

( 2 ) INFORMATION FOR SEQ ID NO:9:

( i ) SEQUENCE CHARACTERISTICS:
        ( A ) LENGTH: 2345 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 369..1973

( x i ) SEQUENCE DESCRIPTION: SEQ ID NO:9:

| CTCTCTCTCT | CTCTCTCTCT | CCCTCTCTCC | TAGCACCTGC | TGCTCAGTAG | GAAGGGCAAG | 60 |
|---|---|---|---|---|---|---|
| AGCAATTCGA | GGCCGGTGCA | TTGTGAGGAG | TCTCCACCCC | TCCTCCTGCG | CTTCCTTCTC | 120 |
| CAGGGAGCCT | CTCAGGCCGC | CCTCACCTGC | CCGAGATAAT | TTTAGTTTCC | CTGGGCCTGG | 180 |
| AATCTGGATA | CGCAGGGCCT | CGCTCTATAT | TCTCCGCCT | CAACATTCCA | AAGGCGGGAT | 240 |
| AGCCTTTCTA | CCATCTGTAG | AGAAGAGAGA | AAGGATTCGA | AATCAAATCC | AAGTGTCTGG | 300 |
| GATCTCTAGA | CAGAGCCAGA | CTTTGGGCCG | GGTGTCCGGC | TCCTTCTGTT | GGAGGTGCTC | 360 |

| CAGGTGCC | ATG | GAA | CTG | GAT | CTG | AGC | CCG | ACT | CAT | CTC | AGC | AGC | TCC | CCA | 410 |
|---|---|---|---|---|---|---|---|---|---|---|---|---|---|---|---|
| | Met | Glu | Leu | Asp | Leu | Ser | Pro | Thr | His | Leu | Ser | Ser | Ser | Pro | |
| | 1 | | | | 5 | | | | | 10 | | | | | |

| GAA | GAT | GTG | TGC | CCA | ACT | CCT | GCT | ACC | CCT | CCT | GAG | ACT | CCT | CCG | CCC | 458 |
|---|---|---|---|---|---|---|---|---|---|---|---|---|---|---|---|---|
| Glu | Asp | Val | Cys | Pro | Thr | Pro | Ala | Thr | Pro | Pro | Glu | Thr | Pro | Pro | Pro | |
| 15 | | | | 20 | | | | | 25 | | | | | 30 | | |

| CCT | GAT | AAC | CCT | CCG | CCA | GGG | GAT | GTG | AAG | CGG | TCG | CAG | CCT | TTG | CCC | 506 |
|---|---|---|---|---|---|---|---|---|---|---|---|---|---|---|---|---|
| Pro | Asp | Asn | Pro | Pro | Pro | Gly | Asp | Val | Lys | Arg | Ser | Gln | Pro | Leu | Pro | |
| | | | | 35 | | | | | 40 | | | | | 45 | | |

| ATC | CCC | AGC | AGC | AGG | AAA | CTT | CGA | GAA | GAG | GAG | TTT | CAG | GCA | ACC | TCT | 554 |
|---|---|---|---|---|---|---|---|---|---|---|---|---|---|---|---|---|
| Ile | Pro | Ser | Ser | Arg | Lys | Leu | Arg | Glu | Glu | Glu | Phe | Gln | Ala | Thr | Ser | |
| | | | 50 | | | | | 55 | | | | | 60 | | | |

| | | | | | | | | | | | | | | | | |
|---|---|---|---|---|---|---|---|---|---|---|---|---|---|---|---|---|
| CTG | CCC | TCC | ATC | CCC | AAC | CCC | TTC | CCT | GAG | CTC | TGC | AGC | CCA | CCT | TCA | 602 |
| Leu | Pro | Ser | Ile | Pro | Asn | Pro | Phe | Pro | Glu | Leu | Cys | Ser | Pro | Pro | Ser | |
| | | | 65 | | | | 70 | | | | 75 | | | | | |
| CAG | AAA | CCC | ATT | CTT | GGT | GGT | TCC | TCC | GGT | GCA | AGG | GGG | TTG | CTT | CCT | 650 |
| Gln | Lys | Pro | Ile | Leu | Gly | Gly | Ser | Ser | Gly | Ala | Arg | Gly | Leu | Leu | Pro | |
| | 80 | | | | | 85 | | | | | 90 | | | | | |
| CGA | GAC | TCC | AGC | CGC | CTC | TGT | GTG | GTG | AAG | GTG | TAC | AGT | GAG | GAT | GGG | 698 |
| Arg | Asp | Ser | Ser | Arg | Leu | Cys | Val | Val | Lys | Val | Tyr | Ser | Glu | Asp | Gly | |
| 95 | | | | | 100 | | | | | 105 | | | | | 110 | |
| GCC | TGC | CGG | TCT | GTG | GAG | GTG | GCA | GCG | GGC | GCC | ACA | GCT | CGT | CAC | GTG | 746 |
| Ala | Cys | Arg | Ser | Val | Glu | Val | Ala | Ala | Gly | Ala | Thr | Ala | Arg | His | Val | |
| | | | | 115 | | | | | 120 | | | | | | 125 | |
| TGT | GAG | ATG | CTG | GTA | CAA | CGA | GCT | CAC | GCC | CTG | AGC | GAC | GAG | AGC | TGG | 794 |
| Cys | Glu | Met | Leu | Val | Gln | Arg | Ala | His | Ala | Leu | Ser | Asp | Glu | Ser | Trp | |
| | | | 130 | | | | | 135 | | | | | 140 | | | |
| GGA | CTA | GTG | GAA | TCC | CAC | CCC | TAC | CTG | GCA | CTG | GAG | CGG | GGT | CTG | GAG | 842 |
| Gly | Leu | Val | Glu | Ser | His | Pro | Tyr | Leu | Ala | Leu | Glu | Arg | Gly | Leu | Glu | |
| | | | 145 | | | | | 150 | | | | | 155 | | | |
| GAC | CAT | GAA | TTT | GTG | GTG | GAA | GTG | CAG | GAG | GCC | TGG | CCT | GTG | GGT | GGA | 890 |
| Asp | His | Glu | Phe | Val | Val | Glu | Val | Gln | Glu | Ala | Trp | Pro | Val | Gly | Gly | |
| | | 160 | | | | | 165 | | | | | 170 | | | | |
| GAT | AGC | CGC | TTC | ATC | TTC | CGT | AAA | AAC | TTC | GCC | AAG | TAT | GAA | CTA | TTC | 938 |
| Asp | Ser | Arg | Phe | Ile | Phe | Arg | Lys | Asn | Phe | Ala | Lys | Tyr | Glu | Leu | Phe | |
| 175 | | | | | 180 | | | | | 185 | | | | | 190 | |
| AAG | AGC | CCC | CCA | CAC | ACC | CTG | TTT | CCA | GAA | AAG | ATG | GTC | TCG | AGC | TGT | 986 |
| Lys | Ser | Pro | Pro | His | Thr | Leu | Phe | Pro | Glu | Lys | Met | Val | Ser | Ser | Cys | |
| | | | | 195 | | | | | 200 | | | | | 205 | | |
| CTG | GAT | GCA | CAA | ACA | GGC | ATA | TCC | CAT | GAA | GAC | CTC | ATC | CAG | AAC | TTC | 1034 |
| Leu | Asp | Ala | Gln | Thr | Gly | Ile | Ser | His | Glu | Asp | Leu | Ile | Gln | Asn | Phe | |
| | | | 210 | | | | | 215 | | | | | 220 | | | |
| CTG | AAC | GCT | GGC | AGC | TTC | CCT | GAG | ATC | CAG | GGC | TTC | CTG | CAG | CTG | CGG | 1082 |
| Leu | Asn | Ala | Gly | Ser | Phe | Pro | Glu | Ile | Gln | Gly | Phe | Leu | Gln | Leu | Arg | |
| | | 225 | | | | | 230 | | | | | 235 | | | | |
| GGA | TCA | GGC | CGG | GGG | TCA | GGT | CGA | AAG | CTT | TGG | AAA | CGT | TTC | TTC | TGC | 1130 |
| Gly | Ser | Gly | Arg | Gly | Ser | Gly | Arg | Lys | Leu | Trp | Lys | Arg | Phe | Phe | Cys | |
| 240 | | | | | 245 | | | | | 250 | | | | | | |
| TTT | CTG | CGT | CGA | TCT | GGC | CTC | TAC | TAC | TCT | ACC | AAG | GGT | ACC | TCC | AAG | 1178 |
| Phe | Leu | Arg | Arg | Ser | Gly | Leu | Tyr | Tyr | Ser | Thr | Lys | Gly | Thr | Ser | Lys | |
| 255 | | | | | 260 | | | | | 265 | | | | | 270 | |
| GAC | CCC | AGA | CAC | CTA | CAG | TAT | GTG | GCA | GAT | GTG | AAT | GAG | TCC | AAT | GTC | 1226 |
| Asp | Pro | Arg | His | Leu | Gln | Tyr | Val | Ala | Asp | Val | Asn | Glu | Ser | Asn | Val | |
| | | | | 275 | | | | | 280 | | | | | 285 | | |
| TAT | GTG | GTG | ACC | CAG | GGC | CGC | AAG | CTG | TAT | GGG | ATG | CCC | ACT | GAC | TTC | 1274 |
| Tyr | Val | Val | Thr | Gln | Gly | Arg | Lys | Leu | Tyr | Gly | Met | Pro | Thr | Asp | Phe | |
| | | | 290 | | | | | 295 | | | | | 300 | | | |
| GGC | TTC | TGT | GTC | AAG | CCC | AAC | AAG | CTT | CGA | AAC | GGC | CAC | AAG | GGG | CTC | 1322 |
| Gly | Phe | Cys | Val | Lys | Pro | Asn | Lys | Leu | Arg | Asn | Gly | His | Lys | Gly | Leu | |
| | | 305 | | | | | 310 | | | | | 315 | | | | |
| CAC | ATC | TTC | TGC | AGT | GAG | GAT | GAG | CAG | ACT | CGG | ACC | TGC | TGG | CTG | GCT | 1370 |
| His | Ile | Phe | Cys | Ser | Glu | Asp | Glu | Gln | Thr | Arg | Thr | Cys | Trp | Leu | Ala | |
| | 320 | | | | | 325 | | | | | 330 | | | | | |
| GCC | TTC | CGG | CTC | TTC | AAG | TAC | GGG | GTA | CAG | CTA | TAT | AAG | AAT | TAT | CAG | 1418 |
| Ala | Phe | Arg | Leu | Phe | Lys | Tyr | Gly | Val | Gln | Leu | Tyr | Lys | Asn | Tyr | Gln | |
| 335 | | | | | 340 | | | | | 345 | | | | | 350 | |
| CAG | GCC | CAG | TCT | CGT | CAC | CTG | CGC | CTA | TCC | TAT | TTG | GGG | TCT | CCA | CCC | 1466 |
| Gln | Ala | Gln | Ser | Arg | His | Leu | Arg | Leu | Ser | Tyr | Leu | Gly | Ser | Pro | Pro | |
| | | | | 355 | | | | | 360 | | | | | 365 | | |
| TTG | AGG | AGC | GTC | TCA | GAC | AAT | ACC | CTA | GTG | GCT | ATG | GAC | TTC | TCT | GGC | 1514 |
| Leu | Arg | Ser | Val | Ser | Asp | Asn | Thr | Leu | Val | Ala | Met | Asp | Phe | Ser | Gly | |
| | | | 370 | | | | | 375 | | | | | 380 | | | |

```
CAT  GCG  GGG  CGT  GTC  ATT  GAT  AAC  CCC  CGG  GAA  GCT  CTG  AGT  GCC  GCC           1562
His  Ala  Gly  Arg  Val  Ile  Asp  Asn  Pro  Arg  Glu  Ala  Leu  Ser  Ala  Ala
               385                      390                     395

ATG  GAG  GAG  GCC  CAG  GCC  TGG  AGG  AAG  AAG  ACA  AAC  CAC  CGT  CTG  AGC           1610
Met  Glu  Glu  Ala  Gln  Ala  Trp  Arg  Lys  Lys  Thr  Asn  His  Arg  Leu  Ser
400                           405                     410

CTG  CCC  ACC  ACA  TGC  TCT  GGC  TCG  AGC  CTC  AGC  GCA  GCC  ATT  CAT  CGC           1658
Leu  Pro  Thr  Thr  Cys  Ser  Gly  Ser  Ser  Leu  Ser  Ala  Ala  Ile  His  Arg
415                      420                     425                          430

ACC  CAG  CCC  TGG  TTT  CAT  GGA  CGC  ATC  TCT  CGG  GAG  GAG  AGC  CAG  CGG           1706
Thr  Gln  Pro  Trp  Phe  His  Gly  Arg  Ile  Ser  Arg  Glu  Glu  Ser  Gln  Arg
                    435                     440                     445

CTA  ATT  GGA  CAG  CAG  GGC  CTG  GTG  GAT  GGT  GTG  TTC  CTG  GTC  CGG  GAG           1754
Leu  Ile  Gly  Gln  Gln  Gly  Leu  Val  Asp  Gly  Val  Phe  Leu  Val  Arg  Glu
               450                     455                     460

AGC  CAG  AGG  AAC  CCA  CAG  GGC  TTT  GTC  CTG  TCC  TTG  TGC  CAT  CTG  CAG           1802
Ser  Gln  Arg  Asn  Pro  Gln  Gly  Phe  Val  Leu  Ser  Leu  Cys  His  Leu  Gln
               465                     470                     475

AAA  GTC  AAG  CAT  TAT  CTC  ATT  TTG  CCA  AGT  GAA  GAT  GAA  GGT  GCC  CTT           1850
Lys  Val  Lys  His  Tyr  Leu  Ile  Leu  Pro  Ser  Glu  Asp  Glu  Gly  Cys  Leu
          480                     485                     490

TAC  TTC  AGC  ATG  GAT  GAG  GGC  CAG  ACC  CGT  TTC  ACA  GAC  CTG  CTG  CAG           1898
Tyr  Phe  Ser  Met  Asp  Glu  Gly  Gln  Thr  Arg  Phe  Thr  Asp  Leu  Leu  Gln
495                      500                     505                          510

CTG  GTA  GAA  TTC  CAC  CAG  CTG  AAC  CGA  GGC  ATC  CTG  CCC  TGC  CTG  CTG           1946
Leu  Val  Glu  Phe  His  Gln  Leu  Asn  Arg  Gly  Ile  Leu  Pro  Cys  Leu  Leu
                    515                     520                     525

CGC  CAC  TGC  TGT  GCC  CGT  GTG  GCC  CTC  TGAGGCCGCA  CAAGCTACTG                       1993
Arg  His  Cys  Cys  Ala  Arg  Val  Ala  Leu
               530                     535

CAGCCATGGG  TTTGCCTACC  ACCCTTCTGT  CCTGTGGACT  CGGTGCAGGT  GGGTGGGGTG                    2053
GTAAACAGTG  AAGAGCTCC   CCCCCCCAAT  TTTATCCCAT  TTTTTTTAAC  CTCTCTCAAC                    2113
CAGTGAAACA  TCCCCTAACC  CTGTCCATCC  CTGACTCCTG  TCCCCAAGGG  AGGCATTGTG                    2173
GTCCTGTCCC  CTTGGTAGAG  CTCCTGAGGT  ACTGTTCCAG  TGAGGGCAT   TATGAGAGGA                    2233
GCGGGGCAGC  CCAGGAGGTC  TCATACCCCA  CCCATAATCT  GTACAGACTG  AGAGGCCAGT                    2293
TGATCTGCTC  TGTTTTATAC  CAGTAACAAT  AAAGATTATT  TTTTGATACA  AA                            2345
```

(2) INFORMATION FOR SEQ ID NO:10:

(i) SEQUENCE CHARACTERISTICS:
        (A) LENGTH: 535 amino acids
        (B) TYPE: amino acid
        (D) TOPOLOGY: unknown (ii) MOLECULE TYPE: protein (xi) SEQUENCE DESCRIPTION: SEQ ID NO:10:

```
Met  Glu  Leu  Asp  Leu  Ser  Pro  Thr  His  Leu  Ser  Ser  Ser  Pro  Glu  Asp
1                   5                     10                     15

Val  Cys  Pro  Thr  Pro  Ala  Thr  Pro  Pro  Glu  Thr  Pro  Pro  Pro  Pro  Asp
               20                     25                     30

Asn  Pro  Pro  Pro  Gly  Asp  Val  Lys  Arg  Ser  Gln  Pro  Leu  Pro  Ile  Pro
               35                     40                     45

Ser  Ser  Arg  Lys  Leu  Arg  Glu  Glu  Glu  Phe  Gln  Ala  Thr  Ser  Leu  Pro
          50                     55                     60

Ser  Ile  Pro  Asn  Pro  Phe  Pro  Glu  Leu  Cys  Ser  Pro  Pro  Ser  Gln  Lys
65                       70                     75                     80
```

```
Pro  Ile  Leu  Gly  Gly  Ser  Ser  Gly  Ala  Arg  Gly  Leu  Leu  Pro  Arg  Asp
                    85                  90                       95

Ser  Ser  Arg  Leu  Cys  Val  Val  Lys  Val  Tyr  Ser  Glu  Asp  Gly  Ala  Cys
                    100                 105                      110

Arg  Ser  Val  Glu  Val  Ala  Ala  Gly  Ala  Thr  Ala  Arg  His  Val  Cys  Glu
                    115                 120                      125

Met  Leu  Val  Gln  Arg  Ala  His  Ala  Leu  Ser  Asp  Glu  Ser  Trp  Gly  Leu
          130                      135                 140

Val  Glu  Ser  His  Pro  Tyr  Leu  Ala  Leu  Glu  Arg  Gly  Leu  Glu  Asp  His
145                      150                 155                           160

Glu  Phe  Val  Val  Glu  Val  Gln  Glu  Ala  Trp  Pro  Val  Gly  Gly  Asp  Ser
                    165                 170                           175

Arg  Phe  Ile  Phe  Arg  Lys  Asn  Phe  Ala  Lys  Tyr  Glu  Leu  Phe  Lys  Ser
                    180                 185                      190

Pro  Pro  His  Thr  Leu  Phe  Pro  Glu  Lys  Met  Val  Ser  Ser  Cys  Leu  Asp
                    195                 200                      205

Ala  Gln  Thr  Gly  Ile  Ser  His  Glu  Asp  Leu  Ile  Gln  Asn  Phe  Leu  Asn
          210                      215                 220

Ala  Gly  Ser  Phe  Pro  Glu  Ile  Gln  Gly  Phe  Leu  Gln  Leu  Arg  Gly  Ser
225                      230                 235                           240

Gly  Arg  Gly  Ser  Gly  Arg  Lys  Leu  Trp  Lys  Arg  Phe  Phe  Cys  Phe  Leu
                    245                 250                      255

Arg  Arg  Ser  Gly  Leu  Tyr  Tyr  Ser  Thr  Lys  Gly  Thr  Ser  Lys  Asp  Pro
                    260                 265                      270

Arg  His  Leu  Gln  Tyr  Val  Ala  Asp  Val  Asn  Glu  Ser  Asn  Val  Tyr  Val
                    275                 280                      285

Val  Thr  Gln  Gly  Arg  Lys  Leu  Tyr  Gly  Met  Pro  Thr  Asp  Phe  Gly  Phe
     290                      295                 300

Cys  Val  Lys  Pro  Asn  Lys  Leu  Arg  Asn  Gly  His  Lys  Gly  Leu  His  Ile
305                      310                 315                           320

Phe  Cys  Ser  Glu  Asp  Glu  Gln  Thr  Arg  Thr  Cys  Trp  Leu  Ala  Ala  Phe
                    325                 330                      335

Arg  Leu  Phe  Lys  Tyr  Gly  Val  Gln  Leu  Tyr  Lys  Asn  Tyr  Gln  Gln  Ala
               340                 345                      350

Gln  Ser  Arg  His  Leu  Arg  Leu  Ser  Tyr  Leu  Gly  Ser  Pro  Pro  Leu  Arg
          355                 360                 365

Ser  Val  Ser  Asp  Asn  Thr  Leu  Val  Ala  Met  Asp  Phe  Ser  Gly  His  Ala
370                 375                      380

Gly  Arg  Val  Ile  Asp  Asn  Pro  Arg  Glu  Ala  Leu  Ser  Ala  Ala  Met  Glu
385                      390                 395                           400

Glu  Ala  Gln  Ala  Trp  Arg  Lys  Lys  Thr  Asn  His  Arg  Leu  Ser  Leu  Pro
               405                 410                      415

Thr  Thr  Cys  Ser  Gly  Ser  Ser  Leu  Ser  Ala  Ala  Ile  His  Arg  Thr  Gln
               420                 425                      430

Pro  Trp  Phe  His  Gly  Arg  Ile  Ser  Arg  Glu  Glu  Ser  Gln  Arg  Leu  Ile
          435                 440                 445

Gly  Gln  Gln  Gly  Leu  Val  Asp  Gly  Val  Phe  Leu  Val  Arg  Glu  Ser  Gln
     450                 455                 460

Arg  Asn  Pro  Gln  Gly  Phe  Val  Leu  Ser  Leu  Cys  His  Leu  Gln  Lys  Val
465                      470                 475                           480

Lys  His  Tyr  Leu  Ile  Leu  Pro  Ser  Glu  Asp  Glu  Gly  Cys  Leu  Tyr  Phe
               485                 490                      495

Ser  Met  Asp  Glu  Gly  Gln  Thr  Arg  Phe  Thr  Asp  Leu  Leu  Gln  Leu  Val
               500                 505                      510
```

```
Glu  Phe  His  Gln  Leu  Asn  Arg  Gly  Ile  Leu  Pro  Cys  Leu  Leu  Arg  His
               515                      520                      525

Cys  Cys  Ala  Arg  Val  Ala  Leu
          530                 535
```

(2) INFORMATION FOR SEQ ID NO:11:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label=A
            / note= "The tyrosine is phosphorylated."

(xi) SEQUENCE DESCRIPTION: SEQ ID NO:11:

```
Glu  Glu  Glu  Glu  Glu  Tyr  Met  Pro  Met  Xaa  Xaa
1                   5                        10
```

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label=A
            / note= "The tyrosine is phosphorylated."

(xi) SEQUENCE DESCRIPTION: SEQ ID NO:12:

```
Glu  Glu  Glu  Glu  Glu  Tyr  Val  Pro  Met  Xaa  Xaa
1                   5                        10
```

(2) INFORMATION FOR SEQ ID NO:13:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Modified-site
        (B) LOCATION: 6
        (D) OTHER INFORMATION: /label=A
            / note= "The tyrosine is phosphorylated."

(xi) SEQUENCE DESCRIPTION: SEQ ID NO:13:

```
Asp  Asp  Asp  Asp  Asp  Tyr  Met  Pro  Met  Xaa  Xaa
1                   5                        10
```

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide ( i x ) FEATURE:
 ( A ) NAME/KEY: Modified-site
 ( B ) LOCATION: 6
 ( D ) OTHER INFORMATION: /label=A
  / note= "The tyrosine is phosphorylated."

( x i ) SEQUENCE DESCRIPTION: SEQ ID NO:14:

| Asp | Asp | Asp | Asp | Asp | Tyr | Val | Pro | Met | Xaa | Xaa |
|-----|-----|-----|-----|-----|-----|-----|-----|-----|-----|-----|
| 1   |     |     |     | 5   |     |     |     |     | 10  |     |

( 2 ) INFORMATION FOR SEQ ID NO:15:

( i ) SEQUENCE CHARACTERISTICS:
  ( A ) LENGTH: 4 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:15:

| Ile | Glu | Gly | Arg |
|-----|-----|-----|-----|
| 1   |     |     |     |

( 2 ) INFORMATION FOR SEQ ID NO:16:

( i ) SEQUENCE CHARACTERISTICS:
  ( A ) LENGTH: 4 amino acids
  ( B ) TYPE: amino acid
  ( D ) TOPOLOGY: unknown ( i i ) MOLECULE TYPE: peptide ( x i ) SEQUENCE DESCRIPTION: SEQ ID NO:16:

| Leu | Val | Pro | Arg |
|-----|-----|-----|-----|
| 1   |     |     |     |

( 2 ) INFORMATION FOR SEQ ID NO:17:

( i ) SEQUENCE CHARACTERISTICS:
  ( A ) LENGTH: 96 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:17:

| Trp | Tyr | Trp | Gly | Asp | Ile | Ser | Arg | Glu | Glu | Val | Asn | Glu | Lys | Leu | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Asp | Thr | Ala | Asp | Gly | Thr | Phe | Leu | Val | Arg | Asp | Ser | Thr | Lys | Met | His |
|     |     |     | 20  |     |     |     |     | 25  |     |     |     |     | 30  |     |     |
| Gly | Asp | Tyr | Thr | Leu | Thr | Leu | Arg | Lys | Gly | Gly | Asn | Asn | Leu | Ile | Lys |
|     |     |     | 35  |     |     |     |     | 40  |     |     |     | 45  |     |     |     |
| Ile | Phe | His | Arg | Asp | Gly | Lys | Tyr | Gly | Phe | Ser | Asp | Pro | Leu | Thr | Phe |
|     |     |     | 50  |     |     |     | 55  |     |     |     |     | 60  |     |     |     |
| Ser | Ser | Val | Val | Glu | Leu | Ile | Asn | His | Tyr | Arg | Asn | Glu | Ser | Leu | Ala |
| 65  |     |     |     |     | 70  |     |     |     |     | 75  |     |     |     |     | 80  |
| Gln | Tyr | Asn | Pro | Lys | Leu | Asp | Val | Lys | Leu | Leu | Tyr | Pro | Val | Ser | Lys |
|     |     |     |     | 85  |     |     |     |     | 90  |     |     |     |     | 95  |     |

( 2 ) INFORMATION FOR SEQ ID NO:18:

( i ) SEQUENCE CHARACTERISTICS:
  ( A ) LENGTH: 97 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:18:

Trp Asn Val Gly Ser Ser Asn Arg Asn Lys Ala Glu Asn Leu Leu Arg
1               5                   10                  15

Gly Lys Arg Asp Gly Thr Phe Leu Val Arg Glu Ser Ser Lys Gln Gly
            20                  25                  30

Cys Tyr Ala Cys Ser Val Val Val Asp Gly Glu Val Lys His Cys Val
            35                  40                  45

Ile Asn Lys Thr Ala Thr Gly Tyr Gly Phe Ala Glu Pro Tyr Asn Leu
        50                  55                  60

Tyr Ser Ser Leu Lys Glu Leu Val Leu His Tyr Gln His Thr Ser Leu
65                  70                  75                  80

Val Gln His Asn Asp Ser Leu Asn Val Thr Leu Ala Tyr Pro Val Tyr
                85                  90                  95

Ala ( 2 ) INFORMATION FOR SEQ ID NO:19:

( i ) SEQUENCE CHARACTERISTICS:
        ( A ) LENGTH: 99 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:19:

Trp Tyr Phe Gly Lys Ile Thr Arg Arg Glu Ser Glu Arg Leu Leu Leu
1               5                   10                  15

Asn Pro Glu Asn Pro Arg Gly Thr Phe Leu Val Arg Glu Ser Glu Thr
            20                  25                  30

Thr Lys Gly Ala Tyr Cys Leu Ser Val Ser Asp Phe Asp Asn Ala Lys
            35                  40                  45

Gly Leu Asn Val Lys His Tyr Lys Ile Arg Lys Leu Asp Ser Gly Gly
        50                  55                  60

Phe Tyr Ile Thr Ser Arg Thr Gln Phe Ser Ser Leu Gln Gln Leu Val
65                  70                  75                  80

Ala Tyr Tyr Ser Lys His Ala Asp Gly Leu Cys His Arg Leu Thr Asn
                85                  90                  95

Val Cys Pro ( 2 ) INFORMATION FOR SEQ ID NO:20:

( i ) SEQUENCE CHARACTERISTICS:
        ( A ) LENGTH: 92 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:20:

Trp Tyr His Gly Pro Val Ser Arg Asn Ala Ala Glu Tyr Lys Lys Ser
1               5                   10                  15

Ser Gly Ile Asn Gly Ser Phe Leu Val Arg Glu Ser Glu Ser Ser Pro
            20                  25                  30

Gly Gln Arg Ser Ile Ser Leu Arg Tyr Glu Gly Arg Val Tyr His Tyr
            35                  40                  45

Arg Ile Asn Thr Ala Ser Asp Gly Lys Leu Tyr Val Ser Ser Glu Ser
        50                  55                  60

```
        Arg   Phe   Asn   Thr   Leu   Ala   Glu   Leu   Val   His   His   His   Ser   Thr   Val   Ala
        65                      70                        75                            80

Asp   Gly   Leu   Ile   Thr   Thr   Leu   His   Tyr   Pro   Ala   Pro
                                85                        90
```

(2) INFORMATION FOR SEQ ID NO:21:

(i) SEQUENCE CHARACTERISTICS:
        (A) LENGTH: 109 amino acids
        (B) TYPE: amino acid
        (D) TOPOLOGY: unknown (ii) MOLECULE TYPE: protein (xi) SEQUENCE DESCRIPTION: SEQ ID NO:21:

```
        Trp   Phe   His   Gly   Lys   Leu   Gly   Ala   Gly   Arg   Asp   Gly   Arg   His   Ile   Ala
        1                       5                         10                            15

Glu   Arg   Leu   Leu   Thr   Glu   Tyr   Cys   Ile   Glu   Thr   Gly   Ala   Pro   Asp   Gly
                                20                        25                            30

Ser   Phe   Leu   Val   Arg   Glu   Ser   Glu   Thr   Phe   Val   Gly   Asp   Tyr   Thr   Leu
                                35                        40                            45

Ser   Phe   Trp   Arg   Asn   Gly   Lys   Val   Gln   His   Cys   Arg   Ile   His   Ser   Arg
                    50                        55                            60

Gln   Asp   Ala   Gly   Thr   Pro   Lys   Phe   Phe   Leu   Thr   Asp   Asn   Leu   Val   Phe
        65                      70                        75                            80

Asp   Ser   Leu   Tyr   Asp   Leu   Ile   Thr   His   Tyr   Gln   Gln   Val   Pro   Leu   Arg
                                85                        90                            95

Cys   Ala   Glu   Phe   Glu   Met   Arg   Leu   Ser   Leu   Pro   Val   Pro
                                100                       105
```

(2) INFORMATION FOR SEQ ID NO:22:

(i) SEQUENCE CHARACTERISTICS:
        (A) LENGTH: 89 amino acids
        (B) TYPE: amino acid
        (D) TOPOLOGY: unknown (ii) MOLECULE TYPE: protein (xi) SEQUENCE DESCRIPTION: SEQ ID NO:22:

```
        Trp   Tyr   His   Ala   Ser   Leu   Thr   Arg   Ala   Gln   Ala   Glu   His   Met   Leu   Met
        1                       5                         10                            15

Arg   Val   Pro   Arg   Asp   Gly   Ala   Phe   Leu   Val   Arg   Lys   Arg   Asn   Glu   Pro
                                20                        25                            30

Asn   Ser   Tyr   Ala   Ile   Ser   Phe   Arg   Ala   Glu   Gly   Lys   Ile   Lys   His   Cys
                    35                        40                            45

Arg   Val   Gln   Gln   Glu   Gly   Gln   Thr   Val   Met   Leu   Gly   Asn   Ser   Glu   Phe
                    50                        55                            60

Asp   Ser   Leu   Val   Asp   Leu   Ile   Ser   Tyr   Tyr   Glu   Lys   His   Pro   Leu   Tyr
        65                      70                        75                            80

Arg   Lys   Met   Lys   Leu   Arg   Tyr   Pro   Ile
                                85
```

(2) INFORMATION FOR SEQ ID NO:23:

(i) SEQUENCE CHARACTERISTICS:
        (A) LENGTH: 94 amino acids
        (B) TYPE: amino acid
        (D) TOPOLOGY: unknown (ii) MOLECULE TYPE: protein (xi) SEQUENCE DESCRIPTION: SEQ ID NO:23:

(2) INFORMATION FOR SEQ ID NO:24:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:23:

```
Trp Tyr His Gly Lys Leu Asp Arg Thr Ile Ala Glu Glu Arg Leu Arg
1               5                   10                  15
Gln Ala Gly Lys Ser Gly Ser Tyr Leu Ile Arg Glu Ser Asp Arg Arg
                20                  25                  30
Pro Gly Ser Phe Val Leu Ser Phe Arg Ser Gln Met Asn Val Val Asn
                35                  40                  45
His Pro Arg Ile Ile Ala Met Cys Gly Asp Tyr Tyr Ile Gly Gly Arg
        50                  55                  60
Arg Phe Ser Ser Leu Ser Asp Leu Ile Gly Tyr Tyr Ser His Val Ser
65                  70                  75                  80
Cys Leu Leu Lys Gly Glu Lys Leu Leu Tyr Pro Val Ala Pro
                85                  90
```

(2) INFORMATION FOR SEQ ID NO:24:

(i) SEQUENCE CHARACTERISTICS:
        (A) LENGTH: 92 amino acids
        (B) TYPE: amino acid
        (D) TOPOLOGY: unknown (ii) MOLECULE TYPE: protein (xi) SEQUENCE DESCRIPTION: SEQ ID NO:24:

```
Trp Tyr His Gly Lys Ile Ser Lys Gln Glu Ala Tyr Asn Leu Leu Met
1               5                   10                  15
Thr Val Gly Gln Val Cys Ser Phe Leu Val Arg Pro Ser Asp Asn Thr
                20                  25                  30
Pro Gly Asp Tyr Ser Leu Tyr Phe Arg Thr Asn Glu Asn Ile Gln Arg
                35                  40                  45
Phe Lys Ile Cys Pro Thr Pro Asn Asn Gln Phe Met Met Gly Gly Arg
        50                  55                  60
Tyr Tyr Asn Ser Ile Gly Asp Ile Ile Asp His Tyr Arg Lys Glu Gln
65                  70                  75                  80
Ile Val Glu Gly Tyr Tyr Leu Lys Glu Pro Val Pro
                85                  90
```

(2) INFORMATION FOR SEQ ID NO:25:

(i) SEQUENCE CHARACTERISTICS:
        (A) LENGTH: 107 amino acids
        (B) TYPE: amino acid
        (D) TOPOLOGY: unknown (ii) MOLECULE TYPE: protein (xi) SEQUENCE DESCRIPTION: SEQ ID NO:25:

```
Trp Tyr Trp Gly Arg Leu Ser Arg Gly Asp Ala Val Ser Leu Leu Gln
1               5                   10                  15
Gly Gln Arg His Gly Thr Phe Leu Val Arg Asp Ser Gly Ser Ile Pro
                20                  25                  30
Gly Asp Phe Val Leu Ser Val Ser Glu Ser Ser Arg Val Ser His Tyr
                35                  40                  45
Ile Val Asn Ser Leu Gly Pro Ala Gly Gly Arg Arg Ala Gly Gly Glu
        50                  55                  60
Gly Pro Phe Ala Pro Gly Leu Asn Pro Thr Arg Phe Leu Ile Gly Asp
65                  70                  75                  80
Asn Val Phe Asp Ser Leu Pro Ser Leu Leu Glu Phe Tyr Lys Ile His
                85                  90                  95
```

-continued

```
Tyr Leu Asp Thr Thr Thr Leu Ile Glu Pro Val
                100                 105
```

( 2 ) INFORMATION FOR SEQ ID NO:26:

( i ) SEQUENCE CHARACTERISTICS:
        ( A ) LENGTH: 70 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:26:

```
Ala Leu Tyr Asp Tyr Lys Lys Glu Arg Glu Glu Asp Ile Asp Leu His
1               5                   10                  15
Leu Gly Asp Ile Leu Thr Val Asn Lys Gly Ser Leu Val Ala Leu Gly
            20                  25                  30
Phe Ser Asp Pro Glu Ala Arg Pro Glu Asp Ile Gly Trp Leu Asn Gly
            35                  40                  45
Tyr Asn Glu Thr Thr Gly Glu Arg Gly Asp Phe Pro Gly Thr Tyr Val
        50                  55                  60
Glu Tyr Ile Gly Arg Lys
65                  70
```

( 2 ) INFORMATION FOR SEQ ID NO:27:

( i ) SEQUENCE CHARACTERISTICS:
        ( A ) LENGTH: 55 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:27:

```
Ala Leu Tyr Asp Tyr Glu Ser Arg Thr Glu Thr Asp Leu Ala Phe Lys
1               5                   10                  15
Lys Gly Glu Arg Leu Gln Ile Val Met Asn Thr Glu Gly Asp Trp Trp
            20                  25                  30
Leu Ala His Ser Leu Thr Thr Gly Gln Thr Gly Tyr Ile Pro Ser Asn
            35                  40                  45
Tyr Val Ala Pro Ser Asp Ser
        50                  55
```

( 2 ) INFORMATION FOR SEQ ID NO:28:

( i ) SEQUENCE CHARACTERISTICS:
        ( A ) LENGTH: 54 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:28:

```
Ala Leu Tyr Asp Phe Val Ala Ser Gly Asp Asn Thr Leu Ser Ile Thr
1               5                   10                  15
Lys Gly Glu Lys Leu Arg Val Leu Gly Tyr Asn His Asn Gly Glu Trp
            20                  25                  30
Cys Glu Ala Gln Thr Lys Asn Gly Gln Gly Trp Val Pro Ser Asn Tyr
            35                  40                  45
Ile Thr Pro Val Asn Ser
        50
```

( 2 ) INFORMATION FOR SEQ ID NO:29:

( i ) SEQUENCE CHARACTERISTICS:
  ( A ) LENGTH: 54 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:29:

| Ala | Leu | Phe | Asp | Tyr | Lys | Ala | Gly | Arg | Glu | Asp | Glu | Leu | Thr | Phe | Thr |
|---|---|---|---|---|---|---|---|---|---|---|---|---|---|---|---|
| 1 | | | | 5 | | | | | 10 | | | | | 15 | |
| Lys | Ser | Ala | Ile | Ile | Gln | Asn | Val | Glu | Lys | Gln | Glu | Gly | Gly | Trp | Trp |
| | | | 20 | | | | | 25 | | | | | 30 | | |
| Arg | Gly | Asp | Tyr | His | His | Lys | Lys | Gln | Leu | Trp | Phe | Pro | Ser | Asn | Tyr |
| | | 35 | | | | | 40 | | | | | 45 | | | |
| Val | Glu | Glu | Met | Val | Ser |
| | | 50 | | | |

( 2 ) INFORMATION FOR SEQ ID NO:30:

( i ) SEQUENCE CHARACTERISTICS:
  ( A ) LENGTH: 56 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:30:

| Ala | Ile | Leu | Asp | Tyr | Thr | Lys | Val | Pro | Asp | Thr | Asp | Glu | Ile | Ser | Phe |
|---|---|---|---|---|---|---|---|---|---|---|---|---|---|---|---|
| 1 | | | | 5 | | | | | 10 | | | | | 15 | |
| Leu | Lys | Gly | Asp | Met | Phe | Ile | Val | Asn | Asn | Glu | Leu | Glu | Asp | Gly | Trp |
| | | | 20 | | | | | 25 | | | | | 30 | | |
| Met | Trp | Val | Thr | Asn | Leu | Arg | Thr | Asp | Glu | Gln | Gly | Leu | Ile | Val | Glu |
| | | | 35 | | | | | 40 | | | | | 45 | | |
| Asp | Leu | Val | Glu | Glu | Val | Gly | Arg |
| | | 50 | | | | | 55 |

( 2 ) INFORMATION FOR SEQ ID NO:31:

( i ) SEQUENCE CHARACTERISTICS:
  ( A ) LENGTH: 55 amino acids
  ( B ) TYPE: amino acid
  ( D ) TOPOLOGY: unknown ( i i ) MOLECULE TYPE: protein ( x i ) SEQUENCE DESCRIPTION: SEQ ID NO:31:

| Ala | Leu | Phe | Asp | Phe | Lys | Gly | Asn | Asp | Asp | Gly | Asp | Leu | Pro | Phe | Lys |
|---|---|---|---|---|---|---|---|---|---|---|---|---|---|---|---|
| 1 | | | | 5 | | | | | 10 | | | | | 15 | |
| Lys | Gly | Asp | Ile | Leu | Lys | Ile | Arg | Asp | Lys | Pro | Glu | Glu | Gln | Trp | Trp |
| | | | 20 | | | | | 25 | | | | | 30 | | |
| Asn | Ala | Glu | Asp | Met | Asp | Gly | Lys | Arg | Gly | Met | Ile | Pro | Val | Pro | Tyr |
| | | 35 | | | | | 40 | | | | | 45 | | | |
| Val | Glu | Lys | Cys | Arg | Pro | Ser |
| | | 50 | | | | | 55 |

( 2 ) INFORMATION FOR SEQ ID NO:32:

( i ) SEQUENCE CHARACTERISTICS:
  ( A ) LENGTH: 949 base pairs
  ( B ) TYPE: nucleic acid
  ( C ) STRANDEDNESS: double
  ( D ) TOPOLOGY: unknown ( i i ) MOLECULE TYPE: cDNA ( i x ) FEATURE:
    ( A ) NAME/KEY: CDS
    ( B ) LOCATION: 1..549

( i x ) FEATURE:
    ( A ) NAME/KEY: CDS
    ( B ) LOCATION: 553..585

( i x ) FEATURE:
    ( A ) NAME/KEY: CDS
    ( B ) LOCATION: 607..642

( i x ) FEATURE:
    ( A ) NAME/KEY: CDS
    ( B ) LOCATION: 646..690

( i x ) FEATURE:
    ( A ) NAME/KEY: CDS
    ( B ) LOCATION: 694..894

( i x ) FEATURE:
    ( A ) NAME/KEY: CDS
    ( B ) LOCATION: 910..942

( x i ) SEQUENCE DESCRIPTION: SEQ ID NO:32:

```
GCCAGTGAAT  TCGGGCCCGA  ATTGGCAGAG  CTTAATGGAA  AAGACGGCTT  CATTCCCAAG      60
AACTACATAG  AAATGAAACC  ACATCCGTGG  TTTTTTGGCA  AAATCCCCAG  AGCCAAGGCA     120
GAAGAAATGC  TTAGCAAACA  GCGGCACGAT  GGGGCCTTTC  TTATCCGAGA  GAGTGAGAGC     180
GCTCCTGGGG  ACTTCTCCCT  CTCTGTCAAG  TTTGGAACGA  TGTGCAGCAC  TTTCAAGGTG     240
CTCCCGAGAT  GGAGCCGGGA  AGTACTTCCT  CTGGTGGTGA  AGTTCAATTC  TTTGAATGAG     300
CTGGTGGATT  ATCACAGATC  TACATCTGTC  TCCAGAAACC  AGCAGATATT  CCTGCGGGAC     360
ATAGAACAGG  TGCCACAGCA  GCCGACATAC  GTCCAGGCCC  TCTTTGACTT  TGATCCCCAG     420
GAGGATGGAG  AGCTGGGCTT  CCGCCGGGGA  GATTTTATCC  ATGTCATGGA  TAACTCAGAC     480
CCCAACTGGT  GGAAAGGAGC  TTGCCACGGG  CAGACCGGCA  TGTTTCCCCG  CGAATTATGT     540
CTCCCCCNGT  GAACCGGAAC  GTCTAAGAGT  CAAGAAGCAA  TTATTTAAAG  AAAGTGAAAA     600
ATGTAAAACA  CATACAAAAG  AATTAAACCC  ACAAGCTGCC  TCTGACAGCA  GCCTGTGAGG     660
GAGTGCAGAA  CACCTGGCCG  GGTCACCCTG  TGACCCTCTC  ACTTTGGTTG  GAACTTTAGG     720
GGGTGGGAGG  GGGCGTTGGA  TTTAAAAATG  CCAAAACTTA  CCTATAAATT  AAGAAGAGTT     780
TTTATTACAA  ATTTTCACTG  CTGCTCCTCT  TTCCCCTCCT  TTGTCTTTTT  TTTTCATCCT     840
TTTTTCTCTT  CTGTCCATCA  GTGCATGACG  TTTAAGGCCA  CGTATAGTCC  TAGCTGACGC     900
CAATAATAAA  AACCGAATTC  GAGCTCGGAT  CCGGGGATCC  TCTAGAGTC                  949
```

( 2 ) INFORMATION FOR SEQ ID NO:33:

( i ) SEQUENCE CHARACTERISTICS:
        ( A ) LENGTH: 183 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:33:

```
Ala  Ser  Glu  Phe  Gly  Pro  Glu  Leu  Ala  Glu  Leu  Asn  Gly  Lys  Asp  Gly
 1                    5                   10                       15

Phe  Ile  Pro  Lys  Asn  Tyr  Ile  Glu  Met  Lys  Pro  His  Pro  Trp  Phe  Phe
               20                   25                        30

Gly  Lys  Ile  Pro  Arg  Ala  Lys  Ala  Glu  Glu  Met  Leu  Ser  Lys  Gln  Arg
          35                        40                   45
```

|  | His | Asp | Gly | Ala | Phe | Leu | Ile | Arg | Glu | Ser | Glu | Ser | Ala | Pro | Gly | Asp |
|--|--|--|--|--|--|--|--|--|--|--|--|--|--|--|--|--|
|  |  | 50 |  |  |  | 55 |  |  |  |  | 60 |  |  |  |  |  |
|  | Phe | Ser | Leu | Ser | Val | Lys | Phe | Gly | Thr | Met | Cys | Ser | Thr | Phe | Lys | Val |
|  | 65 |  |  |  |  | 70 |  |  |  | 75 |  |  |  |  |  | 80 |
|  | Leu | Pro | Arg | Trp | Ser | Arg | Glu | Val | Leu | Pro | Leu | Val | Val | Lys | Phe | Asn |
|  |  |  |  |  | 85 |  |  |  |  | 90 |  |  |  |  | 95 |  |
|  | Ser | Leu | Asn | Glu | Leu | Val | Asp | Tyr | His | Arg | Ser | Thr | Ser | Val | Ser | Arg |
|  |  |  |  | 100 |  |  |  |  | 105 |  |  |  |  | 110 |  |  |
|  | Asn | Gln | Gln | Ile | Phe | Leu | Arg | Asp | Ile | Glu | Gln | Val | Pro | Gln | Gln | Pro |
|  |  |  | 115 |  |  |  |  | 120 |  |  |  |  | 125 |  |  |  |
|  | Thr | Tyr | Val | Gln | Ala | Leu | Phe | Asp | Phe | Asp | Pro | Gln | Glu | Asp | Gly | Glu |
|  |  | 130 |  |  |  |  | 135 |  |  |  |  | 140 |  |  |  |  |
|  | Leu | Gly | Phe | Arg | Arg | Gly | Asp | Phe | Ile | His | Val | Met | Asp | Asn | Ser | Asp |
|  | 145 |  |  |  |  | 150 |  |  |  |  | 155 |  |  |  |  | 160 |
|  | Pro | Asn | Trp | Trp | Lys | Gly | Ala | Cys | His | Gly | Gln | Thr | Gly | Met | Phe | Pro |
|  |  |  |  |  | 165 |  |  |  |  | 170 |  |  |  |  | 175 |  |
|  | Arg | Glu | Leu | Cys | Leu | Pro | Xaa |  |  |  |  |  |  |  |  |  |
|  |  |  |  | 180 |  |  |  |  |  |  |  |  |  |  |  |  |

( 2 ) INFORMATION FOR SEQ ID NO:34:

( i ) SEQUENCE CHARACTERISTICS:
        ( A ) LENGTH: 11 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:34:

|  | Thr | Gly | Thr | Ser | Lys | Ser | Gln | Glu | Ala | Ile | Ile |
|--|--|--|--|--|--|--|--|--|--|--|--|
|  | 1 |  |  |  | 5 |  |  |  |  | 10 |  |

( 2 ) INFORMATION FOR SEQ ID NO:35:

( i ) SEQUENCE CHARACTERISTICS:
        ( A ) LENGTH: 12 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:35:

|  | Asn | Thr | Tyr | Lys | Arg | Ile | Lys | Pro | Thr | Ser | Cys | Leu |
|--|--|--|--|--|--|--|--|--|--|--|--|--|
|  | 1 |  |  |  | 5 |  |  |  |  | 10 |  |  |

( 2 ) INFORMATION FOR SEQ ID NO:36:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:36:

|  | Gln | Gln | Pro | Val | Arg | Glu | Cys | Arg | Thr | Pro | Gly | Arg | Val | Thr | Leu |
|--|--|--|--|--|--|--|--|--|--|--|--|--|--|--|--|
|  | 1 |  |  |  | 5 |  |  |  |  | 10 |  |  |  |  | 15 |

( 2 ) INFORMATION FOR SEQ ID NO:37:

( i ) SEQUENCE CHARACTERISTICS:
        ( A ) LENGTH: 67 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:37:

| Pro | Ser | His | Phe | Gly | Trp | Asn | Phe | Arg | Gly | Trp | Glu | Gly | Ala | Leu | Asp |
| 1 | | | | 5 | | | | | 10 | | | | | 15 | |

| Leu | Lys | Met | Pro | Lys | Leu | Thr | Tyr | Lys | Leu | Arg | Arg | Val | Phe | Ile | Thr |
| | | | 20 | | | | 25 | | | | | 30 | | | |

| Asn | Phe | His | Cys | Cys | Ser | Ser | Phe | Pro | Ser | Phe | Val | Phe | Phe | Phe | His |
| | | 35 | | | | | 40 | | | | | 45 | | | |

| Pro | Phe | Phe | Ser | Ser | Val | His | Gln | Cys | Met | Thr | Phe | Lys | Ala | Thr | Tyr |
| | 50 | | | | | 55 | | | | | 60 | | | | |

| Ser | Pro | Ser |
| 65 | | |

( 2 ) INFORMATION FOR SEQ ID NO:38:

( i ) SEQUENCE CHARACTERISTICS:
( A ) LENGTH: 11 amino acids
( B ) TYPE: amino acid
( D ) TOPOLOGY: unknown ( i i ) MOLECULE TYPE: peptide ( x i ) SEQUENCE DESCRIPTION: SEQ ID NO:38:

| Lys | Pro | Asn | Ser | Ser | Ser | Asp | Pro | Gly | Ile | Leu |
| 1 | | | | 5 | | | | | 10 | |

( 2 ) INFORMATION FOR SEQ ID NO:39:

( i ) SEQUENCE CHARACTERISTICS:
( A ) LENGTH: 236 amino acids
( B ) TYPE: amino acid
( D ) TOPOLOGY: unknown ( i i ) MOLECULE TYPE: protein ( x i ) SEQUENCE DESCRIPTION: SEQ ID NO:39:

| Gln | Pro | Arg | Ala | Gly | Arg | Gly | Ala | Gly | His | Arg | Gly | Leu | Arg | Arg | Pro |
| 1 | | | | 5 | | | | | 10 | | | | | 15 | |

| Ala | Gly | Arg | Gly | Gln | Arg | Val | Arg | Pro | Ala | Gly | Gly | Ala | Ala | Leu | Met |
| | | | 20 | | | | 25 | | | | | 30 | | | |

| Ala | Gly | Gln | Glu | Asp | Ser | Glu | Asp | Arg | Gly | Ser | Trp | Tyr | Trp | Gly | Arg |
| | | 35 | | | | | 40 | | | | | 45 | | | |

| Leu | Ser | Arg | Gly | Asp | Ala | Val | Ser | Leu | Ile | Gln | Gly | Gln | Arg | His | Gly |
| | 50 | | | | | 55 | | | | | 60 | | | | |

| Thr | Phe | Leu | Val | Arg | Asp | Ser | Gly | Ser | Ile | Pro | Gly | Asp | Phe | Val | Leu |
| 65 | | | | | 70 | | | | | 75 | | | | | 80 |

| Ser | Val | Ser | Glu | Ser | Ser | Arg | Val | Ser | His | Tyr | Ile | Val | Asn | Ser | Leu |
| | | | | 85 | | | | | 90 | | | | | 95 | |

| Gly | Pro | Ala | Gly | Gly | Arg | Arg | Ala | Gly | Gly | Glu | Gly | Pro | Gly | Ala | Pro |
| | | | 100 | | | | | 105 | | | | | 110 | | |

| Gly | Leu | Asn | Pro | Thr | Arg | Phe | Leu | Ile | Gly | Asp | Gln | Val | Phe | Asp | Ser |
| | | 115 | | | | | 120 | | | | | 125 | | | |

| Leu | Pro | Ser | Leu | Leu | Glu | Phe | Tyr | Lys | Ile | His | Tyr | Leu | Asp | Thr | Thr |
| | 130 | | | | | 135 | | | | | 140 | | | | |

| Thr | Leu | Ile | Glu | Pro | Val | Ser | Arg | Ser | Arg | Gln | Asn | Ser | Gly | Val | Ile |
| 145 | | | | | 150 | | | | | 155 | | | | | 160 |

| Leu | Arg | Gln | Glu | Glu | Val | Glu | Tyr | Val | Arg | Ala | Leu | Phe | Asp | Phe | Lys |
| | | | | 165 | | | | | 170 | | | | | 175 | |

```
Gly  Asn  Asp  Asp  Gly  Asp  Leu  Pro  Phe  Lys  Lys  Gly  Asp  Ile  Leu  Lys
          180                      185                     190

Ile  Arg  Asp  Lys  Pro  Glu  Glu  Gln  Trp  Trp  Asn  Ala  Glu  Asp  Met  Asp
          195                      200                     205

Gly  Lys  Arg  Gly  Met  Ile  Pro  Val  Pro  Tyr  Val  Glu  Lys  Cys  Arg  Pro
          210                      215                     220

Ser  Ser  Ala  Ser  Val  Ser  Thr  Leu  Thr  Gly  Gly  Arg
225                      230                     235
```

( 2 ) INFORMATION FOR SEQ ID NO:40:

( i ) SEQUENCE CHARACTERISTICS:
        ( A ) LENGTH: 160 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:40:

```
Val  Ile  Glu  Lys  Pro  Glu  Asn  Asp  Pro  Glu  Trp  Trp  Lys  Cys  Arg  Lys
1                   5                      10                      15

Ile  Asn  Gly  Met  Val  Gly  Leu  Val  Pro  Lys  Asn  Tyr  Val  Thr  Val  Met
               20                      25                      30

Gln  Asn  Asn  Pro  Leu  Thr  Ser  Gly  Leu  Glu  Pro  Ser  His  Pro  Pro  Gln
          35                      40                      45

Cys  Asp  Tyr  Ile  Arg  Pro  Ser  Leu  Thr  Gly  Lys  Phe  Ala  Gly  Asn  Pro
          50                      55                      60

Trp  Tyr  Tyr  Gly  Lys  Val  Thr  Arg  His  Gln  Ala  Glu  Met  Ala  Leu  Asn
65                      70                      75                      80

Glu  Arg  Gly  His  Glu  Gly  Asp  Phe  Leu  Ile  Arg  Asp  Ser  Glu  Ser  Ser
               85                      90                      95

Pro  Asn  Asp  Phe  Ser  Val  Ser  Leu  Lys  Ala  Gln  Gly  Lys  Asn  Lys  His
          100                     105                     110

Phe  Lys  Val  Gln  Leu  Lys  Glu  Thr  Val  Tyr  Cys  Ile  Gly  Gln  Arg  Lys
          115                     120                     125

Phe  Ser  Thr  Met  Glu  Glu  Leu  Val  Glu  His  Tyr  Lys  Lys  Ala  Pro  Ile
          130                     135                     140

Phe  Thr  Ser  Glu  Gln  Gly  Glu  Lys  Leu  Tyr  Leu  Val  Lys  His  Leu  Ser
145                     150                     155                     160
```

( 2 ) INFORMATION FOR SEQ ID NO:41:

( i ) SEQUENCE CHARACTERISTICS:
        ( A ) LENGTH: 96 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:41:

```
Trp  Tyr  Phe  Gly  Lys  Leu  Gly  Arg  Lys  Asp  Ala  Glu  Arg  Gln  Leu  Leu
1                   5                      10                      15

Ser  Phe  Gly  Asn  Pro  Arg  Gly  Thr  Phe  Leu  Ile  Arg  Glu  Ser  Glu  Thr
               20                      25                      30

Thr  Lys  Gly  Ala  Tyr  Ser  Leu  Ser  Ile  Arg  Asp  Trp  Asp  Asp  Met  Lys
          35                      40                      45

Gly  Asp  His  Val  Lys  His  Tyr  Lys  Ile  Arg  Lys  Leu  Asp  Asn  Gly  Gly
          50                      55                      60

Tyr  Tyr  Ile  Thr  Thr  Arg  Ala  Gln  Phe  Glu  Thr  Leu  Gln  Gln  Leu  Val
65                      70                      75                      80
```

Gln His Tyr Ser Glu Arg Ala Ala Gly Leu Cys Cys Arg Leu Val Val
                85                      90                      95

(2) INFORMATION FOR SEQ ID NO:42:

(i) SEQUENCE CHARACTERISTICS:
      (A) LENGTH: 92 amino acids
      (B) TYPE: amino acid
      (D) TOPOLOGY: unknown (ii) MOLECULE TYPE: protein (xi) SEQUENCE DESCRIPTION: SEQ ID NO:42:

Lys Gly Lys Gly Lys Arg Trp Lys Asn Leu Tyr Phe Ile Leu Glu Gly
1               5                   10                      15

Ser Asp Ala Gln Leu Ile Tyr Phe Glu Ser Glu Lys Arg Ala Thr Lys
                20                  25                  30

Pro Lys Gly Leu Ile Asp Leu Ser Val Cys Ser Val Tyr Val Val His
            35                  40                  45

Asp Ser Leu Phe Gly Arg Pro Asn Cys Phe Gln Ile Val Val Gln His
        50                  55                  60

Phe Ser Glu Glu His Tyr Ile Phe Tyr Phe Ala Gly Glu Thr Pro Glu
65                  70                  75                      80

Gln Ala Glu Asp Trp Met Lys Gly Leu Gln Ala Phe
                85                  90

(2) INFORMATION FOR SEQ ID NO:43:

(i) SEQUENCE CHARACTERISTICS:
      (A) LENGTH: 223 amino acids
      (B) TYPE: amino acid
      (D) TOPOLOGY: unknown (ii) MOLECULE TYPE: protein (xi) SEQUENCE DESCRIPTION: SEQ ID NO:43:

Pro Lys Pro Ala Arg Ala Ala Pro Pro Pro Pro Pro Pro Pro Pro Pro
1               5                   10                      15

Pro Pro Gly Ala Asp Arg Val Val Lys Ala Val Pro Phe Pro Pro Thr
            20                  25                  30

His Arg Leu Thr Ser Glu Glu Val Phe Asp Leu Asp Gly Ile Pro Arg
        35                  40                  45

Val Asp Val Leu Lys Asn His Leu Val Lys Glu Gly Arg Val Asp Glu
        50                  55                  60

Glu Ile Ala Leu Arg Ile Ile Asn Glu Gly Ala Ala Ile Leu Arg Arg
65                  70                  75                      80

Glu Lys Thr Met Ile Glu Val Glu Ala Pro Ile Thr Val Cys Gly Asp
                85                  90                  95

Ile His Gly Gln Phe Phe Asp Leu Met Lys Leu Phe Lys Val Gly Gly
            100                 105                 110

Ser Pro Ala Asn Thr Arg Tyr Leu Phe Leu Gly Asp Tyr Val Asp Arg
            115                 120                 125

Gly Tyr Phe Ser Ile Glu Cys Val Leu Tyr Leu Trp Val Leu Lys Ile
        130                 135                 140

Leu Tyr Pro Ser Thr Leu Phe Leu Leu Arg Gly Asn His Glu Cys Arg
145                 150                 155                     160

His Leu Thr Glu Tyr Phe Thr Phe Lys Gln Glu Cys Lys Ile Lys Tyr
                165                 170                 175

```
Ser  Glu  Arg  Val  Tyr  Glu  Ala  Cys  Met  Glu  Ala  Phe  Asp  Ser  Leu  Pro
               180                      185                      190

Leu  Ala  Ala  Leu  Leu  Asn  Gln  Gln  Phe  Leu  Cys  Val  His  Gly  Gly  Leu
          195                      200                      205

Ser  Pro  Glu  Ile  His  Thr  Leu  Asp  Asp  Ile  Arg  Arg  Leu  Asp  Arg
          210                      215                      220
```

( 2 ) INFORMATION FOR SEQ ID NO:44:

( i ) SEQUENCE CHARACTERISTICS:
     ( A ) LENGTH: 99 amino acids
     ( B ) TYPE: amino acid
     ( D ) TOPOLOGY: unknown ( i i ) MOLECULE TYPE: protein ( x i ) SEQUENCE DESCRIPTION: SEQ ID NO:44:

```
Trp  Phe  Phe  Gly  Lys  Ile  Pro  Arg  Ala  Lys  Ala  Glu  Glu  Met  Leu  Ser
1               5                        10                       15

Lys  Gln  Arg  His  Asp  Gly  Ala  Phe  Leu  Ile  Arg  Glu  Ser  Glu  Ser  Ala
               20                       25                       30

Pro  Gly  Asp  Phe  Ser  Leu  Ser  Val  Lys  Phe  Gly  Asn  Asp  Val  Gln  His
          35                       40                       45

Phe  Lys  Val  Leu  Arg  Asp  Gly  Ala  Gly  Lys  Tyr  Phe  Leu  Trp  Val  Val
     50                       55                       60

Lys  Phe  Asn  Ser  Leu  Asn  Glu  Leu  Val  Asp  Tyr  His  Arg  Ser  Thr  Ser
65                       70                       75                       80

Val  Ser  Arg  Asn  Gln  Gln  Ile  Phe  Leu  Arg  Asp  Ile  Glu  Gln  Val  Pro
                    85                       90                       95

Gln  Gln  Pro
```

( 2 ) INFORMATION FOR SEQ ID NO:45:

( i ) SEQUENCE CHARACTERISTICS:
     ( A ) LENGTH: 50 amino acids
     ( B ) TYPE: amino acid
     ( D ) TOPOLOGY: unknown ( i i ) MOLECULE TYPE: protein ( x i ) SEQUENCE DESCRIPTION: SEQ ID NO:45:

```
Ala  Lys  Tyr  Asp  Phe  Lys  Ala  Thr  Ala  Asp  Asp  Glu  Leu  Ser  Phe  Lys
1               5                        10                       15

Arg  Gly  Asp  Ile  Leu  Lys  Val  Leu  Asn  Glu  Glu  Cys  Asp  Gln  Asn  Trp
               20                       25                       30

Tyr  Lys  Ala  Glu  Leu  Asn  Gly  Lys  Asp  Gly  Phe  Ile  Pro  Lys  Asn  Tyr
          35                       40                       45

Ile  Glu
     50
```

( 2 ) INFORMATION FOR SEQ ID NO:46:

( i ) SEQUENCE CHARACTERISTICS:
     ( A ) LENGTH: 46 amino acids
     ( B ) TYPE: amino acid
     ( D ) TOPOLOGY: unknown ( i i ) MOLECULE TYPE: protein ( x i ) SEQUENCE DESCRIPTION: SEQ ID NO:46:

```
Ala  Leu  Phe  Asp  Phe  Asp  Pro  Gln  Glu  Asp  Gly  Glu  Leu  Gly  Phe  Arg
1               5                        10                       15
```

```
            Arg  Gly  Asp  Phe  Ile  His  Val  Met  Asp  Asn  Ser  Asp  Pro  Asn  Trp  Trp
                           20                           25                           30

Lys  Gly  Ala  Cys  His  Gly  Gln  Thr  Gly  Met  Phe  Pro  Arg  Asn
                           35                           40                           45
```

( 2 ) INFORMATION FOR SEQ ID NO:47:

( i ) SEQUENCE CHARACTERISTICS:
        ( A ) LENGTH: 228 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:47:

```
    Met  Glu  Ala  Val  Ala  Glu  His  Asp  Phe  Gln  Ala  Gly  Ser  Pro  Asp  Glu
    1                   5                        10                           15

Leu  Ser  Phe  Lys  Arg  Gly  Asn  Thr  Leu  Lys  Val  Leu  Asn  Lys  Asp  Glu
                       20                        25                        30

Asp  Pro  His  Trp  Tyr  Lys  Ala  Glu  Leu  Asp  Gly  Asn  Glu  Gly  Phe  Ile
                   35                        40                        45

Pro  Ser  Asn  Tyr  Ile  Arg  Met  Thr  Glu  Cys  Asn  Trp  Tyr  Leu  Gly  Lys
              50                        55                        60

Ile  Thr  Arg  Asn  Asp  Ala  Glu  Val  Leu  Leu  Lys  Lys  Pro  Thr  Val  Arg
    65                        70                        75                        80

Asp  Gly  His  Phe  Leu  Val  Arg  Gln  Cys  Glu  Ser  Ser  Pro  Gly  Glu  Phe
                            85                        90                        95

Ser  Ile  Ser  Val  Arg  Phe  Gln  Asp  Ser  Val  Gln  His  Phe  Lys  Val  Leu
                       100                       105                       110

Arg  Asp  Gln  Asn  Gly  Lys  Tyr  Tyr  Leu  Trp  Ala  Val  Lys  Phe  Asn  Ser
                   115                       120                       125

Leu  Asn  Glu  Leu  Val  Ala  Tyr  His  Arg  Thr  Ala  Ser  Val  Ser  Arg  Thr
              130                       135                       140

His  Thr  Ile  Leu  Leu  Ser  Asp  Met  Asn  Val  Glu  Thr  Lys  Phe  Val  Gln
    145                       150                       155                       160

Ala  Leu  Phe  Asp  Phe  Asn  Pro  Gln  Glu  Ser  Gly  Glu  Leu  Ala  Phe  Lys
                            165                       170                       175

Arg  Gly  Asp  Val  Ile  Thr  Leu  Ile  Asn  Lys  Asp  Asp  Pro  Asn  Trp  Trp
                       180                       185                       190

Glu  Gly  Gln  Leu  Asn  Asn  Arg  Arg  Gly  Ile  Phe  Pro  Ser  Asn  Tyr  Val
                   195                       200                       205

Cys  Pro  Tyr  Asn  Ser  Asn  Lys  Ser  Asn  Ser  Asn  Val  Ala  Pro  Gly  Phe
              210                       215                       220

Asn  Phe  Gly  Asn
    225
```

( 2 ) INFORMATION FOR SEQ ID NO:48:

( i ) SEQUENCE CHARACTERISTICS:
        ( A ) LENGTH: 3372 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:48:

```
CCAGTGAATT  CGGGTTTTTT  TTTTATTGAA  TAAAGCAGCT  TTGAAGCTTA  TCAGGCACTG      60

CCCAACAAAA  CAGTCCAAAA  AAAATCTGTT  ATGAACTTTT  TAACCTTGGG  CTAACAGCAA     120
```

```
GTACTCTGTA   CAAGAAAAAC   TGTAAAATAT   TTCATAGTTT   TAATTCTGAA   GCCATTTTTT        180
TTTTTACTGG   CATCCTGTAC   ATTTATTTTT   AAAAAGGAT    AACAAAAATG   AATATTAACA        240
AAAATCCGGG   ACAACAATAT   TTTCAAGCAA   CAAAAACTGG   GGTGGGGAAG   CTTATTCTGA        300
AGGTACATTT   AAAACTGAAA   TAACAACTTA   ATGAAAATTA   AGAATTGCAT   AGCGCTGTGA        360
ATTTAGCCTT   CAGCAAAACA   AAACAGAAGC   TATTTGGTAT   TGATACAAAT   CCATCTATTT        420
GATAGTTAGT   CATCCAATAT   TATGTACATA   TTTTATATAC   TGAATGTCAT   TTTAAGTCCT        480
GTTTTCCAAA   CTCCATTTTT   CTGTTGCTGG   GTTTTGTTT    TTTGACAAGT   TAAACACTTT        540
CTGGCACTTT   CTATGACAGA   ATTTCTTCTG   AACATACATG   AACTGACATT   CTCCCAAAGC        600
GTCCCTTGTG   AGTGGACGTG   CCTTTCTGCT   ACATATCGTT   CATTTGTTAC   AAAATGAAAT        660
AATCCACAGT   GCGATGTGTC   TGGGTCCACC   GTGCACAGCA   ACATCCAGGC   TAAACCAGGC        720
TGGACCAAAC   CTTCTCAGGC   CAGGGTTCTT   CTGCCTCTCT   CTCCTCCGCT   CTCCAGAGTC        780
CCAACTTTCA   GCTGGTAAAG   CTTCAGAAAG   CATTAACAAG   CACCATGGTT   AAAGGCCTCT        840
TTGTCCCTGC   ACGCAGAGAT   TTTTGCATTT   CTTTTCTCT    TTGTGTTGTA   TGTGGTTGTG        900
GCTTTAAATT   AAACCAAAGA   AAAAAGAAA    AGAAGGGAT    AAGCACTCCA   GCTTAGGAAC        960
GTGTGGTCAT   CATACAGCCT   TAGGCTGCAT   GTCTTCCCCT   ACTTCTTTTT   TGTCAAAGAA       1020
AGCTCTAGTC   CCATCCAAAG   AAAGATGGCT   TCGTTCTGC    AGCTCAATTC   ACAGATCAGA       1080
CTGGAGAGGA   GCCCTTTGCT   TTCCAGAGGC   CTCAGGGTGG   CTGAACTTCA   GGAGAAGGAT       1140
CAAAGAGTAA   GCGCTTCATC   GCCTCTGCTG   TGCATATACT   GGGTAGGCTA   GTGTGACATT       1200
GAGGGAGTCG   GTGTGCTGCA   CAAGGGAGGT   GTGTTGGTAA   TGTAGCACCA   GTTCTTTCAG       1260
AGAGCTGTAC   AAGTTATAGG   GCTCGGCAAA   GCCATAGCCA   GTTGCTGTTT   TGTTTATGAC       1320
ACAATGCTTT   ACTTCGCCGT   CCACCACTAC   AGAGCAGGCA   TAGCAGCCCT   GTTTACTGCT       1380
CTCCGGACA    AGAAAAGTGC   CATCTCGCTT   CCCTCGCAAC   AGGTTTTCAG   CTTTGTTTCG       1440
GTTGCTGCTT   CCAACATTCC   ATGTCTTCTC   ATCATGATGG   GGCAAATCTT   CATCATCTTC       1500
CACCAGTGAA   TATTGGTCTT   CAGTGTTTTC   ATTGCCCAAC   CACTCGTTCA   ACTTCTTTTG       1560
CCGAACACCT   TTTTGAGTCA   ACCACATCAA   GTATTGGTCT   CTCGTCTTTC   TCAGCTGGAT       1620
AAGGTCTGGT   TTAATGCTGT   TCATACGTTT   GTCAATTTCT   CGATACTCAG   CTGCCTGCTT       1680
CTTCAAGTCT   TCTTCCAATC   TTCTTCTACT   GTCAATAATT   TCACTGATTC   GAGACTTCAA       1740
CTTATCATAA   TTATGCATAA   TCCTTTGTAT   TTCTTTCTCA   TTGCCTTCAC   GTTTAAACTT       1800
TTCTATGTAT   TCTTTGCTGT   ACCGCTCTTG   GGTCTGGCAC   TGTTCTTCAA   ATATTTTAT        1860
GGTTTCATTA   AATGCTTCAA   TAGCTGTCCT   TTTCATTTGG   ATTTCCTGGG   ATGTGCGGGT       1920
ATATTCTTCA   TATAATCTAT   CATATTCTCG   ACTTTTTCT    TGAAACTGAG   TGTTATATTC       1980
ATGTAATTTT   TTCCCTACAG   CTTCAATATT   ATCTTCTTTG   ACAACTTGAT   CCTGTTGGTA       2040
TTTGGATACT   GGATAAAGTA   ATTTCACATC   CAATTTGGGA   TTATACTGAG   CTAGAGATTC       2100
ATTCCGGTAG   TGGTTTATTA   ATTCAACCAC   AGAACTGAAG   GTTAATGGGT   CAGAGAAGCC       2160
ATATTTCCCA   TCTCGATGAA   ATATTTTGAT   TAATTTGTTA   TTTCCCCCTT   TCCTTAGTGT       2220
AAGAGTATAA   TCACCATGCA   TTTTAGTAGA   CGCATCTCGT   ACCAAAAAGG   TCCCGTCTGC       2280
TGTATCTCGA   AGTTTTTCAT   TCACTTCTTC   CCTCGAGATA   TCTCCCAGT    ACCATTCAGC       2340
ATTTTGTAAG   GACATATTGT   TATTCATACC   GTTGTTGGCT   ACAGTAGTAG   GTTTTGGTGG       2400
TTTAGGAGGC   AGTGCTGGTG   CAGGCTGTCG   TTCATTCCAT   TCAGTTGAGA   TTAAAATTTC       2460
TATAACTTTT   ATGAGGTTTT   CAGTATTATC   AGAGCTGGCT   GCTGAGAATC   TGAAAAGCAT       2520
```

| | | | | | | |
|---|---|---|---|---|---|---|
| AGGGCTGAAA | ATTTCAGAGA | GTACTCTTGC | ATTCAACAGA | TTTTTGCTGG | ACGTTTGAGA | 2580 |
| GAGCTTGAAG | AAATGTTTTA | ACAAATACTG | AAGCGTAAGC | CAATACTGAT | GAGGTATGCT | 2640 |
| AGGCGACCTA | ATAAGCTTCT | TCAATAGCTG | AATATATTCT | TCGGAGCTTT | GTACTTCTGG | 2700 |
| AGCTAAAGAA | ATCATTTCAC | TGTAAACGGC | TGCTGGAATG | ACAGGATTTG | GTAAGTCCAG | 2760 |
| GAGATAGCGT | TTGAAAGCGT | CAGCCAAAAC | GTGCACATCG | ATCATTTCCA | AGTCCACGGA | 2820 |
| GGGTGTATCA | CAATCAAGAA | GCTGTCGTAA | TTCTGCCAGG | TTGCTGGAGC | TCTGTGTTCT | 2880 |
| GTATAGAGTT | GAACATTCCA | GACCTTTCTT | TTCAATGGCT | TCCACGAGCT | TGATAAGAAG | 2940 |
| AGGCGGGGCA | ATGTCAGGAG | GGGCAAACTG | CTCTGCAAGA | TCCGGGAGAG | TCAAAGCTTG | 3000 |
| TTGTTCAACA | TCTGCTTCAG | TTTTCGAAGA | ACCTGGTGCA | ACAGGAAGAG | GCCGAGGTGG | 3060 |
| CCGGGGCTTT | GGTGTGGGAG | GCGAGATTTT | TTTCCTTCCA | ATATATTCTA | CGTAAGTTCC | 3120 |
| CGGAAAGTCC | CCCTTTTCCC | CTGTGGTTTC | ATTATAGCCA | TTTAACCAGC | CATTTCTTCG | 3180 |
| AGGCCTGGCT | TCCTGTCCAT | CACTGAATCC | AAGAGCTACT | AAGGACCCTT | TATTCACAGT | 3240 |
| CAATATGTCA | CCCAAGTGCA | AGTCAATATC | TTCTTCTCTT | TCCTTTTTAT | AATCATACAG | 3300 |
| CGCTCTGTAC | TGGTACCCCT | CAGCACTCAT | GTTTGCAAAT | CTGCTACCAT | GCAACAGTTG | 3360 |
| AGCCTGGTTG | TA | | | | | 3372 |

(2) INFORMATION FOR SEQ ID NO:49:

(i) SEQUENCE CHARACTERISTICS:
        (A) LENGTH: 1072 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:49:

| | | | | | | |
|---|---|---|---|---|---|---|
| ATTATTGGCG | TCAGCTAGGA | CTATACGTGG | CCTTAAACGT | CATGCACTGA | TGGACAGAAG | 60 |
| AGAAAAAAGG | ATGAAAAAAA | AGACAAAGGA | GGGGAAAGAG | GAGCAGCAGT | GAAAATTTGT | 120 |
| AATAAAAACT | CTTCTTAATT | TATAGGTAAG | TTTTGGCATT | TTTAAATCCA | ACGCCCCTC | 180 |
| CCACCCCCTA | AAGTTCCAAC | CAAAGTGAGA | GGGTCACAGG | GTGACCCGGC | CAGGTGTTCT | 240 |
| GCACTCCCTC | ACAGGCTGCT | GTCAGAGGCA | GCTTGTGGGT | TTAATTCTTT | TGTATGTGTT | 300 |
| TTACATTTTT | CACTTTCTTT | AAATAATTGC | TTCTTGACTC | TTAGACGTTC | CGGTTCACGG | 360 |
| GGGTGACATA | ATTGCGGGGA | AACATGCCGG | TCTGCCCGTG | GCAAGCTCCT | TTCCACCAGT | 420 |
| TGGGGTCTGA | GTTATCCATG | ACATGGATAA | AATCTCCCCG | GCGGAAGCCC | AGCTCTCCAT | 480 |
| CCTCCTGGGG | ATCAAAGTCA | AAGAGGGCCT | GGACGTATGT | CGGCTGCTGT | GGCACCTGTT | 540 |
| CTATGTCCCG | CAGGAATATC | TGCTGGTTTC | TGGAGACAGA | TGTAGATCTG | TGATAATCCA | 600 |
| CCAGCTCATT | CAAAGAATTG | AACTTCACCA | CCCAGAGGAA | GTACTTCCCG | GCTCCATCTC | 660 |
| GGAGCACCTT | GAAGTGCTGC | ACATCGTTTC | CAAACTTGAC | AGAGAGGGAG | AAGTCCCCAG | 720 |
| GAGCGCTCTC | ACTCTCTCGG | ATAAGAAAGG | CCCCATCGTG | CCGCTGTTTG | CTAAGCATTT | 780 |
| CTTCTGCCTT | GGCTCTGGGG | ATTTTGCCAA | AAAACCACGG | ATGTGGTTTC | ATTTCTATGT | 840 |
| AGTTCTTGGG | AATGAAGCCG | TCTTTTCCAT | TAAGCTCTGC | CTTGTACCAG | TTCTGATCAC | 900 |
| ATTCTTCGTT | CAAAACCTTG | AGGATGTCCC | CCCTTTTGAA | GCTCAGCTCG | TCGTCTGCAG | 960 |
| TAGCTTTGAA | GTCATATTTG | GCGATGGCTT | CCATTCTGAG | CGCTGCTCAG | TGCTCAGCAG | 1020 |
| CCTGAAGCAG | GGGGAAGGGA | GGGAGGAGGG | CTGAGCCCCC | GAATTCACTG | GC | 1072 |

(2) INFORMATION FOR SEQ ID NO:50:

(i) SEQUENCE CHARACTERISTICS:
(A) LENGTH: 949 base pairs
(B) TYPE: nucleic acid
(C) STRANDEDNESS: double
(D) TOPOLOGY: unknown (ii) MOLECULE TYPE: cDNA (xi) SEQUENCE DESCRIPTION: SEQ ID NO:50:

```
GACTCTAGAG GATCCCCGGA TCCGAGCTCG AATTCGGTTT TTATTATTGG CGTCAGCTAG        60
GACTATACGT GGCCTTAAAC GTCATGCACT GATGGACAGA AGAGAAAAAA GGATGAAAAA       120
AAAAGACAAA GGAGGGGAAA GAGGAGCAGC AGTGAAAATT TGTAATAAAA ACTCTTCTTA       180
ATTTATAGGT AAGTTTTGGC ATTTTTAAAT CCAACGCCCC CTCCCACCCC CTAAAGTTCC       240
AACCAAAGTG AGAGGGTCAC AGGGTGACCC GGCCAGGTGT TCTGCACTCC CTCACAGGCT       300
GCTGTCAGAG GCAGCTTGTG GGTTTAATTC TTTTGTATGT GTTTACATT  TTTCACTTTC       360
TTTAAATAAT TGCTTCTTGA CTCTTAGACG TTCCGGTTCA CNGGGGGAGA CATAATTCGC       420
GGGGAAACAT GCCGGTCTGC CCGTGGCAAG CTCCTTTCCA CCAGTTGGGG TCTGAGTTAT       480
CCATGACATG GATAAAATCT CCCCGGCGGA AGCCCAGCTC TCCATCCTCC TGGGGATCAA       540
AGTCAAAGAG GGCCTGGACG TATGTCGGCT GCTGTGGCAC CTGTTCTATG TCCCGCAGGA       600
ATATCTGCTG GTTTCTGGAG ACAGATGTAG ATCTGTGATA ATCCACCAGC TCATTCAAAG       660
AATTGAACTT CACCACCAGA GGAAGTACTT CCCGGCTCCA TCTCGGGAGC ACCTTGAAAG       720
TGCTGCACAT CGTTCCAAAC TTGACAGAGA GGGAGAAGTC CCCAGGAGCG CTCTCACTCT       780
CTCGGATAAG AAAGGCCCCA TCGTGCCGCT GTTTGCTAAG CATTTCTTCT GCCTTGGCTC       840
TGGGGATTTT GCCAAAAAAC CACGGATGTG GTTTCATTTC TATGTAGTTC TTGGGAATGA       900
AGCCGTCTTT TCCATTAAGC TCTGCCAATT CGGGCCCGAA TTCACTGGC                   949
```